US011123285B2

(12) United States Patent
Lichter et al.

(10) Patent No.: US 11,123,285 B2
(45) Date of Patent: Sep. 21, 2021

(54) AURIS FORMULATIONS FOR TREATING OTIC DISEASES AND CONDITIONS

(71) Applicants: Otonomy, Inc., San Diego, CA (US); The Regents of the University of California, Oakland, CA (US)

(72) Inventors: Jay Lichter, San Diego, CA (US); Andrew M. Trammel, Olathe, KS (US); Fabrice Piu, San Diego, CA (US); Qiang Ye, San Diego, CA (US); Luis A. Dellamary, San Diego, CA (US); Carl Lebel, Malibu, CA (US); Jeffrey P. Harris, La Jolla, CA (US)

(73) Assignees: Otonomy, Inc., San Diego, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/389,213

(22) Filed: Apr. 19, 2019

(65) Prior Publication Data

US 2019/0307678 A1    Oct. 10, 2019

Related U.S. Application Data

(63) Continuation of application No. 15/099,336, filed on Apr. 14, 2016, which is a continuation of application
(Continued)

(51) Int. Cl.
| | | |
|---|---|---|
| *A61K 9/00* | (2006.01) | |
| *A61K 9/06* | (2006.01) | |
| *A61K 9/14* | (2006.01) | |
| *A61K 9/16* | (2006.01) | |
| *A61K 38/18* | (2006.01) | |
| *A61K 47/32* | (2006.01) | |
| *A61K 9/127* | (2006.01) | |
| *C07K 16/24* | (2006.01) | |
| *A61K 31/05* | (2006.01) | |
| *A61K 31/13* | (2006.01) | |
| *A61K 31/137* | (2006.01) | |
| *A61K 31/325* | (2006.01) | |
| *A61K 31/43* | (2006.01) | |

(Continued)

(52) U.S. Cl.
CPC .............. *A61K 9/0046* (2013.01); *A61K 9/06* (2013.01); *A61K 9/127* (2013.01); *A61K 9/14* (2013.01); *A61K 9/16* (2013.01); *A61K 31/05* (2013.01); *A61K 31/13* (2013.01); *A61K 31/137* (2013.01); *A61K 31/325* (2013.01); *A61K 31/43* (2013.01); *A61K 31/436* (2013.01); *A61K 31/519* (2013.01); *A61K 31/5513* (2013.01); *A61K 31/5517* (2013.01); *A61K 38/18* (2013.01); *A61K 38/185* (2013.01); *A61K 38/1808* (2013.01); *A61K 38/1825* (2013.01); *A61K 38/1858* (2013.01); *A61K 38/1883* (2013.01); *A61K 47/14* (2013.01); *A61K 47/18* (2013.01); *A61K 47/32* (2013.01); *A61K 47/38* (2013.01); *C07K 16/241* (2013.01); *A61K 2039/505* (2013.01); *C07K 2317/21* (2013.01); *C07K 2317/76* (2013.01)

(58) Field of Classification Search
CPC ................ A61K 38/18; A61K 38/1808; A61K 38/1825; A61K 38/185; A61K 38/1858; A61K 38/1883; A61K 31/05; A61K 31/113; A61K 31/137; A61K 31/325; A61K 31/43; A61K 31/436; A61K 31/519; A61K 31/5513; A61K 31/5517; A61K 47/14; A61K 47/18; A61K 47/32; A61K 47/38; A61K 9/0046; A61K 9/06; A61K 9/127; A61K 9/14; A61K 9/16; A61K 2039/505; A61P 25/02; A61P 25/22; A61P 27/16; A61P 31/04; A61P 37/02; A61P 43/00; C07K 16/241; C07K 2317/21; C07K 2317/76
See application file for complete search history.

(56) References Cited

U.S. PATENT DOCUMENTS

| | | |
|---|---|---|
| 4,188,373 A | 2/1980 | Krezanoski |
| 4,478,822 A | 10/1984 | Haslam et al. |

(Continued)

FOREIGN PATENT DOCUMENTS

| | | |
|---|---|---|
| EP | 1107791 B1 | 5/2007 |
| JP | 2001520188 A | 10/2001 |

(Continued)

OTHER PUBLICATIONS

Ahn et al. Lipoic acid rescues DBA mice from early-onset age-related hearing impairment. Neuroreport 19(13):1265-1269 (2008).
Arnold et al. Novel slow- and fast-type drug release round-window microimplants for local drug application to the cochlea: an experimental study in guinea pigs. Audiol Neurootol 10(1):53-63 (2005).
Atar et al. Therapeutics of hearing loss: expectations vs reality. Drug Discovery Today 10(19):1323-1330 (2005).
Auris Medical. Press release reporting initiating of phase I/II clinical trial with AM-101. (1 pg.) (Feb. 22, 2007).

(Continued)

*Primary Examiner* — Sarah Pihonak
(74) *Attorney, Agent, or Firm* — Procopio, Cory, Hargreaves & Savitch LLP

(57) ABSTRACT

Disclosed herein are compositions and methods for the treatment of otic disorders with immunomodulating agents and auris pressure modulators. In these methods, the auris compositions and formulations are administered locally to an individual afflicted with an otic disorder, through direct application of the immunomodulating and/or auris pressure modulating compositions and formulations onto the auris media and/or auris interna target areas, or via perfusion into the auris media and/or auris interna structures.

17 Claims, 4 Drawing Sheets

Specification includes a Sequence Listing.

Related U.S. Application Data

No. 14/745,160, filed on Jun. 19, 2015, now Pat. No. 10,272,034, which is a continuation of application No. 12/427,663, filed on Apr. 21, 2009, now Pat. No. 9,132,087.

(60) Provisional application No. 61/087,905, filed on Aug. 11, 2008, provisional application No. 61/055,625, filed on May 23, 2008, provisional application No. 61/086,105, filed on Aug. 4, 2008, provisional application No. 61/073,716, filed on Jun. 18, 2008, provisional application No. 61/140,033, filed on Dec. 22, 2008, provisional application No. 61/127,713, filed on May 14, 2008, provisional application No. 61/101,112, filed on Sep. 29, 2008, provisional application No. 61/094,384, filed on Sep. 4, 2008, provisional application No. 61/074,583, filed on Jun. 20, 2008, provisional application No. 61/060,425, filed on Jun. 10, 2008, provisional application No. 61/048,878, filed on Apr. 29, 2008, provisional application No. 61/046,543, filed on Apr. 21, 2008, provisional application No. 61/076,567, filed on Jun. 27, 2008, provisional application No. 61/076,576, filed on Jun. 27, 2008, provisional application No. 61/160,233, filed on Mar. 13, 2009, provisional application No. 61/086,094, filed on Aug. 4, 2008, provisional application No. 61/083,830, filed on Jul. 25, 2008, provisional application No. 61/083,871, filed on Jul. 25, 2008, provisional application No. 61/087,951, filed on Aug. 11, 2008, provisional application No. 61/088,275, filed on Aug. 12, 2008, provisional application No. 61/082,450, filed on Jul. 21, 2008.

(51) Int. Cl.
*A61K 31/436* (2006.01)
*A61K 31/519* (2006.01)
*A61K 31/5513* (2006.01)
*A61K 31/5517* (2006.01)
*A61K 47/14* (2017.01)
*A61K 47/18* (2017.01)
*A61K 47/38* (2006.01)
*A61K 39/00* (2006.01)

(56) References Cited

U.S. PATENT DOCUMENTS

| | | | |
|---|---|---|---|
| 4,530,840 A | 7/1985 | Tice et al. | |
| 4,900,552 A | 2/1990 | Sanvordeker et al. | |
| 4,938,763 A | 7/1990 | Dunn et al. | |
| 4,968,507 A | 11/1990 | Zentner et al. | |
| 5,292,516 A | 3/1994 | Viegas et al. | |
| 5,324,519 A | 6/1994 | Dunn et al. | |
| 5,451,399 A | 9/1995 | Gimbrone, Jr. et al. | |
| 5,503,848 A | 4/1996 | Perbellini et al. | |
| 5,702,716 A | 12/1997 | Dunn et al. | |
| 5,714,167 A | 2/1998 | Milstein et al. | |
| 5,744,153 A | 4/1998 | Yewey et al. | |
| 5,814,330 A | 9/1998 | Putteman et al. | |
| 5,837,681 A | 11/1998 | Magal | |
| 5,861,174 A | 1/1999 | Stratton et al. | |
| 5,929,041 A | 7/1999 | Magal | |
| 5,985,848 A | 11/1999 | Furneaux et al. | |
| 5,990,194 A | 11/1999 | Dunn et al. | |
| 6,004,543 A | 12/1999 | Galey | |
| 6,043,221 A | 3/2000 | Magal et al. | |
| 6,066,722 A | 5/2000 | Furneaux et al. | |
| 6,117,949 A | 9/2000 | Rathi et al. | |
| 6,139,870 A | 10/2000 | Verrecchia | |
| 6,156,728 A | 12/2000 | Gao | |
| 6,177,434 B1 | 1/2001 | Kopke et al. | |
| 6,201,072 B1 | 3/2001 | Rathi et al. | |
| 6,221,367 B1 | 4/2001 | Milstein et al. | |
| 6,225,282 B1 | 5/2001 | Gao | |
| 6,228,847 B1 | 5/2001 | Furneaux et al. | |
| 6,287,588 B1 | 9/2001 | Shih et al. | |
| 6,306,789 B1 | 10/2001 | Dettmar et al. | |
| 6,316,011 B1 | 11/2001 | Ron et al. | |
| 6,319,513 B1 | 11/2001 | Dobrozsi | |
| 6,348,502 B1 | 2/2002 | Gardiner et al. | |
| 6,392,036 B1 | 5/2002 | Karlsson et al. | |
| 6,492,347 B2 | 12/2002 | Furneaux et al. | |
| 6,509,028 B2 | 1/2003 | Williams et al. | |
| 6,548,527 B2 | 4/2003 | Rahman et al. | |
| 6,562,363 B1 | 5/2003 | Mantelle et al. | |
| 6,589,549 B2 | 7/2003 | Shih et al. | |
| 6,638,521 B2 | 10/2003 | Dobrozsi | |
| 6,649,621 B2 | 11/2003 | Kopke et al. | |
| 6,740,664 B2 | 5/2004 | Cagle et al. | |
| 6,803,455 B2 | 10/2004 | Furneaux et al. | |
| 7,001,615 B1 | 2/2006 | Singh et al. | |
| 7,018,645 B1 | 3/2006 | Piao et al. | |
| 7,151,191 B2 | 12/2006 | Boyd et al. | |
| 7,279,499 B2 | 10/2007 | Durst et al. | |
| 7,524,834 B2 | 4/2009 | Karlsson et al. | |
| 7,589,110 B2 | 9/2009 | Puel et al. | |
| 8,030,297 B2 | 10/2011 | Lighter et al. | |
| 8,197,461 B1 | 6/2012 | Arenberg et al. | |
| 8,318,817 B2 | 11/2012 | Lighter et al. | |
| 8,349,353 B2 | 1/2013 | Lighter et al. | |
| 8,399,018 B2 | 3/2013 | Lighter et al. | |
| 8,496,957 B2 | 7/2013 | Lighter et al. | |
| 8,648,119 B2 | 2/2014 | Lighter et al. | |
| 8,784,870 B2 | 7/2014 | Lighter et al. | |
| 8,846,770 B2 | 9/2014 | Lighter et al. | |
| 9,132,087 B2 | 9/2015 | Lighter et al. | |
| 9,744,126 B2 | 8/2017 | Lighter et al. | |
| 10,092,580 B2 | 10/2018 | Lighter et al. | |
| 10,272,034 B2 | 4/2019 | Lighter et al. | |
| 2001/0019823 A1 | 9/2001 | Schramm et al. | |
| 2002/0044920 A1 | 4/2002 | Rahman et al. | |
| 2002/0061898 A1 | 5/2002 | Furneaux et al. | |
| 2002/0132783 A1 | 9/2002 | Sauve et al. | |
| 2003/0092776 A1 | 5/2003 | Ron et al. | |
| 2003/0096830 A1 | 5/2003 | Furneaux et al. | |
| 2003/0099709 A1* | 5/2003 | Shah | A61K 9/06 424/469 |
| 2003/0129240 A1 | 7/2003 | Reeve et al. | |
| 2003/0149261 A1 | 8/2003 | Schramm et al. | |
| 2003/0229333 A1 | 12/2003 | Ashton et al. | |
| 2004/0053944 A1 | 3/2004 | Furneaux et al. | |
| 2004/0082509 A1 | 4/2004 | Bonny | |
| 2004/0101560 A1 | 5/2004 | Sawchuk et al. | |
| 2004/0110772 A1 | 6/2004 | Furneaux et al. | |
| 2004/0181063 A1 | 9/2004 | Furneaux et al. | |
| 2004/0185047 A1 | 9/2004 | Giles-Komar et al. | |
| 2004/0192763 A1 | 9/2004 | Chenard et al. | |
| 2004/0247575 A1 | 12/2004 | Caplice et al. | |
| 2005/0123541 A1 | 6/2005 | Heavner et al. | |
| 2005/0137122 A1 | 6/2005 | Sharif | |
| 2005/0147585 A1 | 7/2005 | Schwarz | |
| 2005/0153984 A1 | 7/2005 | Chen et al. | |
| 2005/0214338 A1 | 9/2005 | Guitton et al. | |
| 2005/0215572 A1 | 9/2005 | Kelly et al. | |
| 2005/0220831 A1 | 10/2005 | Jorsal | |
| 2005/0227986 A1 | 10/2005 | Bo et al. | |
| 2005/0272931 A1 | 12/2005 | Bo et al. | |
| 2005/0277631 A1 | 12/2005 | Doherty et al. | |
| 2005/0277643 A1 | 12/2005 | Kelly et al. | |
| 2005/0277646 A1 | 12/2005 | Doherty et al. | |
| 2006/0013858 A1 | 1/2006 | Trune | |
| 2006/0030618 A1 | 2/2006 | Bo et al. | |
| 2006/0034889 A1 | 2/2006 | Jo et al. | |
| 2006/0046970 A1 | 3/2006 | Bowman et al. | |
| 2006/0063802 A1 | 3/2006 | Guitton et al. | |
| 2006/0074083 A1 | 4/2006 | Kalvinsh et al. | |
| 2006/0100490 A1 | 5/2006 | Wang et al. | |
| 2006/0105967 A1 | 5/2006 | Hsu et al. | |

(56) References Cited

U.S. PATENT DOCUMENTS

| | | |
|---|---|---|
| 2006/0194801 A1 | 8/2006 | Kelly et al. |
| 2006/0205773 A1 | 9/2006 | Kelly et al. |
| 2006/0205980 A1 | 9/2006 | Hanazawa et al. |
| 2006/0211741 A1 | 9/2006 | Hanazawa et al. |
| 2006/0264897 A1 | 11/2006 | Lobl et al. |
| 2006/0269602 A1 | 11/2006 | Dasch et al. |
| 2006/0270682 A1 | 11/2006 | Inoue et al. |
| 2006/0276393 A1 | 12/2006 | Milburn et al. |
| 2007/0021352 A1 | 1/2007 | Anderson et al. |
| 2007/0110788 A1 | 5/2007 | Hissong et al. |
| 2007/0128177 A1 | 6/2007 | Burstein et al. |
| 2007/0178051 A1 | 8/2007 | Pruitt et al. |
| 2007/0190043 A1 | 8/2007 | Sych et al. |
| 2007/0249538 A1 | 10/2007 | Sazani et al. |
| 2007/0281978 A1 | 12/2007 | Nakada et al. |
| 2007/0299113 A1 | 12/2007 | Kalvinsh et al. |
| 2008/0015183 A1 | 1/2008 | Bakthavatchalam et al. |
| 2008/0085901 A1 | 4/2008 | Caldwell et al. |
| 2008/0088713 A1 | 4/2008 | Jung et al. |
| 2008/0089883 A1 | 4/2008 | Kandimalla et al. |
| 2008/0103118 A1 | 5/2008 | Clement et al. |
| 2008/0153857 A1 | 6/2008 | Bakthavatchalam et al. |
| 2008/0175794 A1 | 7/2008 | Caldwell et al. |
| 2009/0324552 A1 | 12/2009 | Lighter et al. |
| 2009/0325938 A1 | 12/2009 | Lighter et al. |
| 2010/0015228 A1 | 1/2010 | Lighter et al. |
| 2010/0015263 A1 | 1/2010 | Lighter et al. |
| 2010/0016218 A1 | 1/2010 | Lighter et al. |
| 2010/0016450 A1 | 1/2010 | Lighter et al. |
| 2010/0197800 A1 | 8/2010 | Friedman et al. |
| 2011/0166960 A1 | 7/2011 | Simons et al. |
| 2016/0228357 A1 | 8/2016 | Lighter et al. |
| 2016/0243028 A1 | 8/2016 | Lighter et al. |

FOREIGN PATENT DOCUMENTS

| | | |
|---|---|---|
| JP | 2005220070 A | 8/2005 |
| JP | 2006509791 A | 3/2006 |
| JP | 2006097031 A | 4/2006 |
| KR | 101449785 B1 | 10/2014 |
| WO | WO-9504533 A2 | 2/1995 |
| WO | WO-9738698 A1 | 10/1997 |
| WO | WO-9901441 A1 | 1/1999 |
| WO | WO-9924051 A2 | 5/1999 |
| WO | WO-0100610 A1 | 1/2001 |
| WO | WO-0130774 A1 | 5/2001 |
| WO | WO-0158890 A1 | 8/2001 |
| WO | WO-0168648 A1 | 9/2001 |
| WO | WO-0224679 A1 | 3/2002 |
| WO | WO-0230353 A2 | 4/2002 |
| WO | WO-0230423 A1 | 4/2002 |
| WO | WO-0241843 A2 | 5/2002 |
| WO | WO-0244153 A1 | 6/2002 |
| WO | WO-0246171 A2 | 6/2002 |
| WO | WO-02056890 A1 | 7/2002 |
| WO | WO-02060386 A1 | 8/2002 |
| WO | WO-02094265 A1 | 11/2002 |
| WO | WO-02094322 A2 | 11/2002 |
| WO | WO-03010163 A1 | 2/2003 |
| WO | WO-03017990 A2 | 3/2003 |
| WO | WO-03024935 A2 | 3/2003 |
| WO | WO-03024936 A1 | 3/2003 |
| WO | WO-03029242 A1 | 4/2003 |
| WO | WO-03034979 A2 | 5/2003 |
| WO | WO-03071986 A2 | 9/2003 |
| WO | WO-03076447 A1 | 9/2003 |
| WO | WO-2004058754 A1 | 7/2004 |
| WO | WO-2005009987 A1 | 2/2005 |
| WO | WO-2005113544 A1 | 12/2005 |
| WO | WO-2006076318 A1 | 7/2006 |
| WO | WO-2006099325 A2 | 9/2006 |
| WO | WO-2007031098 A1 | 3/2007 |
| WO | WO-2007031280 A2 | 3/2007 |
| WO | 2007038949 A1 | 4/2007 |
| WO | WO-2007037874 A2 | 4/2007 |
| WO | WO-2007037886 A2 | 4/2007 |
| WO | WO-2007038949 A1 | 4/2007 |
| WO | WO-2007045876 A1 | 4/2007 |
| WO | WO-2007119098 A2 | 10/2007 |
| WO | WO-2007150016 A2 | 12/2007 |
| WO | WO-2008076556 A2 | 6/2008 |
| WO | WO-2010048095 A2 | 4/2010 |
| WO | WO-2010048095 A3 | 7/2010 |

OTHER PUBLICATIONS

Auris Medical press release reporting results of phase I/II clinical trial with AM-111. (1 pg.)(Jun. 21, 2006).

Author Unknown. Hormone-Replacement Therapy Hurts Hearing, Study Finds. University of Rochester Medical Center https://www.urmc.rochester.edu/news/story/1216/hormone-replacement-therapy-hurts-hearing-study-finds.aspx (publ. online Sep. 5, 2006) (3 pgs.).

Barkdull et al. AM-111 Reduces Hearing Loss in a Guinea Pig Model of acute Labryinthitis. The Laryngoscope 117(12):2174-2182 (2007).

Bartfai et al. A low molecular weight mimic of the Toll/IL-1 receptor/resistance domain inhibits IL-1 receptor-mediated responses. PNAS 100(13):7971-7976 (2003).

Battaglia et al. Combination therapy (intratympanic dexamethasone + high-dose prednisone taper) for the treatment of idiopathic sudden sensorineural hearing loss. Otol Neurotol 29(4):453-460 (2008).

Beitz et al. Aquaporin-Mediated Fluid Regulation in the Inner Ear. Cellular and Molecular Neurobiology 23(3):315-329 (2003).

Benoit et al. Riluzole specifically blocks inactivated Na channels in myelinated nerve fibre. Pfluigers Arch. 419:603-609 (1991).

Caggiano. WAY-VNA-932: Treatment of Central Diabetes Inspidus Treatment of Nocturnal Enuresis Treatment of Nocturia Vasopressin V2 Agonist. Drugs Gut 27(3):248-253 (2002).

Campbell et al. Oral-D-methionine (MRX-1024) significantly protects against cisplatin-induced hearing loss: a phase II study in humans. Abst 32nd Ann MidWinter Res Meeting, ARO Abstracts 32:7 (Feb. 14-19, 2009).

Car et al. Society of Toxicology, 46th Annual Meeting, Charlotte, North Carolina. Mar. 25-29, 2007 (496 pgs).

Carfrae et al. 3 Tesla delayed contrast magnetic resonance imaging evaluation of Ménière's disease. Laryngoscope 118:501-505 (Mar. 2008).

Chen et al. Design and preparation of thermosensitive in situ gel of dexamethasone sodium phosphate. J Guangdong Coll Pharm 23(5):518-521 (2007) (English abstract).

Chen et al. Estrogen-related receptor beta/NR3B2 controls epithelial cell fate and endolymph production by the stria vascularis. Dev Cell 13(3):325-337 (2007).

Chen et al. Evaluation of thermosensitive in situ gel using dynamic rheological experiment, Chin Pharm J 43(6):444-447 (2008) (English abstract).

Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).

Chen et al. In vivo distribution and pharmacokinetics of dexamethasone sodium phosphate thermosensitive in situ gel following intratympanic injection. Sichuan Da Xue Xue Bao Yi Xue Ban 37(3):456-459 (2006) (English translation).

Chen et al. Preliminary study on brain-targeted drug delivery via inner ear. Acta Pharmaceutica Sinica 42:1102-1106 (2007) (English Abstract).

Chen et al. Preparation and characterization of dexamethasone acetate-loaded solid lipid nanoparticles. Chinese J Pharm 39(4):261-264 (2008) (English abstract).

Chen et al. Study on dexamethasone thermosensitive in situ gel for treating deafness. Chin Pharm J 41(9):685-688 (2006) (English abstract).

Chi et al. The quantification of endolymphatic hydrops in an experimental animal model with guinea pigs. J Oto-Rhino-Larynol 66:56-61 (2004).

CIPRODEX. product label 2009 (3 pgs.).

(56) References Cited

OTHER PUBLICATIONS

Cohen et al. Etanercept Treatment for Autoimmune Inner Ear Disease: Results of a Pilot Placebo-Controlled Study. Otology & Neurotology 26:903-907 (2005).
Conway et al. Inhibition of tumor necrosis factor-alpha (TNF-alpha) production and arthritis in the rat by GW3333, a dual inhibitor of TNF-alpha-converting enzyme and matrix metalloproteinases. J. Pharmacol. Exp. Ther. 298:900 (2001).
Daijie et al. Intratympanic Dexamethasone for Refractory Sudden Deafness. J. Clin. Otorhinolaryngol Head Neck Surg (China). 22(7):5 pgs (Apr. 2008).
Definition of Neurotrophins. Stedman's Medical Dictionary. 27th Ed. (2 pgs.) (2000).
Derin et al. The effects of L-carnitine on presbyacusis in the rat model. Clin Otolaryngol Allied Sci 29(3):238-241( 2004).
Doble. The pharmacology and mechanism of action of riluzole. Neurology 47(Suppl. 4):S233-S241 (1996).
Doleviczenyi et al.Cochlear dopamine release is modulated by group II metobotropic glutamate receptors via GABAergic neurotransmission. Neuroscience Letters 385:93-98 (2005).
Dourmishev et al. Waardenburg syndrome. Intl J Dermatol 39:656-663 (1999).
Dumortier et al. A Review of Poloxamer 407 Pharmaceutical and Pharmacological Characteristics. Pharm Res 23(12):2709-2728 (2006).
Duprat et al. The neuroprotective agent riluzole activates the two P domain K(+) channels TREK-1 and TRAAK. Mol Pharmacol 57:906-912 (2002).
Endo et al. Novel strategy for treatment of inner ears using a biodegradable gel. Laryngoscope 115(11):2016-2020 (2005).
Feng et al. Effect of Poloxamer 407 on the cochlear orphology and hearing function after perfusion in round window: experiment with guinea pigs. National Medical Journal of China 87(32):2289-2291 (2007) (English Translation).
Feng et al. Effect of poloxamer 407 on the middle ear and inner ear after regional perfusion in guinea pigs. Zhonghua Er Bi Yan Hou Tou Jing Wai Ke Za Zhi 42(6):443-446 (2007) (English translation).
Feng et al. In vitro and in vivo biodegradation of sustained-release vehicle poloxamer 407 in situ gel. Journal of Clinical Otorhinolaryngology Head Neck Surgery 22(1):28-31 (2008) (English Abstract).
Fernandez et al. Self-curing controlled release systems for steroids. Application of prednisolone-based polymeric systems to ear diseases. Biomaterials 26(16):3311-3318 (2005).
Friedman et al. GRM7 variants confer susceptibility to age-related hearing impairment. Hum Mol Genet 18(4):785-796. (2009).
Garcia-Berrocal et al. Does the serological study for viral infection in autoimmune inner ear disease make sense? O.R.L. 70:16-20 (2008).
Garduno-Anaya et al. Dexamethasone inner ear perfusion by intratympanic injection in unilateral Ménière's disease: a two-year prospective, placebo-controlled, double-blind, randomized trial. Otolaryngol Head Neck Surg 133(2):285-294 (2005).
Gloddek et al. Role of Lymphokines in the Immune response of the Inner Ear. Acta Otolaryngol. 108:68-75 (1989).
Greco et al. Meniere's disease might be an autoimmune condition. Autoimmunity Reviews 11:731-738 (2012).
Greengrass et al. Binding characteristics of 3H-prazosin to rat brain alpha-adrenergic receptors. Eur J Pharmacol 55:323-326 (1979).
Gross et al. The treatment of hyponatraemia using vasopressin antagonists. Exp. Physiol. 85:Spec No. 253S-257S (2000).
Grunnet et al. Pharmacological modulation of SK3 channels. Neuropharmacology 40:879-887 (2001).
Gubbels et al. Functional auditory hair cells produced in the mammalian cochlea by in utero gene transfer. Nature 455(7212):537-541 (2008).
Guyot et al. Intratympanic application of an antiviral agent for the treatment of Meniere's disease. ORL J Otorhinolaryngol Relat Spec 70(1):21-6; discussion 26-27 (2008).
Hall et al. Anti-Pneumocystis activities of aromatic diamidoxime prodrugs. Antimicrobial Agents & Chemother. 42(3):666-674 (1998).
Hargunani et al. Intratympanic injection of dexamethasone: time course of inner ear distribution and conversion to its active form. Otol Neurotol 27(4):564-569 (2006).
Harris et al. Immunology of the inner ear: Response of the inner ear to antigen challenge. Otolaryngol. Head Neck Surgery 91:18-32 (1983).
Harris et al. Prevention of noise-induced hearing loss with Src-PTK inhibitors. Hear Res 208(1-2): 14-25 (2005).
Harris et al. Spiral Modiolar Vein: Its Importance in Inner Ear Inflammation. Acta Otolaryngol. (1990) 110:357-365.
Harris et al. Treatment of corticosteroid-responsive autoimmune inner ear disease with methotrexate: a randomized controlled trial. JAMA 290(14):1875-1883 (2003).
Hashimoto et al. Innate immunity contributes to cochlear adaptive immune responses. Audiol. Neurootol. (2005) 10:35-43.
Hill et al. Cisplation-Induced Ototoxicity: Effect of Intratympanic Dexamethasone Injections. Otol. Neurotol. 29(7):1005-1011 (2008).
Hoffer et al. Transtympanic management of tinnitus. Otolaryngol Clin North Am 36(2):353-358 (2003).
Hoshino et al. The non-steroidal anti-inflammatory drugs protect mouse cochlea against acoustic injury. Tohoku J Exp Med 216(1):53-59 (2008).
Hubert et al. Antagonism by riluzole of entry of calcium evoked by NMDA and veratridine in rat cultured granule cells: evidence fora dual mechanism of action. Br J Pharmacol 113:261-267 (1994).
Inaoka et al. Local application of hepatocyte growth factor using gelatin hydrogels attenuates noise-induced hearing loss in guinea pigs. Acta Otolaryngol 129(4):453-457 (2009).
Iwai et al. Cochlear Protection by Local Insulin-Like Growth Factor-1 Application Using Biodegradable Hydrogel. Laryngoscope 116(4):529-533 (2006).
Jeong et al. Biodegradable block copolymers as injectable drug-delivery systems. Nature 388:860-862 (1997).
Jeong et al. Drug release from biodegradable injectable thermosensitive hydrogel of PEG-PLGA-PEG triblock copolymers. Journal of Controlled Release 63:155-163 (2000).
Jeong et al. Thermosensitive sol-gel reversible hydrogels. Advanced Drug Delivery Reviews 54:37-51 (2002).
Jia et al. Intratympanic dexamethasone for refractory sudden deafness. Lin Chung Er Bi Yan Hou Tou Jing Wai Ke Za Zhi 22(7):309-311 (2008) (English translation).
Jung et al. Molecular characterization of an aquaporin cDNA from brain: candidate osmoreceptor and regulator of water balance. PNAS USA 91:13052-13056 (1994).
Karin et al. The IKK NF-kappa B system: a treasure trove for drug development. Nature Reviews Drug Discovery 3:17-26 (2004).
Karin. How NF-kappaB is activated: the role of the IkappaB kinase (IKK) complex. Oncogene 18:6867-6874 (1999).
Karin. The beginning of the end: IkappaB kinase (IKK) and NF-kappaB activation. J. Biol. Chem 274:27339-27342 (1999).
Karolewicz et al. Thermosensitive polymers in drug form technology H. Possibilities of use of thermosensitive polymers as active substance carriers. Polimery W Medycynie 38(1):15-26 (2008) (English abstract).
Katakam et al. Controlled Release of human growth hormone in rats following parental administration of poloxamer gels. J Controlled Release 49(1):21-26 (1997).
Kazama et al. Lithium effectively complements vasopressin V2 receptor antagonist in the treatment of hyponatraemia of SIADH rats. Nephrol Dial Transplant 22(1):68-76 (2007).
Keithley et al. GDNF protects the cochlea against noise damage. Neuroreport 9(10):2183-2187 (1998).
Kim et al. Effects of tumor necrosis factor alpha antagonist, platelet activating factor antagonist, and nitric oxide synthase inhibitor on experimental otitis media with effusion. Ann Otol Rhinol Laryngol 115(8):617-623 (2006).
Kim et al. Oral administration of collagen conjugated with cholera toxin induces tolerance to type II collagen and suppresses chondritis in an animal model of autoimmune ear disease. Ann Otol Rhinal Larynogol 110:646-654 (2001).
Kim et al. Roles of NADPH Oxidases in Cisplatin-Induced Reactive Oxygen Species Generation and Ototoxicity. J. Neurosci 30(11):3933-3946 (2010).

(56) References Cited

OTHER PUBLICATIONS

Kitahara et al. Up-regulation of cochlear aquaporin-3 mRNA expression after intra-endolymphatic sac application of dexamethasone. Neurol Res. 25(8):865-870 (2003).
Kitano et al.Vasopressin and oxytocin receptor mRNAs are expressed in the rat inner ear. Neuroreport 8:2289-2292 (1997).
Kondo et al. Novel design of nonpeptide AVP V(2) receptor agonists: structural requirements for an agonist having 1-(4-aminobenzoyl)-2,3,4, 5-tetrahydro-1H-1-benzazepine as a template. J Med Chem 43:4388-4397 (2000).
Lamm et al. The effect of prednisolone and non-steroidal anti-inflammatory agents on the normal and noise-damaged guinea pig inner ear. Hear Res 115(1-2):149-161 (1998).
Lavreysen et al. Therapeutic potential of group III metabotropic glutamate receptors. Curr Med Chern 15(7):671-84 (2008).
Lee et al. Novel therapy for hearing loss: delivery of insulin-like growth factor 1 to the cochlea using gelatin hydrogel. Otol Neurotol 28(7):976-981 (2007).
Lee et al. Regional delivery of vancomycin using pluronic F-127 to inhibit methicillin resistant *Staphylococcus aureus* (MRSA) growth in chronic otitis media in vitro and in vivo. J Control Release 96(1):1-7 (2004).
Liu et al. Calcineurin is a common target of cyclophilin-cyclosporin A and FKBP-FK506 complexes. Cell66:807-815 (1991).
Liu et al. Permeability of different Dexamethasone drugs through round window membrane. Zhonghua Er Bi Yan Hou Tou Jing Wai Ke Za Zhi 41(3):211-215 (2006) (English abstract).
Luetje et al. Plasmapheresis in autoimmune inner ear disease: long-term follow-up. Am. J Otol. 18:572-576 (1997).
Luzzi. Microencapsulation. Pharm Psy 59:1367-1376 (1970).
Mahindrakar. A case of carcinoma of middle ear treated with cytotoxic perfusion. J. Laryngol. Otol. 79:921-925 (1965).
Majithiya et al. Thermoreversible-mucoadhesive gel for nasal delivery of sumatriptan. AAPS PharmSciTech 7(3):Article 67:E1-E6 (2006).
Martin et al. Selective V2-receptor vasopressin antagonism decreases urinary aquaporin-2 excretion in patients with chronic heart failure. J. Am. Soc. Nephrol. 10(10):2165-2170 (1999).
Martini et al. An animal model based on the Sprague Dawley rat for the evaluation of ototoxicity. Ann. N.Y. Acad. Sci. 884:85-98 (1999).
McCarthy et al. Alport syndrome: a review. Clinical Eye and Vision Care 12:139-150 (2000).
McGuinness et al. Exogenous BDNF rescues rat spiral ganglion neurons in vivo. Otol Neurotol 26(5):1064-1072 (2005).
Meltser et al. Estrogen receptor beta protects against acoustic trauma in mice. J Clin Invest 118(4): 1563-1570 (2008).
Mercurio et al. IKK-1 and IKK-2: cytokine-activated IkappaB kinases essential for NF-kappaB activation. Science 278:860-866 (1997).
Merkus et al. Lymphoma in the ear. J. Otorhinolaryngol. Relat. Spec 62:274-277 (2000).
Mestre et al. Frequency-independent blockade of cardiac Na+ channels by riluzole: comparison with established anticonvulsants and class I anti-arrhythmics. Fundam Clin Pharmacol 14:107-117 (2000).
Miceli et al. Molecular pharmacology and therapeutic potential of neuronal Kv7-modulating drugs. Curr Opin Pharmacol 8(1):65-74 (2008).
Mitsukawa et al. A selective metabotropic glutamate receptor 7 agonist: activation of receptor signaling via an allosteric site modulates stress parameters in vivo. PNAS USA 102(51):18712-18717 (2005).
Miyazaki et al. Thermally reversible xyloglucan gels as vehicles for rectal drug delivery. Journal of Controlled Release (Elsevier, Amsterdam, NL) 56(1-3):75-83 (1998).
Morin et al.The D136A mutation of the V2 vasopressin receptor induces a constitutive activity which permits discrimination between antagonists with partial agonist and inverse agonist activities. FEBS Letters 441(3):470-475 (1998).
Musso et al. N-hydroxyformamide peptidomimetics as TACE/matrix metalloprotease inhibitors: oral activity via P1' isobutyl substitution. Bioorg. Med. Chem. Lett. 11:2147-2151 (2001).
Nakagawa et al. Local drug delivery to inner ear for treatment of hearing loss. Curr Drug Ther 3:143-147 (2008).
Nakamura et al. Antidiuretic effects of a nonpeptide vasopressin V(2)-receptor agonist, OPC-51803, administered orally to rats. J Pharmacal Exp Ther 295(3):1005-1011 (2000).
Nakamura et al. Characterization of a novel nonpeptide vasopressin V(2)-agonist, OPC-51803, in cells transfected human vasopressin receptor subtypes. Br J Pharmacal 129(8):1700-1706 (2000).
Nance et al. The Genetics of Deafness. Mental Retardation and Developmental Disabilities 9:109-119 (2003).
Nemeth et al. Antifoaming action of polyoxeethy lene-polyoxypropyiene-polyoxyethylene-type triblock copolymers on BSA foams. Colloids and Surfaces A: Physicochemical and Engineering Aspects 127(1-3):151-162 (1997).
Nishimaki et al. Reduction of metabotropic glutamate receptor-mediated heterosynaptic inhibition of developing MNTB-LSO inhibitory synapses. Eur J Neurosci 26(2):323-330 (2007).
Norman et al. Conivaptan Hydrochloride: Treatment of Heart Failure, Treatment of Hyponatremia, Vasopressin V1a/V2 Antagonist. Drugs Fut 25(11):1121-1130 (2000).
Nouvian et al. Degeneration of sensory outer hair cells following pharmacological blockade of cochlear KCNQ channels in the adult guinea pig. Eur J Neurosci 17(12):2553-2562 (2003).
O'Brien et al. A family of highly selective allosteric modulators of the metabotropic glutamate receptor subtype 5. Mol. Pharmacol. 64(3):731-740 (2003).
Oldstone. Virus-induced autoimmunity: molecular mimicry as a route to autoimmune disease. J. Autoimmune 2(suppl):187-194 (1989).
Oliveira et al. Viral etiology for inner ear diseases: proven, unproven, unlikely. ORL 70:42-51 (2008).
Palm et al. V2-vasopressin receptor antagonists-mechanism of effect and clinical implications in hyponatraemia. Nephrol Dial Transplant 14:2559-2562 (1999).
Pappas et al. Topical Antibiotic Ear Drops: Are They Safe? Int J Clin Pract. 60:1115-1119 (2006).
Park et al. Effect of inhibitor of tumor necrosis factor-alpha and oxatomide on immune mediated otitis media. Laryngoscope 116(9):1642-1646 (2006).
Parker et al. Triazolo-tetrahydrofluorenones as selective estrogen receptor beta agonsits. Bioorg & Med. Chem. Ltrs,16:4652-4656 (2006).
Parnes et al. Corticosteroid pharmacokinetics in the inner ear fluids: an animal study followed by clinical application. Laryngoscope 109(7 Pt 2 Supplement No. 91):1-17 (1999).
Patel et al. Association of proinflammatory cytokine gene polymorphisms with susceptibility to otitis media. Pediatrics118:2273-2279 (2006).
Paulson et al. A novel controlled local drug delivery system for inner ear disease. Laryngoscope 118(4):706-711 (2008).
PCT/US2008/061330 International Search Report dated Jul. 31, 2008.
PCT/US2009/041320 International Search Report dated Nov. 26, 2009.
PCT/US2009/061190 International Search Report dated May 14, 2010.
PCT/US2009/067552 International Search Report dated Aug. 18, 2010.
PCT/US2019/012941 International Search Report and Written Opinion dated Mar. 26, 2019.
Peng et al. Clinical investigation of different routes of administration of dexamethasone on sudden deafness. Lin Chung Er Bi Yan Hou Tou Jing Wai Ke Za Zhi 22(10):442-445. (2008) (English translation).
Peng et al. Group I metabotropic glutamate receptors in spiral Ganglion neutrons contribute to excitatory neurotransmissions in the cochlea. Neuroscience 123:221-230 (2004).
Piu et al. OTO-104: A Sustained-Release Dexamethasone Hydrogel for the Treatment of Otic Disorders. Otol & Neurology 32(1):171-179 (2011).

(56) References Cited

OTHER PUBLICATIONS

Plontke et al. Rapid clearance of methylprednisolone after intratympanic application in humans. Comment on: Bird PA. Begg EJ. Zhang M. et al. Intratympanic versus intravenous delivery of methylprednisolone to cochlear perilymph. Otol Neurotol (2007); 28:1124-30. Otol Neurotol 29(5):732-733 (2008).
Pondugula et al. Glucocorticoid regulation of genes in the amiloride-sensitive sodium transport pathway by semicircular canal duct epithelium of neonatal rat. Physiol Genomics 24(2):114-123 (2006).
Pondugula et al. Glucocorticoids stimulate cation absorption by semicircular canal duct epithelium via epithelial sodium channel. Am J Physiol Renal Physiol 286(6):F1127-1135 (2004).
Psillas et al. Potential efficacy of early treatment of acute acoustic trauma with steroids and piracetam after gunshot noise. Eur Arch Otorhinolaryngol 265(12):1465-1469 (2008).
Puel. Chemical synaptic transmission in the cochlea. Prog Neurobiol 47(6):449-476 (1995).
Queille-Roussel et al. The new topical ascomycin derivative SDZ ASM 981 does not induce skin atrophy when applied to normal skin for 4 weeks: a randomized, double-blind controlled study. Br. J. Dermatol. 144:507-513 (2001).
Rahmen et al. Etanercept therapy for immune-mediated cochleovestibular disorders: preliminary results in a pilot study. Otol. Neural.22:619-624 (2001).
Richard et al. Effects of sterilizing-grade filters on the physicochemical properties of onion like vesicles. Int J Pharm 312(1-2):144-150 (2006).
Ross et al. Aqueous Solubilities of some variously Substituted Quinolone Antimicrobials. Int'l of Pharm 63:237-250 (1990).
Rothwarf et al. IKK-gamma is an essential regulatory subunit of the IkappaB kinase complex. Nature 395:297-300 (1998).
Salt et al. Local Inner Ear Drug Delivery and Pharmacokinetics. Drug Discovery Today NIH 10(19): 1299-1306 (2005).
Sanghi et al. Vasopressin antagonism: a future treatment option in heart failure. Eur. Heart J. 26:538-543 (2005).
Satoh et al. Proinflammatory cytokine expression in the endolymphatic sac during inner ear inflammation. J Assoc. Res. Otolaryngol.4:139-147 (2003).
Satoh et al. Tumor necrosis factor-alpha, an initiator, and etanercept, an inhibitor of cochlear inflammation. Laryngoscope 112:1627-1634 (2002).
Schoepp et al. Pharmacological agents acting at subtypes of metabotropic glutamate receptors. Neuropharmacology 38(10):1431-1476 (1999).
Schreiber et al. The mechanism of action of cyclosporin A and FK506. Immunol. Today 13:136-142 (1992).
Schuknecht. Ablation therapy for the relief of Ménière's disease. Laryngoscope 66:859-870 (1956).
Seidman et al. Anti-intercellular adhesion molecule-1 antibody's effect on noise damage. Laryngoscope 119(4):707-712 (2009).
She et al. A short term study on the efficacies of intratympanic prednisolone and dexamethasone injection for subjective tinnitus. Lin Chung Er Bi Yan Hou Tou Jing Wai Ke Za Zhi 22(19):871-873 (2008) (English translation).
Shepherd et al. Neurotrophins and electrical stimulation for protection and repair of spiral ganglion neurons following sensorineural hearing loss. Hear Res 242(1-2):100-109 (2008).
Shinohara et al. Neurotrophic factor intervention restores auditory function in deafened animals. PNAS USA 99(3):1657-1660 (2002).
Shore et al. Trigeminal ganglion Innervates the Auditory Brainstem. J. Comp. Neurology10:271-285 (2000).
Sismanis et al. Methotrexate management of immune-mediated cochleovestibular disorders. Otolaryngol116:146-152 (1997).
Sismanis et al. Methotrexate therapy for autoimmune hearing loss: a preliminary report. Laryngoscope104:932-934 (1994).
Skotnicki et al. Chapter 16: TNF-α Converting Enzyme (TACE) as a Therapeutic Target. Annual Reports in Medicinal Chemistry 38:153-162 (2003).
Smith et al. Sensorineural hearing loss in children. Lancet 365(9462):879-890 (2005).
Stefani et al. Differential inhibition by riluzole, lamotrigine, and phenytoin of sodium and calcium currents in cortical neurons: implications for neuroprotective strategies. Exp Neurol 147:115-122 (1997).
Stuetz et al. Discovery of topical calcineurin inhibitors and pharmacological profile of pimecrolimus. Int. Arch. Allergy Immunol. (141:199-212 (2006).
Sun et al. A new class of reverse signaling costimulators belongs to the TNF family. J. Immunology 179:4307-4312(2007).
Sun et al. In vitro permeability of round window membrane to transforming dexamethasone with delivery vehicles—a dosage estimation. Chin Med J 120(24):2284-2289 (2007) (English translation).
Suzuki et al. Pharmacological Characterization of a New, orally Active and Potent Allosteric Metabotropic Glutamate receptor 1 Antagonist, 4-[1-2{Fluorophyridin-3-yl)-5-methyl-1H-1,2,3-triazol-4-yl]-N-isopropyl-N-methyl-3,6-dihydropyricine-1(2H)-carboxamide (FTIDC). J Pharmacol Exp Ther 321 (3):1144-1153 (2007).
Synphora AB. website printout for JB004/A 2009 (1 pg.).
Tabuchi et al. Hearing impairment in TRPV4 knockout mice. Neurosci Lett 382(3):304-308 (2005).
Taguchi et al. Expressions of aquaporin-2. vasopressin type 2 receptor, transient receptor potential channel vanilloid (TRPV)1. and TRPV4 in the human endolymphatic sac. Laryngoscope 117(4):695-698 (2007).
Tahera et al. NF-kB mediated glucocorticoid response in the inner ear after acoustic trauma. J Neurosci Res 83(6):1066-1076 (2006).
Takeda et al. A comparison of dehydration effects of V2-antagonist (OPC-31260) on the inner ear between systemic and round window applications. Hearing Res 218:89-97 (2006).
Takeda et al. Aquaporins as potential drug targets for Meniere's disease and its related diseases. Handb Exp Pharmacol 190:171-184 (2009).
Takeda et al. Decompression effects of erythritol on endolymphatic hydrops. Auris Nasus Larynx 36(2):146-151 (2009).
Takeda et al. Endolymphatic hydrops induced by chronic administration of vasopressin. Hear Res 140:1-6 (2000).
Takeda et al. The effects of V2 antagonist (OPC-31260) on endolymphatic hydrops. Hear Res 182(1-2):9-18. (2003).
Takemura et al. Direct inner ear infusion of dexamethasone attenuates noise-induced trauma in guinea pig. Hear Res 196(1-2):58-68 (2004).
Taktak et al. Assay of Pyrogens by Interleukin-6 Release from Monocytic Cell Lines. J. Pharm. Pharmacol. 43:578-582 (1991).
Takumida et al. Nitric oxide in the inner ear. Cur Opin Neurol 15(1):11-15 (2002).
Tang et al. COUP-TFI controls Notch regulation of hair cell and support cell differentiation. Development 133(18):3683-3693 (2006).
The Royal National Institute for Deaf People (RNID) advertisement insert in Nature Reviews Drug Discovery, May 2009 (4 pgs.).
Thorne et al. Potential role of purinergic signalling in cochlear pathology. Audiol Neurootol 7(3):180-184 (2002).
U.S. Appl. No. 12/427,663 Office Action dated Apr. 29, 2014.
U.S. Appl. No. 12/427,663 Office Action dated Oct. 27, 2014.
U.S. Appl. No. 12/466,310 Office Action dated Jan. 12, 2011.
U.S. Appl. No. 12/504,553 Office Action dated Feb. 14, 2012.
U.S. Appl. No. 12/506,091 Office Action dated Feb. 22, 2012.
U.S. Appl. No. 14/745,160 Office Action dated Jun. 22, 2016.
U.S. Appl. No. 14/745,160 Office Action dated Mar. 1, 2017.
U.S. Appl. No. 14/745,160 Office Action dated Sep. 28, 2017.
U.S. Appl. No. 15/099,336 Office Action dated Feb. 16, 2018.
U.S. Appl. No. 15/099,336 Office Action dated Mar. 28, 2017.
U.S. Appl. No. 15/099,336 Office Action dated Oct. 21, 2016.
U.S. Appl. No. 15/622,633 Office Action dated Jun. 6, 2019.
U.S. Appl. No. 15/710,727 Office Action dated May 1, 2019.
Van Wijk et al. Local perfusion of the tumor necrosis factor alpha blocker infliximab to the inner ear improves autoimmune neurosensory hearing loss. Audiol Neurootol 11(6):357-365 (2006).
Vass et al. Direct evidence of trigeminal innervation of the cochlear blood vessels. Neuroscience 84:559-567 (1998).

(56) References Cited

OTHER PUBLICATIONS

Wang et al. A novel dual inhibitor of calpains and lipid peroxidation (BN82270) rescues the cochlea from sound trauma. Neuropharmacology 52(6):1426-1437 (2007).
Wang et al. Blockage of Immune-Mediated Inner Ear Damage by Etanercept. Otology and Neurotology 24:52-57 (2003).
Wang et al. Over-expression of X-linked inhibitor of apoptosis protein slows presbycusis in C57BL/6J mice. Neurobiol Aging 12 pgs. (2008).
Wang et al. Principles of Inner Ear Sustained Release Following Intratympanic Administration, Laryngoscope 121:385-391 (2011).
Watanabe et al. Inhibition of inducible nitric oxide synthase lowers the cochlear damage by lipopolysaccharide in guinea pigs. Free Radic Res 32(4):363-370. (2000).
Watanabe et al. Nitric oxide synthase inhibitor reduces the apoptotic change in the cisplatin-treated cochlea of guinea pigs. Anticancer Drugs 11 (9):731-735 (2000).
Watanabe et al. Nitric oxide synthase inhibitor suppresses the ototoxic side effect of cisplatin in guinea pigs. Anticancer Drugs 11(5):401-406. (2000).
Wei et al. Salicylate-induced degeneration of cochlea spiral ganglion neurons-apoptosis signaling. Neuroscience 168(1):288-299 (Jun. 16, 2010).
Wong et al. Sphincter of Oddi Manometry: Comparison of Post-Procedure Abdominal Pain and Post-Procedure Pancreatitis SGW. Gastroent 118(4 Suppl. 2, Part 1) (2000).
Woronicz et al. IkappaB kinase-beta: NF-kappaB activation and complex formation with IkappaB kinase-alpha and NIK. Science 278:866-869 (1997).
Wu et al. Characterization of riluzole-induced stimulation of large-conductance calcium-activated potassium channels in rat pituitary GH3 cells. J Investig Med 47(9):484-495 (1999).
Xu et al. Neuroprotective Agent Riluzole Dramatically Slows Inactivation of Kv1.4 Potassium Channels by a Voltage-Dependent Oxidative Mechanism. J Pharmacol Exp Ther 299:227-237 (2001).
Yamamoto et al. Inhibition of Notch/RBP-J signaling induces hair cell formation in neonate mouse cochleas. J Mol Med 84(1):37-45 (2006).
Yang et al. Intratympanic immunosuppressives for prevention of immune-mediated sensorineural hearing loss. Am J Otol 21(4):499-504 (2000).
Yildirim et al. Effect of intratympanic dexamethasone on noise-induced temporary threshold shift. Laryngoscope 115(7):1219-1222 (2005).
Zadeh et al. Diagnosis and treatment of sudden-onset sensorineural hearing loss: a study of 51 patients. Otolaryngol Head Neck Surg 128(1):92-98 (2003).
Zandi et al. The IkappaB kinase complex (IKK) contains two kinase subunits, IKKalpha and IKKbeta, necessary for IkappaB phosphorylation and NF-kappaB activation. Cell91:243-252 (1997).
Zardoya et al. A phylogenetic framework for the aquaporin family in eukaryotes. J Mol Evol 52:391-404 (2001).
Zheng et al. Vanilloid receptors in hearing: altered cochlear sensitivity by vanilloids and expression of TRPV1 in the organ of corti. J Neurophysiol 90(1):444-455 (2003).
Zhou et al. Intratympanic administration of methylprednisolone reduces impact of experimental intensive impulse noise trauma on hearing. Acta Oto-Laryngologica 129:602-607 (2009).
Endo et al., Novel Strategy for Treatment of Inner Ears using a Biodegradable Gel; Laryngoscope Nov. 2005; 115(11):2016-2020.
Gregory C. Barkdull et al, "AM-111 Reduces Hearing Loss in a Guinea Pig Model of Acute Labyrinthitis", The Laryngoscope, (Dec. 1, 2007), vol. 117, No. 12, doi:10.1097/MLG.0b013e3181461f92, ISSN 0023-852X, pp. 2174-2182, XP055143103 [Y] 1-15.
Gilles Dumortier et al., "A Review of Poloxamer407 Pharmaceutical and Pharmacological Characteristics", Pharmaceutical Research, Kluwer Academic Publishers-Plenum Publishers, NL, (Nov. 11, 2006), vol. 23, No. 12, doi:10.1007/S11095-006-9104-4, ISSN 1573-904X, pp. 2709-2728, XP019453318 [A] 1-15.
Wang et al., Otology and Neurotology, 2003, Lippincott Williams and Wilkins, vol. 24pp. 52-57.
Otolaryngol Head Neck Surg . Aug. 2005;133(2):285-94.
Drug Discov Today . Oct. 1, 2005;10(19):1299-306.

* cited by examiner

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgaattaat                                                         10
```

AURIS FORMULATIONS FOR TREATING OTIC DISEASES AND CONDITIONS

RELATED APPLICATIONS

This patent application is a continuation application of U.S. patent application Ser. No. 15/099,336, filed Apr. 14, 2016, which is a continuation application of Ser. No. 14/745,160, filed Jun. 19, 2015; which is a continuation application of U.S. patent application Ser. No. 12/427,663, filed Apr. 21, 2009, now U.S. Pat. No. 9,132,087, issued on Sep. 15, 2015; which claims the benefit of U.S. Provisional Application Ser. No. 61/087,905, filed on Aug. 11, 2008, 61/055,625 filed on May 23, 2008, 61/086,105 filed on Aug. 4, 2008, 61/073,716 filed on Jun. 18, 2008, 61/140,033 filed on Dec. 22, 2008, 61/127,713 filed on May 14, 2008, 61/101,112 filed on Sep. 29, 2008, 61/094,384 filed on Sep. 4, 2008, 61/074,583 filed on Jun. 20, 2008, 61/060,425 filed on Jun. 10, 2008, 61/048,878 filed on Apr. 29, 2008, 61/046,543 filed on Apr. 21, 2008, 61/076,567 filed on Jun. 27, 2008, 61/076,576 filed on Jun. 27, 2008, 61/160,233 filed on Mar. 13, 2009, 61/086,094 filed on Aug. 4, 2008, 61/083,830 filed on Jul. 25, 2008, 61/083,871 filed on Jul. 25, 2008, 61/087,951 filed on Aug. 11, 2008, 61/088,275 filed on Aug. 12, 2008, 61/082,450 filed on Jul. 21, 2008 the disclosures of all of which are herein incorporated by reference in their entirety.

JOINT RESEARCH AGREEMENT

The claimed invention was made as a result of activities undertaken within the scope of a joint research agreement between Jay Benjamin Lichter, Benedikt K. Vollrath, Otonomy, Inc., and Avalon Ventures VIII GP, LLC that was in effect on or before the date the invention was made.

SEQUENCE LISTING

The instant application contains a Sequence Listing which has been submitted via EFS-Web and is hereby incorporated by reference in its entirety. Said ASCII copy, created on Sep. 16, 2018, is named 37173-823.304-Sequence.txt and is 1607 bytes in size.

BACKGROUND OF THE INVENTION

Described herein are formulations for enhanced drug delivery into the external, middle and/or inner ear, including the cochlea and vestibular labyrinth; preferably with little or no systemic release of the drug.

SUMMARY OF THE INVENTION

The auris formulations and therapeutic methods described herein have numerous advantages that overcome the previously-unrecognized limitations of formulations and therapeutic methods described in prior art.

Sterility

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., immunomodulators, aural pressure modulators, antimicrobials) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes can trigger infections and related physiological changes in the isolated microenvironment of the inner ear.

Due to the susceptibilty of the inner ear to infections, auris formulations require a level of sterility that has not been recognized hitherto in prior art. Provided herein are auris formulations that are sterilized with stringent sterilty requirements and are suitable for administration to the middle and/or inner ear. In some embodiments, the auris compatible compositions described herein are substantially free of pyrogens and/or microbes.

Compatibility with Inner Ear Environment

Described herein are otic formulations with an ionic balance that is compatible with the perilymph and/or the endolymph and does not cause any change in cochlear potential. In specific embodiments, osmolarity/osmolality of the present formulations is adjusted, for example, by the use of appropriate salt concentrations (e.g., concentration of sodium salts) or the use of tonicity agents which renders the formulations endolymph-compatible and/or perilymph-compatible (i.e. isotonic with the endolymph and/or perilymph). In some instances, the endolymph-compatible and/or perilymph-compatible formulations described herein cause minimal disturbance to the environment of the inner ear and cause minimum discomfort (e.g, vertigo) to a mammal (e.g., a human) upon administration. Further, the formulations comprise polymers that are biodegradable and/or dispersable, and/or otherwise non-toxic to the inner ear environment. In some embodiments, the formulations described herein are free of preservatives and cause minimal disturbance (e.g., change in pH or osmolarity, irritation) in auditory structures. In some embodiments, the formulations described herein comprise antioxidants that are non-irritating and/or non-toxic to otic structures.

Dosing Frequency

The current standard of care for auris formulations requires multiple administrations of drops or injections (e.g. intratympanic injections) over several days (e.g., up to two weeks), including schedules of receiving multiple injections per day. In some embodiments, auris formulations described herein are controlled release formulations, and are administered at reduced dosing frequency compared to the current standard of care. In certain instances, when an auris formulation is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. The formulations described herein provide a constant, sustained, extended, delayed or pulsatile rate of release of an active agent into the inner ear environment and thus avoid any variability in drug exposure in treatment of otic disorders.

Therapeutic Index

Auris formulations described herein are administered into the ear canal, or in the vestibule of the ear. Access to, for example, the vestibular and cochlear apparatus will occur through the auris media including the round window membrane, the oval window/stapes footplate, the annular ligament and through the otic capsule/temporal bone. Otic administration of the formulations described herein avoids toxicity associated with systemic administration (e.g., hepatotoxicity, cardiotoxicity, gastrointestinal side effects, renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid formulations is their propensity to drip into the eustachian tube and cause rapid clearance of the formulation from the inner ear. Provided herein, in certain embodiments, are auris formulations comprising polymers that gel at body temperature and remain in contact with the target auditory surfaces (e.g., the round window) for extended periods of time. In some embodiments, the formulations further comprise mucoadhesives that allow the formulations to adhere to otic mucosal surfaces. In some instances, the auris formulations described herein avoid attenuation of therapeutic benefit due to drainage or leakage of active agents via the eustachian tube.

Description of Certain Embodiments

Accordingly, provided herein, in some embodiments, are pharmaceutical formulations for use in the treatment of an otic disease or condition formulated to provide a therapeutically effective amount of an immunomodulating agent across the round window membrane into the cochlea, the formulation comprising:
between about 0.2% to about 6% by weight of an immunomodulating agent, or pharmaceutically acceptable prodrug or salt thereof;
between about 16% to about 21% by weight of a polyoxyethylene-polyoxypropylene triblock copolymer of general formula E106 P70 E106;
sterile water, q.s., buffered to provide a perilymph-suitable pH between about 6.0 and about 7.6;
and substantially low degradation products of the immunomodulating agent;
wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

Provided herein, in some embodiments, are pharmaceutical formulations for use in the treatment of an otic disease or condition formulated to provide a therapeutically effective amount of an immunomodulating agent across the round window membrane into the cochlea, the formulation comprising:
between about 0.1 mg/mL to about 70 mg/mL of an immunomodulating agent, or pharmaceutically acceptable prodrug or salt thereof;
between about 16% to about 21% by weight of a polyoxyethylene-polyoxypropylene triblock copolymer of general formula E106 P70 E106;
sterile water, q.s., buffered to provide a perilymph-suitable pH between about 6.0 and about 7.6;
and substantially low degradation products of the immunomodulating agent;
wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

In some embodiments, the immunomodulating agent is released from the formulation for a period of at least 3 days. In some embodiments, the pharmaceutical formulation is an auris-acceptable thermoreversible gel. In some embodiments, the polyoxyethylene-polyoxypropylene triblock copolymer is biodegradable. In some embodiments, the formulations further comprise a mucoadhesive. In some embodiments, the formulations further comprise a penetration enhancer. In some embodiments, the formulations further comprise a thickening agent. In some embodiments, the formulations further comprise a dye.

In further embodiments, provided herein are formulations further comprising a drug delivery device selected from a needle and syringe, a pump, a microinjection device, a wick, an in situ forming spongy material or combinations thereof.

In some embodiments of the formulations described herein, the immunomodulating agent, or pharmaceutically acceptable salt thereof, has limited or no systemic release, systemic toxicity, poor PK characteristics, or combinations thereof. In some embodiments, the immunomodulating agent is in the form of a free base, salt, a prodrug, or a combination thereof. In some embodiments, the immunomodulating agent comprises multiparticulates. In some embodiments, the immunomodulating agent is essentially in the form of micronized particles.

In some embodiments, the immunomodulating agent is an anti-TNF agent, a calcineurin inhibitor, an IKK inhibitor, an interleukin inhibitor, a TNF-α converting enzyme (TACE) inhibitor, or a toll-like receptor inhibitor.

In some embodiments, the formulations further comprise an immunomodulating agent, or pharmaceutically acceptable salt thereof, as an immediate release agent.

In some embodiments, the formulations described herein further comprise an additional therapeutic agent. In some embodiments, the additional therapeutic agent is a Na/K ATPase modulator, a chemotherapeutic agent, a collagen, a gamma-globulin, an interferon, an anti-microbial agent, an antibiotic, a local acting anesthetic agent, a platelet activator factor antagonist, a nitric oxide synthase inhibitor, an anti-vertigo agent, a vasopressin antagonist, an anti-viral, an anti-emetic agent or combinations thereof.

In some embodiments, the pH of the composition is between about 6.0 to about 7.6. In some embodiments, the ratio of a polyoxyethylene-polyoxypropylene triblock copolymer of general formula E106 P70 E106 to a thickening agent is from about 40:1 to about 10:1. In some embodiments, the thickening agent is carboxymethyl cellulose.

In some embodiments, the otic disease or condition is Meniere's disease, sudden sensorineural hearing loss, noise induced hearing loss, age-related hearing loss, auto immune ear disease or tinnitus.

Also provided herein is a method of treating an otic disease or condition comprising administering to an individual in need thereof an intratympanic composition comprising
between about 0.2% to about 6% by weight of an immunomodulating agent, or pharmaceutically acceptable prodrug or salt thereof;

between about 16% to about 21% by weight of a polyoxyethylene-polyoxypropylene triblock copolymer of general formula E106 P70 E106;

sterile water, q.s., buffered to provide a perilymph-suitable pH between about 6.0 and about 7.6;

and substantially low degradation products of the immunomodulating agent;

wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

In some embodiments of the method, the immunomodulating agent is an anti-TNF agent, a calcineurin inhibitor, an IKK inhibitor, an interleukin inhibitor, a TNF-a converting enzyme (TACE) inhibitor, or a toll-like receptor inhibitor. In some embodiments of the method, the immunomodulating agent is released from the composition for a period of at least 3 days. In some embodiments of the method, the composition is administered across the round window. In some embodiments of the method, the otic disease or condition is Meniere's disease, sudden sensorineural hearing loss, age-related hearing loss, noise induced hearing loss, auto immune ear disease or tinnitus.

Also provided herein, in some embodiments, are pharmaceutical formulations for use in the treatment of an otic disease or condition formulated to provide a therapeutically effective amount of an aural pressure modulating agent across the round window membrane into the cochlea, the formulation comprising:

between about 0.2% to about 6% by weight of an aural pressure modulating agent, or pharmaceutically acceptable prodrug or salt thereof;

between about 16% to about 21% by weight of a polyoxyethylene-polyoxypropylene triblock copolymer of general formula E106 P70 E106;

sterile water, q.s., buffered to provide a perilymph-suitable pH between about 6.0 and about 7.6;

substantially low degradation of the aural pressure modulating agent;

wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

Also provided herein, in some embodiments, are pharmaceutical formulations for use in the treatment of an otic disease or condition formulated to provide a therapeutically effective amount of an aural pressure modulating agent across the round window membrane into the cochlea, the formulation comprising:

between about 0.1 mg/mL to about 70 mg/mL of an aural pressure modulating agent, or pharmaceutically acceptable prodrug or salt thereof;

between about 16% to about 21% by weight of a polyoxyethylene-polyoxypropylene triblock copolymer of general formula E106 P70 E106;

sterile water, q.s., buffered to provide a perilymph-suitable pH between about 6.0 and about 7.6;

and substantially low degradation products of the aural pressure modulating agent;

wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

In some embodiments, the aural pressure modulating agent is released from the formulation for a period of at least 3 days. In some embodiments, the pharmaceutical formulation is an auris-acceptable thermoreversible gel. In some embodiments, the polyoxyethylene-polyoxypropylene triblock copolymer is biodegradable. In some embodiments, the formulations further comprise a round window membrane mucoadhesive. In some embodiments, the formulations further comprise a round window membrane penetration enhancer. In some embodiments, the formulations further comprise thickening agent. In some embodiments, the formulations further comprise a dye.

In some embodiments of the formulations described herein, the formulations further comprise a drug delivery device selected from a needle and syringe, a pump, a microinjection device, a wick, an in situ forming spongy material or combinations thereof.

In some embodiments, the aural pressure modulating agent, or pharmaceutically acceptable salt thereof, has limited or no systemic release, systemic toxicity, poor PK characteristics, or combinations thereof. In some embodiments, the aural pressure modulating agent is administered in the form of a free base, salt, a prodrug, or a combination thereof. In some embodiments, the aural pressure modulating agent comprises multiparticulates. In some embodiments, the aural pressure modulating agent is essentially in the form of micronized particles.

In some embodiments, the aural pressure modulating agent is a modulator of aquaporin, an estrogen related receptor beta modulator, a gap junction protein modulator, an NMDA receptor modulator, an osmotic diuretic, a progesterone receptor modulator, a prostaglandin modulator, or a vasopressin receptor modulator.

In some embodiments, the formulations described herein further comprise an aural pressure modulating agent, or pharmaceutically acceptable salt thereof, as an immediate release agent.

In some embodiments, the formulations described herein further comprise an additional therapeutic agent. In some embodiments, the additional therapeutic agent is Na/K ATPase modulator, a chemotherapeutic agent, a collagen, a gamma-globulin, an interferon, an anti-microbial agent, an antibiotic, a local acting anesthetic agent, a platelet activator factor antagonist, a nitric oxide synthase inhibitor, an anti-vertigo medicine, a vasopressin antagonist, an anti-viral, an anti-emetic agent or combinations thereof.

In some embodiments, the pH of the composition is between about 6.0 to about 7.6. In some embodiments, the ratio of a polyoxyethylene-polyoxypropylene triblock copolymer of general formula E106 P70 E106 to a thickening agent is from about 40:1 to about 10:1. In some embodiments, the thickening agent is carboxymethyl cellulose.

In some embodiments, the otic disease or condition is Meniere's disease, sudden sensorineural hearing loss, age-related hearing loss, noise induced hearing loss, auto immune ear disease or tinnitus.

Also provided herein is a method of treating an otic disease or condition comprising administering to an individual in need thereof an intratympanic composition comprising between about 0.2% to about 6% by weight of an aural pressure modulating agent, or pharmaceutically acceptable prodrug or salt thereof;

between about 16% to about 21% by weight of a polyoxyethylene-polyoxypropylene triblock copolymer of general formula E106 P70 E106;

sterile water, q.s., buffered to provide a perilymph-suitable pH between about 6.0 and about 7.6;

and substantially low degradation products of the aural pressure modulating agent;

wherein the pharmaceutical formulation has a perilymph-suitable osmolarity between about 250 and 320 mOsm/L, less than about 50 colony forming units (cfu) of microbiological agents per gram of formulation, and less than about 5 endotoxin units (EU) per kg of body weight of a subject.

In some embodiments, the aural pressure modulating agent is a modulator of aquaporin, an estrogen related receptor beta modulator, a gap junction protein modulator, an NMDA receptor modulator, an osmotic diuretic, a progesterone receptor modulator, a prostaglandin modulator, or a vasopressin receptor modulator.

In some embodiments of the method, the aural pressure modulating agent is released from the composition for a period of at least 3 days. In some embodiments of the method, the composition is administered across the round window.

In some embodiments of the method, the otic disease or condition is Meniere's disease, sudden sensorineural hearing loss, age-related hearing loss, noise induced hearing loss, auto immune ear disease or tinnitus.

In any of the aforementioned embodiments, the term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent.

Other objects, features, and advantages of the methods and compositions described herein will become apparent from the following detailed description. It should be understood, however, that the detailed description and the specific examples, while indicating specific embodiments, are given by way of illustration only.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
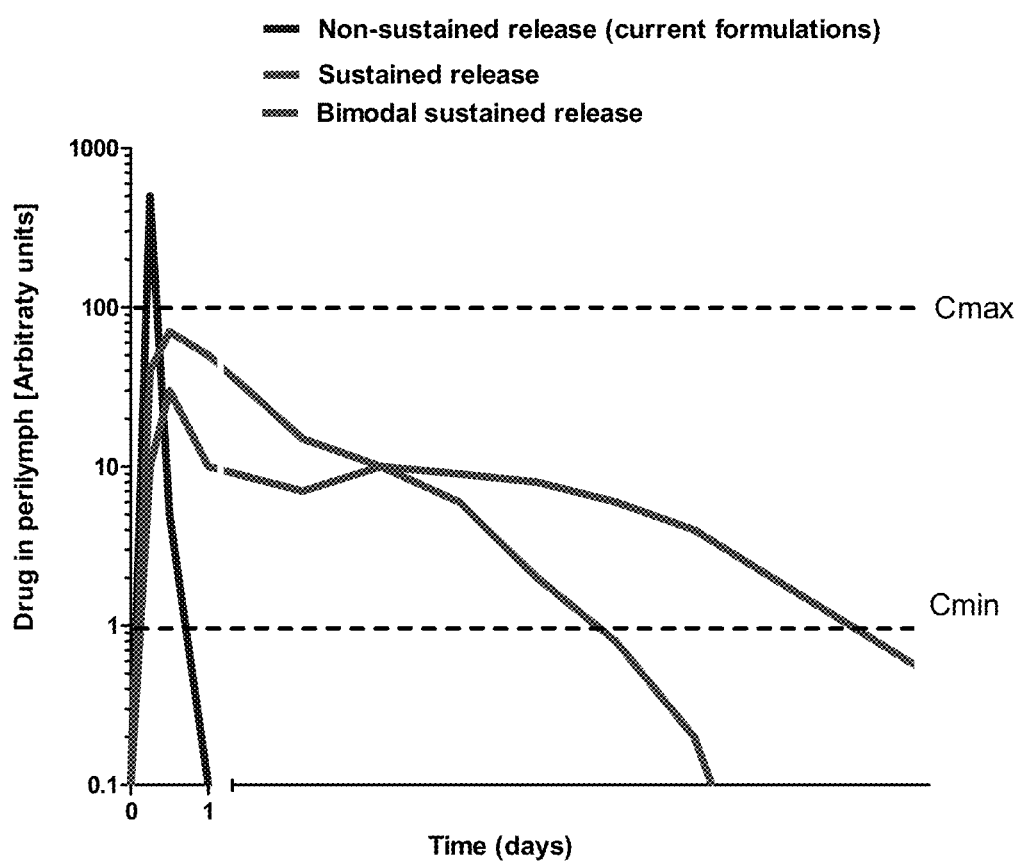
FIG. 1 illustrates a comparison of non-sustained release formulations and sustained release formulations.

Systemic administration of active agents is, in some instances, ineffectual in the treatment of diseases that affect inner ear structures. The cochlear canals and the cochlea, for example, are isolated from the circulatory system limiting systemic delivery of active agents to target sites in the inner ear. In some instances, systemic drug administration creates a potential inequality in drug concentration with higher circulating levels in the serum, and lower levels in the target auris interna organ structures. In certain instances, large amounts of drug are required to overcome this inequality in order to deliver sufficient, therapeutically effective quantities of a drug to auditory structures. In some instances, systemic drug administration also increases the likelihood of secondary systemic accumulation and consequent adverse side effects.

Currently available treatment for inner ear diseases also carries the risk of attendant side effects. For example, available methods require multiple daily doses (e.g., intratympanic injection or infusion) of drugs. In certain instances, multiple daily intratympanic injections cause patient discomfort and non-compliance. In certain instances, delivery of active agents to the inner ear via otic drops administered in the ear canal or via intratympanic injection is hindered by the biological barrier presented by the blood-labyrinth-barrier (BLB), the oval window membrane and/or the round window membrane. In some instances, delivery of active agents to the inner ear via otic drops or intratympanic injection causes osmotic imbalance in inner ear structures, introduces infections or other immune disorders as a result of microbial or endotoxin presence, or results in permanent structural damage (e.g. perforation of the tympanic membrane), resulting in hearing loss and the like.

Clinical studies with steroids such as prednisolone or dexamethasone have demonstrated the benefit of having long term exposure of the steroids to the perilymph of the cochlea; this has been shown by improved clinical efficacy in improving sudden hearing loss when the steroid in question is given on multiple occasions.

U.S. Application Publication Nos. 2006/0063802 and 2005/0214338 disclose compositions comprising arylcycloalkylamine NMDA antagonists for local administration to the inner ear. There is no disclosure of controlled release formulations, osmolarity or pH requirements, or sterility requirements for the compositions. WO 2007/038949 discloses compositions comprising arylcycloalkylamine NMDA antagonists in the treatment of inner ear disorders. No guidance is provided on pyrogenicity, sterility requirements, viscosity levels and/or controlled release characteristics of the formulation.

Fernandez et al. *Biomaterials,* 26: 3311-3318 (2005) describes compositions which comprise prednisolone useful to treat inner ear disease such as Meniere's disease. Fernandez et al. do not disclose osmolarity, pyrogenicity, pH, or sterility levels of the compositions described therein. Paulson et al. *The Laryngoscope,* 118: 706 (2008) describe sustained release compositions which comprise dexamethasone useful in treatment of, inter alia, inner ear diseases such as Meniere's disease. Again, Paulson et al. do not disclose osmolarity, pyrogenicity, pH, or sterility requirements for the compositions described therein.

C. Gang et al., *J. Sichuan Univ.* 37:456-459 (2006) describe a dexamethasone sodium phosphate (DSP) preparation. The formulation described in Gang et al. comprises preservatives and adhesives and is sterilized under conditions that likely lead to breakdown of DSP. There is also no disclosure regarding osmolarity, pyrogenicity, pH, or sterility requirements for the compositions described therein.

Feng et al., *Zhonghua Er Bi Yan Hou Tou Jing Wai Ke Za Zhi* 42:443-6 (June 2007) and Feng et al., *Zhonghua Yi Xue Za Zhi* 87:2289-91 (August 2007) describe 20% and 25% poloxamer 407 solutions as non-toxic to otic structures. There is no active agent in the solutions described therein, and there is no disclosure regarding osmolarity, pyrogenicity, pH, or sterility requirements for the solutions described therein. J. Daijie et al., *J. Clin. Otorhinolaryngol Head Neck Surg* (China) 22(7) (April 2008), P. Yikun et al., *J. Clin. Otorhinolaryngol Head Neck Surg* (China) 22(10) (May 2008), and S. Wandong et al., *J. Clin. Otorhinolaryngol Head Neck Surg* (China) 22(19) (October 2008) describe intratympanic solution injections. However, Daijie et al, Yikun et al. and Wandong et al. do not disclose any otic formulations that are polymer based, or any otic formulations that are sustained release formulations. There is also no disclosure regarding osmolarity, pyrogenicity, pH, or sterility requirements for the compositions described therein.

Intratympanic injection of therapeutic agents is the technique of injecting a therapeutic agent behind the tympanic membrane into the auris media and/or auris interna. Despite early success with this technique (Schuknecht, Laryngoscope (1956) 66, 859-870) some challenges do remain. For example, access to the round window membrane, the site of drug absorption into the auris interna, can be challenging.

However, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intratympanic compositions: the inner ear provides sui generis formulation challenges. Thus, compositions developed for other parts of the body have little to no relevance for an intra-tympanic composition.

There is no guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic formulations that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the formulations described herein comprise dyes and aid visualization of the administered compositions obviating the need for invasive procedures (e.g., removal of perilymph) during preclinical and/or clinical development of intratympanic therapeutics.

Accordingly, provided herein, in certain embodiments, are controlled release auris-acceptable formulations and compositions that locally treat auris target structures and provide extended exposure of otic active agents to the target auris structures. In certain embodiments, the auris formulations described herein are polymer based formulations designed for stringent osmolarity and pH ranges that are compatible with auditory structures and/or the endolymph and perilymph. In some embodiments, the formulations described herein are controlled release formulations that provide extended release for a period of at least 3 days and meet stringent sterility requirements. In some instances, otic compositions described herein contain lower endotoxin levels (e.g. <0.5 EU/mL when compared to typically acceptable endotoxin levels of 0.5 EU/mL. In some instances, the otic formulations described herein contain low levels of colony forming units (e.g., <50 CFUs) per gram of the formulation. In some instances, the auris formulations described herein are substantially free of pyrogens and/or microbes. In some instances the auris formulations described herein are formulated to preserve the ionic balance of the endolymph and/or the perilymph. The stringent requirement for sterility and compatibility with inner ear fluids for otic formulations has not been addressed hereto.

The formulations described herein represent an advantage over currently available therapeutics because they are sterile controlled release otic formulations that are compatible with auris structures (e.g., the perilymph) and are safe for long term administration to humans in need thereof. In some instances, by providing a slow extended release of an active agent, the formulations described herein prevent an initial burst release upon administration to the inner ear; i.e., the formulations avoid causing a dramatic change in the pH of the endolymph or perilymph and subsequently reduce the impact on balance and/or hearing upon administration.

In some instances, local administration of the compositions described herein avoids potential adverse side effects as a result of systemic administration of active agents. In some instances, the locally applied auris-acceptable formulations and compositions described herein are compatible with auris structures, and administered either directly to the desired auris structure, e.g. the cochlear region, or administered to a structure in direct communication with areas of the auris structure; in the case of the cochlear region, for example, including but not limited to the round window membrane, the crista fenestrae cochleae or the oval window membrane.

In certain instances, an advantage of the controlled release formulations described herein is that they provide a constant rate of release of a drug from the formulation and provide a constant prolonged source of exposure of an otic active agent to the inner ear of an individual or patient suffering from an otic disorder, reducing or eliminating any variabilities associated with other methods of treatment (such as, e.g., otic drops and/or multiple intratympanic injections).

The drug formulations described herein provide extended release of the active ingredient(s) into the middle and/or inner ear (auris interna), including the cochlea and vestibular labyrinth. A further option includes an immediate or rapid release component in combination with a controlled release component.

Certain Definitions

The term "auris-acceptable" with respect to a formulation, composition or ingredient, as used herein, includes having no persistent detrimental effect on the auris media (or middle ear) and the auris interna (or inner ear) of the subject being treated. By "auris-pharmaceutically acceptable," as used herein, refers to a material, such as a carrier or diluent, which does not abrogate the biological activity or properties of the compound in reference to the auris media (or middle ear) and the auris interna (or inner ear), and is relatively or is reduced in toxicity to the auris media (or middle ear) and the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

As used herein, the terms "immunomodulating agent" or "immunomodulator" or "immunomodulator agent" or "immune-modulating agent" are used as synonyms.

The term "anti-TNF agent" or "anti tumor necrosis factor agent" or "TNF modulator" or "TNF modulating agent" or "TNF-alpha modulator" or "anti-TNF alpha agent" are used as synonyms. The term "anti-TNF agent" and its synonyms generally refer to agents that counteract the biological effect of TNF-α or the biological effect of pro-TNF-α stimulus including agents which bind to and antagonize the molecular target; here, tumor necrosis factor alpha or TNF-alpha (TNF-α), agents which inhibit release of TNF-α, or agents which interfere with TNF-α gene expression due to pro-TNF-α stimulus. Also included are agents that indirectly antagonize the biological activity of TNF-α by modulating targets in the general pathway of TNF-α activation, including but not limited to targets upstream of the pathway of TNF-alpha activation, including but not limited to agents which increase TNF-alpha expression, activity or function.

As used herein, the terms "aural pressure modulating agent" or "aural pressure modulator" are used as synonyms and do not define the degree of efficacy. The aural pressure modulator also includes compounds that modulate the expression or post-transcriptional processing of a fluid homeostasis protein, including vasopressin and estrogen-related receptor beta protein. Additionally, vasopressin receptor or estrogen-related receptor beta modulators include compounds that influence vasopressin receptor or estrogen-related receptor beta signalling or downstream functions under the control of the vasopressin receptor or estrogen-related receptor beta, such as aquaporin function. Vasopressin receptor or estrogen-related receptor beta modulating agents includes compounds that increase and/or decrease vasopressin receptor or estrogen-related receptor beta function, including antagonists, inhibitors, agonists, partial agonists and the like.

"Modulator of neuron and/or hair cells of the auris" and "auris sensory cell modulating agent" are synonyms. They include agents that promote the growth and/or regeneration of neurons and/or the hair cells of the auris, and agents that destroy neurons and/or hair cells of the auris.

As used herein, the term "antimicrobial agent" refers to compounds that inhibit the growth, proliferation, or multiplication of microbes, or that kill microbes. Suitable "antimicrobial agents" are antibacterial agents (effective against bacteria), antiviral agents (effective against viruses), antifungal agents (effective against fungi), antiprotozoal (effective against protozoa), and/or antiparasitic to any class of microbial parasites. "Antimicrobial agents" may work by any suitable mechanism against the microbes, including by being toxic or cytostatic.

The phrase "antimicrobial small molecule" refers to antimicrobial compounds that are of relatively low molecular weight, e.g., less than 1,000 molecular weight, that are effective for the treatment of otic disorders, particularly otic disorders caused by pathogenic microbes, and are suitable for use in the formulations disclosed herein. Suitable "antimicrobial small molecules" include antibacterial, antiviral, antifungal, antiprotozoal, and antiparasitic small molecules.

"Modulator of free-radicals" and "free-radical modulating agent" are synonyms. They refer to agents that modulate the production of and/or damage caused by free radicals, especially reactive oxygen species.

As used herein, the terms "ion channel modulating agent", "modulator of ion channels" or "ion channel modulator" are used as synonyms and do not define the degree of efficacy. The ion channel modulator also includes compounds that modulate the expression or post-transcriptional processing of a fluid homeostasis protein, including vasopressin and estrogen-related receptor beta protein. Additionally, vasopressin receptor or estrogen-related receptor beta modulators include compounds that influence vasopressin receptor or estrogen-related receptor beta signalling or downstream functions under the control of the vasopressin receptor or estrogen-related receptor beta, such as aquaporin function. Vasopressin receptor or estrogen-related receptor beta modulating agents includes compounds that increase and/or decrease vasopressin receptor or estrogen-related receptor beta function, including antagonists, inhibitors, agonists, partial agonists and the like.

As used herein, the term "otic agent" or "otic structure modulating agent" or "otic therapeutic agent" or "otic active agent" or "active agent" refers to compounds that are effective for the treatment of otic disorders, e.g., otitis media, otosclerosis, autoimmune diseases of the ear and cancer of the ear, and are suitable for use in the formulations disclosed herein. An "otic agent" or "otic structure modulating agent" or "otic therapeutic agent" or "otic active agent" or "active agent" includes, but is not limited to, compounds that act as an agonist, a partial agonist, an antagonist, a partial antagonist, an inverse agonist, a competitive antagonist, a neutral antagonist, an orthosteric antagonist, an allosteric antagonist, or a positive allosteric modulator of an otic structure modulating target, or combinations thereof.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, Ramsay Hunt's Syndrome, Meniere's Disease, mal de debarquement, benign paroxysmal positional vertigo, and labyrinthitis.

"CNS modulator" and "CNS modulating agent" are synonyms. They refer to agents that decrease, diminish, partially suppress, fully suppress, ameliorate, antagonize, agonize, stimulate or increase the activity of the CNS. For example, they may increase the activity of GABA by, for example, increasing the sensitivity of the GABA receptors, or they may alter the depolarization in neurons.

"Local anesthetic" means a substance which causes a reversible loss of sensation and/or a loss of nociception. Often, these substances function by decreasing the rate of the depolarization and repolarization of excitable membranes (for example, neurons). By way of non-limiting example, local anesthetics include lidocaine, benzocaine, prilocaine, and tetracaine.

"Modulator of the $GABA_A$ receptor," "modulator of the GABA receptor," "$GABA_A$ receptor modulator," and "GABA receptor modulator," are synonyms. They refer to substances which modulate the activity of the GABA neurotransmitter, by, for example, increasing the sensitivity of the GABA receptor to GABA.

As used herein, the term "cytotoxic agent" refers to compounds that are cytotoxic (i.e., toxic to a cell) effective for the treatment of otic disorders, e.g., autoimmune diseases of the ear and cancer of the ear, and are suitable for use in the formulations disclosed herein.

The phrase "cytotoxic small molecule" refers to cytotoxic compounds that are of relatively low molecular weight, e.g., less than 1,000, or less than 600-700, or between 300-700 molecular weight, that are effective for the treatment of otic disorders, e.g., autoimmune diseases of the ear and cancer of the ear, and are suitable for use in the formulations disclosed herein. Suitable "cytotoxic small molecules" include methotrexate, cyclophosphamide, and thalidomide, as well as metabolites, salts, polymorphs, prodrugs, analogues, and derivatives of methotrexate, cyclophosphamide, and thalidomide. In certain embodiments, preferred cytotoxic small molecules are the pharmaceutically active metabolites of cytotoxic agents. For example, in the case of cyclophosphamide, preferred metabolites are pharmaceutically active metabolites of cyclophosphamide, including but not limited to 4-hydroxycyclophosphamide, aldophosphamide, phosphoramide mustard, and combinations thereof.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the otic agents disclosed herein.

"Auris interna" refers to the inner ear, including the cochlea and the vestibular labyrinth, and the round window that connects the cochlea with the middle ear.

"Auris-interna bioavailability" or "Auris media bioavailability" refers to the percentage of the administered dose of compounds disclosed herein that becomes available in the inner or middle ear, respectively, of the animal or human being studied.

"Auris media" refers to the middle ear, including the tympanic cavity, auditory ossicles and oval window, which connects the middle ear with the inner ear.

"Blood plasma concentration" refers to the concentration of compounds provided herein in the plasma component of blood of a subject.

"Auris-interna bioavailability" refers to the percentage of the administered dose of compounds disclosed herein that becomes available in the inner ear of the animal or human being studied.

The term "auris-acceptable penetration enhancer" with respect to a formulation, composition or ingredient, as used herein, refers to the property of reducing barrier resistance.

"Carrier materials" are excipients that are compatible with the otic agent, the auris media, the auris interna and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" are chemical compounds that are used to dilute the otic agent prior to delivery and which are compatible with the auris media and/or auris interna.

"Dispersing agents," and/or "viscosity modulating agents" and/or "thickening agents" are materials that control the diffusion and homogeneity of the otic agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. optional dispersing agents useful in liposomal dispersions and self-emulsifying dispersions of the otic agents disclosed herein are dimyristoyl phosphatidyl choline, natural phosphatidyl choline from eggs, natural phosphatidyl glycerol from eggs, cholesterol and isopropyl myristate.

"Drug absorption" or "absorption" refers to the process of movement of the otic agent from the localized site of administration, by way of example only, the round window membrane of the inner ear, and across a barrier (the round window membranes, as described below) into the auris interna or inner ear structures. The terms "co-administration" or the like, as used herein, are meant to encompass administration of the otic agent to a single patient, and are intended to include treatment regimens in which the otic agents are administered by the same or different route of administration or at the same or different time.

The terms "effective amount" or "therapeutically effective amount," as used herein, refer to a sufficient amount of the otic agent being administered that would be expected to relieve to some extent one or more of the symptoms of the disease or condition being treated. For example, the result of administration of the otic agents disclosed herein is reduction and/or alleviation of the signs, symptoms, or causes of AIED. For example, an "effective amount" for therapeutic uses is the amount of the otic agent, including a formulation as disclosed herein required to provide a decrease or amelioration in disease symptoms without undue adverse side effects. The term "therapeutically effective amount" includes, for example, a prophylactically effective amount. An "effective amount" of a otic agent composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate-release dosing format based upon pharmacokinetic and pharmacodynamic considerations.

The terms "enhance" or "enhancing" refers to an increase or prolongation of either the potency or duration of a desired effect of the otic agent, or a diminution of any adverse symptomatology. For example, in reference to enhancing the effect of the otic agents disclosed herein, the term "enhancing" refers to the ability to increase or prolong, either in potency or duration, the effect of other therapeutic agents that are used in combination with the otic agents disclosed herein. An "enhancing-effective amount," as used herein, refers to an amount of an otic agent or other therapeutic agent that is adequate to enhance the effect of another therapeutic agent or otic agent in a desired system. When used in a patient, amounts effective for this use will depend on the severity and course of the disease, disorder or condition, previous therapy, the patient's health status and response to the drugs, and the judgment of the treating physician.

The term "penetration enhancer" refers to an agent that reduces barrier resistance (e.g., barrier resistance of the round window membrane, BLB or the like).

The term "inhibiting" includes preventing, slowing, or reversing the development of a condition, for example, AIED, or advancement of a condition in a patient necessitating treatment.

The terms "kit" and "article of manufacture" are used as synonyms.

The term "modulate" includes the interaction with a target, for example, with the TNF-alpha agents disclosed herein, the activity of TNF-alpha, or other direct or indirect targets that alter the activity of TNF-alpha, including, by way of example only, to inhibit the activity of TNF-alpha, or to limit the activity of the TNF-alpha.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

In prophylactic applications, compositions containing the otic agents described herein are administered to a patient susceptible to or otherwise at risk of a particular disease, disorder or condition, for example, AIED, or patients that are suffering from diseases associated with AIED, including by way of example only, Ankylosing spondylitis, Systemic Lupus Erythematosus (SLE), Sjögren's Syndrome, Cogan's disease, ulcerative colitis, Wegener's granulomatosis, inflammatory bowel disease, rheumatoid arthritis, scleroderma and Behçet's disease. Such an amount is defined to be a "prophylactically effective amount or dose." In this use, the precise amounts also depend on the patient's state of health, weight, and the like.

A "prodrug" refers to the otic agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refers to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, Transcutol®, propylene glycol, and dimethyl isosorbide and the like.

"Stabilizers" refers to compounds such as any antioxidation agents, buffers, acids, preservatives and the like that are compatible with the environment of the auris media and/or auris interna. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the auris media and/or auris interna is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject are used interchangeably.

"Surfactants" refers to compounds that are auris-acceptable, such as sodium lauryl sulfate, sodium docusate, Tween 60 or 80, triacetin, vitamin E TPGS, phospholipids, lecithins, phosphatidyl cholines (c8-c18), phosphatidylethanolamines (c8-c18), phosphatidylglycerols (c8-c18), sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition, for example AIED, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or controlling or stopping the symptoms of the disease or condition either prophylactically and/or therapeutically.

The ear serves as both the sense organ that detects sound and the organ that maintains balance and body position. The ear is generally divided into three portions: the outer ear, middle ear and the inner ear (or auris interna). As shown in the illustration above, the outer ear is the external portion of the organ and is composed of the pinna (auricle), the auditory canal (external auditory meatus) and the outward facing portion of the tympanic membrane, also known as the ear drum. The pinna, which is the fleshy part of the externa ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by a membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window is correspondingly pushed out and away from the cochlear fluid. This movement of the round window allows movement of fluid within the cochlea, which eventually leads in turn to movement of the cochlear inner hair cells, allowing hearing signals to be transduced. Stiffness and rigidity in the round window leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled inner ear, or auris interna, consists of two major components: the cochlear and the vestibular apparatus.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The Organ of Corti, the sensory organ for hearing, is located on the basilar membrane and extends upward into the cochlear duct. The Organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the membrane on the round window to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the Organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista amupllaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The drug formulation will first be placed in the middle or inner ear, including the cochlea and vestibular labyrinth: one option is to use a syringe/needle or pump and inject the formulation across the tympanic membrane (the eardrum). For cochlear and vestibular labyrinth delivery, one option is to deliver the active ingredient across the round window membrane or even by microinjection directly into the auris interna also known as cochlear microperfusion.

Animal Models and Human Clinical Trials

There are, at present, no intratympanic therapeutics approved for administration to humans. In some instances, a lack of suitable animal models for inner ear diseases has hindered development of intratympanic therapeutics for human use.

In some instances, the use of animal models for inner ear diseases that are utilized for testing the efficacy of the formulations described herein is not accurately predictive of the efficacy of such formulations in humans. Rodent animal models for inner ear disease (e.g., inner ear disease models in guinea pigs) are not amenable to allometric scaling in humans because rodents are different anatomically in the organization of the middle and inner ear. The middle ear of the guinea pig (or bulla) is a cavity that contains all of the cochlea; the cochlea is anchored to the bulla via the basal turn, its apex residing in the cavity. In contrast, the human cochlea is imbedded into the temporal bone and the only access to the human cochlea is through the round window. In some instances, from a pharmacokinetics perspective, studies in guinea pigs that overfill the bulla and/or inject formulations towards the anterior quadrant of the tympani, or more generally away from the round window niche, will result in high perilymph exposure because of drug diffusion through the cochlea apex. This situation is not possible in humans because the human cochlea is imbedded into the temporal bone and as such the only access to the cochlea is on and/or through the round window or the elliptical/oval window. In addition, the ossicle chains in guinea pigs are adjacent to the round window. In some instances, the location of the ossicle chains next to the round window in guinea pig ears adversely affects the ABR threshold in experiments with guinea pigs. In contrast, the human ear is anatomically different from rodent ears; the ossicle chains and/or stapes are anatomically located away from the round window. In certain instances, an auris formulation injected intratympanically into a human ear does not make contact with the stapes and does not adversely affect the ABR threshold. Thus, in certain instances, the reliability of animal models of inner ear diseases as a predictor of efficacy in human clinical trials is limited by the anatomical difference between the human ear and animal ears.

In some instances, a guinea pig animal model for inner ear disease utilizes an injection via a hole drilled into the bulla, i.e., the cavity surrounding the cochlear bones. In some instances, the bulla procedure leads to a local inflammatory reaction and a rapid accumulation of fluids within the bulla cavity, a condition that lasts for several days. In some instances, an accumulation of significant volumes of fluids in the bulla (about a ⅓-½ of the total bulla volume) seen with the bulla injection rapidly erodes any auris formulation injected, primarily by diluting the formulation and reverting a formulation (e.g., a gel formulation) to a liquid that drains away via the eustachian tube. For example, a gel formulation comprising a poloxamer will not form a gel at concentration below 12-14%, and at concentrations less than 15% concentration will gel at temperatures higher than 37° C. In some instances, a guinea pig model is of limited utility for testing the efficacy of an auris formulation for administration to humans due the accelerated clearance of the gel from the bulla compartment of a guinea pig. For example, in some instances, a 17% Pluronic F-127 gel injection is cleared from the bulla of a guinea pig in less than 2 days.

In some instances, a guinea pig animal model for inner ear disease utilizes an injection through the tympanic membrane. In certain instances, in guinea pigs, an intratympanic injection is not associated with fluid accumulation at any of the time points evaluated (up to 10 days). In some instances, injection of an auris formulation described herein (e.g. a gel formulation) via the tympanic route allows for detectable amounts of the formulation (e.g., a gel) in the inner ear of a guinea pig up to at least 5 days.

In some instances, animal models (e.g., guinea pig models for inner ear diseases) utilizing intratympanic injections are limited by the volume that can be injected through the tympanic route. In the guinea pig, the round window niche and membrane are located just opposite the tympanic membrane in the posterior superior quadrant. In certain instances, about 50 mL can be injected within this quadrant in a 250-350 g guinea pig. In some instances, a larger volume (up to 70 mL) can be injected in the posterior inferior quadrant; however most of the gel migrates towards the round window. In some instances larger volumes (100-120 mcl) are injected in the anterior quadrant, but this action fills the bulla cavity and promotes drug transfer across the apical part of the cochlea (due to the bone structure thinness of the cochlea in rodents). In certain animal models, injection of larger volumes in any of these quadrants leads to tympanic perforation and presence of the gel in the external ear canal. In some instances, the volume injected has an impact on the hearing threshold (measured by ABR). In the guinea pig ear for example, intratympanic injections volumes up to 50 mL do not produce any shift in hearing threshold; but volumes of 90 and 120 mL produce an ABR threshold shift within 1 day. In some instances, the anatomical difference between human and animal ears and the variability in experimental outcomes lends a low predictive value to animal testing data for use in subsequent human clinical trials. Further, the invasive procedures used in animal models of inner ear disease are not applicable in a clinical setting.

Visualization of Otic Formulations

Provided herein are otic formulations that comprise a dye (e.g., a Trypan blue dye, Evans blue dye) or other tracer compound. In some instances, addition of an auris-compatible dye to an otic formulation described herein aids visualization of any administered formulation in a ear (e.g., a rodent ear and/or a human ear). In certain embodiments, an otic composition comprising a dye or other tracer compound eliminates the need for invasive procedures that are currently used in animal models to monitor the concentrations of drugs in the endolymph and/or perilymph.

In some instances, intratympanic injections require the need of a specialist and the formulation needs to be delivered to a specific site of the ear to maximize efficiency of the medication delivered. In certain instances, a visualization technique for any formulation described herein allows for visualization of a dosing site (e.g., the round window) so that the medication is applied in the proper place. In some instances, a formulation comprising a dye allows visualization of the formulation during administration of the formulation to an ear (e.g., a human ear), ensures that the medication will be delivered at the intended site, and avoids any complications due to incorrect placement of a formulation. The inclusion of a dye to help enhance the visualization of the gel when applied, and the ability to visually inspect the location of the gel after administration without further intervention, represents an advance over currently available methods for testing intratympanic therapeutics in animal models and/or human trials. In some embodiments, dyes that are compatible with the otic compositions described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g, FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like (e.g., Gadolinium-based MRI dyes, iodine-base dyes, barium-based dyes or the like) are also contemplated for use with any otic formulation described herein. Other dyes that are compatible with any formulation described herein are listed in the Sigma-Aldrich catalog under dyes (which is included herein by reference for such disclosure). In some embodiments, concentration of a dye in any otic formulation described herein is less than 2%, less than 1.5%, less than 1%, less than 0.5%, less than 0.25%, less than 0.1%, or less than 100 ppm of the total weight and/or volume of any formulation described herein.

In certain embodiments of such auris-compatible formulations that comprise a dye, the ability to visualize a controlled release otic formulation comprising a dye in an ear meets a long standing need for suitable testing methods that are applicable to the development of intratympanic otic compositions suitable for human use. In certain embodiments of such auris-compatible formulations that comprise a dye, the ability to visualize a controlled release otic formulation comprising a dye allows for testing of any otic formulation described herein in human clinical trials.

Diseases of the Ear

The formulations described herein are suitable for the treatment and/or prevention of diseases or conditions associated with the middle and inner ear, including the cochlea, including vertigo, tinnitus, hearing loss, otosclerosis, balance disorders, and Meniere's disease (endolymphatic hydrops).

The formulations described herein reduce, reverse and/or ameliorate symptoms of otic disorders (e.g., auris interna disorders) which include but are not limited to hearing loss, nystagmus, vertigo, tinnitus, inflammation, swelling, infection and congestion. These disorders may have many causes, such as infection, injury, inflammation, tumors and adverse response to drugs or other chemical agents.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. The cause of Meniere's disease is likely related to an imbalance of auris interna fluid homeostasis, including an increase in production or a decrease in resorption of auris interna fluid.

The cause of symptoms associated with Meniere's disease is likely an imbalance of inner ear fluid homeostasis, including an increase in production or a decrease in reabsorption of inner ear fluid.

Although the cause of Meniere's disease is unknown, certain evidence suggests a viral etiology for the disease. Specifically, histopathologic analysis of temporal bones in patients with Meniere's disease revealed viral ganglionitis. Also, viral DNA has been observed in the ganglia of patients with Meniere's disease at a higher rate than in healthy patients. Oliveira et al. *ORL* (2008) 70: 42-51. Based on these studies, a pilot study of intratympanic injection of the antiviral agent ganciclovir was conducted, resulting in an improvement of patients suffering from Meniere's disease. Guyot et al. *ORL* (2008) 70: 21-27. Accordingly, controlled release formulations disclosed herein comprising antiviral agents, e.g., ganciclvir, acyclovir, famovir, and valgancyclovir, is administered to the ear for localized treatment of Meniere's disease.

Recent studies of the vasopressin (VP)-mediated aquaporin 2 (AQP2) system in the auris interna suggest a role for VP in inducing endolymph production, thereby increasing pressure in the vestibular and cochlear structures. (Takeda et al. *Hearing Res.* (2006) 218:89-97). VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of $V_2$-R) into the scala tympani resulted in a marked reduction of Meniere's disease symptoms. (Takeda et al. *Hearing Res.* (2003) 182:9-18). Other VP antagonists include WAY-140288, CL-385004, tolvaptan, conivaptan, SR 121463A and VPA 985. (Sanghi et al. *Eur. Heart J.* (2005) 26:538-543; Palm et al. *Nephrol. Dial Transplant* (1999) 14:2559-2562).

Other studies suggest a role for estrogen-related receptor β/NR3B2 (ERR/Nr3b2) in regulating endolymph production, and therefore pressure in the vestibular/cochlear apparatus. (Chen et al. *Dev. Cell.* (2007) 13:325-337). Knock-out studies in mice demonstrate the role of the protein product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume. Treatment with antagonists to ERR/Nr3b2 may assist in reducing endolymphatic volume, and thus alter pressure in the auris interna structures.

Other treatments are aimed at dealing with the immediate symptoms and prevention of recurrence. Low-sodium diets, avoidance of caffeine, alcohol, and tobacco have been advocated. Medications that may temporarily relieve vertigo attacks include antihistamines (including meclizine (Antivert, Bonine, Dramamine, Driminate) and other antihistamines), and central nervous system agents, including barbiturates and/or benzodiazepines, including lorazepam or diazepam. Other examples of drugs that are useful in relieving symptoms include muscarinic antagonists, including scopolamine. Nausea and vomiting are relieved by suppositories containing antipsychotic agents, including the phenothiazine agent prochlorperazine (Compazine, Buccastem, Stemetil and Phenotil).

Surgical procedures have also been used to relieve symptoms of Meniere's disease, including destruction of vestibular function to relieve vertigo symptoms. These procedures aim to either reduce fluid pressure in the inner ear and/or to destroy inner ear balance function. An endolymphatic shunt procedure, which relieves fluid pressure, are placed in the inner ear to relieve symptoms of vestibular dysfunction. Severing of the vestibular nerve may also be employed, which may control vertigo while preserving hearing.

Another approach to destruction of vestibular function for the treatment of severe Meniere's disease is intratympanic application of an agent that destroys sensory hair cell function in the vestibular system, thereby eradicating inner ear balance function. Various antimicrobial agents are used in the procedure, including aminoglycosides such as gentamicin and streptomycin. The agents are injected through the tympanic membrane using a small needle, a tympanostomy tube with or without a wick, or surgical catheters. Various dosing regimens are used to administer the antimicrobial agents, including a low dose method in which less of the agents are administered over longer periods of time (e.g., one month between injections), and high dose methods in which more of the agents are administered over a shorter time frame (e.g., every week). Although the high dose method is typically more effective, it is more risky, as it may result in hearing loss.

Accordingly, formulations disclosed herein are also useful for administration of antimicrobial agents, e.g., gentamicin and streptomycin, for disabling the vestibular apparatus to treat Meniere's disease. The formulations disclosed herein are used to maintain a steady release of the active agents inside the tympanic membrane, thereby avoiding the need for multiple injections or the insertion of a tympanostomy tube. Further, by keeping the active agents localized in the vestibular system, the formulations disclosed herein can also be used to administer higher doses of the antimicrobial agents with a decreased risk of hearing loss.

Meniere's Syndrome

Meniere's Syndrome, which displays similar symptoms as Meniere's disease, is attributed as a secondary affliction to another disease process, e.g. thyroid disease or auris interna inflammation due to syphillis infection. Meniere's syndrome, thus, are secondary effects to various process that interfere with normal production or resportption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Sensorineural Hearing Loss

Sensorineural hearing loss is a type of hearing loss which results from defects (congenital and acquired) in the vestibulocochlear nerve (also known as cranial nerve VIII), or sensory cells of the inner ear. The majority of defects of the inner ear are defects of otic hair cells.

Aplasia of the cochlea, chromosomal defects, and congenital cholesteatoma are examples of congenital defects which can result in sensorineural hearing loss. By way of non-limiting example, inflammatory diseases (e.g. suppurative labyrinthitis, meningitis, mumps, measles, viral syphilis, and autoimmune disorders), Meniere's Disease, exposure to ototoxic drugs (e.g. aminoglycosides, loop diuretics, antimetabolites, salicylates, and cisplatin), physical trauma, presbyacusis, and acoustic trauma (prolonged exposure to sound in excess of 90 dB) can all result in acquired sensorineural hearing loss.

If the defect resulting in sensorineural hearing loss is a defect in the auditory pathways, the sensorineural hearing loss is called central hearing loss. If the defect resulting in sensorineural hearing loss is a defect in the auditory pathways, the sensorineural hearing loss is called cortical deafness.

In some instances, sensorineural hearing loss occurs when the components of the auris interna or accompanying neural components are affected, and may contain a neural, i.e. when the auditory nerve or auditory nerve pathways in the brain are affected, or sensory component. Sensory hearing loss are hereditary, or it are caused by acoustic trauma (i.e. very loud noises), a viral infection, drug-induced or Meniere's disease. Neural hearing loss may occur as a result of brain tumors, infections, or various brain and nerve disorders, such as stroke. Some hereditary diseases, such as Refsum's disease (defective accumulation of branched fatty acids), may also cause neural disorders affecting hearing loss. Auditory nerve pathways are damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG peripheral neuropathy.

The incidence of sudden deafness, or sensorineural hearing loss, occurs in about 1 in 5000 individuals, and are caused by viral or bacterial infections, e.g. mumps, measles, influenza, chickenpox, cytomegalovirus, syphillis or infectious mononucleosis, or physical injury to the inner ear organ. In some cases, no cause can be identified. Tinnitus and vertigo may accompany sudden deafness, which subsides gradually. Oral corticosteroids are frequently prescribed to treat sensorineural hearing loss. In some cases, surgical intervention are necessary. Other treatments include AM-101 and AM-111, compounds under development for the treatment of auris interna tinnitus and acute sensorineural hearing loss. (Auris Medical AG, Basel, Switzerland).

Noise Induced Hearing Loss

Noise induced hearing loss (NIHL) is caused upon exposure to sounds that are too loud or loud sounds that last a long time. Hearing loss may occur from prolonged exposure to loud noises, such as loud music, heavy equipment or machinery, airplanes or gunfire Long or repeated or impulse exposure to sounds at or above 85 decibels can cause hearing loss. NIHL causes damage to the hair cells and/or the auditory nerve. The hair cells are small sensory cells that convert sound energy into electrical signals that travel to the brain. Impulse sound can result in immediate hearing loss that are permanent. This kind of hearing loss are accompanied by tinnitus—a ringing, buzzing, or roaring in the ears or head—which may subside over time. Hearing loss and tinnitus are experienced in one or both ears, and tinnitus may continue constantly or occasionally throughout a lifetime. Permanent damage to hearing loss is often diagnosed. Continuous exposure to loud noise also damages the structure of hair cells, resulting in hearing loss and tinnitus, although the process occurs more gradually than for impulse noise.

In some embodiments, an otoprotectant can reverse, reduce or ameliorate NIHL. Examples of otoprotectants that treat or prevent NIHL include, but are not limited to, D-methionine, L-methionine, ethionine, hydroxyl methionine, methioninol, amifostine, mesna (sodium 2-sulfanylethanesulfonate), a mixture of D and L methionine, normethionine, homomethionine, S-adenosyl-L-methionine), diethyldithiocarbamate, ebselen (2-phenyl-1,2-benzisoselenazol-3(2H)-one), sodium thiosulfate, AM-111 (a cell permeable JNK inhibitor, (Laboratoires Auris SAS)), leucovorin, leucovorin calcium, dexrazoxane, or combinations thereof.

Although there is currently no treatment for noise-induced hearing loss, several treatment regimens have been experimentally developed, including treatment with insulin-like growth factor 1 (IGF-1) and antioxidant therapy, including treatment with alpha lipoic acid. (Lee et al. *Otol. Neurotol.* (2007) 28:976-981).

Tinnitus

Tinnitus is defined as the perception of sound in the absence of any external stimuli. It may occur in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus.

In certain instances, tinnitus results from damage to otic structures (e.g. stereocillia), the dysfunction of one or more molecular receptors, and/or the dysfunction of one or more neural pathways. In certain instances, tinnitus results from excitotoxicity caused by abnormal activity of an NMDA receptor. In certain instances, tinnitus results from by dysfunction of an α9 and/or α10 acetylcholine receptor. In certain instances, tinnitus results from damage to the vestibulocochlear nerve. In certain embodiments, a reduction in neurotransmitter reuptake (e.g. the increase in extracellular neurotransmitters) treats, and/or ameliorates the symptoms of tinnitus. In certain embodiments, antagonism of an NK1 receptor treats, and/or ameliorates the symptoms of tinnitus. In certain embodiments, a reduction in neurotransmitter reuptake and antagonism of an NK1 receptor treats, and/or ameliorates the symptoms of tinnitus.

There are several treatments for tinnitus. Lidocaine, administered by IV, reduces or eliminates the noise associated with tinnitus in about 60-80% of sufferers. Selective neurotransmitter reuptake inhibitors, such as nortriptyline, sertraline, and paroxetine, have also demonstrated efficacy against tinnitus. Benzodiazepines are also prescribed to treat tinnitus.

Autoimmune Inner Ear Disease

Autoimmune inner ear disease (AIED) is one of the few reversible causes of sensorineural hearing loss. It is a rare disorder appearing in both adults and children that often involves a bilateral disturbance of the audio and vestibular functions of the auris interna. The origin of AIED is likely autoantibodies and/or immune cells attacking inner ear structures, but are associated with other autoimmune conditions. In many cases, AIED occurs without systemic autoimmune symptoms, but up to one-third of patients also suffer from a systemic autoimmune illness, such as inflammatory bowel disease, rheumatoid arthritis, Ankylosing spondylitis, Systemic Lupus Erythematosus (SLE), Sjögren's Syndrome, Cogan's disease, ulcerative colitis, Wegener's granulomatosis and scleroderma. Behçet's disease, a multisystem disease, also commonly has audiovestibular problems. There is some evidence for food-related allergies as a cause for cochlear and vestibular autoimmunity, but there is presently no agreement as to its importance in the aetiology of the disease. A classification scheme for AIED has been developed (Harris and Keithley, (2002) Autoimmune inner ear disease, in *Otorhinolaryngology Head and Neck Surgery.* 91, 18-32).

The immune system normally performs a cruical role in protecting the auris interna from invasive pathogens such as bacteria and viruses. However, in AIED the immune system itself begins to damage the delicate auris interna tissues. It is well established that the auris interna is fully capable of mounting a localized immune response to foreign antigens. (Harris, *Otolaryngol. Head Neck Surg.* (1983) 91, 18-32). When a foreign antigen enters the auris interna, it is first processed by immunocompetent cells which reside in and around the endolymphatic sac. Once the foreign antigen has been processed by these immunocompetent cells, these cells secrete various cytokines which modulate the immune response of the auris interna. One result of this cytokine release is to facilitate the influx of inflammatory cells which are recruited from the systemic circulation. These systemic inflammatory cells enter the cochlea via diapedesis through the spiral modiolar vein and its tributaries and begin to participate in antigen uptake and deregulation just as it occurs in other parts of the body (Harris, *Acta Otolaryngol.* (1990) 110, 357-365). Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotet T-cells into helper, cytotoxic and suppressor T-cell subtypes. IL-2 also assists T helper cells in the activation of B lymphocytes and probably plays a pivotal role in the immunoregulation of the immune response of the auris interna. IL-2 has been identified within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge (Gloddek, *Acta Otolaryngol.* (1989) 108, 68-75).

Both IL-1β and tumor necrosis factor-α (TNF-α) may play a key role in the initiation and amplification of the immune response. IL-1β is expressed by the fibrocytes of the spiral ligament in the presence of trauma such as surgical trauma or acoustic trauma in a nonspecific response. THF-α is expressed either by infiltrating systemic cells or by resident cells contained within the endolymphatic sac in the presence of antigen. THF-α is released as part of the adaptive (specific) immune response in animal models. When antigen is injected into the auris internas of mice, IL-1β and TNF-α are both expressed and a vigouous immune response occurs. However, when antigen is introduced to the auris interna via the cerebral spinal fluid without trauma to the auris interna, only TNF-α is expressed and the immune response in minimal (Satoh, *J. Assoc. Res. Otolaryngol.* (2003), 4, 139-147). Importantly, cochlear trauma in isolation also results in a minimal immune response. These results suggest that both the nonspecific and specific components of the immune response may act in concert in the auris interna to achieve a maximal response.

Accordingly, if the cochlea is traumatized and an antigen is injected (or in the case of autoimmune disease, the patient has immune cells directed against auris interna antigens), both the nonspecific and the specific immune responses can be activated simultaneously. This results in the concurrent production of IL-1β as well as THF-α which causes a greatly amplified level of inflammation leading to substantial damage to the auris interna. Subsequent experiments in animal models confirm that an important step in immune-mediated damage requires that the auris interna be conditioned by the non-specific innate immune response before the specific adaptive immune response can lead to enough inflammation to result in damage (Hashimoto, *Audiol. Neurootol.* (2005), 10, 35-43). As a result, agents which downregulate or block the specific immune response, and in particular the effect of TNF-α, might be able to prevent the excessive immune response seen when both the specific and nonspecific immune responses are simultaneously activated (Satoh, *Laryngoscope* (2002), 112, 1627-1634).

Treatment of autoimmune ear disease, thus, may consist of anti-TNF agents. Trials using etanercept (ENBREL®), an anti-TNF drug, is emerging as a promising agent for treatment of autoimmune inner ear disease. (Rahmen et al., *Otol. Neurol.* (2001) 22:619-624; Wang et al., *Otology & Neurotology* (2003) 24:52-57). Additionally, the anti-TNF agents infliximab (REMICADE®) and adalimumab (HUMIRA®) may also be useful in treatment of autoimmune auris interna disorders. Trial protocols include injections of anti-TNF agents as an injection on a twice-weekly basis.

In addition, steroids have been used, e.g. prednisone or decadron, have also been tried with some success. Chemotherapeutic agents, e.g. cytoxan, azathiaprine or methotrexate are used on a long-term basis to treat autoimmune inner ear disorders. (Sismanis et al., *Laryngoscope* (1994) 104: 932-934; Sismanis et al., *Otolaryngol* (1997) 116:146-152; Harris et al. *JAMA* (2003) 290:1875-1883). Plasmapheresis procedures have also been tried with some success. (Luetje et al. *Am. J. Otol.* (1997) 18:572-576). Treatment with oral collagen (Kim et al. *Ann. Otol. Rhinol. Larynogol.* (2001) 110: 646-654), gamma globulin infusions or other immune modulating drugs (e.g. beta-interferon, alpha interferon or copaxone) may also be used to treat autoimmune inner ear disorders.

Certain evidence suggests that viral infection is a factor in the initiation of the inflammatory response that results in AIED. Various autoimmune conditions are induced or enhanced by a variety of DNA and RNA virus infections. Acute or persistent viral infections induce or enhance autoimmune diseases in animal models as well. Similar antigenic determinants have also been observed on viruses and host components. Oldstone, M. B. A. *J. Autoimmun.* (1989) 2(suppl): 187-194. Further, serological tests have identified viral infection in at least one patient diagnosed with a systemic autoimmune disorder that is often associated with AIED (Cogan's syndrome). García-Berrocal, et al. *O.R.L.* (2008) 70: 16-20.

Accordingly, in some embodiments, controlled release antimicrobial agent compositions and formulations disclosed herein are administered for the treatment of AIED. Particularly, in certain embodiments, formulations disclosed herein comprising antiviral agents are administered for treatment of AIED. In other embodiments, the antimicrobial agent formulations disclosed herein are administered for the treatment of AIED in conjunction with other pharmaceutical agents useful for treating the same conditions or symptoms of the same conditions, including steroids, cytotoxic agents, collagen, gamma globulin infusion, or other immune modulating drugs. Steroids include, e.g., prednisone or decadron. Cytotoxic agents for the treatment of AIED include, e.g., methotrexate, cyclophosphamide, and thalidomide. Plasmapheresis procedures are optionally used. Treatment with oral collagen, gamma globulin infusions, or other immune modulating drugs (e.g. beta-interferon, alpha-interferon or copaxone) is also optionally used in combination with the antimicrobial agent formulations disclosed herein. The additional pharmaceutical agents are optionally administered together with the controlled release formulations disclosed herein, or through other modes of administration, e.g., orally, by injection, topically, nasally or through any other suitable means. The additional pharmaceutical agents are optionally co-administered, or administered at different time periods.

Auditory Nerve Tumors

Auditory nerve tumors, including acoustic neuroma, acoustic neurinoma, vestibular schwannoma and eighth nerve tumor) are tumors that originate in Schwann cells, cells that wrap around a nerve. Auditory nerve tumors account for approximately 7-8% of all tumors originating in the skull, and are often associated with the diagnosis of neurofibromatosis in a patient. Depending upon the location of the tumor, some symptoms include hearing loss, tinnitus, dizziness and loss of balance. Other more serious symptoms may develop as the tumor becomes larger, which may compress against the facial or trigemminal nerve, which may affect connections between the brain and the mouth, eye or jaw. Smaller tumors are removed by microsurgery, or sterotactic radiosurgical techniques, including fractionated sterotactic radiotherapy. Malignant Schwannomas are treated with chemotherapeutic agents, including vincristine, adriamycin, cyclophosphamide and imidazole carboxamide.

Benign Paroxysmal Positional Vertigo

Benign paroxysmal positional vertigo is caused by the movement of free floating calcium carbonate crystals (otoliths) from the utricle to one of the semicircular canals, most often the posterior semicircular canal. Movement of the head results in the movement of the otoliths causing abnormal endolymph displacement and a resultant sensation of vertigo. The episodes of vertigo usually last for about a minute and are rarely accompanied by other auditory symptoms.

Cancer of the Ear

Although the cause is unknown, cancer of the ear is often associated with long-term and untreated otitis, suggesting a link between chronic inflammation and development of the cancer, at least in some cases. Tumors in the ear can be benign or malignant, and they can exist in the external, middle, or inner ear. Symptoms of ear cancer include otorrhea, otalgia, hearing loss, facial palsy, tinnitus, and vertigo. Treatment options are limited, and include surgery, radiotherapy, chemotherapy, and combinations thereof. Also, additional pharmaceutical agents are used to treat symptoms or conditions associated with the cancer, including corticosteroids in the case of facial palsy, and antimicrobial agents when otitis is present.

Systemic administration of conventional cytoxic agents have been used to treat cancer of the ear, including systemic administration of cyclophosphamide (in CHOP chemotherapy) in combination with radiotherapy and methotrexate, Merkus, P., et al. *J. Otorhinolaryngol. Relat. Spec.* (2000) 62:274-7, and perfusion of methotrexate through the external carotid artery, Mahindrakar, N. H. *J. Laryngol. Otol.* (1965) 79:921-5. However, treatments requiring systemic administration of the active agents suffer from the same drawbacks discussed above. Namely, relatively high doses of the agents are required to achieve the necessary therapeutic doses in the ear, which result in an increase of undesired, adverse side effects. Accordingly, local administration of the cytotoxic agents in the compositions and formulations disclosed herein results in treatment of cancer of the ear with lower effective doses, and with a decrease in the incidence and/or severity of side effects. Typical side effects of systemic administration of cytotoxic agents, e.g., methotrexate, cyclophosphamide, and thalidomide, for the treatment of cancer of the ear include anemia, neutropenia, bruising, nausea, dermatitis, hepatitis, pulmonary fibrosis, teratogenicity, peripheral neuropathy, fatigue, constipation, deep vein thrombosis, pulmonary edema, atelectasis, aspiration pneumonia, hypotension, bone marrow suppression, diarrhea, darkening of skin and nails, alopecia, changes in hair color and texture, lethargy, hemorrhagic cystitis, carcinoma, mouth sores, and decreased immunity.

In certain embodiments, the cytotoxic agents are methotrexate (RHEUMATREX®, Amethopterin) cyclophosphamide (CYTOXAN®), and thalidomide (THALIDOMID®). All of the compounds can be used to treat cancer, including cancer of the ear. Further, all of the compounds have anti-inflammatory properties and can be used in the formulations and compositions disclosed herein for the treatment of inflammatory disorders of the ear, including AIED.

Although systemic administration of methotrexate, cyclophosphamide, and thalidomide is currently used to treat or is being investigated for the treatment of otic disorders, such as inflammatory otic disorders, including AIED, Meniere's disease, and Behçet's disease, as well as cancer of the ear, the cytotoxic agents are not without the potential for serious adverse side effects. Moreover, cytotoxic agents which demonstrate efficacy but are otherwise not approvable because of safety considerations is also contemplated within the embodiments disclosed herein. It is contemplated that localized application of the cytotoxic agents to the target otic structures for treatment of autoimmune and/or inflammatory disorders, as well as cancer of the ear, will result in the reduction or elimination of adverse side effects experienced with systemic treatment. Moreover, localized treatment with the cytotoxic agents contemplated herein will also reduce the amount of agent needed for effective treatment of the targeted disorder due, for example, to increased retention of the active agents in the auris interna and/or media, to the existence of the biological blood barrier in the auris interna, or to the lack of sufficient systemic access to the auris media.

In some embodiments, cytotoxic agents used in the compositions, formulations, and methods disclosed herein are metabolites, salts, polymorphs, prodrugs, analogues, and derivatives of cytotoxic agents, including methotrexate, cyclophosphamide, and thalidomide. Particularly preferred are metabolites, salts, polymorphs, prodrugs, analogues, and derivatives of cytotoxic agents, e.g., methotrexate, cyclophosphamide, and thalidomide, that retain at least partially the cytotoxicity and anti-inflammatory properties of the parent compounds. In certain embodiments, analogues of thalidomide used in the formulations and compositions disclosed herein are lenalidomide (REVLIMID®) and CC-4047 (ACTIMID®).

Cyclophosphamide is a prodrug that undergoes in vivo metabolism when administered systemically. The oxidized metabolite 4-hydroxycyclophosphamide exists in equilibrium with aldophosphamide, and the two compounds serve as the transport forms of the active agent phosphoramide mustard and the degradation byproduct acrolein. Thus, in some embodiments, preferred cyclophosphamide metabolites for incorporation into the formulations and compositions disclosed herein are 4-hydroxycyclophosphamide, aldophosphamide, phosphoramide mustard, and combinations thereof.

Other cytotoxic agents used in the compositions, formulations, and methods disclosed herein, particularly for the treatment of cancer of the ear, are any conventional chemotherapeutic agents, including acridine carboxamide, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar.

Cholesteatoma

A cholesteatoma is a hyperproliferative cyst often found in the middle ear. Cholesteatoma are classified as congenital or acquired. Acquired cholesteatomas result from retraction of the ear drum (primary) and/or a tear in the ear drum (secondary).

The most common primary cholesteatoma results from the pars flaccida retracting into the epitympanum. As the pars flaccida continues to retract, the lateral wall of the epitympanum slowly erodes. This produces a defect in the lateral wall of the epitympanum that slowly expands. A less common type of primary acquired cholesteatoma results from the retraction of the posterior quadrant of the tympanic membrane retracts into the posterior middle ear. As the tympanic membrane retracts, squamous epithelium envelops the stapes and retracts into the sinus tympani. Secondary cholesteatomas result from injury to the tympanic membrane (e.g. a perforation resulting from otitis media; trauma; or a surgically-induced injury).

Complications associated with a growing cholesteatoma include injury to the osteoclasts and, in some cases, deterioration of the thin bone layer separating the top of the ear from the brain. Damage to the osteoclasts results from the persistent application of pressure to the bones resulting from the expansion of the cholesteatoma. Additionally, the presence of multiple cytokines (e.g. TNF-α, TGF-β1, TGF-β2, Il-1, and IL-6) in the epithelium of the cholesteatoma can result in further degradation of the surrounding bones.

Patients with a cholesteatoma often present with earache, hearing loss, mucopurulent discharge, and/or dizziness. Physical examination can confirm the presence of a cholesteatoma. Symptoms which can be identified upon physical examination include damage to the ossicles, and a canal filled with mucopus and granulation tissue.

There is currently no effective medical therapy for cholesteatomas. As a cholesteatoma has no blood supply, it cannot be treated with systemic antibiotics. Topical administration of antibiotics often fails to treat a cholesteatoma.

Drug-Induced Inner Ear Damage

Damage from the administration of drugs, including certain antibiotics, diuretics (e.g. ethacrynic acid and furosemide), aspirin, aspirin-like substances (e.g. salicylates) and quinine Deterioration of the auris interna organ are hastened by impaired kidney function, which results in decreased clearance of the affecting drugs and their metabolites. The drugs may affect both hearing and equilibrium, but likely affects hearing to a greater extent.

For example, neomycin, kanamycin, amikacin have a greater effect on hearing than on balance. The antibiotics viomycin, gentamicin and tobramycin affect both hearing and equilibrium. Streptomycin, another commonly administered antibiotic, induces vertigo more than loss of hearing, and can lead to Dandy's syndrome, where walking in the dark becomes difficult and induces a sensation of the environment moving with each step. Aspirin, when taken in very high doses, may also lead to temporary hearing loss and tinnitus, a condition where sound is perceived in the absence of external sound. Similarly, quinine, ethacryinic acid and furosemide can result in temporary or permanent hearing loss.

Excitotoxicity

Excitotoxicity refers to the death or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. Certain events (e.g. ischemia or stroke) can damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, $Na^+$ and $Ca^{2+}$ ions flow into the neuron and $K^+$ ions flow out of the neuron.

The NMDA receptor is activated by the binding of both glutamate and NMDA. Activation of the NMDA receptor, results in the opening of ion channels located in the plasma membrane of the neuron. However, these channels are blocked by $Mg^{2+}$ ions. Activation of the AMPA receptor results in the expulsion of $Mg^{2+}$ ions from the ion channels into the synapse. When the ion channels open, and the $Mg^{2+}$ ions evacuate the ion channels, $Na^+$ and $Ca^{2+}$ ions flow into the neuron, and $K^+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca^{2+}$ and $Na^+$ to enter the neuron. The influx of these levels of $Ca^{2+}$ and $Na^+$ into the neuron causes the neuron to fire more often, resulting in a rapid buildup of free radicals and inflammatory compounds within the cell. The free radicals eventually damage the mitochondria, depleting the cell's energy stores. Furthermore, excess levels of $Ca^{2+}$ and $Na^+$ ions activate excess levels of enzymes including, but not limited to, phospholipases, endonucleases, and proteases. The over-activation of these enzymes results in damage to the cytoskeleton, plasma membrane, mitochondria, and DNA of the sensory neuron.

Endolymphatic Hydrops

Endolymphatic hydrops refers to an increase in the hydraulic pressure within the endolymphatic system of the inner ear. The endolymph and perilymph are separated by thin membranes which contain multiple nerves. Fluctuation in the pressure stresses the membranes and the nerves they house. If the pressure is great enough, disruptions may form in the membranes. This results in a mixing of the fluids which can lead to a depolarization blockade and transient loss of function. Changes in the rate of vestibular nerve firing often lead to vertigo. Further, the Organ of Corti may also be affected. Distortions of the basilar membrane and the inner and outer hair cells can lead to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus may also be present. Treatment includes systemic administration of benzodiazepine, diuretics (to decrease the fluid pressure), corticosteroids, and/or anti-bacterial, anti-viral, or anti-fungal agents.

Hereditary Disorders

Hereditary disorders, including Scheibe, Mondini-Michelle, Waardenburg's, Michel, Alexander's ear deformity, hypertelorism, Jervell-Lange Nielson, Refsum's and Usher's sydromes, are found in approximately 20% of patients with sensorineural hearing loss. Congenital ear malformations may result from defects in the development of the membranous labyrinthine, the osseous labyrinthine, or both. Along with profound hearing loss and vestibular function abnormalities, hereditary deformities may also be associated with other dysfunctions, including development of recurring menigitis, cerebral spinal fluid (CSF) leaks, as well as perilymphatic fistulas. Treatment of chronic infections are necessitated in hereditary disorder patients.

Inflammatory Disorders of the Auris Media

Otitis media (OM), which includes acute otitis media (AOM), otitis media with effusion (OME) and chronic otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viral causes, as well as other microbial agents, may also account for OM conditions.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Genetic studies supports this link between cytokines and OM by demonstrating a correlation in the occurrence of TNF-α SNP (single-nucleotide polymorphisms) and an increased susceptibility for OM in pediatric patients suffering from AOM and with a subsequent need for placement of tympanostomy tubes. (Patel et al. *Pediatrics* (2006) 118:2273-2279). In animal models of OM induced with pneumococci innoculations, TNF-α and interleukins levels were found to increase in early developmental phase of OM, with TNF-α levels steadily increasing 72 hours after innoculation. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines may play in the origin and maintenance of OM in the auris media.

Because OM can be caused by a virus, bacteria or both, it is often difficult to identify the exact cause and thus the most appropriate treatment. Treatment options of OM in the auris media include treatment with antibiotics, such as amoxicillin, clavulanate acid, trimethoprim-sulfamethoxazole, cefuroxime, clarithromycin and azithromycin and other cephalosporins, macrolides, penicillins or sulfonamides. Surgical intervention is also available, including a myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, may also be prescribed to treat accompanying fever or pain effects. Pre-treatment with TNF-α inhibitors in experimental lipopolysaccharide (LPS)-induced OM animal models has been shown to suppress development of OM, suggesting a role in the treatment of OM or OME. In addition, treatment of such conditions include use of TNF-α inhibitors in combination with other inflammatory response mediators, including platelet activating factor antagonists, nitric oxide synthase inhibitors and histamine antagonists.

As discussed above, methotrexate, cyclophosphamide, and thalidomide are all cytotoxic small molecule agents that are systemically administered to treat AIED. Thus, the compounds are useful in the compositions and formulations disclosed herein for the treatment of inflammatory disorders of the auris media, including OM, by having a direct anti-inflammatory effect, particularly by interfering with TNF activity. In other embodiments, metabolites, salts, polymorphs, prodrugs, analogues, and derivatives of methotrexate, cyclophosphamide, and thalidomide that retain the ability of the parent cytotoxic agents to treat inflammatory disorders of the auris media, including OM, are useful in the formulations disclosed herein for the treatment of inflammatory disorders of the auris media, including OM. In certain embodiments, preferred metabolites of cyclophosphamide for incorporation into the compositions and formulations disclosed herein include 4-hydroxycyclophosphamide, aldophosphamide, phosphoramide mustard, or combinations thereof.

In addition, other otic disorders have inflammatory response aspects or are tangentially related to autoimmune conditions, including Meniere's disease and non-sudden hearing loss or noise induced hearing loss. These disorders are also explicitly contemplated as benefiting from the cytotoxic agent formulations disclosed herein, and therefore are within the scope of the embodiments disclosed.

Inflammatory Disorders of the Auris externa

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE may cause temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin and ciprofloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. Ear drops are often used as the vehicle for administration of the active agents. In the case that ear swelling has progressed substantially and ear drops do not penetrate significantly into the ear canal, a wick can be inserted into the ear canal to facilitate penetration of the treatment solutions. Oral antibiotics are also administered in the case of extensive soft tissue swelling that extends to the face and neck. When the pain of OE is extremely severe such that it interferes with normal activity, e.g., sleeping, pain relievers such as topical analgesics or oral narcotics are given until the underlying inflammation and infection are alleviated.

Notably, some types of topical ear drops, such as ear drops containing neomycin, are safe and effective for use in the ear canal, but can be irritating and even ototoxic to the auris media, prompting concern that such topical preparations should not be used unless the tympanic membrane is known to be intact. Utilization of the formulations disclosed herein for the treatment of OE allows for use of active agents that are potentially damaging to the auris media, even when the tympanic membrane is not intact. Specifically, the controlled release formulations disclosed herein can be applied locally in the external ear with improved retention time, thus eliminating concern that the active agents will leak out of the ear canal into the auris media. Furthermore, otoprotectants can be added when ototoxic agents, such as neomycin, are used.

Treatment of severe OE with the compositions disclosed herein, particularly highly viscous and/or mucoadhesive formulations, also obviates the need for extended use of an ear wick. Specifically, the compositions disclosed herein have increased retention time in the ear canal as a result of the formulation technology, thus eliminating the need for a device to maintain their presence in the outer ear. The formulations can be applied in the outer ear with a needle or an ear dropper, and the active agents can be maintained at the site of inflammation without the aid of an ear wick.

In some embodiments, the treatment of OE with antimicrobial formulations disclosed herein encompasses the treatment of granular myringitis, a specific form of OE characterized by chronic inflammation of the pars tensa of the tympanic membrane. The outer epithelial and underlying fibrous layers of the tympanic membrane are replaced by a proliferating granulation tissue. The predominant symptom is foul-smelling otorrhea. A variety of bacteria and fungi cause the condition, including *Proteus* and *Psuedomonas* species. Accordingly, antimicrobial agent formulations disclosed herein comprising antibacterial or antifungal agents are useful for the treatment of granular myringitis.

In some embodiments, the treatment of OE with antimicrobial formulations disclosed herein encompasses the treatment of chronic stenosing otitis externa. Chronic stenosing otitis externa is characterized by repeated infections, typically caused by bacteria or fungi. The primary symptoms are pruritus in the ear canal, otorrhea, and chronic swelling. Antimicrobial agent formulations disclosed herein comprising antibacterial or antifungal agents are useful for the treatment of chronic stenosing otitis externa.

In some embodiments, the treatment of OE with antimicrobial formulations disclosed herein encompasses the treatment of malignant or necrotizing external otitis, an infection involving the temporal and adjacent bones. Malignant external otitis is typically a complication of external otitis. It occurs primarily in persons with compromised immunity, especially in older persons with diabetes mellitus. Malignant external otitis is often caused by the bacteria *Pseudomonas aeruginosa*. Treatment typically involves correction of immunosuppression when possible, in conjunction with antibacterial therapy and pain relievers. According, antimicrobial agent formulations disclosed herein are useful for the treatment of malignant or necrotizing external otitis.

Otitis media (OM), which includes acute otitis media (AOM), chronic otitis media, otitis media with effusion (OME), secretory otitis media, and chronic secretory otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viruses, as well as other microbes, may also account for OM conditions.

Because OM can be caused by a virus, bacteria or both, it is often difficult to identify the exact cause and thus the most appropriate treatment. Treatment options for OM include antibiotics, such as penicillins (e.g., amoxicillin and amoxicillin-clavulanate), clavulanate acid, trimethoprim-sulfamethoxazole, cephalosporins (e.g., cefuroxime, ceflacor, cefprozil, loracarbef, cefindir, cefixime, cefpodoxime proxetil, cefibuten, and ceftriaxone), macrolides and azalides (e.g., erythromycin, clarithromycin, and azithromycin), sulfonamides, and combinations thereof. Surgical intervention is also available, including myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, may also be prescribed to treat accompanying fever or pain effects.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines may play in the origin and maintenance of OM in the auris media. Thus, treatment of OM includes the use of antimicrobial agents in conjunction with anti-inflammatory agents to eliminate the pathogen and treat the symptoms of inflammation. Such treatments include use of steroids, TNF-α inhibitors, platelet activating factor antagonists, nitric oxide synthase inhibitors, histamine antagonists, and combinations thereof in conjunction with the antimicrobial formulations disclosed herein.

Mastoiditis is an infection of the mastoid process, which is the portion of the temporal bone behind the ear. It is typically caused by untreated acute otitis media. Madtoiditis are acute or chronic. Symptoms include pain, swelling, and tenderness in the mastoid region, as well as otalgia, erythematous, and otorrhea. Mastoiditis typically occurs as bacteria spread from the middle ear to the mastoid air cells, where the inflammation causes damage to the bony structures. The most common bacterial pathogens are *Streptococcus pneumoniae, Streptococcus pyogenes, Staphylococcus aureus*, and gram-negative bacilli. Accordingly, antimicrobial agent formulations disclosed herein comprising antibacterial agents effective against the bacteria are useful for the treatment of mastoiditis, including acute mastoiditis and chronic mastoiditis.

Bullous myringitis is an infection of the tympanic membrane, caused by a variety of bacteria and viruses, including *Mycoplasma* bacteria. The infection leads to inflammation of the tympanic membrane and nearby canal, and causes the formation of blisters on the ear drum. The primary symptom of Bullous myringitis is pain, which are relieved through the administration of analgesics. Antimicrobial formulations disclosed herein comprising antibacterial and antiviral agents are useful for the treatment of Bullous myringitis.

Eustachian tubal catarrh, or Eustachian salpingitis, is caused from inflammation and swelling of the Eustachian tubes, resulting in a build-up of catarrh. Accordingly, antimicrobial formulations disclosed herein are useful for the treatment of Eustachian salpingitis.

Labyrinthitis, e.g., serous labyrinthitis, is an inflammation of the inner ear that involves one or more labyrinths housing the vestibular system. The primary symptom is vertigo, but the condition is also characterized by hearing loss, tinnitus, and nystagmus. Labrynthitis maybe acute, lasting for one to six weeks and being accompanied by severe vertigo and vomiting, or chronic, with symptoms lasting for months or even years. Labyrinthitis is typically caused by viral or bacterial infection. Accordingly, antimicrobial formulations disclosed herein comprising antibacterial and antiviral agents are useful for the treatment of labyrinthitis.

Facial nerve neuritis is a form of neuritis, an inflammation of the peripheral nervous system, afflicting the facial nerve. The primary symptoms of the condition are a tingling and burning sensation, and stabbing pains in the affected nerves. In severe cases, there are numbness, loss of sensation, and paralysis of the nearby muscles. The condition is typically caused by herpes zoster or herpes simplex viral infection, but has also been associated with bacterial infection, e.g., leprosy. Accordingly, antimicrobial formulations disclosed herein comprising antibacterial and antiviral agents are useful for the treatment of facial nerve neuritis.

In some embodiments, antimicrobial formulations disclosed herein are also useful for the treatment of temporal bone osteoradionecrosis.

Kinetosis

Kinetosis, also known as motion sickness, is a condition in which there is a disconnection between visually perceived movement and the vestibular system's sense of movement. Dizziness, fatigue, and nausea are the most common symptoms of kinetosis. Dimenhydrinate, cinnarizine, and meclizine are all systemic treatments for kinetosis. Additionally, benzodiazepines and antihistamines have demonstrated efficacy in treating kinetosis.

Labyrinthitis

Labyrinthitis is an inflammation of the labyrinths of the ear which contain the vestibular system of the inner ear. Causes include bacterial, viral, and fungal infections. It may also be caused by a head injury or allergies. Symptoms of labyrinthitis include difficulty maintaining balance, dizziness, vertigo, tinnitus, and hearing loss. Recovery may take one to six weeks; however, chronic symptoms are present for years.

There are several treatments for labyrinthitis. Prochlorperazine is often prescribed as an antiemetic. Serotonin-reuptake inhibitors have been shown to stimulate new neural growth within the inner ear. Additionally, treatment with antibiotics is prescribed if the cause is a bacterial infection, and treatment with corticosteroids and antivirals is recommended if the condition is caused by a viral infection.

Mal de Debarquement

Mal de debarquement is a condition which usually occurs subsequent to a sustained motion event, for example, a cruise, car trip, or airplane ride. It is characterized by a persistent sense of motion, difficulty maintaining balance, fatigue, and cognitive impairment. Symptoms may also include dizziness, headaches, hyperacusis, and/or tinnitus. Symptoms often last in excess of a month. Treatment includes benzodiazepines, diuretics, sodium channel blockers, and tricyclic antidepressants.

Microvascular Compression Syndrome

Microvascular compression syndrome (MCS), also called "vascular compression" or "neurovascular compression", is a disorder characterized by vertigo and tinnitus. It is caused by the irritation of Cranial Nerve VII by a blood vessel. Other symptoms found in subjects with MCS include, but are not limited to, severe motion intolerance, and neuralgic like "quick spins". MCS is treated with carbamazepine, TRILEPTAL®, and baclofen. It can also be surgically treated.

Other Microbial Infections Causing Cochleovestibular Disorders

Other microbial infections are known to cause cochleovestibular disorders, including hearing loss. Such infections include rubella, cytomegalovirus, mononucleosis, varicella zoster (chicken pox), pneumonia, *Borrelia* species of bacteria (Lyme disease), and certain fungal infections. Accordingly, controlled release antimicrobial agent formulations disclosed herein are also used for localized treatment of these infections in the ear.

Otic Disorders Caused by Free Radicals

Free radicals are highly reactive atoms, molecules, or ions the reactivity of which results from the presence of unpaired electrons. Reactive oxygen species ("ROS") form as a result of sequential reduction of molecular oxygen. Examples of reactive oxygen species of interest ("ROS") include, but are not limited to, superoxide, hydrogen peroxide, and hydroxyl radicals. ROS are naturally produced as a by-product of the production of ATP. ROS can also result from the use of cisplatin, and aminoglycosides. Further, stress to stereocila caused by acoustic trauma results in otic hair cells producing ROS.

ROS can damage cells directly by damaging nuclear DNA and mitochondrial DNA. Damage to the former can lead to mutations which impair the functioning of auditory cells and/or apoptosis. Damage to the latter often results in decreased energy production and increased ROS production both of which can lead to impaired cellular functioning or apoptosis. Further, ROS can also damage or kill cells by oxidizing the polydesaturated fatty acids which comprise lipids, oxidizing the amino acids which comprise proteins, and oxidizing co-factors necessary for the activity of enzymes. Antioxidants can ameliorate damage by caused by ROS by preventing their formation, or scavenging the ROS before they can damage the cell.

Damage to mitochondria by ROS is often seen in hearing loss, especially hearing loss due to aging. The loss of ATP correlates to a loss in neural functioning in the inner ear. It can also lead to physiological changes in the inner ear. Further, damage to mitochondria often results in an increased rate of cellular degradation and apoptosis of inner ear cells. The cells of the stria vascularis are the most metabolically active due to the vast energy requirements needed to maintain the ionic balance of fluids in the inner ear. Thus, the cells of the stria vascularis are most often damaged or killed due to damage of the mitochondria.

Otosclerosis

Otosclerosis is an abnormal growth of bone in the middle ear, which prevents structures within the ear from transducing vibration, which causes hearing loss. Otoscelorosis usually effects the ossicles, in particular the stapes, which rests in the entrance to the cochlea in the oval window. The abnormal bone growth fixates the stapes onto the oval window, preventing sound passing waves from traveling to the cochlea. Otoscelorosis may cause a sensorineural hearing loss, i.e. damaged nerve fibers or hearing hair cells, or conductive hearing loss.

Treatment of otoscelrosis may include surgery to remove the fixated stapes bone, called a stapedectomy. Fluoride treatment may also be used, which will not reverse the hearing loss but may slow the development of otoscelorosis.

Ototoxicity

Ototoxicity refers to hearing loss caused by a toxin. The hearing loss are due to trauma to otic hair cells, the cochlea, and/or the cranial nerve VII. Multiple drugs are known to be ototoxic. Often ototoxicity is dose-dependent. It are permanent or reversible upon withdrawal of the drug.

Known ototoxic drugs include, but are not limited to, the aminoglycoside class of antibiotics (e.g. gentamicin, and amikacin), some members of the macrolide class of antibiotics (e.g erythromycin), some members of the glycopeptide class of antibiotics (e.g. vancomycin), salicylic acid, nicotine, some chemotherapeutic agents (e.g. actinomycin, bleomycin, cisplatin, carboplatin and vincristine), and some members of the loop diuretic family of drugs (e.g. furosemide).

Cisplatin and the aminoglycoside class of antibiotics induce the production of reactive oxygen species ("ROS"). ROS can damage cells directly by damaging DNA, polypeptides, and/or lipids. Antioxidants prevent damage of ROS by preventing their formation or scavenging free radicals before they can damage the cell. Both cisplatin and the aminoglycoside class of antibiotics are also thought to damage the ear by binding melanin in the stria vascularis of the inner ear.

Salicylic acid is classified as ototoxic as it inhibits the function of the polypeptide prestin. Prestin mediates outer otic hair cell motility by controlling the exchange of chloride and carbonate across the plasma membrane of outer otic hair cells. It is only found in the outer otic hair cells, not the inner otic hair cells. Accordingly, disclosed herein is the use of controlled release auris-compositions comprising antioxidants to prevent, ameliorate or lessen ototoxic effects of chemotherapy, including but not limited to cisplatin treatment, aminoglycoside or salicylic acid administration, or other ototoxic agents.

Postural Vertigo

Postural vertigo, otherwise known as positional vertigo, is characterized by sudden violent vertigo that is triggered by certain head positions. This condition are caused by damaged semicircular canals caused by physical injury to the auris interna, otitis media, ear surgery or blockage of the artery to the auris interna.

Vertigo onset in patients with postural vertigo usually develops when a person lies on one ear or tilts the head back to look up. Vertigo is accompanied by nystagmus. In severe cases of postural vertigo, the vestibular nerve is severed to the affected semicircular canal. Treatment of vertigo is often identical to Meniere's disease, and may include meclizine, lorazepam, prochlorperazine or scopolamine. Fluids and electrolytes may also be intravenously administered if the vomiting is severe.

Presbycusis (Age Related Hearing Loss)

Presbycusis (or presbyacusis or age related hearing loss (ARHL)) is the progressive bilateral loss of hearing that results from aging. Most hearing loss occurs at higher frequencies (i.e. frequencies above 15 or 16 Hz) making it difficult to hear a female voice (as opposed to male voice), and an inability to differentiate between high-pitched sounds (such as "s" and "th"). It is difficult to filter out background noise. The disorder is most often treated by the implantation of a hearing aid and/or the administration of pharmaceutical agents which prevent the build up of ROS.

The disorder is caused by changes in the physiology of the inner ear, the middle ear, and/or the VII nerve. Changes in the inner ear resulting in presbycusis include epithelial atrophy with loss of otic hair cells and/or stereocilia, atrophy of nerve cells, atrophy of the stria vascularis, and the thickening/stiffening of the basilar membrane. Additional changes which can contribute to presbycusis include the accumulation of defects in the tympanic membrane and the ossicles.

Changes leading to presbycusis can occur due to the accumulation of mutations in DNA, and mutations in mitochondrial DNA; however, the changes are exacerbated by exposure to loud noise, exposure to ototoxic agents, infections, and/or the lessening of blood flow to the ear. The latter is attributable to atherosclerosis, diabetes, hypertension, and smoking.

Presbycusis, or age-related hearing loss, occurs as a part of normal aging, and occurs as a result of degeneration of the receptor cells in the spiral Organ of Corti in the auris interna. Other causes may also be attributed to a decrease in a number of nerve fibers in the vestibulocochlear nerve, as well as a loss of flexibility of the basilar membrane in the cochlea. There is currently no known cure for permanent hearing damage as a result of presbycusis or excessive noise, although treatment regimens have been proposed, including treatment with antioxidants such as alpha lipoic acid. (Seidman et al. *Am. J. Otol.* (2000) 21:161-167).

Ramsay Hunt's Syndrome (Herpes Zoster Infection)

Ramsay Hunt's syndrome is caused by a herpes zoster infection of the auditory nerve. The infection may cause severe ear pain, hearing loss, vertigo, as well as blisters on the outer ear, in the ear canal, as well as on the skin of the face or neck supplied by the nerves. Facial muscles may also become paralyzed if the facial nerves are compressed by the swelling. Hearing loss are temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy may also be employed to ameliorate herpes zoster infection. Analgesics or narcotics may also be administered to relieve the pain, and diazempam or other central nervous system agents to suppress vertigo. Capsaicin, lidocaine patches and nerve blocks may also be used. Surgery may also be performed on compressed facial nerves to relieve facial paralysis.

Recurrent Vestibulopathy

Recurrent vestibulopathy is a condition wherein the subject experiences multiple episodes of severe vertigo. The episodes of vertigo may last for minutes or hours. Unlike Meniere's Disease, it is not accompanied by hearing loss. In some cases it may develop into Meniere's Disease or Benign Paroxysmal Positional Vertigo. Treatment is similar to that of Meniere's Disease.

Syphillis Infection

Syphillis infection may also lead to congenital prenatal hearing loss, affecting approximately 11.2 per 100,000 live births in the United States, as well as sudden hearing loss in adults. Syphilis is a venereal disease, caused by the spirochete *Treponema pallidum*, which in its secondary and tertiary stages may result in auditory and vestibular disorders due to membranous labyrinthis, and secondarily include meningitis.

Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes. Syphilis infection may lead to congenital prenatal hearing loss, affecting approximately 11.2 per 100,000 live births in the United States, as well as sudden hearing loss in adults.

Treatment with steroids and antibiotics, including penicillins (e.g. benzathine penicillin G (BICILLIN LA®), are effective in eradicating the spirochete organism. However, Treponemas may remain in the cochlear and vestibular endolymph even after eradication from other sites in the body. Accordingly, long term treatment with penicillins are warranted to achieve complete eradication of the spirochete organism from the endolymph fluid.

Treatment of otosyphilis (syphilis presenting otic symptoms) typically includes a combination of steroids (e.g., prednisilone) and antibacterial agents (e.g., benzathine penicillin G (BICILLIN LA®), penicillin G procaine, doxycycline, tetracycline, ceftriaxone, azithromycin). Such treatments are effective in eradicating the spirochete organism. However, *Treponemas* may remain in the cochlear and vestibular endolymph even after eradication from other sites in the body. Accordingly, long term treatment with penicillins are required to achieve complete eradication of the spirochete organism from the endolymph fluid. Also, in the case of a severe or advanced case of syphilis, a uricosuric drug, such as probenecid, are administered in conjunction with the antibacterial agent to increase its efficacy.

Temporal Bone Fractures

The temporal bone, which contains part of the ear canal, the middle ear and the auris interna, is subject to fractures from blows to the skull or other injuries. Bleeding from the ear or patchy bruising is symptomatic of a fracture to the temporal bone, and may a computed tomography (CT) scan for accurate diagnosis. Temporal bone fractures may rupture the eardrum, causing facial paralysis and sensorineural hearing loss.

Treatment of detected temporal bone fractures includes an antibiotic regimen to prevent meningitis, or an infection of brain tissue. In addition, surgery are performed to relieve any subsequent pressure on the facial nerve due to swelling or infection.

Temporomandibular Joint Disease

Some evidence exists for a relationship between temporomandibular joint disease (TMD) and auris interna disorders. Anatomical studies demonstrate the possible involvement of the trigeminal nerve, where trigemminal innervation of the vascular system has been shown to control cochlear and vestibular labyrinth function. (Vass et al. *Neuroscience* (1998) 84:559-567). Additionally, projections of ophthalmic fibers of the trigeminal Gasser ganglion to the cochlea through the basilar and anterior inferior cerebellar arteries can play an important role in the vascular tone in quick vsaodilatatory response to metabolic stresses, e.g. intense noise. Auris interna diseases and symptoms, such as sudden hearing loss, vertigo and tinnitus, may originate from reduction of the cochlear blood flow due to the presence of abnormal activity in the trigeminal ganglion, for example from migraine or by the central excitatory effect originated in chronic or deep pain produced by TMD.

Similarly, other researchers have found that the trigeminal ganglion also innervates the ventral cochlear nucleus and the superior olivary complex, which may interfere with authditory pathways leading to the auditory cortex where constant peripheral somatic signals from the opthalmic and mandibular trigenimal peripheral innvervation occurs in TMD cases. (Shore et al. *J. Comp. Neurology* (2000) 10:271-285). These somatosensoory and auditory system interactions via the central nervous system may explain otic symptoms in the absence of existing disease in the ear, nose or throat.

Accordingly, forceful muscle contractions in TMD may elicit modulations in the neurological and auditory and equilibrium function. For example, the auditory and vestibular modulations may occur as a result of hyerptonicity and muscular spasm, which in turn irritates nerves and blood vessels that affect auris interna function by muscular trapping. Relief of the affected nerve or muscular contractions may act to relieve auditory or vestibular symptoms. Medications, including barbiturates or diazepam, may thus relieve auditory or vestibular dysfunction in TMD patients.

Utricular Dysfunction

The utricle is one of the two otoliths found in the vestibular labyrinth. It is responsive to both gravity and linear acceleration along the horizontal plane. Utricular dysfunction is a disorder caused by damage to the utricle. It is often characterized by a subject's perception of tilting or imbalance.

Vertigo

Vertigo is described as a feeling of spinning or swaying while the body is stationary. There are two types of vertigo. Subjective vertigo is the false sensation of movement of the body. Objective vertigo is the perception that one's surrounding are in motion. It is often accompanied by nausea, vomiting, and difficulty maintaining balance.

While not wishing to be bound by any one theory, it is hypothesized that vertigo is caused by an over-accumulation of fluid in the endolymph. This fluid imbalance results in increased pressure on the cells of the inner ear which leads to the sensation of movement. The most common cause of vertigo is benign paroxysmal positional vertigo, or BPPV. It can also be brought on by a head injury, or a sudden change of blood pressure. It is a diagnostic symptom of several diseases including superior canal dehiscence syndrome.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection, and acute localized ischemia of the vestibular nerve and/or labyrinth. Vestibular neuronitis is characterized by sudden vertigo attacks, which may present as a single attack of vertigo, a series of attacks, or a persistent condition which diminishes over a matter of weeks. Symptoms typically include nausea, vomiting, and previous upper respiratory tract infections, although there are generally no auditory symptoms. The first attack of vertigo is usually severe, leading to nystagmus, a condition characterized by flickering of the eyes involuntarily toward the affected side. Hearing loss does not usually occur.

In some instances, vestibular neuronitis is caused by inflammation of the vestibular nerve, the nerve that connects the inner ear to the brain, and is likely caused by viral infection. Diagnosis of vestibular neuronitis usually involves tests for nystagmus using electronystamography, a method of electronically recording eye movements. Magnetic resonance imaging may also be performed to determine if other causes may play a role in the vertigo symptoms.

Treatment of vestibular neuronitis typically involves alleviating the symptoms of the condition, primarily vertigo, until the condition clears on its own. Treatment of vertigo is often identical to Meniere's disease, and may include meclizine, lorazepam, prochlorperazine, or scopolamine. Fluids and electrolytes may also be intravenously administered if the vomiting is severe. Corticosteroids, such as prednisilone, are also given if the condition is detected early enough.

Compositions disclosed herein comprising an antiviral agent can be administered for the treatment of vestibular neuronitis. Further, the compositions are administered with other agents that are typically used to treat symptoms of the condition, including anticholinergics, antihistamines, benzodiazepines, or steroids. Treatment of vertigo is identical to Meniere's disease, and may include meclizine, lorazepam, prochlorperazine or scopolamine. Fluids and electrolytes may also be intravenously administered if the vomiting is severe.

The most significant finding when diagnosing vestibular neuronitis is spontaneous, unidirectional, horizontal nystagmus. It is often accompanied by nausea, vomiting, and vertigo. It is, generally, not accompanied by hearing loss or other auditory symptoms.

There are several treatments for vestibular neuronitis. H1-receptor antagonists, such as dimenhydrinate, diphenhydramine, meclizine, and promethazine, diminish vestibular stimulation and depress labyrinthine function through anticholinergic effects. Benzodiazepines, such as diazepam and lorazepam, are also used to inhibit vestibular responses due to their effects on the $GABA_A$ receptor. Anticholinergics, for example scopolamine, are also prescribed. They function by suppressing conduction in the vestibular cerebellar pathways. Finally, corticosteroids (i.e. prednisone) are prescribed to ameliorate the inflammation of the vestibular nerve and associated apparatus.

Advantages of Local Otic Administration

To overcome the toxic and attendant side effects of systemic delivery, disclosed herein are methods and compositions for local delivery of therapeutic agents to auris media and/or auris interna structures. Access to, for example, the vestibular and cochlear apparatus will occur through the auris media including the round window membrane, the oval window/stapes footplate, the annular ligament and through the otic capsule/temporal bone.

In addition, localized treatment of the auris media and/or auris interna also affords the use of previously undesired therapeutic agents, including agents with poor PK profiles, poor uptake, low systemic release and/or toxicity issues. Because of the localized targeting of the otic agent formulations and compositions, as well as the biological blood barrier present in the auris interna, the risk of adverse effects will be reduced as a result of treatment with previously characterized toxic or ineffective otic active agents, (e.g., immunomodulatory agents such as anti-TNF agents). Accordingly, also contemplated within the scope of the embodiments described herein is the use of active agents and/or agents that have been previously rejected by practitioners because of adverse effects or ineffectiveness of the otic agent.

By specifically targeting the auris media or auris interna structures, adverse side effects as a result of systemic treatment are avoided. Moreover, by providing a controlled release otic agent formulation (e.g., immunomodulating agent or auris pressure modulator formulation) or composition to treat otic disorders, a constant, variable and/or extended source of an otic agent is provided to the individual or patient suffering from an otic disorder, reducing or eliminating the variability of treatment. Accordingly, one embodiment disclosed herein is to provide a formulation that enables at least one therapeutic agent to be released in therapeutically effective doses either at variable or constant rates such as to ensure a continuous release of the at least one agent. In some embodiments, the auris active agents disclosed herein are administered as an immediate release formulation or composition. In other embodiments, the auris active agents are administered as a controlled release formulation, released either continuously or in a pulsatile manner, or variants of both. In still other embodiments, the active agent formulation is administered as both an immediate release and controlled release formulation, released either continuously or in a pulsatile manner, or variants of both. The release is optionally dependent on environmental or physiological conditions, for example, the external ionic environment (see, e.g. Oros® release system, Johnson & Johnson).

Also included within the embodiments disclosed herein is the use of additional auris media and/or auris interna agents in combination with the otic agent formulations and compositions disclosed herein. When used, such agents assist in the treatment of hearing or equilibrium loss or dysfunction as a result of an autoimmune disorder, including vertigo, tinnitus, hearing loss, balance disorders, infections, inflammatory response or combinations thereof. Accordingly, agents that ameliorate or reduce the effects of vertigo, tinnitus, hearing loss, balance disorders, infections, inflammatory response or combinations thereof are also contemplated to be used in combination with the otic agents described herein including steroids, anti-emetic agents, local anesthetic agents, corticosteroids, chemotherapeutic agents, including cytoxan, azathiaprine or methotrexate; treatment with collagen, gamma globulin, interferons, copaxone, central nervous system agents, antibiotics, platelet-activating factor antagonists, nitric oxide synthase inhibitors and combinations thereof.

In addition, the auris-compatible pharmaceutical compositions or formulations included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the auris media and/or auris interna. Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, otic pharmaceutical compositions or formulations disclosed herein are optionally targeted to distinct regions of the auris media and/or auris interna, including but not limited to the tympanic cavity, vestibular bony and membranous labyrinths, cochlear bony and membranous labyrinths and other anatomical or physiological structures located within the auris interna.

Treatment

Provided herein are otic compositions suitable for the treatment of any otic condition, disease or disorder (e.g., middle and/or inner ear disorder) described herein, comprising administration of an auris formulation described herein to an individual or patient in need thereof. The formulations described herein are suitable for the treatment of any disease described herein. In some instances, the treatment is long-term treatment for chronic recurring disease. In some instances, the treatment is prophylactic administration of an otic formulation described herein for the treatment of any otic disease or disorder described herein. In some instances, prophylactic administration avoids occurrence of disease in individuals suspected of having a disease or in individuals genetically predisposed to an otic disease or disorder. In some instances the treatment is preventive maintenance therapy. In some instances, preventive maintenance therapy avoids recurrence of a disease.

In some instances, because of their otic compatiblity and improved sterility, the formulations described herein are safe for long-term administration. The auris compositions described herein have very low ototoxicity and provide a steady sustained release of a therapeutic agent for a period of at least one week, two weeks, three weeks or a month.

Provided herein are controlled release compositions and formulations to treat and/or prevent diseases associated with the ear, including the cochlea, the middle ear and inner ear, including autoimmune inner ear disorder (AIED), Ménière's disease (endolymphatic hydrops), noise induced hearing loss (NIHL), sensorineural hearing loss (SNL), tinnnitus, otosclerosis, balance disorders, vertigo and the like.

The etiology of several ear diseases or disorders consists of a syndrome of progressive hearing loss, including noise induced hearing loss and age-related hearing loss, dizziness, nausea, nystagmus, vertigo, tinnitus, inflammation, swelling, infection and/or congestion. These disorders may have many causes, such as infection, exposure to noise, injury, inflammation, tumors and/or adverse response to drugs or other chemical agents. Several causes of hearing and/or equilibrium impairment are attributed to inflammation and/or an autoimmune disorder and/or a cytokine-mediated inflammatory response.

Provided herein are controlled release immunomodulator compositions and formulations to treat inflammation or infection of the auris media, including otitis media. A few therapeutic products are available for the treatment of AIED, including anti-TNF agents; however, systemic routes via oral, intravenous or intramuscular routes are currently used to deliver these therapeutic agents.

Provided herein are controlled release aural pressure modulating compositions and formulations to treat fluid homeostasis disorders of the inner ear, including Meniere's Disease, endolymphatic hydrops, progressive hearing loss, including noise induced hearing loss and age-related hearing loss, dizziness, vertigo, tinnitus and similar conditions.

In some embodiments, the compositions provided herein are CNS modulating compositions and formulations to treat tinnitus, progressive hearing loss, including noise induced hearing loss and age-related hearing loss, and balance disorders. Balance disorders include benign paroxysmal positions vertigo, dizziness, endolymphatic hydrops, kinetosis, labyrinthitis, Mal de debarquement, Meniere's Disease, Meniere's Syndrome, myringitis, otitis media, Ramsay Hunt's Syndrome, recurrent vestibulopathy, tinnitus, vertigo, microvascular compression syndrome, utricular dysfunction, and vestibular neuronitis. A few therapeutic products are available for the treatment of balance disorders, including $GABA_A$ receptor modulators and local anesthetics.

In some embodiments, the compositions provided herein are cytotoxic agent compositions and formulations for the treatment of autoimmune diseases of the ear, including autoimmune inner ear disease (AIED). Also provided herein are controlled release cytotoxic agent compositions for the treatment of disorders of the auris media, including otitis media. The compositions disclosed herein are also useful for the treatment of cancer, particularly cancer of the ear. A few therapeutic products are available for the treatment of AIED, including certain cytotoxic agents. Particularly, the cytotoxic agents methotrexate and cyclophosphamide have been tested and are used for systemic treatment of AIED. Also, thalidomide, while not currently administered for the treatment of AIED, has been used to treat Behçet's disease, which is often associated with AIED.

In some embodiments, the compositions provided herein comprise auris sensory cell modulators for treating or ameliorating hearing loss or reduction resulting from destroyed, stunted, malfunctioning, damaged, fragile or missing hairs in the inner ear. Further disclosed herein are controlled release auris sensory cell modulating agent compositions and formulations to treat ototoxicity, excitotoxicity, sensorineural hearing loss, Meniere's Disease/Syndrome, endolymphatic hydrops, labyrinthitis, Ramsay Hunt's Syndrome, vestibular neuronitis and microvascular compression syndrome.

In some embodiments, the compositions provided herein are antimicrobial agent compositions and formulations for the treatment of otic disorders, including otitis externa, otitis media, Ramsay Hunt syndrome, otosyphilis, AIED, Meniere's disease, and vestibular neuronitis.

In some embodiments, the compositions provided herein prevent, relieve, reverse or ameliorate the degeneration of neurons and/or hair cells of the auris due to free radicals and/or the dysfunction of the mitochondria.

Also provided herein are controlled release ion channel modulating compositions and formulations to treat fluid homeostasis disorders of the inner ear, including Meniere's Disease, endolymphatic hydrops, progressive hearing loss, including noise induced hearing loss and age-related hearing loss, dizziness, vertigo, tinnitus and similar conditions. Systemic routes via oral, intravenous or intramuscular routes are currently used to deliver ion channel modulating therapeutic agents.

Therapeutic Agents

Notwithstanding any therapeutic agent used in the formulations described herein, the otic compositions described herein will have pH and osmolarity that is auris-acceptable. Any otic composition described herein meets the stringent sterility requirements described herein and will be compatible with the endolymph and/or the perilymph. Pharmaceutical agents that are used in conjunction with the formulations disclosed herein include agents that ameliorate or lessen otic disorders, including auris interna disorders, and their attendant symptoms, which include but are not limited to hearing loss, nystagmus, vertigo, tinnitus, inflammation, swelling, infection and congestion. Otic disorders may have many causes, such as infection, injury, inflammation, tumors and adverse response to drugs or other chemical agents that are responsive to the pharmaceutical agents disclosed herein. A skilled practitioner would be familiar with agents that are useful in the amelioration or eradication of otic disorder; accordingly, agents which are not disclosed herein but are useful for the amelioration or eradication of otic disorders are expressly included and intended within the scope of the embodiments presented. In some embodiments, pharmaceutically active metabolites, salts, polymorphs, prodrugs, analogues, and derivatives of the otic agents disclosed herein that retain the ability of the parent antimicrobial agents to treat otic disorders are useful in the formulations.

Active ingredients or otic therapeutic agents include, but are not limited to, anti-inflammatory agents, anti-anti-oxidants, neuroprotective agents, glutamate modulators, TNF-alpha modulators, interleukin 1 beta modulators, retinaldehyde modulators, notch modulators, gamma-secretase modulators, thalidomide, ion and/or fluid (e.g., water) homeostasis modulators, vasopressin inhibitors, inhibitors of the vasopressin-mediated AQP2 (aquaporin 2) system, transcriptional regulators of the inner-ear transcriptional regulatory network (including, e.g., transcriptional regulators of estrogen-related receptor beta), inner ear hair cell growth factors, including BDNF (brain derived and NF-3, and other therapeutic modalities. Agents explicitly include an agonist of an otic target, a partial agonist of an otic target, an antagonist of an otic target, a partial antagonist of an otic target, an inverse agonist of an otic target, a competitive antagonist of an otic target, a neutral antagonist of an otic target, an orthosteric antagonist of an otic target, an allosteric antagonist of an otic target a positive allosteric modulator of an otic target, or combinations thereof.

In addition, because the formulation is designed such that the active ingredient has limited or no systemic release, agents that produce systemic toxicities (e.g., liver toxicity) or have poor PK characteristics (e.g. short half-life) are also optionally used. Thus, pharmaceutical agents which have been previously shown to be toxic, harmful or non-effective during systemic application, for example through toxic metabolites formed after hepatic processing, toxicity of the drug in particular organs, tissues or systems, through high levels needed to achieve efficacy, through the inability to be released through systemic pathways or through poor PK characteristics, are useful in some embodiments herein. The formulations disclosed herein are contemplated to be targeted directly to otic structures where treatment is needed; for example, one embodiment contemplated is the direct application of the aural pressure modulating formulations disclosed herein onto the round window membrane or the

*crista* fenestrae cochlea of the auris interna, allowing direct access and treatment of the auris interna, or inner ear components. In other embodiments, the aural pressure modulating formulation disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the aural pressure modulating formulations through use of a needle and syringe, a pump, a microinjection device, an in situ forming spongy material or any combination thereof.

In still other embodiments, application of any otic agent formulation described herein is targeted to the auris media through piercing of the intratympanic membrane and applying the otic agent formulation directly to the auris media structures affected, including the walls of the tympanic cavity or auditory ossicles. By doing so, the auris active agent formulations disclosed herein are confined to the targeted auris media structure, and will not be lost, for example, through diffusion or leakage through the eustachian tube or pierced tympanic membrane. In some embodiments, the auris-compatible formulations disclosed herein are delivered to the auris externa in any suitable manner, including by cotton swab, injection or ear drops. Also, in other embodiments, the otic formulations described herein are targeted to specific regions of the auris externa by application with a needle and syringe, a pump, a microinjection device, an in situ forming spongy material or any combination thereof. For example, in the case of treatment of otitis externa, antimicrobial agent formulations disclosed herein are delivered directly to the ear canal, where they are retained, thereby reducing loss of the active agents from the target ear structure by drainage or leakage.

In some embodiments, agents which may have been previously rejected as, for example, an antimicrobial agent, may find use herein because of the targeted nature of the embodiments which bypass systemic effects, including toxicity and harmful side effects. By way of example only, onercept, a previously rejected anti-TNF agent due to toxicity and safety issues, is useful as an anti-TNF agent in some of the embodiments disclosed herein. Also contemplated within the scope of embodiments described herein is the administration of higher doses of pharmaceutical agents, for example agents that have dose limiting toxicities, compared to currently approved doses for such pharmaceutical agents Some pharmaceutical agents, either alone or in combination, are ototoxic. For example, some chemotherapeutic agents, including actinomycin, bleomycin, cisplatin, carboplatin and vincristine; and antibiotics, including erythromycin, gentamicin, streptomycin, dihydrostreptomycin, tobramycin, netilmicin, amikacin, neomycin, kanamycin, etiomycin, vancomycin, metronidizole, capreomycin, are mildly to very toxic, and may affect the vestibular and cochlear structures differentially. However, in some embodiments, the combination of an ototoxic drug, for example cisplatin, in combination with an antioxidant is protective and lessen the ototoxic effects of the drug. Moreover, the localized application of the potentially ototoxic drug lessens the toxic effects that might otherwise occur through systemic application through the use of lower amounts with maintained efficacy, or the use of targeted amounts for a shorter period of time. Accordingly, a skilled practitioner choosing a course of therapy for targeted otic disorder will have the knowledge to avoid or combine an ototoxic compound, or to vary the amount or course of treatment to avoid or lessen ototoxic effects.

In certain instances, pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release otic formulation, it is advised to avoid or combine the appropriate excipients, diluents or carriers to lessen or eliminate potential ototoxic components from the formulation, or to decrease the amount of such excipients, diluents or carriers. In some instances, the ototoxicity of the pharmaceutical agents, excipients, diluents, carriers, or formulations and compositions disclosed herein can be ascertained using an accepted animal model. See, e.g., Maritini, A., et al. *Ann. N.Y. Acad. Sci.* (1999) 884:85-98. Optionally, a controlled release otic formulation includes otoprotective agents, such as antioxidants, alpha lipoic acid, calicum, fosfomycin or iron chelators, to counteract potential ototoxic effects that may arise from the use of specific therapeutic agents or excipients, diluents or carriers.

Other agents that are used in the embodiments disclosed herein, either alone or in combination with other auris interna agents, include anti-apoptotic agents, including caspases, JNK inhibitors (by way of example only CEP/KT-7515, AS601245, SPC9766 and SP600125), antioxidants, NSAIDs, neuroprotectants, glutamate modulators, interleukin 1 modulators, interleukin-1 antagonists, including tumor necrosis factor-α coverting enzyme (TACE) and caspases, retinaldehyde modulator, notch modulator, gamma secretase modulator, thalidomide, latanoprost (Xalatan®) for reducing internal pressure and combinations thereof.

Immunomodulating Agents

Anti-TNF Agents

Contemplated for use with the formulations disclosed herein are agents which reduce or ameliorate symptoms or effects as a result of an autoimmune disease and/or inflammatory disorder, including AIED or OM. Accordingly, some embodiments incorporate the use of agents which block the effects of TNF-α, including anti-TNF agents. By way of example only, anti-TNF agents include protein-based therapeutics, such as etanercept (ENBREL®), infliximab (REMICADE®), adalimumab (HUMIRA®) and golimumab (CNTO 148), and small molecule therapeutics, such as TACE inhibitors, IKK inhibitors or calcineurin inhibitors or combinations thereof.

Infliximab and adalimumab are anti-TNF monoclonal antibodies, and etanercept is a fusion protein designed to bind specifically to the TNF protein. All are currently approved for use in the treatment of rheumatoid arthritis. Golimumab, which is currently in Phase 3 clinical trials for rheumatoid arthritis, psoriatic arthritis and ankylosing spondylitis, is a fully-humanized anti-TNF-alpha IgG1 monoclonal antibody that targets and neutralizes both the soluble and the membrane-bound form of TNF-α. Other antagonists to TNF, by way of example only, include TNF receptors (pegylated soluble TNF receptor type 1; Amgen); TNF binding factors (Onercept; Serono); TNF antibodies (US Patent App. No. 2005/0123541; US Patent App. No. 2004/0185047); single domain antibodies against the p55 TNF receptor (US Patent App. No. 2008/00088713); soluble TNF receptors (US Patent App. No. 2007/0249538); fusion polypeptides binding to TNF (US Patent App. No. 2007/0128177); and flavone derivatives (US Patent App. No. 2006/0105967), all of which are incorporated by reference for such disclosure. The use of onercept, a soluble TNF p55 receptor, was discontinued in 2005. Three phase-III clinical trials reported patients diagnosed with fatal sepsis. A risk to benefit analysis was subsequently performed, resulting in the discontinuation of the clinical trials. As discussed above, the embodiments herein specifically contemplate the use of anti-TNF agents which have been previously shown to have limited or no systemic release, systemic toxicity, poor PK characteristics of combinations thereof.

Although etanercept, infliximab and adalimumab are currently approved systemic therapies for use in rheumatoid arthritis, these anti-TNF agents are not without serious adverse side effects. It is contemplated that the localized application of the anti-TNF agents to the target otic structures for treatment of autoimmune and/or inflammatory disorders will result in the reduction or elimination of these adverse side effects experienced with systemic treatment. Moreover, localized treatment with the anti-TNF agents contemplated herein will also reduce the amount of agent needed for effective treatment of the targeted disorder due, for example, to the existence of the biological blood barrier in the auris interna or to the lack of sufficient systemic access to the auris media.

Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the $C_H2$ domain, the $C_H3$ domain and hinge region, but not the $C_H1$ domain of IgG1. Etanercept is a recombinant protein consisting of 934 amino acids, with an apparent molecular weight of approximately 150 kilodaltons. Etanercept binds specifically to tumor necrosis factor (TNF), and acts by inhibiting the interaction of TNF with cell surface TNF receptors. Serious side effects with etanercept have been reported with systemic administration, including serious infections and sepsis that resulted in fatalities. Other side effects observed upon intravenous administration of etanercept include contraction of tuberculosis; onset or exacerbation of central nervous system disorders, including mental status changes, transverse myelitis, optic neuritis, multiple sclerosis and seizures resulting in permanent disability; adverse hematologic events, including pancytopenia, aplastic anemia with fatal outcomes, blood dyscrasias, persistent fever, bruising, bleeding and pallor, neutropenia and cellulitis. Treatment with etanercept may also result in the formation of autoantibodies, which may develop into a lupus-like syndrome, as well as development of malignant disorders. Moreover, over one-third of patients systemically treated with etanercept experience injection site reactions including mild to moderate erythema and/or itching, pain and/or swelling. Injection site bleeding and bruising has also been observed. Other side effects from the systemic administration of etanercept include headache, nausea, rhinitis, dizziness, pharyngitis, cough, asthenia, abdominal pain, rash, peripheral edema, respiratory disorder, dyspepsia, sinusitis, vomiting, mouth ulcer, alopecia and pneumonitis. Infrequent side effects include heart failure, myocardial infarction, myocardial ischemia, hypertension, hypotension, deep vein thrombosis, thrombophlebitis, cholecystitis, pancreatitis, gastrointestinal hemorrhage, bursitis, polymyositis, cerebral ischemia, depression, dyspnea, pulmonary embolism, and membranous glomerulonephropathy in rheumatoid arthritis patients. Varicella infections, gastroenteritis, depression/personality disorder, cutnaeous ulcer, esophagitis/gastritis, group A streptococcal septic shock, type I diabetes mellitus, and soft tissue and post-operative wound infection was also seen in juvenile rheumatoid arthritis patients.

Infliximab is a chimeric human-mouse IgG1κ monoclonal antibody with an approximate molecular weight of 149 kilodaltons. Infliximab binds specifically to TNFα with an association constant of $10^{10}$ $M^{-1}$. Infliximab is produced by a recombinant cell line cultured by continuous perfusion. Infliximab acts to neutralize the binding activity of TNFα by inhibiting binding of TNF to its cell surface receptors. Serious side effects as a result of systemic intravenous infusions or injections have been reported with the use of infliximab, including fatal sepsis and serious infections. Cases of histoplasmosis, listeriosis, pneumocystosis and tuberculosis have also been observed. Hypersensitivity, including urticaria, dyspnea and hypotension have occurred upon treatment with infliximab. Infusion reactions include cardiopulmonary reactions (primarily chest pain, hypotension, hypertension or dyspnea), pruritus, and combined reactions. Other hypersensitivity symptoms include fever, rash, headache, sore throat, myalgias, polyarthralgias, hand and facial edema and/or dysphagia, anaphylaxis, convulsions, erythematous rash, laryngeal/pharyngeal edema and severe bronchospasm. Neurologic adverse events include optic neuritis, seizure and new onset or exacerbation and/or radiographic evidence of central nervous system demyelinating disorders, including multiple sclerosis. The formation of autoantibodies have also been observed, including symptoms suggestive of a lupus-like syndrome following treatment. Other serious adverse events include worsening rheumatoid arthritis, rheumatoid nodules, abdominal hernia, asthenia, chest pain, diaphragmatic hernia, pancytopenia, splenic infarction, splenomegaly, syncope, cerebral hypoxia, convulsions, dizziness, encephalopathy, hemiparesis, spinal stenosis, upper motor neuron lesion, ceruminosis, endophthalmitis, and other infrequent-occurring side effects.

Adalimumab is a recombinant human IgG1 monoclonal antibody specific for human TNF. Adalimumab was created using phage display technology resulting in an antibody with human derived heavy and light chain variable regions and human IgG1:κ constant regions, and consists of 1330 amino acids with a molecular weight of approximately 148 kilodaltons. Adalimumab binds specifically to TNF-α and blocks its interaction with both the p55 and p75 TNF cell surface receptors. Adalimumab also lyses TNF expressing cells in vitro in the presence of complement. Adalimumab does not bind or inactivate lymphotoxin (TNF-β). Serious side effects from systemic administration have been reported with the intravenous administration or injection of adalimumab, including fatal sepsis and serious infections, including upper respiratory infections, bronchitis, urinary tract infections, pneumonia, septic arthritis, prosthetic and post-surgical infections, erysipelas cellulitis, diverticulitis, pyelonephritis, tuberculosis, and invasive opportunistic infections caused by *histoplasma, aspergillus* and *nocardia*. Other serious adverse reactions were neurologic events, including confusion, multiple sclerosis, paresthesia, subdural hematoma, and tremor, and the development of malignancies, including lymphoma development. The formation of autoantibodies has also been observed, including symptoms suggestive of a lupus-like syndrome following treatment. The most common adverse reaction was injection site reactions, with 20% of patients developing erythema and/or itching, hemorrhage, pain and/or swelling. Other adverse events as a result of systemic administration of adalimumab include clinical flare reaction, rash and pneumonia. Other adverse events included sinusitis, flu syndrome, nausea, abdominal pain, hypercholesterolemia, hyperlipidemia, hematuria, increased alkaline phosphatase levels, back pain, hypertension, as well as more infrequent serious adverse events, including pain, pelvic pain, thorax pain, arrthythmia, atrial fibrillation, cardiovascular disorder, congestive heart failure, coronary artery disorder, heart arrest, hypertensive encelphalopathy, myocardial infact, palpitation, pericardial effusion, pericarditis, syncope, tachycardia, vascular disorders, and other disorders.

Calcineurin Inhibitors

Calcineurin inhibitors are a group of structurally diverse small molecule immunomodulators which function through the inhibition of calcineurin function. Calcineurin is a calcium-activated protein phosphatase which catalyses the dephosphorylation of cytoplasmic NFAT. Upon dephosphorylation, NFAT migrates to the nucleus and forms a regulatory complex involved in the transcription of cytokines, such as TNF-α, IL-2, IL-3 and IL-4. Inhibition of calcineurin function blocks the dephosphorylation event and subsequent cytokine transcription. An unusual aspect of calcineurin inhibition is that cyclosporine, tacrolimus and pimecrolimus are required to form a complex with an immunophilin for the inhibitory properties to be realized (Schreiber et al, Immunol. Today (1992), 13:136-42; Liu et al, Cell (1991), 66:807-15). For cyclosporine the immunophilin is cyclophilin; tacrolimus and pimecrolimus bind to the FK506-binding protein (FKBP).

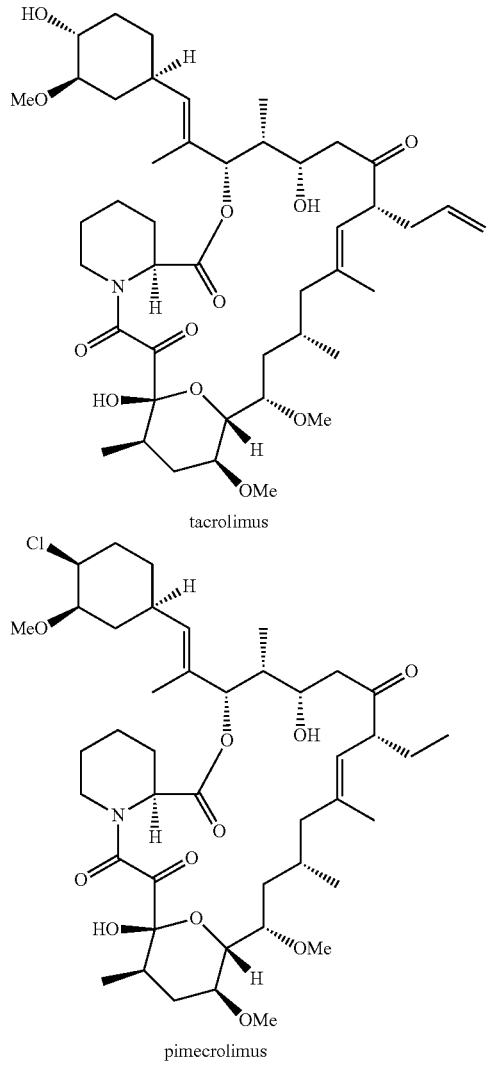

tacrolimus pimecrolimus

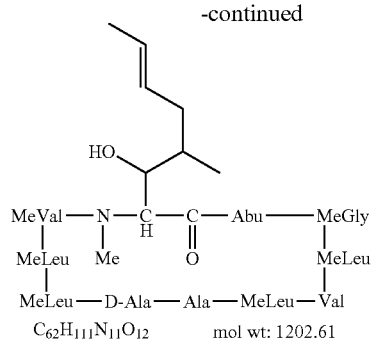

cyclosporine A

Cyclosporine is an 11-residue cyclic peptide produced as a metabolite of the fungus *Beauveria nivea* and has the chemical name cyclo[[(E)-(2S,3R,4R)-3-hydroxy-4-methyl-2-(methylamino)-6-octenoyl]-L-2-aminobutyryl-N-methyl-glycyl-N-methyl-L-leucyl-L-valyl-N-methyl-L-leucyl-L-alanyl-D-alanyl-N-methyl-L-leucyl-N-methyl-L-leucyl-N-methyl-L-valyl. It is provided in several formulations for both systemic or local administration. Sandimmune® provides cyclosporine in three different formulations: soft gelatin capsules, an oral solution or a formulation for injection. Sandimmune® is indicated for prevention of organ rejection in kidney, liver or heart transplants. Neoral® and Gengraf® provide cyclosporine in two formulations: soft gelatin capsules and an oral solution. They are indicated for prevention of organ rejection in kidney, liver or heart transplants, for treatment of patients with severe active, rheumatoid arthritis, or for treatment of severe psoriasis. Compared to Sandimmune®, Neoral® and Gengraf® provide increased bioavailability of cyclosporine. Restasis® provides cyclosporine in an ophthalmic emulsion formulation. It is indicated to increase tear production in patients with reduced tear production due to ocular inflammation associated with keratoconjunctivitis sicca.

Tacrolimus, also known as FK-506 or fujimycin, is a 23-membered macrolide natural product produced by *Streptomyces tsukubaensis* and has the chemical name [3S-[3R*[E(1S*,3S*,4S*)], 4S*,5R*,8S*,9E,12R*,14R*,15S*, 16R*,18S*,19S*,26aR*]]-5,6,8,11,12,13,14,15,16,17,18, 19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-39c][1,4]oxaazacyclotricosine-1,7, 20,21(4H,23H)-tetrone monohydrate. It is provided in formulations suitable for systemic or topical administration. For systemic administration, the Prograf® formulation provides an oral capsule or a sterile solution for injection. Prograf® is indicated for prevention of organ rejection in liver, kidney or heart transplants. For topical administration, the Protopic® formulation is indicated for the treatment of moderate-to-severe atopic dermatitis.

Pimecrolimus is a semi-synthetic analog of tacrolimus and has the chemical name (1R,9S,12S,13R,14S,17R,18E, 21S,23S,24R,25S,27R)-12-[(1E)-2-{(1R,3R,4S)-4-chloro-3-methoxycyclohexyl}-1-methylvinyl]-17-ethyl-1,14-dihydroxy-23,25-dimethoxy-13,19,21,27-tetramethyl-11,28-dioxa-4-aza-tricyclo[22.3.1.04,9]octacos-18-ene-2,3,10,16-tetraone. It is provided in a formulation suitable for topical application and is indicated for the treatment of mild-to-moderate atopic dermatitis.

Studies have shown that tacrolimus and pimecrolimus do not suppress Langerhans' cells or dermal connective tissue and therefore do not cause atrophy of the skin, unlike corticosteroids (Stuetz et al, Int. Arch. Allergy Immunol. (2006), 141:199-212; Queille-Roussel et al, Br. J. Dermatol. (2001), 144:507-13). Because of the importance of calcineurin, systemic administration of calcineurin inhibitors leads to significant side effects. Systemic side effects are related to dose, exposure levels and duration of therapy. Prolonged elevated blood levels result in hypertension, nephrotoxicity, psychiatric disorders, hyperlipidemia, and profound immunosuppression. Topical application of tacrolimus or pimecrolimus has shown to afford very little, if any, systemic exposure, with tacrolimus having demonstrated less than 0.5% bioavailability after topical application.

In one embodiment, the auris-acceptable controlled release immunomodulating formulation comprises a calcineurin inhibitor. In another embodiment, the auris-acceptable controlled release immunomodulating formulation comprises cyclosporine. In another embodiment, the auris-acceptable controlled release immunomodulating formulation comprises tacrolimus. In another embodiment, the auris-acceptable controlled release immunomodulating formulation comprises pimecrolimus. In another embodiment, the auris-acceptable controlled release immunomodulating formulation comprises a calcineurin inhibitor which induces toxicity upon systemic administration.

Other pharmaceutical agents that are optionally used in combination with immunomodulating-α agents for the treatment of autoimmune and/or inflammatory disorders include other agents that have been used to treat autoimmune and inflammatory disorders, including corticosteroids, local anesthetic agents, chemotherapeutic agents, including cytoxan, azathiaprine or methotrexate; treatment with collagen, gamma globulin, interferons, copaxone, or combinations thereof. Accordingly, also contemplated within the scope of the embodiments herein is the use of other pharmaceutical agents in combination with the immunomodulating compositions and formulations disclosed in the treatment of autoimmune otic disorders. In addition, other pharmaceutical agents are optionally used to treat attendant symptoms of AIED or other autoimmune disorder, including vomiting, dizziness and general malaise.

IKK Inhibitors

The transcription of TNF-α is dependent on the transcription factor NF-κB. In unstimulated cells, NF-κB is in the cytoplasm as part of a protein complex with the protein inhibitor of NF-κB, also known as IκB. Activation of NF-κB depends on phosphorylation-induced ubiquitination of the IκB. Once poly-ubiquitinated, the IκB undergoes a rapid degradation through the 26S proteasome and the free NF-κB migrates to the nucleus to activate pro-inflammatory gene transcription. The phosphorylation event which releases NF-κB is mediated by the IκB kinase (IKK) complex, composed of IKK kinases. Two IKK enzymes, generally referred to as IKK-α and IKK-β (Woronicz et al. Science (1997), 278:866; Zandi et al. Cell (1997), 91:243) or IKK-1 and IKK-2 (Mercurio et al. Science (1997), 278:860) have been discovered. Both forms of IKK can exist as homodimers and as IKK-α/IKK-β heterodimers. Another component of the IκB kinase complex is a regulatory protein, known as IKK-γ or NEMO (NF-κB-Essential Modulator) (Rothwarf et al. Nature (1998), 395:297). NEMO does not contain a catalytic domain, and thus it appears to have no direct kinase activity and it probably serves a regulatory function. Existing data suggests that the predominant form of IKK in cells is an IKK-α/IKK-β heterodimer associated with either a dimer or a trimer of NEMO (Rothwarf et al. Nature (1998) 395:297). Biochemical and molecular biology experiments have identified IKK-α and IKK-β as the most likely mediators of TNF-α-induced IκB phosphorylation and degradation, which results in NF-κB activation and upregulation of families of genes involved in inflammatory processes (Woronicz et al. Science (1997); Karin, Oncogene (1999) 18:6867; Karin, J. Biol. Chem. (1999) 274:27339).

Many IKK-β inhibitors have been identified. SPC-839 has been extensively studied. It inhibits IKK-β with an $IC_{50}$ of 62 nM and reduces paw edema in a rat arthritis model at 30 mg/kg. Carboline PS-1145 inhibits the IKK complex with an $IC_{50}$ of 150 nM and reduces the production of TNF-α in LPS-challenged mice. BMS-345541, an allosteric inhibitor, inhibits IKK-β with an $IC_{50}$ of 0.3 μM. In the mouse collagen-induced arthritis model it significantly reduced the severity of disease at a 30 mg/kg dose. A scientific review of IKK inhibitors has been published (Karin et al., Nature Reviews Drug Discovery (2004), 3, 17-26), incorporated herein by reference for such disclosure.

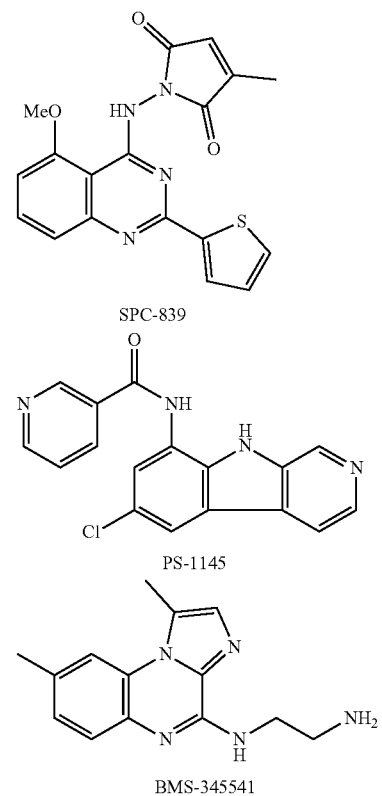

SPC-839

PS-1145

BMS-345541

In one embodiment, the auris-acceptable controlled release immunomodulating formulation comprises an IKK inhibitor. In a further embodiment, the auris-acceptable controlled release immunomodulating formulation comprises a IKK-β inhibitor. In another embodiment, the auris-acceptable controlled release immunomodulating formulation comprises a IKK inhibitor which induces toxicity upon systemic administration. In an additional embodiment, the auris-acceptable controlled release immunomodulating formulation comprises a IKK inhibitor which is not orally absorbed. In an additional embodiment, the auris-acceptable controlled release immunomodulating formulation comprises an IKK inhibitor selected from SPC-839, PS-1145, BMS-345541, or SC-514. In an additional embodiment, the auris-acceptable controlled release immunomodulating formulation comprises an IKK inhibitor selected from compounds disclosed in the following group of patent publications: WO199901441, WO2001068648, WO2002060386, WO2002030353, WO2003029242, WO2003010163, WO2001058890, WO2002044153, WO2002024679, WO2002046171, WO2003076447, WO2001030774, WO2001000610, WO2003024936, WO2003024935, WO2002041843, WO200230423, WO2002094265, WO2002094322, WO2005113544 and WO2006076318, all of which are incorporated by reference herein for such disclosure.

Interleukin Inhibitors

Interleukins are a class of cytokines. In certain instances, they are signaling molecules secreted by leukocytes having encountered a pathogen. In certain instances, the secretion of interleukins activates and recruits additional leukocytes to the site of infection. In certain instances, the recruitment of additional leukocytes to the site of infection results in inflammation (due to the increase in leukocyte containing lymph). IL-1α, IL-1β, IL-2, and IL-8 are found in middle ear effusions. In certain instances, IL-1α and IL-1β are also found in the epithelium of cholesteatomas.

Il-1 is a class of interleukins comprised of IL-1α, and IL-1β. IL-1 is made by macrophages, B cells, monocytes, and dendritic cells (DC). It binds to receptors IL1R1/CD121a and IL1R2/CD121b. The binding of IL-1 to its receptors results in an increase in cell-surface adhesion factors. This enables the migration of leukocytes to the site of infection.

IL-2 is made by TH-1 cells and binds to the receptors CD25/IL2Ra, CD122IL2Rb, and CD132/IL2Rg. 11-2 secretion is stimulated by the binding of an antigen to a TH-1 cell. The binding of IL-2 to a receptor stimulates the growth, and differentiation of memory T cells.

IL-8 is made by macrophages, lymphocytes, epithelial cells, and endothelial cells. It binds to CXCR1/IL8Ra and CXCR2/IL8Ra/CD128. Secretion of IL-8 initiates neutrophil chemotaxis to the site of infection.

In some embodiments, a subject in need thereof is administered an inhibitor of a pro-inflammatory interleukin. In some embodiments, the pro-inflammatory interleukin is IL-1α, IL-1β, IL-2, or IL-8. In some embodiments, the inhibitor of a pro-inflammatory interleukin is a WS-4 (an antibody against IL-8); [Ser IL-8]$_{72}$; or [Ala IL-8]$_{77}$ (See U.S. Pat. No. 5,451,399 which is hereby incorporated by reference for disclosures relating to these peptides); IL-1RA; SB 265610 (N-(2-Bromophenyl)-N'-(7-cyano-1H-benzotriazol-4-yl)urea); SB 225002 (N-(2-Bromophenyl)-N'-(2-hydroxy-4-nitrophenyl)urea); SB203580 (4-(4-Fluorophenyl)-2-(4-methylsulfinyl phenyl)-5-(4-pyridyl) 1H-imidazole); SB272844 (GlaxoSmithKline); SB517785 (GlaxoSmithKline); SB656933 (GlaxoSmithKline); Sch527123 (2-hydroxy-N,N-dimethyl-3-{2-[[(R)-1-(5-methyl-furan-2-yl)-propyl]amino]-3,4-dioxo-cyclobut-1-enylamino}-benzamide); PD98059 (2-(2-amino-3-methoxyphenyl)-4H-1-Benzopyran-4-one); reparixin; N-[4-chloro-2-hydroxy-3-(piperazine-1-sulfonyl)phenyl]-N'-(2-chloro-3-fluorophenyl)urea p-toluenesulfonate (See WO/2007/150016 which is hereby incorporated by reference for disclosures relating to this compound); sivelestat; bG31P (CXCL8((3-74))K11R/G31P); basiliximab; cyclosporin A; SDZ RAD (40-O-(2-hydroxyethyl)-rapamycin); FR235222 (Astellas Pharma); daclizumab; anakinra; AF12198 (Ac-Phe-Glu-Trp-Thr-Pro-Gly-Trp-Tyr-Gln-L-azetidine-2-carbonyl-Tyr-Ala-Leu-Pro-Leu-NH2); or combinations thereof.

Platelet Activating Factor Antagonists

Platelet activating factor antagonists are contemplated for use in combination with the immunomodulating formulations disclosed herein. Platelet activating factor antagonists include, by way of example only, kadsurenone, phomactin G, ginsenosides, apafant (4-(2-chlorophenyl)-9-methyl-2[3 (4-morpholinyl)-3-propanol-1-yl[6H-thieno[3.2-f[[1.2.4]triazolo]4,3-1]]1.4]diazepine), A-85783, BN-52063, BN-52021, BN-50730 (tetrahedra-4,7,8,10 methyl-1 (chloro-1 phenyl)-6 (methoxy-4 phenyl-carbamoyl)-9 pyrido[4',3'-4,5]thieno[3,2-f]triazolo-1,2,4 [4,3-a]diazepine-1,4), BN 50739, SM-12502, RP-55778, Ro 24-4736, SR27417A, CV-6209, WEB 2086, WEB 2170, 14-deoxyandrographolide, CL 184005, CV-3988, TCV-309, PMS-601, TCV-309 and combinations thereof.

TNF-α Converting Enzyme (TACE) Inhibitors

TNF-α is initially expressed on the cell surface as a 26 kDa, 233-amino acid, membrane-bound precursor protein. Proteolytic cleavage of the membrane-bound TNF-α by the matrix metalloproteinase TNF-α converting enzyme occurs between Ala-76 and Val-77 and results in a 17 kDa mature TNF-α which exists as a soluble trimer. Inhibition of the proteolytic cleavage could provide an alternative to the use of protein-based therapeutics in anti-inflammatory therapy. One potential complication, however, is that TACE is thought to be involved in the processing of other proteins in addition to TNF-α. For example, in a phase II clinical trial, indications of toxic effects in the liver occurred as a result of TACE inhibition. (Car et al, Society of Toxicology, 46$^{th}$ Annual Meeting, Charlotte, N.C., Mar. 25-29, 2007). The hypothesis for this mechanism-based toxicity is that TACE also acts on other membrane bound proteins, such as TNFRI and TNFRII.

While toxicities following oral administration are problematic for a drug administered systemically, local delivery to the site of action overcomes this problem. Inhibitor GW3333 has a TACE IC$_{50}$ of 40 nM and an IC$_{50}$ of 0.97 μM for inhibiting TNF-α production in the LPS-induced human PBMC cells (Conway et al, J. Pharmacol. Exp. Ther. (2001), 298:900). Nitroarginine analog A has an IC$_{50}$ TACE IC$_{50}$ of 4 nM and an IC$_{50}$ of 0.034 μM for inhibiting TNF-α production in the LPS-induced MonoMac-6 cells (Musso et al, Bioorg. Med. Chem. Lett. (2001), 11:2147), but lacks oral activity. A scientific review of TNF-α converting enzyme inhibitors has been published (Skotnicki et al., Annual Reports in Medicinal Chemistry (2003), 38, 153-162), incorporated by reference herein for such disclosure.

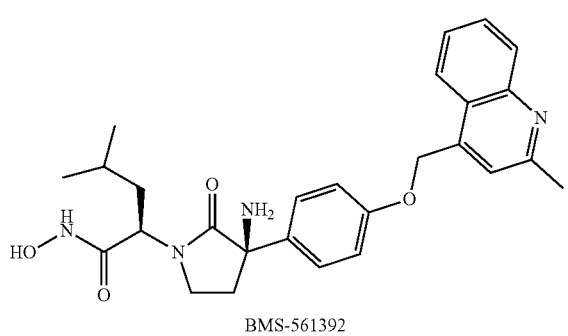

BMS-561392

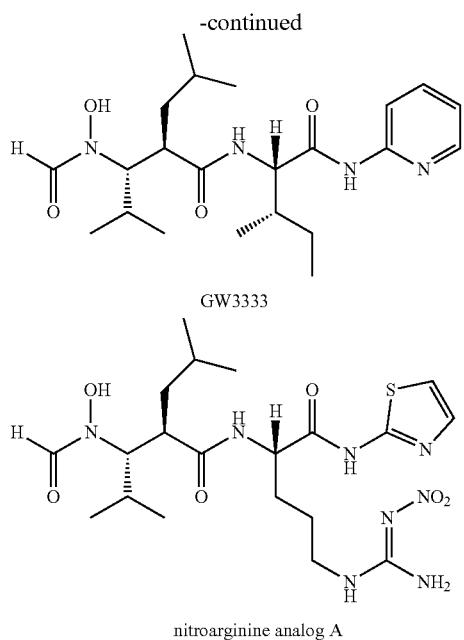

GW3333 nitroarginine analog A

Accordingly, in one embodiment, the auris-acceptable controlled release anti-TNF formulation comprises a TACE inhibitor. In another embodiment, the auris-acceptable controlled release anti-TNF formulation comprises a TACE inhibitor which induces toxicity upon systemic administration. In additional embodiments, the auris-acceptable controlled release anti-TNF formulation comprise a TACE inhibitor which is not orally absorbed. In another embodiment, the auris-acceptable controlled release anti-TNF formulation comprises a TACE inhibitor selected from Nitroarginine analog A, GW3333, TMI-1, BMS-561392, DPC-3333, TMI-2, BMS-566394, TMI-005, apratastat, GW4459, W-3646, IK-682, GI-5402, GI-245402, BB-2983, DPC-A38088, DPH-067517, R-618, or CH-138.

Toll-Like Receptor Inhibitors

Toll-like receptors (TLR) are a family of at least 12 pattern recognition cell-surface and intracellular receptors. The family is defined by the presence of two domains: a ligand-binding domain with multiple leucine-rich repeats, and a short Toll/Il-1 receptor domain; the latter controlling the initiation of downstream-signaling cascades. In certain instances, the receptors are activated by the binding of structurally conserved molecules (i.e. the "patterns") found on pathogens. Each receptor recognizes and binds to specific conserved molecules found on pathogens (e.g. TLR2—lipopeptides; TLR3—viral dsRNA; TLR4—LPS; TLR5—flagellin; TLR9—CpG DNA). In certain instances, the binding of a TLR to a pathogen, initiates the TLR signaling cascade which ultimately leads to the activation of various cytokines, chemokines, and antigen-specific and non-specific immune responses. In certain instances, the expression of TLR2 and/or TLR4 is up-regulated upon exposure to nontypeable *Hemophilus influenzae* (NTHi). Infection by NTHi is a common cause of otitis media.

Toll-like receptors belong to a class of single membrane-spanning non-catalytic receptors that recognize structurally conserved molecules derived from breached microbes are believed to play a key role in the innate immune system. Toll-like receptors thus recognize molecules that are broadly shared by pathogens, but are distinguishable from the host molecules. These receptors form a superfamily with Interleukin-1 receptors, and have in common a Toll-like receptor domain. Toll-like receptor agonists, such as CQ-07001, can stimulate Toll-like receptor 3 function, triggering anti-inflammatory and tissue regeneration activity. Toll-like receptor modulators, thus, have implication for use in both auris interna disorders, including AIED, and auris media diseases, including otitis media. In some embodiments, toll-like receptor modulators include toll-like receptor antagonist, partial agonist, inverse agonist, neutral or competitive antagonist, allosteric antagonist, and/or orthosteric antagonist. Other toll-like receptor modulators include but are not limited to polyinosinic-polycytidylic acid [poly(I:C)], polyAU, other nucleic acid molecules, including dsRNA agonists (such as AMPLIGEN®, Hemispherx, Inc., Rockville Md.; and POLYADENUR®, Ipsen), and are also contemplated within the scope of the embodiments disclosed herein.

In some embodiments, the TLR inhibitor is an ST2 antibody; sST2-Fc (functional murine soluble ST2-human IgG1 Fc fusion protein; see Biochemical and Biophysical Research Communications, 29 Dec. 2006, vol. 351, no. 4, 940-946 which is herein incorporated by reference for disclosures related to sST2-Fc); CRX-526 (Corixa); lipid IV$_A$; RSLA (*Rhodobacter sphaeroides* lipid A); E5531 ((6-O-{2-deoxy-6-O-methyl-4-O-phosphono-3-O—[(R)-3-Z-dodec-5-endoyloxydecl]-2-[3-oxo-tetradecanoylamino]-β-O-phosphono-α-D-glucopyranose tetrasodium salt); E5564 (α-D-Glucopyranose,3-O-decyl-2-deoxy-6-O-[2-deoxy-3-O-[(3R)-3-methoxydecyl]-6-O-methyl-2-[[(11Z)-1-oxo-11-octadecenyl]amino]-4-O-phosphono-β-D-glucopyranosyl]-2-[(1,3-dioxotetradecyl)amino]-1-(dihydrogen phosphate), tetrasodium salt); compound 4a (hydrocinnamoyl-L-valyl pyrrolidine; see PNAS, Jun. 24, 2003, vol. 100, no. 13, 7971-7976 which is herein incorporated by reference for disclosures related to compound 4a); CPG 52364 (Coley Pharmaceutical Group); LY294002 (2-(4-Morpholinyl)-8-phenyl-4H-1-benzopyran-4-one); PD98059 (2-(2-amino-3-methoxyphenyl)-4H-1-Benzopyran-4-one); chloroquine; and an immune regulatory oligonucleotide (for disclosures relating to IROs see U.S. Patent Application Publication No. 2008/0089883).

Auto-Immune Agents

Also contemplated for use with the formulations disclosed herein are agents which reduce or ameliorate symptoms or effects as a result of autoimmune disease, including auto-immune inner ear disease (AIED). Accordingly, some embodiments may incorporate the use of agents which block the effects of TNF-α, including but not limited to anti-TNF agents. By way of example only, some anti-TNF agents include etanercept (ENBREL®), infliximab (REMICADE®) and adalimumab (HUMIRA®), or combinations thereof. Other pharmaceutical agents to treat autoimmune disorders include chemotherapeutic agents, including cytoxan, azathiaprine or methotrexate; treatment with collagen, gamma globulin, interferons, copaxone, or combinations thereof.

IL-1 Modulators

Interleukin-1 (IL-1) is a pleiotropic cytokine that plays a role in the modulation of local as well as systemic inflammation, immune regulation and hemopoiesis. IL-1β, a member of the IL-1 family, has been implicated in angiogenesis processes, including tumor angiogenesis. In addition, IL-1 has been shown to stimulate the synthesis of inflammatory eicosanoids in macrophages, fibroblasts, synovial cells and chondrocytes, and is believed to contribute to leukocyte activation and tissue destruction in arthritic models. Interfering with IL-1 activity, therefore, is an approach for developing a disease modifying therapy for chronic inflammatory diseases, such as AIED and otitis media. In some embodiments, IL-1 modulators include an IL-1 antagonist, partial agonist, inverse agonist, neutral or competitive antagonist, allosteric antagonist, and/or orthosteric antagonist. In some embodiments, IL-1 modulators include but are not limited to antibodies that specifically recognize IL-1 subunits or its receptors, proteins, peptides, nucleic acids, and small molecule therapeutics. In some embodiments, ILL-1 modulators are IL-1 antagonists, including, for example, AF12198, IL-1 natural antagonists, inactive receptor fragments that bind to IL-1 molecule, and antisense molecules or factors that block expression of IL-1 cytokine proteins. In some embodiments, IL-1 antagonists are IL-1 antibodies including, by way of example, anakinra (Kinaret®) and ACZ885 (Canakinumab®). In some embodiments, modulators of IL-1 are antibodies that modulate cytokines and/or growth factors that affect the release and/or expression of IL-1, including, by way of example, ranibizumab, tefibazumab, and bevacizumab. In some embodiments, IL-1 modulators are IL-1 traps that attach to IL-1 and neutralize IL-1 before it can bind to cell surface receptors and include, but are not limited to, rilonocept (Arcalyst®).

RNAi

In some embodiments, where inhibition or down-regulation of a target is desired (e.g. genes encoding one or more calcineurins, IKKs, TACEs, TLRs, or cytokines), RNA interference are utilized. In some embodiments, the agent that inhibits or down-regulates the target is an siRNA molecule. In certain instances, the siRNA molecule inhibits the transcription of a target by RNA interference (RNAi). In some embodiments, a double stranded RNA (dsRNA) molecule with sequences complementary to a target is generated (e.g. by PCR). In some embodiments, a 20-25 bp siRNA molecule with sequences complementary to a target is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into a controlled-release auris-acceptable microsphere or microparticle, hydrogel, liposome, actinic radiation curable gel, solvent-release gel, xerogel, paint, foam, in situ forming spongy material, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, actinic radiation curable gel, solvent-release gel, hydrogel, liposome, or thermoreversible gel is injected through the round window membrane. In some embodiments, the auris-acceptable microsphere, hydrogel, liposome, paint, foam, in situ forming spongy material, actinic radiation curable gel, solvent-release gel, nanocapsule or nanosphere or thermoreversible gel is injected into the cochlea, the Organ of Corti, the vestibular labyrinth, or a combination thereof.

In certain instances, after administration of the dsRNA or siRNA molecule, cells at the site of administration (e.g. the cells of cochlea, Organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary target mRNA sequence. In certain instances, the RISC cleaves the target mRNA. In certain instances, the expression of the target gene is down-regulated.

In some embodiments, a sequence complementary to a target is ligated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and anti-sense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g pSUPER; pSUPER.neo; pSUPER.neo+gfp).

In some embodiments, the vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the Organ of Corti, the vestibular labyrinth, or a combination thereof.

Aural Pressure Modulators

Aquaporin

Contemplated for use with the formulations disclosed herein are agents that treat disorders of the auris, and/or modulate the cells and structures of the auris. In certain instances, an aquaporin is involved in fluid homeostasis. In certain instances, AQP2 mRNA is elevated in rats treated with vasopressin above the levels observed in control animals. In certain instances, Aquaporin-1 is expressed in the cochlea and endolymphatic sac. In certain instances, Aquaporin-1 is expressed in the spiral ligament, the Organ of Corti, the scala tympani, and the endolymphatic sac. Aquaporin-3 is expressed in the stria vascularis, the spiral ligament, the Organ of Corti, the spiral ganglion and the endolymphatic sac. In certain instances, aquaporin 2 (AQP2) mRNA is elevated above normal levels in individuals with endolymphatic hydrops.

Accordingly, some embodiments incorporate the use of agents that modulate an aquaporin. In some embodiments, the aquaporin is aquaporin 1, aquaporin 2 and/or aquaporin 3. In some embodiments, the agent that modulates an aquaporin (e.g. aquaporin 1, aquaporin 2 or aquaporin 3) is an aquaporin antagonist, partial agonist, inverse agonist, neutral or competitive antagonist, allosteric antagonist, and/or orthosteric antagonist. In some embodiments, the aquaporin antagonist, partial agonist, inverse agonist, neutral or competitive antagonist, allosteric antagonist, and/or orthosteric antagonist includes, but is not limited to, substance P; RU-486; tetraethylammonium (TEA); an anti-aquaporin antibody; a vasopressin and/or a vasopressin receptor antagonist, partial agonist, inverse agonist, neutral or competitive antagonist, allosteric antagonist, and/or orthosteric antagonist; or combinations thereof.

Estrogen-Related Receptor Beta Modulators

Estrogen-related receptor beta (ERR-beta; also known as Nr3b2), an orphan nuclear receptor, is specifically expressed in and controls the development of the endolymph-producing cells of the inner ear: the strial marginal cells in the cochlea and the vestibular dark cells in the ampulla and utricle. (Chen et al. Dev. Cell. (2007) 13:325-337). Nr3b2 expression has been localized in the endolymph-secreting strial marginal cells and vestibular dark cells of the cochlea and vestibular apparatus, respectively. Studies in knockout mice have shown that strial marginal cells in these animals fail to express multiple ion channel and transporter genes, suggesting a role in the development and/or function of endolymph producing epithelia. Moreover, conditional knockout of the Nr3b2 gene results in deafness and diminished endolymphatic fluid volume.

Other studies suggest a role for estrogen-related receptor β/NR3B2 (ERR/Nr3b2) in regulating endolymph production, and therefore pressure in the vestibular/cochlear apparatus. Treatment with antagonists to ERR/Nr3b2 may assist in reducing endolymphatic volume, and thus alter pressure in the auris interna structures. Accordingly, agents which antagonize ERR/Nr3b2 expression, protein production or protein function are contemplated as useful with the formulations disclosed herein.

GAP Junction Proteins

Contemplated for use with the formulations disclosed herein are agents that treat disorders of the auris, and/or modulate the cells and structures of the auris. Gap junctions are intracellular connections. In certain instances, a gap junction connects the cytoplasm of two cells. In certain instances, a gap junction facilitates the passage of small molecules (e.g. $IP_3$) and ions between the cells. In certain instances, gap junctions are formed of connexins (e.g. six connexins form a connexon and two connexons form a gap junction). There are multiple connexins (e.g. Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, and Cx62).

In certain instances, of Cx26 and Cx43 are expressed in a spiral limbus, a spiral ligament, a stria vascularis, cells of the Organ of Corti. In certain instances, non-syndromic deafness is associated with mutations in genes (e.g. GJB2) encoding connexins (e.g. Cx26). In certain instances, sensorineural hearing loss is associated with mutations in genes encoding connexins (e.g. Cx26). In certain instances, the expression of Cx26 and Cx43 is upregulated in a cholesteatoma. In certain instances, the expression of Cx26 is upregulated following acoustic trauma. In certain instances, gap junctions facilitate the movement of $K^+$ ions in endolymph.

Accordingly, some embodiments disclosed herein incorporate the use of agents that modulate gap junction proteins. In some embodiments, the gap junction protein is a connexin. In some embodiments, the agent that modulates a connexin is a connexin agonist, partial agonist, and/or positive allosteric modulator of a connexin. In some embodiments, the connexin agonist, partial agonist, and/or positive allosteric modulator includes, but is not limited to, astaxanthin; rotigaptide; adenosine; corticotropin-releasing hormone; or combinations thereof.

Vasopressin and the Vasopressin Receptor

Vasopressin (VP) is a hormone that plays an important part in circulatory and water homoeostasis. This hormone is synthesised by neurosecretory cells located predominantly in two specific hypothalamic nuclei—the supraoptic nucleus and the paraventricular nucleus. These neurons have axons that terminate in the neural lobe of the posterior pituitary gland (neurohypophysis) in which they release vasopressin. The three vasopressin receptor subtypes (VP1a, VP1b and VP2) all belong to the G-protein coupled receptor family and have differing tissue distributions. The VP1a receptor is predominantly located in the vascular smooth muscle, hepatocytes and blood platelets. The VP1b receptors are found in the anterior pituitary. The VP2 receptors are localized in the collecting duct of the kidney and regulate the presentation of aquaporin-2 channels at the apical cell surface. The effect of modulation of the VP2 subtype provides readily observed changes in urine volume and electrolyte levels to determine the pharmacological effects of anti-diuresis.

Vasopressin regulates systemic osmolality by controlling urinary volume and composition.

Vasopressin is secreted in response to increases in plasma tonicity (very sensitive stimulus) or to decreases in plasma volume (less sensitive stimulus). Vasopressin mainly regulates urinary volume by binding to the VP receptor in the collecting duct of the kidney. The VP receptor also exists in the inner ear of rodents, and aquaporin-2 (AQP2), a VP mediated water channel protein, is also expressed (Kitano et al. Neuroreport (1997), 8:2289-92). Water homeostasis of the inner ear fluid was confirmed to be regulated using the VP-AQP2 system (Takeda et al. Hear Res (2000), 140:1-6; Takeda et al. Hear Res. (2003), 182:9-18). A recent study looked at tissue expression of VP2 and AQP2 in human endolymphatic sac by immunohistochemistry and noted that VP2 and AQP2 were located in the epithelial layer of the endolymphatic sac but not in surrounding connective tissue (Taguchi et al, Laryngoscope (2007), 117:695-698). Studies on the systemic administration of vasopressio in the guinea pig showed the development of endolymphatic hydrops (Takeda et al. Hear Res (2000), 140:1-6). Additionally, the aquaporin-4 knockout mouse, while otherwise healthy, is deaf (Beitz et al., Cellular and Molecular Neurobiology (2003) 23(3):315-29). This suggests that transport of water and solutes in a manner similar to that of the kidney may play a role in fluid homeostasis of the endolymphatic sac. A mutant human VP2 receptor protein (D136A) has been identified and characterized as constitutively active (Morin et al., FEBS Letters (1998) 441(3):470-5). This hormone-independent activation of the VP2 receptor could play a role in the etiology of conditions such as Meniere's disease.

Contemplated for use with the formulations disclosed herein are agents that treat disorders of the auris, and/or modulate the cells (e.g., auris sensory cells) and structures of the auris. In certain instances, VP is involved in fluid homeostasis. In certain instances, VP is involved in endolymph and/or perilymph homeostasis. In certain instances, an increase in endolymph volume increases pressure in the vestibular and cochlear structures. In certain instances, plasma levels of VP are elevated above normal levels in endolymphatic hydrops and/or Meniere's Disease.

Vasopressin Receptor Modulators

Vasopressin receptor modulators can be differentiated based upon their efficacy relative to the vasopressin peptide hormone. A vasopressin receptor full agonist is a mimic of the native peptide. A vasopressin receptor antagonist blocks the effect of the native peptide. A partial agonist can serve as a mimic of the native peptide and induce a partial response, or in the presence of elevated levels of the native peptide, a partial agonist competes with the native peptide for receptor occupancy and provides a reduction in efficacy, relative to the native peptide alone. For a vasopressin receptor with constitutive activity, an inverse agonist serves to reverse the activity of the receptor.

Accordingly, some embodiments incorporate the use of agents that modulate vasopressin and/or a vasopressin receptor. In some embodiments, the agent that modulates vasopressin and/or a vasopressin receptor is a vasopressin and/or a vasopressin receptor antagonist, partial agonist, inverse agonist, neutral or competitive antagonist, allosteric antagonist, and/or orthosteric antagonist. In some embodiments, the vasopressin and/or a vasopressin receptor antagonist, partial agonist, inverse agonist, neutral or competitive antagonist, allosteric antagonist, and/or orthosteric antagonist includes, but is not limited to, an anti-vasopressin antibody; an anti-vasopressin receptor antibody; lithium; OPC-31260 ((±)-5-dimethylamino-1-(4-[2-methylbenzoylamino]benzoyl)-2,3,4,5-tetrahydro-1H-benzazepin hydrochloride); WAY-140288 (N-[4-[3-(Dimethylaminomethyl)-10,11-dihydro-5H-pyrrolo[2,1-c][1,4]benzodiazepin-10-ylcarbonyl]-2-methoxyphenyl]biphenyl-2-carboxamide); CL-385004 (5-Fluoro-2-methyl-N-[5-(5H-pyrrolo[2,1-c][1,4]benzodiazepine-10(11H)-yl carbonyl)-2-pyridinyl]benzamide); relcovaptan, lixivaptan (VPA-985); tolvaptan; conivaptan; SR 121463A (1-(4-(N-tert-butylcarbamoyl)-2-methoxybenzenesulfonyl)-5-ethoxy-3-spiro-(4-(2-morpholinoethoxy)cyclohexane)indol-2-one fumarate); SR-49059 ((2S)-1-[[(2R,3S)-5-Chloro-3-(2-chlorophenyl)-1-[(3,4-di methoxyphenyl)sulfonyl]-2,3-dihydro-3-hydroxy-1H-indol-2-yl]carbonyl]-2-pyrrolidinecarboxamide), Lixivaptan (VPA 985); AC-94544 (ACADIA Pharmaceuticals Inc.); AC-88324 (ACADIA Pharmaceuticals Inc.); AC-110484 (ACADIA Pharmaceuticals Inc.); or combinations thereof.

Recent studies have suggested a role for vasopressin in regulating auris interna pressure by regulating endolymph production, therapy mediating the pressure present in vestibular and cochlear structures. (Takeda et al. *Hearing Res.* (2006) 218:89-97). Treatment with vasopressin antagonists, including OPC-31260, resulted in the marked reduction of Meniere's disease symptoms. Accordingly, vasopressin antagonists are contemplated as useful with the formulations disclosed herein. Examples of vasopressin antagonists include, but are not limited to OPC-31260, WAY-140288, CL-385004, tolvaptan, conivaptan, SR 121463A, VPA 985, valium (diazepam), benzodiazepines and combinations thereof. Testing of vasopressin antagonists may include testing and calculating hydrops reduction with treatment in a guinea pig animal model. See, e.g., Chi et al. "The quantification of endolymphatic hydrops in an experimental animal model with guinea pigs", *J. Oto-Rhino-Larynol.* (2004) 66:56-61.

Agonists of the VP2 receptor are known, including OPC-51803 and related analogs (Kondo et al., J. Med. Chem. (2000) 43:4388; Nakamura et al., Br. J. Pharmacol. (2000) 129(8):1700; Nakamure et al., J. Pharmacol. Exp. Ther. (2000) 295(3):1005) and WAY-VNA-932 (Caggiano, Drugs Gut (2002) 27(3):248). Antagonists of the VP2 receptor include lixivaptan, tolvaptan, conivaptan, SR-121463 and OPC-31260 (Martin et al., J. Am. Soc. Nephrol. (1999) 10(10):2165; Gross et al., Exp. Physiol. (2000) 85: Spec No 253S; Wong et al., Gastroent April 2000, vol 118, 4 Suppl. 2, Part 1); Norman et al., Drugs Fut. (2000), 25(11):1121; Inoue et al., Clin. Pharm. Therap. (1998) 63(5):561). In testing against the constitutively activated D136A mutant VP2 receptor, SR-1211463 and OPC-31260 behaved as inverse agonist (Morin et al., FEBS Letters (1998) 441(3): 470-75).

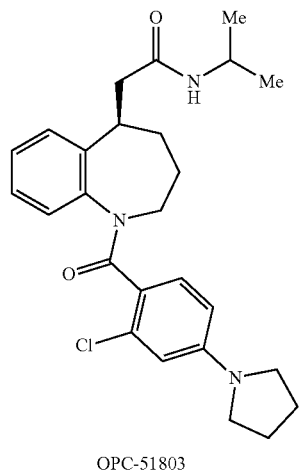

OPC-51803

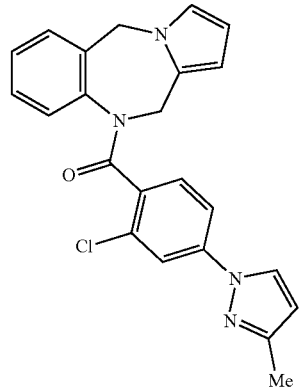

WAY-VNA-932

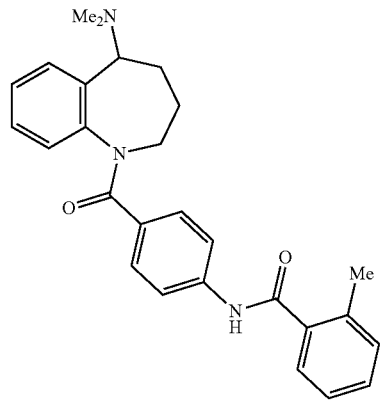

OPC-31260

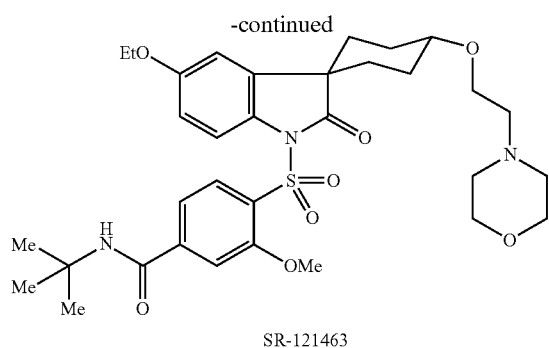

SR-121463

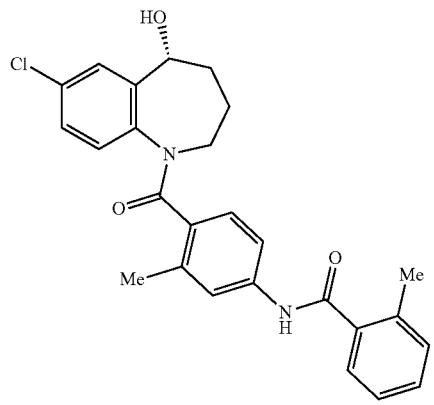

Tolvaptan (OPC-41061)

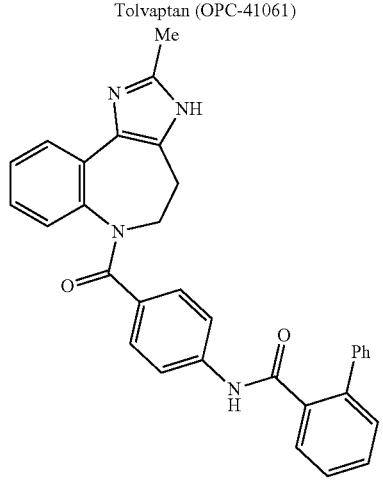

Conivaptan

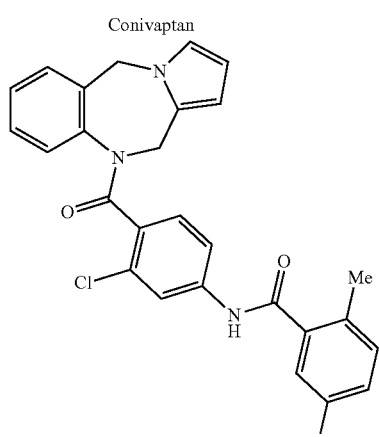

Lixivaptan

NMDA Receptor Modulators

Contemplated for use with the formulations disclosed herein are agents that modulate the degeneration of neurons and/or hair cells of the auris, and agents for treating or ameliorating hearing disorders such as tinnitus. Accordingly, some embodiments incorporate the use of agents which modulate NMDA receptors.

In certain instances, the over-activation of the NMDA glutamate receptors by the binding of excessive amounts of glutamate, results in the excessive opening of the ion channels under their control. In certain instances, this results in abnormally high levels of $Ca^{2+}$ and $Na^+$ entering the neuron. In certain instances, the influx of $Ca^{2+}$ and $Na^+$ into the neuron activates multiple enzymes including, but not limited to, phospholipases, endonucleases, and proteases. In certain instances, the over-activation of these enzymes results in tinnitus, and/or damage to the cytoskeleton, plasma membrane, mitochondria, and DNA of the neuron. In certain instances, the NMDA receptor modulator neramexane treats, and/or ameliorates the symptoms of tinnitus.

In some embodiments, the agent that modulates the NMDA receptor is an NMDA receptor antagonist. In some embodiments, the agent that modulates an NMDA receptor is an NMDA receptor antagonist, partial agonist, inverse agonist, neutral or competitive antagonist, allosteric antagonist, and/or orthosteric antagonist. In some embodiments, the agent which antagonizes the NMDA receptor includes, but is not limited to, 1-aminoadamantane, dextromethorphan, dextrorphan, ibogaine, ketamine, nitrous oxide, phencyclidine, riluzole, tiletamine, memantine, neramexane, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxyphenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophe-nyl)-4-hydroxypiperidin-1-yl-)-chroman-4,7-diol; (1R*, 2R*)-1-(4-hydroxy-3-methylphenyl)-2-(4-(4-fluoro-phe-nyl)-4-hydroxypiperidin-1-yl)-propan-1-ol-mesylate; and/or combinations thereof.

ENaC Receptor Modulators

The epithelial sodium channel (ENaC, sodium channel non-neuronal 1 (SCNN1) or amiloride sensitive sodium channel (ASSC)) is a membrane-bound ion-channel that is permeable for $Li^+$-ions, protons and Nations. The ENaC is located in the apical membrane of polarized epithelial cells and is involved in transepithelial $Na^+$-ion transport. $Na^+$/$K+$-ATPase is also involved in $Na^+$ transport and ion homeostasis.

ENaC plays a role in the Na+- and K+-ion homeostasis of blood, epithelia and extraepithelial fluids by resorption of Na+-ions. Modulators of the activity of ENaC modulate aural pressure and include, by way of example, the mineralcorticoid aldosterone, triamterene, and amiloride.

Osmotic Diuretics

Contemplated for use with the compositions disclosed herein, are agents which regulate aural pressure. Accordingly, some embodiments comprise osmotic diuretics. An osmotic diuretic is a substance that produces an osmotic gradient between two spaces. In certain instances, an osmotic diuretic produces an osmotic gradient between the endolymphatic and perilymphatic spaces. In certain instances, an osmotic gradient between the endolymphatic and perilymphatic spaces exerts a dehydrating effect on the endolymphatic space. In certain instances, dehydrating the endolymphatic space decreases aural pressure.

Accordingly, in some embodiments of the compositions and formulations disclosed herein, the aural pressure modulator is an osmotic diuretic. In some embodiments, the osmotic diuretic is erythritol, mannitol, glucose, isosorbide, glycerol; urea; or combinations thereof.

In some instances, contemplated for use in combination with the aural pressure modulating formulations disclosed herein are diuretic agents. A diuretic agent is a drug that elevates the rate of urination. Such diuretics include triamterene, amiloride, bendroflumethiazide, hydrochlorothiazide, furosemide, torsemide, bumetanide, acetazolamide, dorzolamide and combinations thereof.

Progesterone Receptors

Contemplated for use with the formulations disclosed herein are otic therapeutic agents that treat disorders (e.g., inflammation) of the auris, and/or modulate the cells and structures of the auris. Progesterone is a steroidal hormone. In certain instances, progesterone is a ligand for a progesterone receptor. In certain instances, progesterone is found in the brain. In certain instances, progesterone affects synaptic functioning. In certain instances, progesterone is associated with partial or complete loss of hearing. In certain instances, females taking progesterone and estrogen experienced greater hearing loss than females taking estrogen alone (e.g. about 10% to about 30%).

Accordingly, some embodiments incorporate the use of agents that modulate progesterone and/or a progesterone receptor. In some embodiments, the agent that modulates progesterone and/or a progesterone receptor is a progesterone and/or progesterone receptor antagonist, a partial agonist, an inverse agonist, a neutral or competitive antagonist, an allosteric antagonist, and/or an orthosteric antagonist. In other embodiments, the agent that modulates progesterone and/or a progesterone receptor includes, but is not limited to, RU-486 ((11b,17 b)-11-[4-(Dimethylamino)phenyl]-17-hydroxy-17-(1-propyn yl)-estra-4,9-dien-3-one); CDB-2914 (17α-acetoxy-11β-[4-N,N-dimethylaminophenyl]-19-norpregna-4,9-diene-3,20-dione); CDB-4124 (17α-acetoxy-21-methoxy-11β-[4-N,N-dimethylaminophenyl]-19-norpregna-4,9-diene-3,20-dione); CDB-4453 (17α-acetoxy-21-methoxy-11β-[4-N-methylaminophenyl]-19-norpregna-4,9-diene-3,20-dione); RTI 3021-022 (Research Triangle Institute); ZK 230211 (11-(4-acetylphenyl)-17-hydroxy-17-(1,1,2,2,2-pentafluoroethyl)estra-4,9-dien-3-one); ORG 31710 (11-(4-dimethylaminophenyl)-6-methyl-4',5'-dihydro(estra-4,9-diene-17,2'-(3H)-furan)-3-one); ORG 33628 (Organon); onapristone (ZK 98299); asoprisnil; ulipristal; a anti-progesterone antibody; an anti-progesterone receptor antibody; or combinations thereof.

Prostaglandins

Prostaglandins are members of a group of fatty-acid derived compounds and depending upon the subtype, participate in a variety of functions, including control of constriction or dilation in vascular smooth muscle cells, aggregation or disaggregation of platelets, sensitization of spinal neurons to pain, increase or decrease in intraocular pressure, regulation of inflammatory mediation, regulation of calcium movement, control of hormone regulation and control of hormonal regulation. Prostaglandins have both paracrine and autocrine functions, and are a subclass of eicosanoid compounds.

Prostaglandin analogues, such as latanoprost, travoprost, unoprostone, minprostin F2 alpha and bimtoprost, have been shown in reduce intra-ocular pressure in glaucoma patients by enhancing the uveoscleral outflow, possibly through vasodilation mechanisms, in addition to effects on the trabecular meshwork. In sensorineural hearing loss animal models, noise exposure induces 8-isoprostaglandin F2a production in the cochlea, concomitant with an increase in vasoconstriction and reduced blood flow. Treatment with SQ29548, a specific antagonist of 8-isoprostaglandin F2α, prevents these noise-induced changes in cochlear blood flow and vascular conductance. Further, the prostaglandin analogue JB004/A improves hearing, and treats, and/or the symptoms of tinnitus and vertigo in patients suffering from Ménière's disease. Inhibition of prostaglandin F2α function also reduces tinnitus in patients suffering from Meniere's disease, as well as improvements in hearing and vertigo. Finally, prostaglandins have been implicated in chronic inflammation associated with otitis media.

Accordingly, one embodiment disclosed herein is the use of prostaglandin modulators, including latanoprost, travoprost, unoprostone, minprostin F2-alpha, bimtoprost and SQ29548, and JB004/A (Synphora AB) to ameliorate or decrease inner ear and middle ear disorders, including Meniere's disease, tinnitus, vertigo, hearing loss and otitis media.

RNAi

In some embodiments, where inhibition or down-regulation of a target is desired (e.g. genes ERR, and Nr3b2), RNA interference are utilized. In some embodiments, the agent that inhibits or down-regulates the target is an siRNA molecule. In certain instances, the siRNA molecule is as described herein.

Cytotoxic Agents

In some instances, immunomodulators and/or aural pressure modulators are useful in treatment of inflammatory otic disorders.

Any cytotoxic agent useful for the treatment of otic disorders, e.g., inflammatory diseases of the ear or cancer of the ear, is suitable for use in the formulations and methods disclosed herein. In certain embodiments, the cytotoxic agent is an antimetabolite, an antifolate, an alkylating agent, a DNA intercalator, an anti-TNF agent, an anti-angiogenic agent, an anti-inflammatory agent, and/or an immunomodulatory agent. In some embodiments, the cytotoxic agent is a protein, a peptide, an antibody, DNA, a carbohydrate, an inorganic molecule, or an organic molecule. In certain embodiments, the cytotoxic agents are cytotoxic small molecules. Typically, cytotoxic small molecules are of relatively low molecular weight, e.g., less than 1,000, or less than 600-700, or between 300-700 molecular weight. In some embodiments, the cytotoxic small molecules will also have anti-inflammatory properties.

In certain embodiments, the cytotoxic agents are methotrexate (RHEUMATREX®, Amethopterin) cyclophosphamide (CYTOXAN®), and thalidomide (THALIDOMID®). All of the compounds can be used to treat cancer, including cancer of the ear. Further, all of the compounds have anti-inflammatory properties and can be used in the formulations and compositions disclosed herein for the treatment of inflammatory disorders of the ear, including AIED.

Although systemic administration of methotrexate, cyclophosphamide, and thalidomide is currently used to treat or is being investigated for the treatment of otic disorders, such as inflammatory otic disorders, including AIED, Meniere's disease, and Behçet's disease, as well as cancer of the ear, the cytotoxic agents are not without the potential for serious adverse side effects. Moreover, cytotoxic agents which demonstrate efficacy but are otherwise not approvable because of safety considerations is also contemplated within the embodiments disclosed herein. It is contemplated that localized application of the cytotoxic agents to the target otic structures for treatment of autoimmune and/or inflammatory disorders, as well as cancer of the ear, will result in the reduction or elimination of adverse side effects experienced with systemic treatment. Moreover, localized treatment with the cytotoxic agents contemplated herein will also reduce the amount of agent needed for effective treatment of the targeted disorder due, for example, to increased retention of the active agents in the auris interna and/or media, to the existence of the biological blood barrier in the auris interna, or to the lack of sufficient systemic access to the auris media.

In some embodiments, cytotoxic agents used in the compositions, formulations, and methods disclosed herein are metabolites, salts, polymorphs, prodrugs, analogues, and derivatives of cytotoxic agents, including methotrexate, cyclophosphamide, and thalidomide. Particularly preferred are metabolites, salts, polymorphs, prodrugs, analogues, and derivatives of cytotoxic agents, e.g., methotrexate, cyclophosphamide, and thalidomide, that retain at least partially the cytotoxicity and anti-inflammatory properties of the parent compounds. In certain embodiments, analogues of thalidomide used in the formulations and compositions disclosed herein are lenalidomide (REVLIMID®) and CC-4047 (ACTIMID®).

Cyclophosphamide is a prodrug that undergoes in vivo metabolism when administered systemically. The oxidized metabolite 4-hydroxycyclophosphamide exists in equilibrium with aldophosphamide, and the two compounds serve as the transport forms of the active agent phosphoramide mustard and the degradation byproduct acrolein. Thus, in some embodiments, preferred cyclophosphamide metabolites for incorporation into the formulations and compositions disclosed herein are 4-hydroxycyclophosphamide, aldophosphamide, phosphoramide mustard, and combinations thereof.

Other cytotoxic agents used in the compositions, formulations, and methods disclosed herein, particularly for the treatment of cancer of the ear, are any conventional chemotherpeutic agents, including acridine carboxamide, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar.

Auris Sensory Cell Modulators

In some instances, immunomodulators and/or aural pressure modulators modulate the function of neurons and/or auris sensory cells. Contemplated for use with the formulations disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which promote the survival of neurons and otic hair cells, and/or the growth of neurons and otic hair cells. In some embodiments, the agent which promotes the survival of otic hair cells is a growth factor. In some embodiments, the growth factor modulator is a growth factor modulator antagonist, partial agonist, inverse agonist, neutral or competitive antagonist, allosteric antagonist, and/or orthosteric antagonist.

Amifostine

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which rescue neurons and otic hair cells from cisplatin-induced ototoxicity.

Amifostine (also known as WR-2721, or ETHYOL®) is a cytoprotective agent. In certain instances, it prevents or ameliorates the damage to neuron and otic hair cells caused by cisplatin. In certain instances, doses at or above 40 mg/kg are needed to protect against or ameliorate the ototoxic effects of cisplatin.

Anti-Intercellular Adhesion Molecule-1 Antibody

Contemplated for use with the formulations disclosed herein are antibodies to anti-intercellular adhesion molecule (ICAM). In some instances, ICAM blocks the cascade of reactive oxygen species associated with exposure to noise. In some instances modulation of the cascade of reactive oxygen species associated with exposure to noise ameliorates or reduces the degeneration of neurons and/or hair cells of the auris. Accordingly, some embodiments incorporate the use of agents that are antibodies to ICAMs (e.g., anti-ICAM-1 Ab, anti-ICAM-2 Ab or the like).

Modulation of Atoh/Math1

Contemplated for use with the formulations disclosed herein are agents that promote the growth and/or regeneration of neurons and/or otic hair cells. Atoh1 is a transcription factor which binds to an E-box. In certain instances, it is expressed during the development of the hair cells of the vestibular and auditory systems. In certain instances, mice with Atoh1 knocked-out did not develop otic hair cells. In certain instances, adenoviruses expressing Atoh1 stimulate the growth and/or regeneration of otic hair cells in guinea pigs treated with ototoxic antibiotics. Accordingly, some embodiments incorporate modulation of the Atoh1 gene.

In some embodiments, a subject is administered a vector engineered to carry the human Atoh1 gene (the "Atoh1 vector"). For disclosures of techniques for creating the Atoh1 vector see U.S. Pub. No. 2004/02475750, which is hereby incorporated by reference for those disclosures. In some embodiments, the Atoh1 vector is a retrovirus. In some embodiments, the Atoh1 vector is not a retrovirus (e.g. it is an adenovirus; a lentivirus; or a polymeric delivery system such as METAFECTENE, SUPERFECT®, EFFECTENE®, or MIRUS TRANSIT).

In some embodiments, the Atoh1 vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the Organ of Corti, the vestibular labyrinth, or a combination thereof.

In certain instances, after administration of the Atoh1 vector, the Atoh1 vector infects the cells at the site of administration (e.g. the cells of cochlea, Organ of Corti, and/or the vestibular labyrinth). In certain instances the Atoh1 sequence is incorporated into the subject's genome (e.g. when the Atoh1 vector is a retrovirus). In certain instances the therapy will need to be periodically re-administered (e.g. when the Atoh1 vector is not a retrovirus). In some embodiments, the therapy is re-administered annually. In some embodiments, the therapy is re-administered semi-annually. In some embodiments, the therapy is re-administered when the subject's hearing loss is moderate (i.e. the subject cannot consistently hear frequencies less than 41 db to 55 dB) to profound (i.e. the subject cannot consistently hear frequencies less than 90 dB).

In some embodiments, a subject is administered the Atoh1 polypeptide. In some embodiments, the Atoh1 polypeptide is incorporated into controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the Organ of Corti, the vestibular labyrinth, or a combination thereof. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is placed in contact with the round window membrane.

In some embodiments, a subject is administered a pharmaceutically acceptable agent which modulates the expression of the Atoh1 gene or activity of the Atoh1 polypeptide. In some embodiments, the expression of the Atoh1 gene or activity of the Atoh1 polypeptide is up-regulated. In some embodiments, the expression of the Atoh1 gene or activity of the Atoh1 polypeptide is down-regulated.

In certain instances, a compound which agonizes or antagonizes Atoh1 is identified (e.g. by use of a high throughput screen). In some embodiments, a construct is designed such that a reporter gene is placed downstream of an E-box sequence. In some embodiments, the reporter gene is luciferase, CAT, GFP, β-lactamase or β-galactosidase. In certain instances, the Atoh1 polypeptide binds to the E-box sequence and initiates transcription and expression of the reporter gene. In certain instances, an agonist of Atoh1 aids or facilitates the binding of Atoh1 to the E-box sequence, thus increasing transcription and expression of the reporter gene relative to a pre-determined baseline expression level. In certain instances, an antagonist of Atoh1 blocks the binding of Atoh1 to the E-box, thus decreasing transcription and expression of the reporter gene relative to a pre-determined baseline expression level.

BRN-3 Modulators

Contemplated for use with the formulations disclosed herein are agents that promote the growth and/or regeneration of neurons and/or otic hair cells. BRN-3 is a group of transcription factors that include, but are not limited to, BRN-3a, BRN-3b, and BRN-3c. In certain instances, they are expressed in postmitotic hair cells. In certain instances, the hair cells of mice with BRN-3c knocked-out did not develop stereocilia and/or underwent apoptosis. In certain instances, BRN3 genes regulate the differentiation of inner ear supporting cells into inner ear sensory cells. Accordingly, some embodiments incorporate modulation of the BRN3 genes, and/or polypeptides.

In some embodiments, a subject is administered a vector engineered to carry a human BRN-3 gene (the "BRN3 vector"). In some embodiments, the BRN3 vector is a retrovirus. In some embodiments, the BRN3 vector is not a retrovirus (e.g. it is an adenovirus; a lentivirus; or a polymeric delivery system such as METAFECTENE®, SUPERFECT®, EFFECTENE®, or MIRUS' TRANSIT®).

In some embodiments, the subject is administered the BRN3 vector before, during, or after exposure to an ototoxic agent (e.g an aminoglycoside or cisplatin), or a sound of sufficient loudness to induce acoustic trauma.

In some embodiments, the BRN3 vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the Organ of Corti, the vestibular labyrinth, or a combination thereof.

In certain instances, after administration of the BRN3 vector, the BRN3 vector infects the cells at the site of administration (e.g. the cells of cochlea, Organ of Corti, and/or the vestibular labyrinth). In certain instances the BRN3 sequence is incorporated into the subject's genome (e.g. when the BRN3 vector is a retrovirus). In certain instances the therapy will need to be periodically re-administered (e.g. when the BRN3 vector is not a retrovirus).

In some embodiments, a subject is administered a BRN3 polypeptide. In some embodiments, the BRN3 polypeptide is incorporated into controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the Organ of Corti, the vestibular labyrinth, or a combination thereof. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is placed in contact with the round window membrane.

In some embodiments, a subject is administered a pharmaceutically acceptable agent which modulates the expression of the BRN3 gene or activity of the BRN3 polypeptide. In some embodiments, the expression of the BRN3 gene or activity of the BRN3 polypeptide is up-regulated. In some embodiments, the expression of the BRN3 gene or activity of the BRN3 polypeptide is down-regulated.

In some embodiments, a compound which agonizes or antagonizes BRN3 is identified (e.g. by use of a high throughput screen). In some embodiments, a construct is designed such that a reporter gene is placed downstream of a BRN3 binding site. In some embodiments, the BRN3 binding site has the sequence ATGAATTAAT (SEQ ID NO: 1) (SBNR3). In some embodiments, the reporter gene is luciferase, CAT, GFP, β-lactamase or β-galactosidase. In certain instances, the BRN3 polypeptide binds to the SBNR3 sequence and initiates transcription and expression of the reporter gene. In certain instances, an agonist of BRN3 aids or facilitates the binding of BRN3 to the SBNR3 sequence, thus increasing transcription and expression of the reporter gene relative to a pre-determined baseline expression level. In certain instances, an antagonist of BRN3 blocks the binding of BRN3 to the SBNR3, thus decreasing transcription and expression of the reporter gene relative to a pre-determined baseline expression level.

Carbamates

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. In certain instances, carbamate compounds protect neurons and otic hair cells from glutamate-induced excitotoxicity. Accordingly, some embodiments incorporate the use of carbamate compounds. In some embodiments, the carbamate compounds are 2-phenyl-1,2-ethanediol monocarbomates and dicarbamates, derivatives thereof, and/or combinations thereof.

Estrogen Receptors

In some embodiments, the agent that promotes the survival of otic hair cells is an Estrogen Receptor agonist. In some embodiments, the estrogen receptor agonist is a partial agonist or inverse agonist.

In certain instances, Estrogen Receptor β (ERβ) is expressed in an outer hair cell, an inner hair cell, a spiral ganglion neuron, or combinations thereof. In certain embodiments, agonism of ERα and/or ERβ ameliorates hearing loss resulting from acoustic trauma. In certain embodiments, agonism of ERα and/or ERβ increases and/or up-regulates the expression of a neurotroph gene and/or the activity of a neurotroph polypeptide (e.g. BDNF). In certain embodiments, antagonism of ERα and/or ERβ increases hearing loss resulting from acoustic trauma. In certain embodiments, antagonism of ERα and/or ERβ down-regulates the expression of a neurotroph gene and/or the activity of a neurotroph polypeptide (e.g. BDNF).

In some embodiments, the ERα agonist is PPT (4,4',4"-(4-Propyl-[1H]-pyrazole-1,3,5-triyl)trisphenol); SKF-82958 (6-chloro-7,8-dihydroxy-3-allyl-1-phenyl-2,3,4,5-tetrahydro-1H-3-benzazepine); estrogen; estradiol; estradiol derivatives, including but not limited to 17-β estradiol, estrone, estriol, synthetic estrogen compositions or combinations thereof. In some embodiments, the ERβ agonist is ERβ-131, phytoestrogen, MK 101 (bioNovo); VG-1010 (bioNovo); DPN (diarylpropiolitrile); ERB-041; WAY-202196; WAY-214156; genistein; estrogen; estradiol; estradiol derivatives, including but not limited to 17-β estradiol, estrone, estriol, synthetic estrogen compositions or combinations thereof. Other ERβ agonists include select benzopyrans and triazolo-tetrahydrofluorenones, disclosed in U.S. Pat. No. 7,279,499, and Parker et al., Bioorg. & Med. Chem. Ltrs. 16: 4652-4656 (2006), each of which is incorporated herein by reference for such disclosure. In some embodiments, a neurotroph is administered before, after, or simultaneously with an Estrogen Receptor β (ERβ) agonist. In some embodiments, the neurotroph is BDNF, CNTF, GDNF, neurotrophin-3, neurotrophin-4, and/or combinations thereof.

Fatty Acids

Contemplated for use with the formulations disclosed herein are agents that relieve, prevent, reverse or ameliorate the degeneration of neurons and/or hair cells of the auris. Accordingly, some embodiments incorporate the use of fatty acids. In certain instances, the membrane surrounding auditory neurons and the vestibulocochlear nerve comprise fatty acids. In certain instances, a deficiency in omega-3 fatty acid results in a decreased response to auditory stimuli. In certain instances, maternal deficiency of alpha-linolenic acid (ALA) leads to offspring with hearing deficiency. In some embodiments, the fatty acid includes but is not limited to an omega-3 fatty acid, an omega-6 fatty acid, or combinations thereof. In some embodiments, the omega-3 fatty acid is α-Linolenic acid, Stearidonic acid, Eicosatrienoic acid, Eicosatetraenoic acid, Eicosapentaenoic acid, Docosapentaenoic acid, Clupanodonic acid, Docosahexaenoic acid, Tetracosapentaenoic acid, Tetracosahexaenoic acid (Nisinic acid), or combinations thereof. In some embodiments, the omega-3 fatty acid is α-Linolenic acid, docosahexaenoic acid, eicosapentaenoic acid, or combinations thereof. In some embodiments, the omega-6 fatty acid is Linoleic acid, Gamma-linolenic acid, Eicosadienoic acid, Dihomo-gamma-linolenic acid, Arachidonic acid, Docosadienoic acid, Adrenic acid, Docosapentaenoic acid, Calendic acid, or combinations thereof.

Gamma-Secretase Inhibitors

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which inhibit Notch 1 signaling. Notch 1 is a transmembrane polypeptide which participates in cell development. In some embodiments, the agents which inhibit Notch 1 signaling are γ-secretase inhibitors. In certain instances, the inhibition of Notch 1 by a γ-secretase inhibitor, following treatment with an ototoxic agent, results in the production of otic hair cells. In some embodiments, the γ-secretase inhibitor is LY450139 (hydroxylvaleryl monobenzocaprolactam), L685458 (1S-benzyl-4R[1-[1-S-carbamoyl-2-phenethylcarbamoyl)-1S-3-methylbutylcarbamoyl]-2R-hydroxy-5-phenylpentyl}carbamic acid tert-butyl ester); LY411575 ($N^2$-[(2S)-2-(3,5-difluorophenyl)-2-hydroxyethanoyl]-$N^1$[(7S)-5-methyl-6-oxo-6,7-dihydro-5H-dibenzo[bid]azepin-7yl]-L-alaninamide), MK-0752 (Merck), tarenflurbil, and/or BMS-299897 (2-[(1R)-1-[[(4-chlorophenyl) sulfony](2,5-difluorophenyl) amino]ethyl]-5-fluorobenzenepropanoic acid).

Glutamate-Receptor Modulators

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which modulate glutamate receptors. In some embodiments, the glutamate receptor is the AMPA receptor, the NMDA receptor, and/or a group II or III mGlu receptor.

In some embodiments, the agent that modulates the AMPA receptor is an AMPA receptor antagonist. In some embodiments, the agent which antagonizes the AMPA receptors is CNQX (6-cyano-7-nitroquinoxaline-2,3-dione); NBQX (2,3-dihydroxy-6-nitro-7-sulfamoyl-benzo[f]quinoxaline-2,3-dione); DNQX (6,7-dinitroquinoxaline-2,3-dione); kynurenic acid; 2,3-dihydroxy-6-nitro-7-sulfamoyl-benzo-[f]quinoxaline; or combinations thereof.

In some embodiments, the agent that modulates the NMDA receptor is an NMDA receptor antagonist. In some embodiments, the agent which antagonizes the NMDA receptor is 1-aminoadamantane, dextromethorphan, dextrorphan, ibogaine, ketamine, nitrous oxide, phencyclidine, riluzole, tiletamine, memantine, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2 S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*, 2R*)-1-(4-hydroxy-3-methylphenyl)-2-(4-(4-fluoro-phenyl)-4-hydroxypiperidin-1-yl)-propan-1-ol-mesylate; and/or combinations thereof.

In certain instances, the over-activation of the AMPA and NMDA glutamate receptors by the binding of excessive amounts of glutamate, results in the excessive opening of the ion channels under their control. In certain instances, this results in abnormally high levels of $Ca^{2+}$ and $Na^+$ entering the neuron. In certain instances, the influx of $Ca^{2+}$ and $Na^+$ into the neuron activates multiple enzymes including, but not limited to, phospholipases, endonucleases, and proteases. In certain instances, the over-activation of these enzymes results in damage to the cytoskeleton, plasma membrane, mitochondria, and DNA of the neuron. Further, in certain instances, the transcription of multiple pro-apoptotic genes and anti-apoptotic genes are controlled by $Ca^{2+}$ levels.

The mGlu receptors, unlike the AMPA and NMDA receptors, do not directly control an ion channel. However, in certain instances, they indirectly control the opening of ion channels by the activation of biochemical cascades. The mGlu receptors are divided into three groups. In certain instances, the members of groups II and III reduce or inhibit post-synaptic potentials by preventing or decreasing the formation of cAMP. In certain instances, this causes a reduction in the release of neurotransmitters, especially glutamate. GRM7 is the gene which encodes the mGlu7 receptor, a group III receptor. In certain instances, the agonism of mGlu7 results in a decrease in synaptic concentrations of glutamate. This ameliorates glutamate excitotoxicity.

In some embodiments, the glutamate receptor is a group II mGlu receptor. In some embodiments, the agent which modulates the group II mGlu receptor is a group II mGlu receptor agonist. In some embodiments, the group II mGlu receptor agonist is LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); and/or combinations thereof.

In some embodiments, the mGlu receptor is a group III mGlu receptor. In some embodiments, the group III mGlu receptor is mGlu7. In some embodiments, the agent which modulates the group III mGlu receptor is a group III mGlu receptor agonist. In some embodiments, the group III mGlu receptor agonist is ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (,N'-bis(diphenylmethyl)-1,2-ethanediamine dihydrochloride); DCG-IV ((2S,2'R,3'R)-2-(2',3'-dicarboxycyclopropyl)glycine); and/or combinations thereof. In some embodiments, the mGlu receptor is mGlu7. In some embodiments, the agonist of mGlu7 is AMN082. In some embodiments, the mGlu receptor modulator is 3,5-Dimethyl pyrrole-2,4-dicarboxylic acid 2-propyl ester 4-(1,2,2-trimethyl-propyl) ester (3,5-dimethyl PPP); 3,3'-difluorobenzaldazine (DFB), 3,3'-dimlethoxybenzaldazine (DMeOB), 3,3'-dichlorobenzaldazine (DCB) and other allosteric modulators of mGluR$_5$ disclosed in Mol. Pharmacol. 2003, 64, 731-740; (E)-6-methyl-2-(phenyldiazenyOpyridin-3-ol (SIB 1757); (E)-2-methyl-6-styrylpyridine (SIB 1893); 2-methyl-6-(phenylethynyl)pyridine (MPEP), 2-methyl-4-((6-methylpyridin-2-yl)ethynyl)thiazole (MTEP); 7-(Hydroxyimino)cyclopropa[b]chromen-1α-carboxylate ethyl ester (CPCCOEt), N-cyclohexyl-3-methylbenzo[d]thiazolo[3,2-a]imidazole-2-carboxamide (YM-298198), tricyclo[3.3.3.1]nonanyl quinoxaline-2-carboxamide (NPS 2390); 6-methoxy-N-(4-methoxyphenyl) quinazolin-4-amine (LY 456239); mGluR1 antagonists disclosed in WO2004/058754 and WO2005/009987; 2-(4-(2,3-dihydro-1H-inden-2-ylamino)-5,6,7,8-tetrahydroquinazolin-2-ylthio)ethanol; 3-(5-(pyridin-2-yl)-2H-tetrazol-2-yl)benzonitrile, 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 6-(3-methoxy-4-(pyridin-2-yl) phenyl)imidazo[2,1-b]thiazole; (S)-(4-fluorophenyl)(3-(3-(4-fluorophenyl)-1,2,4-oxadiazol-5-yl)piperidin-1-yl) methanone (ADX47273) and/or combinations thereof.

In some embodiments, a glutamate receptor modulator is a nootropic agent. Contemplated for use with the formulations disclosed herein are nootropic agents that modulate neuronal signalling by activating glutamate receptors. In some instances, nootropic agents treat or ameliorate hearing loss (e.g, NIHL) or tinnitus. Accordingly, some embodiments incorporate the use of nootropic agents including, and not limited to, piracetam, Oxiracetam, Aniracetam, Pramiracetam, Phenylpiracetam (Carphedon), Etiracetam, Levetiracetam, Nebracetam, Nicoracetam, Rolziracetam, Nebracetam, Fasoracetam, Coluracetam, Dimiracetam, Brivaracetam, Seletracetam, and/or Rolipram for the treatment of NIHL or tinnitus.

Growth Factors

Contemplated for use with the formulations disclosed herein are agents that modulate the degeneration of neurons and/or hair cells of the auris, promote the survival and/or growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which promote the survival of neurons and otic hair cells, and/or the growth of neurons and otic hair cells. In some embodiments, the agent which promotes the survival of otic hair cells is a growth factor. In some embodiments, the growth factor is a neurotroph. In certain instances, neurotrophs are growth factors which prevent cells from initiating apoptosis, repair damaged neurons and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof. In some embodiments, the growth factor is a fibroblast growth factor (FGF), an insulin-like growth factor (IGF), an epidermal growth factor (EGF), a platlet-derived growth factor (PGF) and/or agonists thereof. In some embodiments, the growth factor is an agonist of the fibroblast growth factor (FGF) receptor, the insulin-like growth factor (IGF) receptor, the epidermal growth factor (EGF) receptor, and/or the platlet-derived growth factor. In some embodiments, the growth factor is hepatocyte growth factor.

In some embodiments, the growth factor is an epidermal growth factor (EGF). In some embodiments, the EGF is heregulin (HRG). In certain instances, HRG stimulates the proliferation of utricular sensory epithelium. In certain instances, HRG-binding receptors are found in the vestibular and auditory sensory epithelium.

In some embodiments, the growth factor is an insulin-like growth factor (IGF). In some embodiments, the IGF is IGF-1. In some embodiments, the IGF-1 is mecasermin. In certain instances, IGF-1 attenuates the damage induced by exposure to an aminoglycoside. In certain instances, IGF-1 stimulates the differentiation and/or maturation of cochlear ganglion cells.

In some embodiments, the FGF receptor agonist is FGF-2. In some embodiments, the IGF receptor agonist is IGF-1. Both the FGF and IGF receptors are found in the cells comprising the utricle epithelium.

In some embodiments, the growth factor is hepatocyte growth factor (HGF). In some instances, HGF protects cochlear hair cells from noise-induced damage and reduces noise-exposure-caused ABR threshold shifts.

Also contemplated for use in the otic formulations described herein are growth factors including Erythropoietin (EPO), Granulocyte-colony stimulating factor (G-CSF), Granulocyte-macrophage colony stimulating factor (GM-CSF), Growth differentiation factor-9 (GDF9), Insulin-like growth factor (IGF), Myostatin (GDF-8), Platelet-derived growth factor (PDGF), Thrombopoietin (TPO), Transforming growth factor alpha (TGF-α), Transforming growth factor beta (TGF-β), Vascular endothelial growth factor (VEGF) or combinations thereof.

Neurotrophs

In some embodiments, the growth factor is a neurotroph. In certain instances, neurotrophs are growth factors which prevent cells from initiating apoptosis, repair damaged neurons and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof.

In some embodiments, the neurotroph is BDNF. In certain instances, BDNF is a neurotroph which promotes the survival of existing neurons (e.g. spiral ganglion neurons), and otic hair cells by repairing damaged cells, inhibiting the production of ROS, and inhibiting the induction of apoptosis. In certain embodiments, it also promotes the differentiation of neural and otic hair cell progenitors. Further, in certain embodiments, it protects the Cranial Nerve VII from degeneration. In some embodiments, BDNF is administered in conjunction with fibroblast growth factor.

In some embodiments, the neurotroph is neurotrophin-3. In certain embodiments, neurotrophin-3 promotes the survival of existing neurons and otic hair cells, and promotes the differentiation of neural and otic hair cell progenitors. Further, in certain embodiments, it protects the VII nerve from degeneration.

In some embodiments, the neurotroph is CNTF. In certain embodiments, CNTF promotes the synthesis of neurotransmitters and the growth of neuritis. In some embodiments, CNTF is administered in conjunction with BDNF.

In some embodiments, the neurotroph is GDNF. In certain embodiments, GDNF expression is increased by treatment with ototoxic agents. Further, in certain embodiments, cells treated with exogenous GDNF have higher survival rates after trauma then untreated cells.

Immune System Cells

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of cells which participate in the repair of otic hair cells and neurons. In some embodiments, the cells which participate in the repair of otic hair cells and neurons are macrophages, microglia, and/or microglia-like cells. In certain instances, the concentration of macrophages and microglia increase in ears damaged by treatment with ototoxic agents. In certain instances, microglia-like cells eliminate waste from the Organ of Corti and participate in the structural repair of hair cells following treatment with the ototoxic antibiotic neomycin.

Ototoxic Agents

Contemplated for use with the formulations disclosed herein are agents that destroy neurons and/or otic hair cells. Accordingly, some embodiments incorporate the use of agents which fatally damage and/or induce apoptosis in the neurons and/or otic hair cells of the auris. In some embodiments, the agents which fatally damage and/or induce apoptosis in the neurons and/or otic hair cells of the auris are the aminoglycoside antibiotics (e.g. gentamicin, and amikacin), the macrolide antibiotics (e.g erythromycin), the glycopeptide antibiotics (e.g. vancomycin), the loop diuretics (e.g. furosemide) salicylic acid, and nicotine.

Retinoblastoma Protein Modulation

Contemplated for use with the formulations disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Further contemplated herein are agents that destroy neurons and/or otic hair cells. Accordingly, some embodiments incorporate the use of agents that modulate retinoblastoma protein (pRB). pRB is a member of the pocket protein family. It is encoded by the RB1 gene. In certain instances, it inhibits transition from G1 to S phase by binding to and inactivating the E2f family of transcription factors. In certain instances, it also regulates differentiation, and survival of hair cells. In certain instances, pRB knock-out mice demonstrate increased prioliferation of hair cells.

In some embodiments, the agent that modulates one or more of the pRB is an agonist of pRB. In some embodiments, the agent that modulates one or more of the pRB is an antagonist of pRB. In certain instances, a compound which agonizes or antagonizes pRB is identified (e.g. by use of a high throughput screen). In some embodiments, a construct is designed such that a reporter gene is placed downstream of an E2F binding sequence. In some embodiments, the binding sequence is TTTCGCGC. In some embodiments, the reporter gene is luciferase, CAT, GFP, β-lactamase or β-galactosidase. In certain instances, E2f binds to the binding sequence causing the transcription and expression of the reporter gene. In certain instances, an agonist of pRB causes an increase in the binding of pRB to E2f. In certain instances, the increase in binding of pRB and E2f results in a decrease in the transcription and expression of the reporter gene. In certain instances, an antagonist of pRB causes a decrease in the binding of pRB to E2f. In certain instances, the decrease in binding of pRB and E2f results in a increase in the transcription and expression of the reporter gene.

In some embodiments, the agent that modulates pRB is an siRNA molecule. In certain instances, the siRNA molecule is as described herein.

Salicylic Acid

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of salicylic acid. In certain instances, when administered before treatment with an aminoglycoside, it protects otic hair cells and spiral ganglion neurons from aminoglycoside ototoxicity.

Sodium Channel Blockers

Contemplated for use with the formulations disclosed herein are agents that modulate the degeneration of neurons and hair cells, and agents for treating or ameliorating hearing loss or reduction resulting from destroyed, stunted, malfunctioning, damaged, fragile or missing hairs in the inner ear. In certain instances, excitotoxicity causes the excessive opening of $Na^+$ channels. In certain instances, this results in excess $Na^+$ ions entering the neuron. In certain instances, the excess influx of $Na^+$ ions into the neuron causes the neuron to fire more often. In certain instances, this increased firing yields a rapid buildup of free radicals and inflammatory compounds. In certain instances, the free radicals damage the mitochondria, depleting the cell's energy stores. Further, in certain instances, excess levels of $Na^+$ ions activate excess levels of enzymes including, but not limited to, phospholipases, endonucleases, and proteases. In certain instances, the over-activation of these enzymes results in damage to the cytoskeleton, plasma membrane, mitochondria, and DNA of the neuron. Accordingly, some embodiments incorporate the use of agents which antagonize the opening of $Na^+$ channels. In some embodiments, sodium channel blockers are as described herein.

Stem Cells and Differentiated Auris Sensory Cells

Contemplated for use with the formulations disclosed herein are transplants of cells that supplement and/or replace the pre-existing neurons and/or hair cells of the auris. In some embodiments, the agent is a stem cell. In some embodiments, the agent is a partially or fully differentiated auris sensory cell. In some embodiments, the differentiated auris sensory cell is derived from a human donor. In some embodiments, the differentiated auris sensory cell is derived from a stem cell, the differentiation of which was induced under artificial (e.g. laboratory) conditions.

Stem cells are cells that possess the capacity to differentiate into multiple cell types. Totipotent stem cells can differentiate into embryonic cells or extraembryonic cells. Pluripotent cells can differentiate into cells of any of endoderm, mesoderm, or ectoderm origin. Multipotent cells can differentiate into closely related cells (e.g hematopoietic stem cells). Unipotent cells can differentiate into only one type of cell, but like other stem cells have the characteristic of self-renewal. In some embodiments, the stem cell is totipotent, pluripotent, multipotent, or unipotent. Further, stem cells can undergo mitotic division without themselves differentiating (i.e. self-renewal).

Embryonic stem (ES) cells are stem cells derived from the epiblast tissue of the inner cell mass of a blastocyst or earlier stage embryo. ES cells are pluripotent. In some embodiments, the stem cell is an ES cell. Adult stem cells (also known as somatic cells or germline cells) are cells isolated from a developed organism wherein the cells possess the characteristic of self-renewal, and the ability to differentiate into multiple cell types. Adult stem cells are pluripotent (for example, stem cells found in umbilical cord blood), multipotent or unipotent. In some embodiments, the stem cell is an adult stem cell.

In some embodiments, a stem cell and/or a differentiated auris sensory cell is administered in combination with a differentiation stimulating agent. In some embodiments, the differentiation stimulating agent is a growth factor. In some embodiments, the growth factor is a neurotrophin (e.g. nerve growth factor (NGF), brain-derived neurotrophic factor (BDNF), neurotrophin-3 (NT-3), neurotrophin-4 (NT-4), or novel neurotrophin-1 (NNT1). In some embodiments, the growth factor is FGF, EGF, IGF, PGF, or combinations thereof.

In some embodiments, a stem cell and/or a differentiated auris sensory cell is administered to a subject in need thereof as a controlled release agent. In some embodiments, a stem cell and/or a differentiated auris sensory cell is administered to a subject in need thereof as an immediate release agent (e.g. in a cell suspension) in combination with a controlled release auris sensory cell modulating agent. In some embodiments, a controlled release auris sensory cell modulating agent is a vector comprising an Atoh1 or BRN3 gene, an siRNA sequence targeting RB1, a growth factor, or combinations thereof.

In some embodiments, a stem cell and/or a differentiated auris sensory cell is administered to the cochlea or vestibular labyrinth. In some embodiments, a stem cell and/or a differentiated auris sensory cell is administered by via intratympanic injection, and/or a post-auricular incision. In some embodiments, a stem cell and/or a differentiated auris sensory cell is contacted with the Organ of Corti, vestibulocochlear nerve, and/or crista ampullaris.

Thyroid Hormone Receptor Modulation

Contemplated for use with the formulations disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents that modulate Thyroid Hormone (TH) receptors. The TH receptors are a family of nuclear hormone receptors. The family includes, but is not limited to TRα1 and TRβ. In certain instances, TRβ knockout mice demonstrate a decreased responsiveness to auditory stimuli, and a decrease in $K^+$ current in hair cells.

In some embodiments, the agent that modulates one or more of the TH receptors is an agonist of the one or more TH receptors. In some embodiments, the agonist of one or more of the TH receptors is $T_3$ (3,5,3'-triiodo-L-thyronine); KB-141 (3,5-dichloro-4-(4-hydroxy-3-isopropylphenoxy) phenylacetic acid); GC-1 (3,5-dimethyl-4-(4'-hydroxy-3'-isopropylbenzyl)-phenoxy acetic acid); GC-24 (3,5-dimethyl-4-(4'-hydroxy-3'-benzyl)benzylphenoxyacetic acid); sobetirome (QRX-431); 4-OH-PCB106 (4-OH-2',3,3',4',5'-pentachlorobiphenyl); MB07811 ((2R,4S)-4-(3-chlorophenyl)-2-[(3,5-dimethyl-4-(4-hydroxy-3-isopropylbenzyl)phenoxy)methyl]-2-oxido-[1,3,2]-dioxaphosphonane); MB07344 (3,5-dimethyl-4-(4-hydroxy-3-isopropylbenzyl) phenoxy)methylphosphonic acid); and combinations thereof. In certain instances, KB-141; GC-1; sobetirome; and GC-24 are selective for TRβ.

TRPV Modulation

Contemplated for use with the formulations disclosed herein are agents that modulate the degeneration of neurons and hair cells, and agents for treating or ameliorating hearing loss or reduction resulting from destroyed, stunted, malfunctioning, damaged, fragile or missing hairs in the inner ear. Accordingly, some embodiments incorporate the use of agents that modulate TRPV receptors. The TRPV (Transient Receptor Potential Channel Vanilloid) receptors are a family of non-selective ion channels permeable to calcium, amongst other ions. There are six members of the family: TRPV1-6. In certain instances, following treatment with kanamycin, TRPV 1 is upregulated. Additionally, in certain instances, antagonism of the TRPV 4 receptor makes mice vulnerable to acoustic trauma. Further, in certain instances, capsaicin, an agonist of TRPV 1, prevents hyperlocomotion following an ischemic event.

In some embodiments, the agent that modulates one or more of the TRPV receptors is an agonist of the one or more TRPV receptors. In some embodiments, the agonist of one or more of the TRPV receptors is capsaicin, resiniferatoxin, or combinations thereof. In some embodiments, TRPV modulating include the TRPV modulators disclosed in US application publications 2005/0277643, 2005/0215572, 2006/0194801, 2006/0205773, 2006/0194801, 2008/0175794, 2008/0153857, 2008/0085901, 20080015183, 2006/0030618, 2005/0277646, 2005/0277631, 2005/0272931, 2005/0227986, 2005/0153984, 2006/0270682, 2006/0211741, 2006/0205980, and 2006/0100490, and/or combinations thereof.

Sensory Hair Cell Restorative Agents

In some instances, immunomodulators and/or aural pressure modulators modulate the function of neurons and/or auris sensory cells. Therapeutic agents which assist in restoring sensory hair cell presence or function are also contemplated herein. These therapeutic agents assist in the treatment of hearing loss in patients, including sensorineural hearing loss, presbycusis and hearing loss from excessive noise. Recent studies have demonstrated the use of insulin-like growth factor 1 (IGF-1) in the restoration of auditory function for noise-induced hearing loss patients. (Lee et al. *Otol. Neurotol.* (2007) 28:976-981). Accordingly, agents IGF-1, IGF-1 agonists or agents which upregulate the expression, production or function of IGF-1 are optionally included with the formulations described herein.

Adenosine Modulators

Adenosine is comprised of adenine attached to ribofuranose via a β-N9-glycosidic bond. In certain instances, adenosine is an inhibitory neurotransmitter. In certain instances, it functions as a ligand for four GPCRs—adenosine receptor $A_1$, adenosine receptor $A_{2A}$, adenosine receptor $A_{2B}$, and adenosine receptor $A_3$. In certain instances, the binding of adenosine to an adenosine receptor results in (either partially or fully) an anti-inflammatory effect. In certain instances, the binding of adenosine to an adenosine receptor results in (either partially or fully) vasodialation. In certain instances, it is produced in response to cellular damage (e.g., hypoxia, and ischemia). For example, depolarization and asphyxia in the ear induce the release of adenosine into perilymph where it exerts a protective effect.

Accordingly, in some embodiment adensoine modulators are used in the treatment of cochlear and vestibular disorders. In some embodiments, the adenosine modulator is ATL313 (4-(3-(6-amino-9-(5-cyclopropylcarbamoyl-3,4-dihydroxytetrahydrofuran-2-yl)-9H-purin-2-yl)prop-2-ynyl) piperidine-1-carboxylic acid methyl ester); GW328267X ((2R,3R,4S,5R)-2-{6-amino-2-[(1-benzyl-2-hydroxyethyl) amino]-9H-purin-9-yl}-5-(2-ethyl-2H-tetrazol-5-yl)tetrahydrofuran-3,4-diol); CGS 21680 hydrochloride (4-[2-[[6-Amino-9-(N-ethyl-b-D-ribofuranuronamidosyl)-9H-purin-2-yl]amino]ethyl]benzenepropanoic acid hydrochloride); CV 1808 (2-Phenylaminoadenosine); p-DITC-APEC (2-[4-[2-[2-[(4-Isothiocyanatophenyl)thiocarbonylamino]ethyl-aminocarbonyl]ethyl]phenethylamino]-5'-N-ethylcarbox-amidadenosine); SDZ WAG994 (N-Cyclohexyl-2'-O-methyladenosine); CVT-3146 (regadenoson; 1-(9-(3,4-dihydroxy-5-(hydroxymethyl)oxolan-2-yl)-6-aminopurin-2-yl)pyrazol-4-yl)-N-methylcarboxamide); ATL-146e (4-{3-[6-Amino-9-(5-ethylcarbamoyl-3,4-dihydroxy-tetrahydro-furan-2-yl)-9H-purin-2-yl]-prop-2-ynyl}-cyclohexanecarboxylic acid methyl ester); 5'-n-Ethyl-carboxamidoadenosine; tecadenoson; CVT-510 (N-(3(R)-tetrahydrofuranyl)-6-aminopurine riboside); CCPA (2-Chloro-N6-cyclopentyladenosine); CPA (N6-Cyclopentyladenosine); GR 79236 (N-[(1S,2S)-2-Hydroxycyclopentyl]adenosine); 2'-MeCCPA; PD 81723 ((2-Amino-4,5-dimethyl-3-thienyl)-[3-(trifluoromethyl)phenyl]methanone); PSB 36 (1-Butyl-8-(hexahydro-2,5-methanopentalen-3a (1H)-yl)-3,7-dihydro-3-(3-hydroxypropyl)-1H-purine-2,6-dione); ribavirin; CHA (N6-cyclohexyladenosine); GW493838 (GSK); (−)-N6-(2-phenylisopropyl) adenosine; GW684067 ((2R,3R,4S,5R)-5-ethynyl-2-[6-tetrahydro-2H-pyran-4-ylamino)-9H-purin-9-yl]tetrahydrofuran-3,4-diol); CVT-3619 (2-(6-((2-hydroxycyclopentyl)amino)purin-9-yl)-5-((2-fluorophenylthio)methyl)oxolane-3,4-diol); 2-Cl-IB-MECA (CF102; 2-chloro-$N^6$-(3-iodobenzyl)-5'-N-methylcarbamoyladenosine); HEMADO; IB-MECA (CF101; $N^6$-(3-iodobenzyl)-5'-N-methylcarbamoyladenosine);

CP-532903 (N$^6$-(2,5-Dichlorobenzyl)-3'-aminoadenosine-5'-N-methylcarboxamide); CF502 (Can-Fite BioPharma); LJ-529 (2-chloro-N(6)-(3-iodobenzyl)-5'-N-methylcarbamoyl-4'-thioadenosine); BAA (8-butylaminoadenosine); 6-Amino-2-chloropurine riboside; 2-Chloroadenosine; NECA (5'-N-ethylcarboxamidoadenosine); APNEA (N6-2-(4-aminophenyl)ethyladenosine); or combinations thereof.

Modulators of Atoh 1

An additional sensory hair cell restorative agents are directed towards modulators to the products of the Atoh1 (atonal; ATOH), Neurod1 and Neurog1 genes. Atoh1 belongs to a family of basic Helix-Loop-Helix (bHLH) genes that are involved in cell fate determination across phyla and systems, typically being expressed in proliferating precursors. In mammals, at least three bHLH transcription factors are essential for sensory neuron development, including hair cells and sensory neurons of the ear: Atoh1, Neurod1 and Neurog1. Atoh1, in particular, is essential for hair cell differentiation, and plays a role as a differentiation factor of postmitotic hair cells. Studies have also shown that expression of Atoh1, in combination with Bdnf, form afferent and efferent innervation in undifferentiated cells of epithelial origin.

Treatment of with ATOH protein supports the role of Atoh1 in sensory hair cell development, inducing the formation of new sensory hair cells in cochlear structures, and restoring hearing and balance function. Gene therapy using vectors inserted with the Atoh1 gene further supports ATOH's role in promoting and maintaining sensory hair cell function. Accordingly, one embodiment disclosed herein is the use of ATOH proteins or manipulation of Atoh1 expression to induce sensory hair cell development in hearing and balance disorders.

In additional embodiments, a neurotrophic growth factor is administered to the auris interna via the formulations described herein to stimulate inner ear hair cell neurotrophic growth factors. The damage caused to spiral ganglion neurons removes not only neural activity, but also neurotrophin support that is normally supplied by hair cells, the absence of which leads to cell death via apopotosis.

In one embodiment, neurotrophic growth factor includes but is not limited to brain-derived neurotrophic fact, neurotrophin-3, glial-derived neurotrophic factor, neurotrophin-4/5, nerve growth factor, chlorphenylthio-cAMP (cptcAMP; a permeant cAMP analog), ciliary derived neurotrophic factor (CNTF) or combinations thereof. In another example, the sensory cell restorative agent is a brain-derived neutrophic factor (BDNF). In yet another example, the neurotrophic growth factor is neurotrophin-3 (NT-3). In other examples, the neurotrophic growth factor is glial-derived neurotrophic factor (GDNF). In some examples, the neurotrophic growth factor is a peptide or protein. In other embodiments, the neurotrophic growth factor stimulates or enhances spiral ganglion neuron survival.

ERR/NR3B2 Antagonists

Studies have also suggested a role for the orphan receptor estrogen related receptor β/Nr3b2 in regulating endolymph production, thereby possibly playing a role in mediating cochlear and vestibular pressure in the endolymph fluid. (Chen et al. *Dev. Cell.* (2007) 13:325-337). Accordingly, agents which antagonize ERR/Nr3b2 expression, protein production or protein function are contemplated as useful with the formulations disclosed herein.

KCNQ Modulators

Modulators of KCNQ are also contemplated within the scope of the embodiments disclosed herein. KCNQ proteins form potassium channels, which play a role by preventing accumulation of potassium in hair cells. Potassium concentrations are high in the endolymph, giving the endocochlear fluid a high positive potential, which in turn provides a large drive force for potassium entry into the hair cell. KCNQ function is correlated with outer hair cell (OHC) survival; inhibition of KCNQ alters potassium homeostasis, resulting eventually in OHC degeneration. Accordingly, treatment of the auris interna with KCNQ modulators, in some cases activators, is contemplated within the scope of the embodiments disclosed herein as useful in the maintenance of sensory hair cell function in both vestibular and cochlear structures.

P2X Modulators

Modulators of P2X channel function are also contemplated within the scope of the embodiments, for use, for example, in auris interna disorders, such as cochlear inflammation and noise-induced hearing loss. P2X channels, which are gated by adenosine triphosphate, are present in a broad distribution of tissues, and are thought to play a role in peripheral and central neuronal transmission, smooth muscle contraction and inflammation. Purine nucleotides are thought to play a role in cochlear disease, where ATP plays a cytotoxic role via both apoptosis and necrosis due to the activation of P2X receptors. For example, chronic perfusion of the perilymphatic space with ATP causes the proliferation of fibrous tissue and neoosterogenesis in the scala tympani. Moreover, noise exposure and hypoxia cause a significant elevation of ATP concentration in the endolymphatic and perilymphatic compartments, which may represent an adaptive response of the cells to injury.

Accordingly, one embodiment is the use of modulators of P2X in the treatment of cochlear and vestibular disorders, including hearing and balance disorders. Antagonists and agonists to P2X channels include BzATP, TNP-ATP, α,β-meATP, A-317491, PPADS, NF279, meSuramin, Reactive Blue II, RO-1, Adamantane amides, RO-3 and 4,5-diarylimidazolines.

CNS Modulating Agents

In some instances, immunomodulators and/or aural pressure modulators modulate central nervous system activity.

Anticholinergics

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which inhibit the release of the neurotransmitter acetylcholine in the CNS. Anticholinergic agents are substances which block acetylcholine in the central and the peripheral nervous system. They treat balance disorders by suppressing conduction in vestibular cerebellar pathways, thus increasing motion tolerance.

In some embodiments, the anticholinergic is glycopyrrolate, homatropine, scopolamine or atropine. In some embodiments, the anticholinergic is glycopyrrolate. In some embodiments, the anticholinergic is homatropine. In some embodiments, the anticholinergic is scopolamine. In some embodiments, the anticholinergic is atropine.

Antihistamines

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which block the action of neurotransmitters in the CNS. Histamine is a neurotransmitter in the CNS. Accordingly, some embodiments incorporate the use of agents which modulate histamine receptors (e.g. the $H_1$ receptor, $H_2$ receptor, and/or the $H_3$ receptor). In some embodiments, anithistamines are as described herein.

Calcium Channel Blockers

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which block or antagonize Ca+ channels. Calcium channels are channels formed in the plasma membrane of neurons (amongst other cells) by integral membrane proteins. These channels conduct $Ca^+$ through a cell's plasma membrane. In neurons, the flow of $Ca^{2+}$ is partly responsible for creating and propagating action potentials in neurons. It can also be responsible for the release of certain neurotransmitters.

In some embodiments, the calcium channel antagonist is cinnarizine, flunarizine, or nimodipine. In some embodiments, the calcium channel antagonist is cinnarizine. In some embodiments, the calcium channel antagonist is flunarizine. In some embodiments, the calcium channel antagonist is nimodipine. Other calcium channel blockers include verapamil, diltiazem, omega-conotoxin, GVIA, amlodipine, felodipine, lacidipine, mibefradil, NPPB (5-Nitro-2-(3-phenylpropylamino)benzoic Acid), flunarizine, and/or combinations thereof GABA Receptor Modulators Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which modulate the action of GABA receptors in the CNS. GABA, or γ-aminobutyric acid, is an inhibitory neurotransmitter in the CNS. It acts at inhibitory synapses of both pre- and postsynaptic neuronal processes. The binding of GABA to its receptors (the $GABA_A$ receptor, the $GABA_B$ receptor, and the $GABA_C$ receptor) results in the opening of ion channels, and the flow of Cl⁻ into the cell and/or K⁺ out of the neuron. The result is hyperpolarization of the neuron. Accordingly, some embodiments incorporate the use of agents which increase or decrease the sensitivity of the GABA receptors, or activate the GABA receptors by mimicking GABA.

The benzodiazepine class of therapeutic agents are agonists of the $GABA_A$ receptor. When a benzodiazepine binds to the $GABA_A$ receptor it induces a conformational change which increases the affinity of GABA for its receptor. The result of the increase in the binding of GABA is an increase in the frequency with which the channels in the neurons open. This causes hyperpolarization of the neural membrane. In some embodiments, the benzodiazepine is selected from the group consisting of: alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam or combinations thereof. In some embodiments, the benzodiazepine is clonazepam, diazepam, lorazepam, or combinations thereof. In some embodiments, the benzodiazepine is diazepam.

In some embodiments, the GABA receptor modulator is a loop diuretic. In some embodiments, the loop diuretic is furosemide, bumetanide, or ethacrynic acid. In some embodiments, the loop diuretic is furosemide. In some embodiments, the loop diuretic is bumetanide. In some embodiments, the loop diuretic is ethacrynic acid. Furosemide, for example, binds to the $GABA_A$ receptor and reversibly antagonizes GABA-evoked currents of the α6, β2, and γ2 receptors. By way of example only, useful loop diuretics include, but are not limited to, furosemide, bumetanide, and ethacrynic acid.

In some embodiments, the modulator of a GABA receptor is a GABA analogue. GABA analogues mimic GABA. Thus, when they bind to a GABA receptor, the receptor acts as though GABA is binding to it and the receptor is activated. In some embodiments, the GABA analog is gabapentin, pregabalin, muscimol, or baclofen. In some embodiments, the GABA analog is gabapentin. In some embodiments, the GABA analog is pregabalin. In some embodiments, the GABA analog is muscimol. In some embodiments, the GABA analogue is baclofen. Baclofen is an analogue of GABA which binds to and activates the $GABA_B$ receptor. Muscimol is also an analogue of GABA. It agonizes the $GABA_A$ receptor.

Neurotransmitter Reuptake Inhibitors

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which inhibit the reuptake of neurotransmitters in the CNS. In some embodiments, the neurotransmitter reuptake modulator is an antagonist of a neurotransmitter reuptake target, partial agonist, inverse agonist, neutral or competitive antagonist, allosteric antagonist, and/or orthosteric antagonist. Neurotransmitter reuptake inhibitors inhibit the reuptake of neurotransmitters into presynaptic cells of the CNS. This increases the concentration of neurotransmitter available to stimulate post-synaptic cells of the CNS.

In some embodiments, the neurotransmitter reuptake inhibitors are tricyclic antidepressants. Tricyclic antidepressants work by inhibiting the re-uptake of the neurotransmitters norepinephrine and serotonin by pre-synaptic cells. This increases the level of serotonin and/or norepinephrine available to bind to the postsynaptic receptor. In some embodiments, the tricyclic antidepressant is amitriptyline, nortriptyline, or trimipramine. In some embodiments, the tricyclic antidepressant is amitriptyline. In some embodiments, the tricyclic antidepressant is nortriptyline. In some embodiments, the tricyclic antidepressant is trimipramine.

In some embodiments, the neurotransmitter reuptake inhibitor is a selective serotonin reuptake inhibitor. By inhibiting the reuptake of serotonin into the presynaptic cells, SSRIs increase the extracellular level of serotonin. This increases the level of serotonin available to bind to the postsynaptic receptor. SSRIs are hypothesized to stimulate new neural growth within the inner ear. In some embodiments, the selective serotonin reuptake inhibitor is fluoxetine, paroxetine, or sertraline. In some embodiments, the selective serotonin reuptake inhibitor is fluoxetine. In some embodiments, the selective serotonin reuptake inhibitor is paroxetine. In some embodiments, the selective serotonin reuptake inhibitor is sertraline.

Contemplated for use with the formulations disclosed herein are agents that ameliorate otic disorders, including vestibular disorders and/or tinnitus, through local modulation of central nervous system (CNS) activity. Accordingly, some embodiments incorporate the use of agents that antagonize neurokinin receptors. There are at least three neurokinin receptors: NK1, NK2 and NK3. In certain embodiments, the binding of a ligand (e.g. a tachykinin peptide, substance P, neurokinin A, and neurokinin B) to a neurokinin receptor induces the activation of phospholipase C. The activation of phospholipase C produces inositol triphosphate. In some embodiments, the neurokinin receptor is the NK1 receptor, the NK2 receptor, the NK3 receptor, or combinations thereof. In some embodiments, the neurokinin receptor is the NK1 receptor. In some embodiments, the antagonist of the NK1 receptor is vestipitant.

In some embodiments, the SSRI inhibitor is administered in combination with a neurokinin receptor antagonist. In some embodiments, the SSRI is paroxetine and the neurokinin receptor is NK1. In some embodiments, the NK1 receptor antagonist is vestipitant. In certain embodiments, the co-administration of paroxetine and vestipitant treats, and/or the symptoms of tinnitus.

Local Anesthetics

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which decrease the rate of the depolarization and repolarization of neurons by, for example, blocking the $Na^+$ channels in cell membranes.

In some embodiments, the CNS modulator is a local anesthetic. In some embodiments, the local anesthetic is selected from the group consisting of: benzocaine, carticaine, cinchocaine, cyclomethycaine, lidocaine, prilocaine, propxycaine, proparacaine, tetracaine, tocainide, and trimecaine. In some embodiments, the local anesthetic is lidocaine. In some embodiments, the local anesthetic is tocainide.

Sodium Channel Blockers

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which block or antagonize Na+ channels. Sodium channels are channels formed in the plasma membrane of neurons (amongst other cells) by integral membrane proteins. These channels conduct $Na^+$ through a cell's plasma membrane. In neurons, the flow of $Na^+$ is partly responsible for creating and propagating action potentials in the neurons.

In some embodiments, the sodium channel blocker is carbamazepine, oxcarbazepine, phenytein, valproic acid, or sodium valproate. In some embodiments, the sodium channel blocker is carbamazepine. In some embodiments, the sodium channel blocker is oxcarbazepine. In some embodiments, the sodium channel blocker is phenytein. In some embodiments, the sodium channel blocker is valproic acid. In some embodiments, the sodium channel blocker is sodium valproate.

In some embodiments, the $Na^+$ channel blocker is vinpocetine ((3a,16a)-Eburnamenine-14-carboxylic acid ethyl ester); sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarbox amide hydrochloride); carbamazepine (5H-dibenzo[b,f]azepine-5-carboxamide); TTX (octahydro-12-(hydroxymethyl)-2-imino-5,9:7,10a-dimethano-10aH-[1,3]dioxocino[6,5-d]pyrimidine-4,7,10,11,12-pentol); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenytoin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl) pyrimidine-2,4-1.1 ethanesulphonate); QX-222 (2-[(2,6-dimethylphenyl)amino]-N,N,N-trimethyl-2-oxoethaniminium chloride); ambroxol (trans-4-[[(2-Amino-3,5-dibromophenyl)methyl]amino]cyclo hexanol hydrochloride); R56865 (N-[1-(4-(4-fluorophenoxy)butyl]-4-piperidinyl-N-methyl-2-benzo-thiazolamine); lubeluzole; ajmaline ((17R,21alpha)-ajmalan-17,21-diol); procainamide (4-amno-N-(2-diethylaminoethyl)benzamide hydrochloride); flecainide; riluzoleor; or combinations thereof.

In some embodiments, agents which decrease the rate of the depolarization and repolarization of neurons by, for example, blocking the $Na^+$ channels in cell membranes include local anesthetics. In some embodiments, the local anesthetic is selected from the group consisting of: benzocaine, carticaine, cinchocaine, cyclomethycaine, lidocaine, prilocaine, propxycaine, proparacaine, tetracaine, tocainide, and trimecaine. In some embodiments, the local anesthetic is lidocaine. In some embodiments, the local anesthetic is tocainide.

Thyrotropin-Releasing Hormone

Contemplated for use with the formulations disclosed herein are agents which ameliorate otic disorders, including vestibular disorders and/or tinnitus, through local modulation of central nervous system (CNS) activity. Accordingly, some embodiments incorporate the use of agents which modulate neurotransmitters. Thyrotropin-releasing hormone is a neurotransmitter which inhibits glutamate-induced excitation of neurons. In some embodiments, the CNS modulator is thyrotropin-releasing hormone.

Antimicrobial Agents

Any antimicrobial agent useful for the treatment of otic disorders, e.g., inflammatory diseases of the ear or cancer of the ear, is suitable for use in the formulations and methods disclosed herein. In some embodiments, the antimicrobial agent is an antibacterial agent, an antifungal agent, an antiviral agent, an antiprotozoal agent, and/or an antiparasitic agent. Antimicrobial agents include agents that act to inhibit or eradicate microbes, including bacteria, fungi, viruses, protozoa, and/or parasites. Specific antimicrobial agents are used to combat specific microbes. Accordingly, a skilled practitioner would know which antimicrobial agent would be relevant or useful depending on the microbe identified, or the symptoms displayed.

In some embodiments, the antimicrobial agent is a protein, a peptide, an antibody, DNA, a carbohydrate, an inorganic molecule, or an organic molecule. In certain embodiments, the antimicrobial agents are antimicrobial small molecules. Typically, antimicrobial small molecules are of relatively low molecular weight, e.g., less than 1,000, or less than 600-700, or between 300-700 molecular weight.

Antibacterial agents include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, AL-15469A (Alcon Research), AL-38905 (Alcon Research) and combinations thereof.

Antiviral agents include acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

Antiparasitic agents include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, pharmaceutically active metabolites, salts, polymorphs, prodrugs, analogues, and derivatives of the antimicrobial agents discussed above that retain the ability of the parent antimicrobial agents to treat otic disorders of the ear are also useful in the formulations disclosed herein.

Free Radical Modulators

In some instances, immunomodulators and/or aural pressure modulators relieve, prevent, reverse or ameliorate the degeneration of neurons and/or hair cells of the auris due to free radicals or the dysfunction of the mitochondria.

Antioxidants

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of agents which prevent and/or ameliorate the damage caused by free radicals. In some embodiments, the agents which prevent and/or ameliorate the damage caused by free radicals is an antioxidant.

Antioxidants, as disclosed herein, are also useful as protectants against ototoxic agents through the prevention of reactive oxygen species, neutralization of toxic products or blockage of the apoptosis pathway. Resveratrol (3,5,4'-Trihydroxystilbene), a representative example of an antioxidant, exerts its effects through a variety of pathways, including the inhibition of MnSOD, which reduces superoxide to $H_2O_2$, which inhibits free radical chain reactions, reducing superoxide levels in the cell. Moreover, resveratrol has been implicated in preventing neuronal cell dysfunction and cell death. Other antioxidants include but are not limited to vitamin E (tocopherol), vitamin C (ascorbic acid), glutathione, lipoic acid, alpha lipoic acid, uric acid, carotenes, ubiquinol, melatonin, tocotrienols, selenium, flavonoids, polyphenols, lycopene, lutein, lignan, butyl hydroxytoluene, coenzyme Q10, salicylate, or combinations thereof.

In certain embodiments, nitrones act synergistically with antioxidants. In certain embodiments, nitrones trap free radicals. In some embodiments, a nitrone (e.g. alpha-phenyl-tert-butylnitrone (PBN), allpurinol) is co-administered with an antioxidant. In certain embodiments, a nitrone co-administered with an antioxidant treats acute acoustic noise-induced hearing loss.

In some embodiments, the antioxidant is N-acetylcysteine; vitamin E (tocopherols and tocotrienols); vitamin C; vitamin A; lutein; selenium glutathione; melatonin; a polyphenol; a carotenoid (e.g. lycopene, carotenes); coenzyme Q-10; Ebselen (2-phenyl-1,2-benzisoselenazol-3(2H)-one (also called PZ 51 or DR3305); L-methionine; azulenyl nitrones (e.g. stilbazulenyl nitrone); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester (CAPE); dimethylthiourea; dimethylsulfoxide; disufenton sodium (NXY-059; disodium 4-[(Z)-(tert-butyl-oxidoazaniumylidene)methyl]benzene-1,3-disulfonate); pentoxifylline; MCI-186 (3-Methyl-1-phenyl-2-pyrazolin-5-one); Ambroxol (trans-4-(2-Amino-3,5-dibromobenzylamino)cyclohexane-HCl; U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol•2HCl); MITOQ (mitoquinone mesylate, Antipodean Pharmaceuticals); Idebenone (2-(10-hydroxydecyl)-5,6-dimethoxy-3-methyl-cyclohexa-2,5-diene-1,4-dione); (+)-cyanidanol-3; or combinations thereof.

Glutamate-Receptor Modulators

Contemplated for use with the formulations disclosed herein are agents that modulate the production of free-radicals and/or inhibit damage to the mitochondria. Accordingly, some embodiments incorporate the use of agents which modulate glutamate receptors. In some embodiments, the glutamate receptor is the AMPA receptor, the NMDA receptor, and/or a group II or III mGlu receptor. In some embodiments, a glutamate receptor modulator is as described herein.

Iron Chelators

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of agents which prevent and/or ameliorate the damage caused by free radicals. In some embodiments, the agents which prevent and/or ameliorate the damage caused by free radicals is an iron chelator. The iron chelator, deferoxamine, prevents ototoxic damage to the ear resulting from treatment with neomycin when it is co-administered with neomycin.

In some embodiments, the iron chelator is desferrioxamine (DFO); hydroxybenzyl ethylene diamine; fullerenol-1, pyrrolidine dithiocarbamate; desferal; Vk-28 (5-[4-(2-hydroxyethyl) piperazine-1-ylmethyl]-quinoline-8-ol); clioquinol; echinochrome; PIH (pyridoxal isonicotinoyl hydrazone); deferasirox; HBED (N,N'-bis(2-hydroxybenzyl)

ethylenediamine-N,N'-diacetic acid); SIH (salicylaldehyde isonicotinoyl hydrazone); deferiprone; L1 (1,2-dimethyl-3-hydroxy-4-pyridone); Kojic acid (5-hydroxy-2-hydroxymethyl-4-pyrone); deferoxamine; 2,3-dihydroxybenzoate; or combinations thereof.

Mitochondrial Modulators

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents that modulate the activity of the mitochondria. In some embodiments, the agent which modulates the activity of the mitochondria is acetylcarnitine; lipoic acid; or combinations thereof.

Nitric Oxide Synthase modulators

Contemplated for use with the compositions disclosed herein are agents for treating or ameliorating hearing loss or reduction resulting from destroyed, stunted, malfunctioning, damaged, fragile or missing hairs in the inner ear. Nitric oxide (NO) is a neurotransmitter. It is synthesized by multiple nitric oxide synthases (NOS) from arginine and oxygen. It is also derived from the reduction of inorganic nitrate. In certain instances, it induces vasodilation; thus, increasing blood flow. In certain instances, it increases cochlear blood flow. In certain instances, NO damages blood vessel walls. In certain instances, NO ameliorates vascular protein leakage in the cochlea. In certain instances, NO increases the sensitivity of hair cells. In certain instances, NO reacts with super-oxide to form the free radical peroxynitrite. Accordingly, some embodiments incorporate the use of agents that modulate nitric oxide and/or nitric oxide synthase (NOS).

In some embodiments, the agent that modulates NO and/or NOS is an antagonist of NO or NOS. In some embodiments, the antagonist of NO and/or NOS is aminoguanidine; 1-Amino-2-hydroxyguanidine p-toluensulfate; GED (guanidinoethyldisulfide); bromocriptine mesylate; dexamethasone; SDMA (symmetric $N^G,N^G$-Dimethyl-L-arginine); ADMA (asymmetric $N^G,N^G$-Dimethyl-L-arginine); L-NMMA ($N^G$-monomethyl-L-arginine); L-NMEA ($N^G$-monoethyl-L-arginine); D-MMA ($N^G$-monomethyl-D-arginine); L-NIL ($N^6$-(1-Iminoethyl)-L-lysine hydrochloride); L-NNA ($N^G$-nitro-L-arginine); L-NPA ($N^G$-propyl-L-arginine); L-NAME ($N^G$-nitro-L-arginine methyl ester dihydrochloride); L-VNIO ($N^5$-(1-imino-3-butenyl)-1-ornithine); diphenyleneiodonium chloride; 2-ethyl-2-thiopseudourea; haloperidol; L-NIO (L-$N^5$-(1-iminoethyl)ornithine); MEG (methylecgonidine); SMT (S-methylisothiourea sulfate); SMTC (S-methyl-L-thiocitrulline); 7-Ni (7-nitroindazole); nNOS inhibitor I ((4S)—N-(4-Amino-5[aminoethyl]aminopentyl)-N'-nitroguanidine); 1,3-PBITU (S,S'-1,3-Phenylenebis(1,2-ethanediyl)-bis-isothiourea); L-thiocitrulline; TRIM (1-(2-trifluoromethylphenyl) imidazole); MTR-105 (S-ethylisothiuronium diethylphosphate); BBS-1; BBS-2; ONO-1714 ((1S,5S,6R,7R)-7chloro-3-amino-5methyl-2-azabicyclo[4.1.0]heptane hydrochloride); GW273629 (3-[[2-[(1-iminoethyl)amino]ethyl]sulphonyl]-L-alanine); GW 274150 ((S)-2-amino-(1-iminoethylamino)-5-thioheptanoic acid); PPA250 (3-(2,4-difluorophenyl)-6-{2-[4-(1H-imidazol-1-ylmethyl) phenoxy]ethoxy}-2-phenylpyridine); AR-R17477 ([N-(4-(2-((3-chlorophenylmethyl)amino)ethyl)phenyl)-2-thiophecarboxamidine dihydrochloride); AR-R18512 (N(2-methyl-1,2,3,4-tetrahydroisoquinoline-7-yl)-2-thiophenecarboximidamide); spiroquinazolone; 1400W (N-[[3-(aminomethyl)phenyl]methyl]-ethanimidamide dihydrochloride); or combinations thereof.

In some embodiments, the agent that modulates NO and/or NOS is an agonist of NO and/or NOS, or a donor of NO. In some embodiments, the agonist of NO and/or NOS, or donor of NO, is S—NC (S-nitrosocysteine); NTG (nitroglycerine); SNP (sodium nitroprusside); thapsigargin; vascular endothelial growth factor (VEGF); bradykinin; ATP; sphingosine-1-phosphate; estrogen; angiopoietin; acetylcholine; SIN-1 (3-morpholinosydnonimine); GEA 3162 (1,2,3,4-oxatriazolium, 5-amino-3-(3,4-dichlorophenyl)-,chloride); GEA 3175 (3-(3-chloro-2-methylphenyl)-5-[[4-methylphenyl)sulphonyl]amino]-)hydroxide); GEA 5024 (1,2,3,4-oxatriazolium,5-amino-3-(30chloro-2-methyl-phenyl)chloride); GEA 5538 (,2,3,4-Oxatriazolium,3-(3-chloro-2-methylphenyl)-5-[[[cyanomethylamino]carbonyl]amino]-hydroxide inner salt); SNAP (S-nitroso-N-acetylpenicillamine); molsidomine; CNO-4 (1-[(4',5'-Bis(carboxymethoxy)-2'-nitrophenyl)methoxy]-2-oxo-3,3, diethyl-1-triazene dipotassium salt); CNO-5 ([1-(4',5'-Bis(carboymethoxy)-2'-nitrophenyl)methoxy]-2-oxo-3,3-diethyl-1-triazine diacetoxymethyl ester); DEA/NO, IPA/NO, SPER/NO, SULFI/NO, OXI/NO, DETA/NO; or combinations thereof.

Sirtuin Modulators

The sirtuins (or Sir2 proteins) comprise class III of the histone deacetylases (HDACs). While they are classified as protein deacetylases some also function as mono-ADP-ribosyltransferases. Each sirtuin protein has a homologous core sequence of 250 amino acids. This sequence is highly conserved over multiple species. Further, in order to catalyze the deacetylation of a protein, each sirtuin requires NAD as a cofactor. There are seven members of the family: Sirt1, Sirt2, Sirt3, Sirt4, Sirt5, Sirt6, and Sirt7. Sirt1 and Sirt3 are protein deacetylases. Sirt2 is involved in mitosis.

Agonism of Sirt1 yields multiple benefits which have previously been identified in subjects undergoing caloric restriction. These benefits include, but are not limited to, decreased glucose levels and improved insulin sensitivity, increased mitochondrial activity, and decreased adiposity (due to the Sirt1 mediated repression of PPAR-γ). Decreases in glucose levels and adiposity can contribute to the amelioration of presbycusis as diabetes and atherosclerosis are both factors which contribute to the development and progression of presbycusis.

Sirt1 can prevent apoptosis by deacetylating the pro-apoptotic genes p53 and Ku-70. Additional substrates for Sirt1 include, but are not limited to, the transcription factors NFκB, Fox01, Fox03a, Fox04, Fox05; the transcription repressor Hic1; and Pgc-1α, which regulates, among other cellular functions, adaptive thermogenesis, glucose metabolism, and triglyceride metabolism. Agonism of Sirt3 results in increased cellular respiration and a decrease in the production of reactive oxygen species (ROS).

The catalysis of deacetylation by sirtuins is NAD (nicotinamide adenine dinucleotide) dependent. Upon binding to an acetylated protein, the sirtuin hydrolyzes NAD by breaking the glycosidic bond between nicotinamide and ADP-ribose. The acetyl group of the acetylated protein is then transferred to ADP-ribose. At the completion of the reaction nicotinamide, the deacetylated protein, and 2'-O-acetyl-ADP-ribose are released.

Multiple compounds modulate the sirtuin catalyzed deacetylation of proteins. Administration of certain polyphenols such as, but not limited to, stilbenes, chalcones, flavones, isoflavones, flavanones, anthocyanidins, catechins, results in the decrease of the $K_m$ of the deacetylation reaction. Further, as free nicotinamide antagonizes the deacetylation reaction, compounds which inhibit the binding of nicotinamide to sirtuins will also agonize the activity of sirtuins.

Administration of the sirtuin agonizing agent resveratrol (trans-3,5,4'-trihydroxystilbene) decreases apoptosis. It also increases glutamate uptake and thus ameliorates excitotoxicity. Further, administration of resveratrol results in lower levels of reactive oxygen species (ROS) and thus ameliorates damage caused by ischemia, excitotoxicity, ototoxicity caused by cisplatin and aminoglycosides, acoustic trauma and presbycusis.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a stilbene. In some embodiments, the stilbene is trans-stilbene, cis-stilbene, resveratrol, piceatannol, rhapontin, deoxyrhapontin, butein, or combinations thereof.

In some embodiments, the stilbene is resveratrol. In some embodiments, the stilbene is an analog of resveratrol. In some embodiments, the analog of resveratrol is SRT-501 (RM-1821). For additional analogs of resveratrol see U.S. Patent App. Pub. No. 2006/0276393, which is hereby incorporated by reference for this disclosure.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a chalcone. In some embodiments, the chalcone is chalcon; isoliquirtigen; butein; 4,2',4'-trihydroxychalcone; 3,4,2',4',6'-pentahydroxychalcone; or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a flavone. In some embodiments, the flavone is flavone, morin, fisetin; luteolin; quercetin; kaempferol; apigenin; gossypetin; myricetin; 6-hydroxyapigenin; 5-hydroxyflavone; 5,7,3',4', 5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3', 4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is an isoflavone. In some embodiments, the isoflavone is daidzein, genistein, or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a flavanone. In some embodiments, the flavanone is naringenin; flavanone; 3,5,7,3',4'-pentahydroxyflavanone; or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is an anthocyanidin. In some embodiments, the anthocyanidin is pelargonidin chloride, cyanidin chloride, delphinidin chloride, or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a catechin. In some embodiments, the catechin is (−)-epicatechin (Hydroxy Sites: 3,5,7,3',4'); (−)-catechin (Hydroxy Sites: 3,5,7, 3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents that modulate the catalytic rate of sirtuin catalyzed deacetylation reactions. In some embodiments, the agent which modulates the catalytic rate of sirtuin catalyzed deacetylation reactions is dipyridamole, ZM 336372 (3-(dimethylamino)-N-[3-[(4-hydroxybenzoyl)-amino]-4-methylphenyl]benzamide), camptothecin, coumestrol, nordihydroguaiaretic acid, esculetin, SRT-1720 (Sirtris), SRT-1460 (Sirtris), SRT-2183 (Sirtris), or combinations thereof.

Contemplated for use with the formulations disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent that modulates sirtuin catalyzed deacetylation reactions is a nicotinamide binding antagonist. In some embodiments, the nicotinamide binding antagonist is isonicotinamide or an analog of isonicotinamide. In some embodiments, the analog of isonicotinamide is β-1'-5-methyl-nicotinamide-2'-deoxyribose; β-D-1'-5-methyl-nico-tinamide-2'-deoxyribofuranoside; β-1'-4, 5-dimethyl-nicotinamide-2'-de-oxyribose; or β-D-1'-4,5-dimethyl-nicotinamide-2'-deoxyribofuranoside. For additional analogs of isonicotinamide see U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/

0096830; 2004/0053944; 2004/0110772; and 2004/0181063, which are hereby incorporated by reference for that disclosure.

Ion Channel Modulators

Potassium Ion Channel Modulators

Contemplated for use with the formulations disclosed herein are agents for treating or ameliorating hearing loss or reduction resulting from destroyed, stunted, malfunctioning, damaged, fragile or missing hairs and neurons in the inner ear. Accordingly, some embodiments incorporate the use of agents that modulate potassium ion concentrations. In some embodiments, the agents that modulate potassium ion concentrations are agonists or antagonists of potassium ion channels. Potassium ion channels are channels that regulate the flow of potassium ions into and out of cells. In the cochlea the transduction current through the sensory cells is carried by potassium ions and depends on the high concentration of potassium ions in the endolymph. Mutations in the genes encoding potassium channel protein result in both acquired and congenital hearing loss.

The KCNQ family of potassium channels is a family of delayed rectifier voltage-gated potassium channels found in the cochlea. KCNQ1 subunits form potassium channels in vestibular dark cells and marginal cells of the stria vascularis. These channels regulate the level of potassium in endolymph. KCNQ4 subunits form channels hair cells. Mice with genes encoding KCNQ subunits knocked-out display a hearing loss during development, starting at four weeks of postnatal life.

In some embodiments, the agent that modulates a potassium channel is an agonist of a potassium channel (e.g. a potassium channel opener). In some embodiments, the agonist of a potassium channel is nicorandil; minoxidil; levcromakalim; lemakalim; cromakalim; L-735,334 (14-hydroxy CAF-603 oleate); retigabine; flupirtine; BMS-204352 (3S)-(+)-(5-Chloro-2-methoxyphenyl)-1,3-dihydro-3-fluoro-6-(trifluoromethyl)-2H-indole-2-one); DMP-543 (10,10-bis((2-fluoro-4-pyridinyl)methyl)-9(10H)-anthracenone); or combinations thereof.

In some embodiments, the agent that modulates a potassium channel is an antagonist of a potassium channel (e.g. a potassium channel blocker). In some embodiments, the antagonist of a potassium channel is linopirdine; XE991 (10,10-bis(4-pyridinylmethyl)-9(10H)-anthracenone); 4-AP (4-aminopyridine); 3,4-DAP (3,4-Diaminopyridine); E-4031 (4'-[[1-[2-(6-methyl-2-pyridyl)ethyl]-4-piperidinyl]carbonyl]-methanesulfonanilide); DIDS (4,4'-diisothiocyanostilbene-2,2'-disulfonic acid); Way 123,398 (N-methyl-N-(2-(methyl(1-methyl-1H-benzimidazol-2-yl)amino)ethyl)-4-((methylsulfonyl)amino)benzenesulfonamide HCl); CGS-12066A (7-Trifluoromethyl-4-(4-methyl-1-piperazinyl)pyrrolo-[1,2-a]quinoxaline); dofetilide; sotalol; apamin; amiodarone; azimilide; bretylium; clofilium; tedisamil; ibutilide; sematilide; nifekalant; tamulustoxin and combinations thereof.

Purigenic Receptor Modulators

Contemplated for use with the formulations disclosed herein are agents for modulating ion channels. Accordingly, some embodiments incorporate the use of agents that modulate the concentration of ions. In some embodiments, the agents that modulate the concentration of ions are agonists or antagonist of purigenic receptors.

Purigenic receptors are a family of plasma membrane-bound receptors. The family includes the P2X, P2Y, and P1 receptors. The P2X receptors comprise ion channels. When ATP binds to the receptor the channel opens. The P2Y receptors comprise G-coupled protein receptors. The ligands for these receptors are ATP, ADP, UTP, UDP, UDP-glucose. The P1 receptors comprise G-coupled protein receptors. The ligand for these receptors is adenosine. Purigenic receptors regulate ion homeostasis in the ear. Endolymph, for example, requires high potassium (10, low sodium ($Na^r$), and low calcium ($Ca^2$) ion levels for normal auditory transduction.

In some embodiments, the agonist of a purigenic receptor is ATP; ADP; UTP; UDP; UDP-glucose; adenosine; 2-MeSATP; 2-MeSADP; αβmeATP; dATPαS; ATPγS; Bz-ATP; MRS2703 (2-MeSADP with the beta-phosphate group blocked by a 1-(3,4-dimethyloxyphenyl)eth-1-ylphosphoester)); denufosol tetrasodium; MRS2365 ([[(1R,2R,3S,4R,5S)-4-[6-amino-2-(methylthio)-9H-purin-9-yl]-2,3-dihydroxybicyclo[3.1.0]hex-1-yl]methyl]diphosphoric acid mono ester trisodium salt); MRS 2690 (diphosphoric acid 1-a-D-glucopyranosyl ester 2-[(4'-methylthio)uridin-5"-yl] ester disodium salt); PSB 0474 (3-(2-Oxo-2-phenylethyl)-uridine-5'-diphosphate disodium salt); or combinations thereof.

In some embodiments, the antagonist of a purigenic receptor is A-317491 ((5-([(3-Phenoxybenzyl)[(1S)-1,2,3,4-tetrahydro-1-naphthalenyl]amino]carbonyl)-1,2,4-benzenetricarboxylic acid)); RO-3 (Roche); suramin; PPADS (pyridoxalphosphate-6-azophenyl-2',4'-disulfonic acid); PPNDS (Pyridoxal-5'-phosphate-6-(2'-naphthylazo-6'-nitro-4',8'-disulfonate)tetrasodium salt); DIDS; pyridoxal-5-phosphate; 5-(3-bromophenyl)-1,3-dihydro-2H-benzofuro-[3,2-e]-1,4-diazepin-2-one; cibacron blue; basilen blue; ivermectin; A-438079 (3-[[5-(2,3-Dichlorophenyl)-1H-tetrazol-1-yl]methyl]pyridine hydrochloride); A-740003 ((N-(1-{[(cyanoimino)(5-quinolinylamino)methyl]amino}-2,2-dimethylpropyl)-2-(3,4-dimethoxyphenyl)acetamide); NF449 (4,4',4'',4'''-(carbonylbis(imino-5,1,3-benzenetriyl-bis(carbonylimino)))tetrakis-benzene-1,3-disulfonic acid); NF110 (para-4,4',4'',4'''-(carbonylbis(imino-5,1,3-benzenetriylbis carbonylimino)))tetrakis-benzenesulfonic acid); MRS 2179 (2'-Deoxy-N6-methyladenosine 3',5'-bisphosphate tetrasodium salt); MRS 2211 (2-[(2-chloro-5-nitrophenyl)azo]-5-hydroxy-6-methyl-3-[(phosphonooxy)methyl]-4-pyridinecarboxaldehyde disodium salt); MRS 2279 ((1R,2S,4S,5S)-4-[2-chloro-6-(methylamino)-9H-purin-9-yl]-2-(phosphonooxy)bicyclo[3.1.0]hexane-1-methanol dihydrogen phosphate ester diammonium salt); MRS 2500 tetrasodium salt ((1R,2S,4S,5S)-4-[2-Iodo-6-(methylamino)-9H-purin-9-yl]-2-(phosphonooxy)bicyclo[3.1.0] hexane-1-methanol dihydrogen phosphate ester tetraammonium salt); NF157 (8,8'-[carbonylbis[imino-3,1-phenylenecarbonylimino(4-fluoro-3,1-phenylene) carbonylimino]]bis-1,3,5-naphthalene trisulfonic acid hexasodium salt); TNP-ATP; tetramethylpyrazine; $Ip_5I$; βγ-carboxymethylene ATP; βγ-chlorophosphomethylene ATP; KN-62 (4-[(2S)-2-[(5-isoquinolinylsulfonyl)methylamino]-3-oxo-3-(4-phenyl-1-piperazinyl)propyl]phenyl isoquinolinesulfonic acid ester); NF023 (8,8'-[carbonylbis (imino-3,1-phenylenecarbonylimino)]bis-1,3,5-naphthalene-trisulphonic acid, hexasodium salt); NF279 (8,8'-[Carbonylbis(imino-4,1-phenylenecarbonylimino-4,1-phenylenecarbonylimino)]bis-1,3,5-naphthalenetrisulfonic acid hexasodium salt); spinorphin; or combinations thereof.

RNAi

In some embodiments, where inhibition or down-regulation of a target is desired (e.g. genes encoding a component of a potassium channel, genes encoding a purigenic receptor), RNA interference is optionally utilized. In some embodiments, the agent that inhibits or down-regulates the target is an siRNA molecule. In certain instances, the siRNA molecule is as described herein.

Combination Therapy

In certain embodiments, any otic active agent (e.g., an immunomodulator or an auris pressure modulator) is administered in combination with one or more of any other otic active agent described herein. In some embodiments, an otic agent is administered with an anti-emetic agent (e.g., when a balance disorder is accompanied by nausea). In some embodiments, an otic agent is administered in combination with one or more otoprotectant (e.g., when the administration of a cytotoxic agent is accompanied by ototoxicity). In certain embodiments, an otic agent is administered in combination with, for example, an anti-emetic, an antimicrobial agent, a nitric oxide synthase inhibitor, an antioxidant, a neurotransmitter reuptake inhibitor, an otoprotectant, a homeostasis modulator (e.g., ion/fluid (e.g., water) homeostasis modulator) or the like.

Anti-Emetic Agents/Central Nervous System Agents

Anti-Emetic agents are optionally used in combination with any otic formulations disclosed herein. Anti-emetic agents include antihistamines and central nervous agents, including anti-psychotic agents, barbiturates, benzodiazepines and phenothiazines Other anti-emetic agents include the serotonin receptor antagonists, which include dolasetron, granisetron, ondansetron, tropisetron, palonosetron, and combinations thereof, dopamine antagonists, including domperidone, properidol, haloperidol, chlorpromazine, promethazine, prochlorperazine and combinations thereof; cannabinoids, including dronabinol, nabilone, sativex, and combinations thereof; anticholinergics, including scopolamine; and steroids, including dexamethasone; trimethobenzamine, emetrol, propofol, muscimol, and combinations thereof.

Optionally, Central Nervous System agents and barbiturates are useful in the treatment of nausea and vomiting symptoms that accompany an autoimmune otic disorder. When used, an appropriate barbiturate and/or central nervous system agent is selected to relieve or ameliorate specific symptoms without possible side effects, including ototoxicity. Moreover, as discussed above, targeting of the drugs to the round window membrane of the auris interna reduces possible side effects and toxicity caused by systemic administration of these drugs. Barbiturates, which act as a central nervous system depressant, include allobarbital, alphenal, amobarbital, aprobarbital, barnexaclone, barbital, brallobarbital, butabarbital, butalbital, butallylonal, butobarbital, corvalol, crotylbarbital, cyclobarbital, cyclopal, ethallobarbital, febarbamate, heptabarbital, hexethal, hexobarbital, metharbital, methohexital, methylphenobarbital, narcobarbital, nealbarbital, pentobarbital, phenobarbital, primidone, probarbital, propallylonal, proxibarbital, reposal, secobarbital, sigmodal, sodium thiopental, talbutal, thialbarbital, thiamylal, thiobarbital, thiobutabarbital, tuinal, valofane, vinbarbital, vinylbital, and combinations thereof.

Other central nervous system agents which are optionally used in conjunction with the otic formulations disclosed herein include benzodiazepines or phenothiazines Useful benzodiazepines include, but are not limited to diazepam, lorazepam, oxazepam, prazepam, alprazolam, bromazepam, chlordiazepoxide, clonazepam, clorazepate, brotizolam, estazolam, flunitrazepam, flurazepam, loprazolam, lormetazepam, midazolam, nimetazepam, nitrazepam, temazepam, triazolam, and combinations thereof. Examples of phenothiazines include prochlorperazine, chlorpromazine, promazine, triflupromazine, levopromazine, methotrimepramazine, mesoridazine, thiroridazine, fluphenazine, perphenazine, flupentixol, trifluoperazine, and combinations thereof.

Antihistamines, or histamine antagonists, act to inhibit the release or action of histamine. Antihistamines that target the H1 receptor are useful in the alleviation or reduction of nausea and vomiting symptoms that are associated with AIED, other autoimmune disorders, as well as anti-inflammatory disorders. Accordingly, some embodiments incorporate the use of agents which modulate histamine receptors (e.g. the $H_1$ receptor, $H_2$ receptor, and/or the $H_3$ receptor).

Such antihistamines include, but are not limited to, meclizine, diphenhydramine, loratadine and quetiapine. Other antihistamines include mepyramine, piperoxan, antazoline, carbinoxamine, doxylamine, clemastine, dimenhydrinate, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and combinations thereof.

In some embodiments, the $H_1$ receptor antagonist is meclizine hydrochloride. In some embodiments, the $H_1$ receptor antagonist is promethazine hydrochloride. In some embodiments, the $H_1$ receptor antagonist is dimenhydrinate. In some embodiments, the $H_1$ receptor antagonist is diphenhydramine. In some embodiments, the $H_1$ receptor antagonist is cinnarizine. In some embodiments, the $H_1$ receptor antagonist is hydroxyzine pamoate.

Antihistamines which target the $H_3$ receptor include, but are not limited to betahistine dihydrochloride.

Antimicrobial Agents

Antimicrobial agents are also contemplated as useful with the formulations disclosed herein. In some embodiments, the antimicrobial agent is as described herein.

Corticosteroids

Contemplated for use in combination with any otic formulation described herein (e.g, aural pressure modulating formulations, immunomodulator formulations described herein) are corticosteroid agents which reduce or ameliorate symptoms or effects as a result of an autoimmune disease and/or inflammatory disorder, including AIED. Such autoimmune response are a contributing factor to otic disorders such as Meniere's disease. In some embodiments, corticosteroids modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which protect otic hair cells from ototoxins. In some embodiments, the agent which protects otic hair cells from ototoxins is a corticosteroid. Such steroids include prednisolone, dexamethasone, dexamethasone phosphate, beclomethasone, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide and combinations thereof. In certain instances, triamcinolone actenoide and dexamethasone protect otic hair cells from damage caused by the naturally occurring toxin 4-hydroxy-2,3-nonenal (HNE), which is produced in the inner ear in response to oxidative stress.

Otoprotectants

In some embodiments, any otic formulation described herein (e.g. auris sensory cell modulating agent formulations disclosed herein) further comprise otoprotectants that reduce, inhibit or ameliorate the ototoxicity of agents such as chemotherapeutic agents and/or antibiotics as described herein, or reduce, inhibit or ameliorate the effects of other environmental factors, including excessive noise and the like. Examples of otoprotectants include, and are not limited to, thiols and/or thiol derivatives and/or pharmaceutically acceptable salts, or derivatives (e.g. prodrugs) thereof (e.g., D-methionine, L-methionine, ethionine, hydroxyl methionine, methioninol, amifostine, mesna (sodium 2-sulfanylethanesulfonate), a mixture of D and L methionine, normethionine, homomethionine, S-adenosyl-L-methionine), diethyldithiocarbamate, ebselen (2-phenyl-1,2-benzisoselenazol-3(2H)-one), sodium thiosulfate, AM-111 (a cell permeable JNK inhibitor, (Laboratoires Auris SAS)), leucovorin, leucovorin calcium, dexrazoxane, piracetam, Oxiracetam, Aniracetam, Pramiracetam, Phenylpiracetam (Carphedon), Etiracetam, Levetiracetam, Nebracetam, Nicoracetam, Rolziracetam, Nebracetam, Fasoracetam, Coluracetam, Dimiracetam, Brivaracetam, Seletracetam, Rolipramand or combinations thereof. Otoprotectants allow for the administration of chemotherapeutic agents and/or antibiotics at doses that are higher than maximal toxic doses; the chemotherapeutic agents and/or antibiotics would otherwise be administered at lower doses due to ototoxicity. Otoprotectants, when optionally administered by itself, also allow for the amelioration, reduction or elimination of the effect of environmental factors that contribute to loss of hearing and attendant effects, including but not limited to noise-induced hearing loss and tinnitus.

The amount of otoprotectant in any formulation described herein on a mole:mole basis in relation to the ototoxic chemotherapeutic agent (e.g. cis platin) and/or an ototoxic antibiotic (e.g. gentamicin) is in the range of from about 5:1 to about 200:1, from about 5:1 to about 100:1, or from about 5:1 to about 20:1. The amount of otoprotectant in any formulation described herein on a molar basis in relation to the ototoxic chemotherapeutic agent (e.g. cis platin) and/or an ototoxic antibiotic (e.g. gentamicin) is about 50:1, about 20:1 or about 10:1. Any the auris sensory cell modulating agent formulation described herein comprises from about 10 mg/mL to about 50 mg/mL, from about 20 mg/mL to about 30 mg/mL, or from about 25 mg/mL of otoprotectant.

Chemotherapeutic Agents

Chemotherapeutic agents are also contemplated for use with the formulations disclosed herein. Chemotherapeutic agents act by killing cancer cells or microorganisms, and may include antineoplastic agents that target cancer or malignant cells. Some chemotherapeutic agents, either alone or in combination, are also ototoxic. For example, cisplatin is a known cochleotoxic agent. However, use of cisplatin in combination with antioxidants are protective and lessen the ototoxic effects of the chemotherapeutic agent. Moreover, the localized application of the cytotoxic drug may lessen the ototoxic effects that might otherwise occur through systemic application through the use of lower amounts with maintained efficacy, or the use of targeted amounts for a shorter period of time. Accordingly, a skilled practitioner choosing a course of therapy for tumor growth will have the knowledge to avoid or combine an ototoxic compound, or to vary the amount or course of treatment to avoid or lessen ototoxic effects.

Chemotherapeutic agents that are used in combination with the formulations disclosed herein include, for example, but are not limited to adriamycin, imidazole carboxamide, cyclophosphamide, mechlorethamine, chlorambucil, melphalan, daunorubicin, doxorubicin, epirubicin, idarubicin, mitoxanthrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and combinations thereof.

Homeostasis Modulators

Homeostatis modulators are contemplated as useful with the formulations described herein. Homeostasis modulators include ion and fluid (e.g. water) homeostasis modulators. In some instances, homeostasis modulators include Na/K-ATPase modulators, ENaC modulators, vasopressin receptor modulators, diuretics or the like as described herein.

Na/K ATPase Modulators

Na/K-ATPase modulators are contemplated for use with the formulations disclosed herein. Cochlear homeostasis is dependent on the electrolyte composition of the endolymph, which is regulated by an active exchange of $Na^+$ and $K^+$ via a ATPase. Examples of Na/K-ATPase modulators include, and are not limited to, nimodipine (a sodium-potassium adenosine triphosphatase stimulator), ouabain, and furosemide.

Presented below (Table 1) are examples of active agents contemplated for use with the formulations disclosed herein.

Active Agents (Including Pharmaceutically Acceptable Salts of these Active Agents) for Use with the Formulations Disclosed Herein

TABLE 1

| Auris Condition | Therapeutic Agent |
|---|---|
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | Methylprednisolone sodium succinate |
| Hearing Loss | N-acetyl cysteine |
| Meniere's Disease | Betahistine |
| Meniere's Disease | Sildenafil |
| Middle Ear Effusion | Pneumonococcal vaccine |
| Otitis Externa | Diclofenac sodium; dexotc |
| Otitis Externa, Acute | AL-15469A/AL-38905 |
| Otitis Media | Amoxicillin/clavulanate |
| Otitis Media | Amoxycillin |
| Otitis Media | Chlorpheniramine maleate |
| Otitis Media | Dornase alfa |

TABLE 1-continued

| Auris Condition | Therapeutic Agent |
| --- | --- |
| Otitis Media | Echinacea purpurea |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Triamcinolone acetonide |
| Otitis Media | Zmax |
| Otitis Media with Effusion | Lansoprazole |
| Otitis Media, Acute | AL-15469A; AL-38905 |
| Otitis Media, Acute | Amoxicillin |
| Otitis Media, Acute | Amoxicillin-clavulanate |
| Otitis Media, Acute | Azithromycin |
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |
| Otitis Media, Suppurative | Telithromycin |
| Otosclerosis | Acetylcysteine |
| Ototoxicity | Aspirin |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

Devices

Also contemplated herein are the use of devices for the delivery of the pharmaceutical formulations disclosed herein, or alternatively for the measurement or surveillance of the function of the auris formulations disclosed herein. For example, in one embodiment pumps, osmotic devices or other means of mechanically delivering pharmaceutical formulations are used for the delivery of the pharmaceutical formulations disclosed herein. Reservoir devices are optionally used with the pharmaceutical drug delivery units, and reside either internally along with the drug delivery unit, or externally of the auris structures.

Other embodiments contemplate the use of mechanical or imaging devices to monitor or survey the hearing, balance or other auris disorder. For example, magnetic resonance imaging (MRI) devices are specifically contemplated within the scope of the embodiments, wherein the MRI devices (for example, 3 Tesla MRI devices) are capable of evaluating Meniere Disease progression and subsequent treatment with the pharmaceutical formulations disclosed herein. See, Carfrae et al. Laryngoscope 118:501-505 (March 2008). Whole body scanners, or alternatively cranial scanners, are contemplated, as well as higher resolution (7 Tesla, 8 Tesla, 9.5 Tesla or 11 Tesla for humans) are optionally used in MRI scanning.

General Methods of Sterilization

Provided herein are otic compositions that ameliorate or lessen otic disorders described herein. Further provided herein are methods comprising the administration of said otic compositions. In some embodiments, the compositions are sterilized. Included within the embodiments disclosed herein are means and processes for sterilization of a pharmaceutical composition disclosed herein for use in humans. The goal is to provide a safe pharmaceutical product, relatively free of infection causing micro-organisms. The U.S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety. No specific guidelines are available for safe pharmaceutical products for treatment of the inner ear.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, said low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation); the remaining excipients (e.g., fluid gel components present in auris formulations) are sterilized in a separate step by a suitable method (e.g. filtration and/or irradiation of a cooled mixture of excipients); the two solutions that were separately sterilized are then mixed aseptically to provide a final auris formulation.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions that ameliorate or lessen otic disorders described herein. Further provided herein are methods comprising the administration of said otic compositions. In some embodiments, the compositions are substantially free of microorganisms. Acceptable sterility levels are based on applicable standards that define therapeutically acceptable otic compositions, including but not limited to United States Pharmacopeia Chapters <1111> et seq. For example, acceptable sterility levels include 10 colony forming units (cfu) per gram of formulation, 50 cfu per gram of formulation, 100 cfu per gram of formulation, 500 cfu per gram of formulation or 1000 cfu per gram of formulation. In addition, acceptable sterility levels include the exclusion of specified objectionable microbiological agents. By way of example, specified objectionable microbiological agents include but are not limited to Escherichia coli (E. coli), Salmonella sp., Pseudomonas aeruginosa (P. aeruginosa) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for E. coli and Salmonella includes the use of lactose broths incubated at 30-35° C. for 24-72 hours, incubation in MacConkey and/or EMB agars for 18-24 hours, and/or the use of Rappaport medium. Testing for the detection of P. aeruginosa includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of E. coli LPS. Humans can develop a response to as little as 5 EU/kg of body weight. The sterility is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

pH and Osmolarity

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (i.e., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 7.0 to 8.0, and a preferred pH range of about 7.2-7.9. In some embodiments, the pH of the auris formulations described herein is adjusted (e.g., by use of a buffer) to a perilymph-compatible pH of about 7.0-7.6, and a preferred pH range of about 7.2-7.4.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system. In some embodiments, from about 5 mM to about 200 mM concentration of a buffer is present in the gel formulation. In certain embodiments, from about a 20 mM to about a 100 mM concentration of a buffer is present. In other embodiments, the concentration of buffer is such that a pH of the formulation is between 3 and 9, between 5 and 8, or alternatively between 6 and 7. In other embodiments, the pH of the gel formulation is about 7. In one embodiment is a buffer such as acetate or citrate at slightly acidic pH. In one embodiment the buffer is a sodium acetate buffer having a pH of about 4.5 to about 6.5. In another embodiment the buffer is a sodium acetate buffer having a pH of about 5.5 to about 6.0. In a further embodiment the buffer is a sodium acetate buffer having a pH of about 6.0 to about 6.5. In one embodiment the buffer is a sodium citrate buffer having a pH of about 5.0 to about 8.0. In another embodiment the buffer is a sodium citrate buffer having a pH of about 5.5 to about 7.0. In one embodiment the buffer is a sodium citrate buffer having a pH of about 6.0 to about 6.5.

In some embodiments, the concentration of buffer is such that a pH of the formulation is between 6 and 9, between 6 and 8, between 6 and 7.6, between 7 and 8. In other embodiments, the pH of the gel formulation is about 6.0, about 6.5, about 7 or about 7.5. In one embodiment is a buffer such as tris(hydroxymethyl)aminomethane, bicarbonate, carbonate or phosphate at slightly basic pH. In one embodiment, the buffer is a sodium bicarbonate buffer having a pH of about 7.5 to about 8.5. In another embodiment the buffer is a sodium bicarbonate buffer having a pH of about 7.0 to about 8.0. In a further embodiment the buffer is a sodium bicarbonate buffer having a pH of about 6.5 to about 7.0. In one embodiment the buffer is a sodium phosphate dibasic buffer having a pH of about 6.0 to about 9.0. In another embodiment the buffer is a sodium phosphate dibasic buffer having a pH of about 7.0 to about 8.5. In one embodiment the buffer is a sodium phosphate dibasic buffer having a pH of about 7.5 to about 8.0.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In a specific embodiment the pH of a composition described herein is between about between about 6.0 and about 7.6, between 7 and about 7.8, between about 7.0 and about 7.6, between about 7.2 and about 7.6, or between about 7.2 and about 7.4. In certain embodiments the pH of a composition described herein is about 6.0, about 6.5, about 7.0, about 7.1, about 7.2, about 7.3, about 7.4, about 7.5, or about 7.6. In some embodiments, the pH of any formulation described herein is designed to be compatible with the targeted otic structure (e.g., endolymph, perilymph or the like).

In some embodiments, any gel formulation described herein has a pH that allows for sterilization (e.g, by filtration or aseptic mixing or heat treatment and/or autoclaving (e.g., terminal sterilization)) of a gel formulation without degradation of the otic agent or the polymers comprising the gel. In order to reduce hydrolysis and/or degradation of the otic agent and/or the gel polymer during sterilization, the buffer pH is designed to maintain pH of the formulation in the 7-8 range during the process of sterilization.

In specific embodiments, any gel formulation described herein has a pH that allows for terminal sterilization (e.g, by heat treatment and/or autoclaving) of a gel formulation without degradation of the otic agent or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. P407, CMC) as described herein.

In some embodiments, a pH of between about 6.0 and about 7.6, between about 7 and about 7.8, between about 7.0 and about 7.6, between about 7.2 and 7.6, between about 7.2 and about 7.4 is suitable for sterilization (e.g, by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any composition described herein.

In some embodiments, the formulations described herein have a pH between about 3 and about 9, or between about 4 and 8, or between about 5 and 8, or between about 6 and about 7, or between about 6.5 and about 7, or between about 5.5 and about 7.5, or between about 7.1 and about 7.7, and have a concentration of active pharmaceutical ingredient between about 0.1 mM and about 100 mM. In some embodiments, the formulations described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 1 and about 100 mM. In some embodiments, the formulations described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 50 and about 80 mM. In some embodiments, the concentration of active pharmaceutical ingredient between about 10 and about 100 mM. In other embodiments, the concentration of active pharmaceutical ingredient between about 20 and about 80 mM. In additional embodiments, the concentration of active pharmaceutical ingredient between about 10 and about 50 mM.

In some embodiments, the formulations have a pH as described herein, and include a thickening agent (i.e, a vicosity enhancing agent) such as, by way of non-limiting example, a cellulose based thickening agent described herein. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein, is about 40:1, about 35:1, about 30:1, about 25:1, about 20:1, about 15:1 or about 10:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1 or about 10:1. In some embodiments, the amount of thermoreversible polymer in any formulation described herein is about 10%, about 15%, about 20%, about 25%, about 30%, or about 35% of the total weight of the formulation. In some embodiments, the amount of thermoreversible polymer in any formulation described herein is about 14%, about 15%, about 16%, about 17%, about 18%, about 19%, about 20%, about 21%, about 22%, about 23%, about 24% or about 25% of the total weight of the formulation. In some embodiments, the amount of thickening agent (e.g., a gelling agent) in any formulation described herein is about 1%, 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In some embodiments, auris compositions described herein are formulated to provide an osmolarity of about 250 to about 320 mM (osmolality of about 250 to about 320 mOsm/kg $H_2O$); and preferably about 270 to about 320 mM (osmolality of about 270 to about 320 mOsm/kg $H_2O$). In specific embodiments, osmolarity/osmolality of the present formulations is adjusted, for example, by the use of appropriate salt concentrations (e.g., concentration of potassium salts) or the use of tonicity agents which renders the formulations endolymph-compatible and/or perilymph-compatible (i.e. isotonic with the endolymph and/or perilymph. In some instances, the endolymph-compatible and/or perilymph-compatible formulations described herein cause minimal disturbance to the environment of the inner ear and cause minimum discomfort (e.g., vertigo and/or nausea) to a mammal upon administration.

In some embodiments, any formulation described herein is isotonic with the perilymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfate anions; suitable salts include sodium chloride, potassium chloride, sodium thiosulfate, sodium bisulfite and ammonium sulfate.

In further embodiments, the tonicity agents are present in an amount as to provide a final osmolality of an otic formulation of about 100 mOsm/kg to about 500 mOsm/kg, from about 200 mOsm/kg to about 400 mOsm/kg, from about 250 mOsm/kg to about 350 mOsm/kg or from about 280 mOsm/kg to about 320 mOsm/kg. In some embodiments, the formulations described herein have a osmolarity of about 100 mOsm/L to about 500 mOsm/L, about 200 mOsm/L to about 400 mOsm/L, about 250 mOsm/L to about 350 mOsm/L, or about 280 mOsm/L to about 320 mOsm/L. In some embodiments, the osmolarity of any formulation described herein is designed to be isotonic with the targeted otic structure (e.g., endolymph, perilymph or the like).

In some embodiments, the formulations described herein have a pH and osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and osmolarity as described herein, and have a concentration of active pharmaceutical ingredient between about 0.2-about 20%, between about 0.2-about 10%, between about 0.2-about 7.5%, between about 0.2-5%, between about 0.2-about 3%, between about 0.1-about 2% of the active ingredient by weight of the formulation. In some embodiments, the formulations described herein have a pH and osmolarity as described herein, and have a concentration of active pharmaceutical ingredient between about 0.1-about 70 mg/mL, between about 1 mg-about 70 mg/mL, between about 1 mg-about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some instances, any formulation described herein comprises mulitparticulates, i.e., a plurality of particle sizes (e.g., micronized particles, nano-sized particles, non-sized particles); i.e, the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about picometer-sized in diameter. In some embodiments, the use of multiparticulates (e.g., micronized particles) of an otic agent allows for extended and/or sustained release of the otic agent from any formulation described herein compared to a formulation comprising non-multiparticulate (e.g, non-micronized) otic agent. In some instances, formulations containing multiparticulate (e.g. micronized) otic agents are ejected from a 1 mL syringe adapted with a 27G needle without any plugging or clogging.

In some instances, any particle in any formulation described herein is a coated particle (e.g., a coated micronized particle) and/or a microsphere and/or a liposomal particle. Particle size reduction techniques include, by way of example, grinding, milling (e.g., air-attrition milling (jet milling), ball milling), coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles. In some embodiments, formulations described herein comprise amorphous particles. In some embodiments, formulations described herein comprise therapeutic agent particles wherein the therapeutic agent is a free base, or a salt, or a prodrug of a therapeutic agent, or any combination thereof.

In some instances, a combination of an otic agent and a salt of the otic agent is used to prepare pulsed release otic agent formulations using the procedures described herein. In some formulations, a combination of a micronized otic agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the otic agent (e.g., micronized otic agent, or free base or salt or prodrug thereof; multiparticulate otic agent, or free base or salt or prodrug thereof) with the aid of cyclodextrins, surfactants (e.g., poloxamers (407, 338, 188), tween (80, 60, 20,81), PEG-hydrogenated castor oil, cosolvents like N-methyl-2-Pyrrolidone or the like and preparing pulsed release formulations using any procedure described herein.

In some specific embodiments, any otic formulation described herein comprises one or more micronized otic agents. In some of such embodiments, a micronized otic agent comprises micronized particles, coated (e.g., with an extended release coat) micronized particles, or a combination thereof. In some of such embodiments, a micronized otic agent comprising micronized particles, coated micronized particles, or a combination thereof, comprises an otic agent as a free base, a salt, a prodrug or any combination thereof.

Controlled Release Otic Formulations

In certain embodiments, any controlled release otic formulation described herein increases the exposure of an otic agent and increases the Area Under the Curve (AUC) in otic fluids (e.g., endolymph and/or perilymph) by about 30%, about 40%, about 50%, about 60%, about 70%, about 80% or about 90% compared to a formulation that is not a controlled release otic formulation. In certain embodiments, any controlled release otic formulation described herein increases the exposure of an otic agent and decreases the $C_{max}$ in otic fluids (e.g., endolymph and/or perilymph) by about 40%, about 30%, about 20%, or about 10%, compared to a formulation that is not a controlled release otic formulation. In certain embodiments, any controlled release otic formulation described herein alters (e.g. reduces) the ratio of $C_{max}$ to $C_{min}$ compared to a formulation that is not a controlled release otic formulation. In certain embodiments, the ratio of $C_{max}$ to $C_{min}$ is 10:1, 9:1, 8:1, 7:1, 6:1, 5:1, 4:1, 3:1, 2:1 or 1:1. In certain embodiments, any controlled release otic formulation described herein increases the exposure of an otic agent and increases the length of time that the concentration of an otic agent is above $C_{min}$ by about 30%, about 40%, about 50%, about 60%, about 70%, about 80% or about 90% compared to a formulation that is not a controlled release otic formulation. In certain instances, controlled release formulations described herein delay the time to $C_{max}$. In certain instances, the controlled steady release of a drug prolongs the time the concentration of the drug will stay above the $C_{min}$. In some embodiments, auris compositions described herein prolong the residence time of a drug in the inner ear. In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, or 1 week).

The otic formulations described herein deliver an active agent to the external, middle and/or inner ear, including the cochlea and vestibular labyrinth. Local otic delivery of the auris compositions described herein allows for controlled release of active agents to auris structures and overcomes the drawbacks associated with systemic administration (e.g, low bioavailability of the drug in the endolymph or perilymph, variability in concentration of the drug in the middle and/or internal ear).

Controlled-release options include gel formulations, liposomes, cyclodextrins, biodegradable polymers, dispersable polymers, emulsions, microspheres or microparticles, hydrogels (e.g., a self-assembling hydrogel displaying thixotropic properties that also functions as an absorption enhancer; including instances in which the penetration enhancer is a surfactant comprising an alkyl-glycoside and/or a saccharide alkyl ester), other viscous media, paints, foams, in situ forming spongy materials, xerogels, actinic radiation curable gels, liposomes, solvent release gels, nanocapsules or nanospheres, and combinations thereof; other options or components include mucoadhesives, penetration enhancers, bioadhesives, antioxidants, surfactants, buffering agents, diluents, salts and preservatives. To the extent viscosity considerations potentially limit the use of a syringe/needle delivery system, thermoreversible gels or post-administration viscosity-enhancing options are also envisioned, as well as alternative delivery systems, including pumps, microinjection devices and the like.

In one embodiment of the auris-acceptable aural pressure modulating formulations described herein, the aural pressure modulator is provided in a gel formulation, also referred to herein as "auris acceptable gel formulations," "auris interna-acceptable gel formulations," "auris gel formulations" or variations thereof. All of the components of the gel formulation must be compatible with the auris interna. Further, the gel formulations provide controlled release of the aural pressure modulator to the desired site within the auris interna; in some embodiments, the gel formulation also has an immediate or rapid release component for delivery of the aural pressure modulator to the desired target site.

Provided herein, in some embodiments, are auris formulations that comprise thermoreversible gelling polymers and/or hydrogels. In some instances, the formulations are liquid at or below room temperature but gel at body temperatures. In some instances, intratympanic injection of cold formulations (e.g., formulation with temperatures of <20° C.) causes a dramatic change in the inner ear environment and causes vertigo in individuals undergoing treatment for inner ear disorders. Preferably, the formulations described herein are designed to be liquids that are administered at or near room temperature and do not cause vertigo or other discomfort when administered to an individual or patient.

In some embodiments, the formulations are bimodal formulations and comprise an immediate release component and an extended release component. In some instances, bimodal formulations allow for a constant rate of release of an immediate release component (multiparticulate agent (e.g., micronized active agent)) from the gelled polymer and a constant rate of release of an extended release component (e.g., an encapsulated active agent that serves as a depot for extending the release of an active agent). In other embodiments, the otic compositions described herein are administered as a controlled release formulation, released either continuously or in a pulsatile manner, or variants of both. In still other embodiments, the active agent formulation is administered as both an immediate release and controlled release formulation, released either continuously or in a pulsatile manner, or variants of both. In certain embodiments, the formulations comprise penetration enhancers that allow for delivery of the active agents across the oval window or the round window of the ear.

In some embodiments, the auris gel formulations are biodegradable. In other embodiments, the auris gel formulations include a mucoadhesive excipient to allow adhesion to the external mucous membrane of the round window. In yet other embodiments, the auris gel formulations include a penetration enhancer excipient; in further embodiments, the auris gel formulation contains a viscosity enhancing agent. In other embodiments, the auris pharmaceutical formulations provide an auris-acceptable microsphere or microparticle; in still other embodiments, the auris pharmaceutical formulations provide an auris-acceptable liposome, in yet other embodiments, the auris pharmaceutical formulations provide an auris-acceptable paint, foam or xerogel. In other embodiments, the auris pharmaceutical formulations provide an auris-acceptable in situ forming spongy material. Further embodiments include a thermoreversible gel or actinic radiation curable gel in the auris pharmaceutical formulation, such that upon preparation of the gel at room temperature or below, the formulation is a fluid, but upon application of the gel into or near the auris interna and/or auris media target site, including the tympanic cavity, round window membrane or the *crista* *fenestrae* *cochleae*, the auris-pharmaceutical formulation stiffens or hardens into a gel-like substance. Some embodiments include the use of a combination of a mucoadhesive and a thermoreversible gel in any otic formulation described herein.

The formulations disclosed herein alternatively encompass an otoprotectant agent in addition to the at least one active agent and/or excipients, including but not limited to such as antioxidants, alpha lipoic acid, calicum, fosfomycin or iron chelators, to counteract potential ototoxic effects that may arise from the use of specific therapeutic agents or excipients, diluents or carriers.

One aspect of the embodiments disclosed herein is to provide a controlled release aural pressure modulating auris-acceptable composition or formulation for the treatment of fluid homeostasis disorders. The controlled release aspect of the compositions and/or formulations disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable microsphere, an auris-acceptable hydrogel, an auris-acceptable liposome, an auris-acceptable nanocapsule or nanosphere, an auris-acceptable thermoreversible gel, or combinations thereof.

Thus, provided herein are pharmaceutical compositions that include at least one auris therapeutic agent and auris-acceptable diluent(s), excipient(s), and/or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

Auris-Acceptable Gel Formulations

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels can further consist of a single-phase or a two-phase system. A single-phase gel consists of organic macromolecules distributed uniformly throughout a liquid in such a manner that no apparent boundaries exist between the dispersed macromolecules and the liquid. Single-phase gels are usually prepared from synthetic macromolecules (e.g., Carbomer®) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. The bases of a hydrophobic gel usually consists of a liquid paraffin with polyethylene or fatty oils gelled with colloidal silica, or aluminum or zinc soaps. In contrast, the bases of hydrophobic gels usually consists of water, glycerol, or propylene glycol gelled with a suitable gelling agent (e.g., tragacanth, starch, cellulose derivatives, carboxyvinylpolymers, and/or magnesium-aluminum silicates).

In certain embodiments, the rheology of the gel formulation is pseudo plastic, plastic, thixotropic, or dilatant.

Thermoreversible Gels

Polymers composed of polyoxypropylene and polyoxyethylene are known to form thermoreversible gels when incorporated into aqueous solutions. These polymers have the ability to change from the liquid state to the gel state at temperatures close to body temperature, therefore allowing useful topical formulations. The liquid state-to-gel state phase transition is dependent on the polymer concentration and the ingredients in the solution.

"ReGel™" is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(ortho ester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly (ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 daltons. The hydrophilic B-block segment is preferably polyethylene glycol (PEG) having an average molecular weight of between about 500 and 2200 daltons.

Additional biodegradable thermoplastic polyesters include AtriGel™ (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly (DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Additional embodiments include Poloxamer thermoreversible copolymers. Poloxamer 407 (PF-127) is a nonionic surfactant composed of polyoxyethylene-polyoxypropylene copolymers. Other commonly used poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. It contains approximately 70% ethylene oxide, which accounts for its hydrophilicity. It is one of the series of poloxamer ABA block copolymers, whose members share the chemical formula shown below.

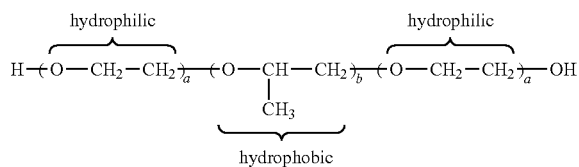

P-F127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a controlled release depot. Furthermore, PF-127 has good solubilizing capacity, low toxicity and is, therefore, considered a good medium for drug delivery systems.

In an alternative embodiment, the thermogel is a PEG-PGLA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PGLA copolymer can range from about 1:1 to about 20:1. The resulting coploymers are soluble in water and form a free-flowing liquid at room temperature, but form a hydrogel at body temperature. A commercially available PEG-PGLA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

In some embodiments, a suitable combination of gelling agents and a thermoreversible gel is utilized in the controlled release formulations described herein. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the thickening agents (i.e., viscosity enhancing agents) described herein are also utilized as the gelling agent for the gel formulations presented herein.

Suitable combinations of thermoreversible gels with a thickening agent include, by way of non-limiting example, a combination of poloxamer thermoreversible copolymers with cellulose based thickening agents described herein. In some instances, the addition of a secondary polymer (e.g., a thickening agent) introduces a diffusional barrier and reduces the rate of release of the otic agent. An appropriate thickening agent (e.g., a cellulose based polymer, e.g., CMC polymer) is selected based on the viscosity of a 2% solution of the secondary polymer (e.g., CMC); the selected secondary polymer (e.g., CMC) provides a 2% polymer solution with viscosity less than 15,000 cP. In specific formulations, the selected secondary polymer (e.g., CMC) provides a 2% polymer solution with viscosity from about 4,000 cP to about 10,000 cP. In some embodiments, the ratio of a thermoreversible poloxamer to a gelling agent is about 50:1, about 40:1, about 35:1, about 30:1, about 25:1, about 20:1, about 15:1 or about 10:1. For example, in certain embodiments, a controlled release formulation described herein comprises a combination of poloxamer 407 (pluronic F127) and carboxymethylcellulose (CMC) in a ratio of about 50:1, 40:1, about 35:1, about 30:1, about 25:1, about 20:1, about 15:1 or about 10:1.

Hydrogels

Chitosan glycerophosphate (CGP) is a biodegradable matrix for the formation of hydrogels. CGP has been shown to be suitable for local delivery of dexamethasone to the inner ear, where 50% of the active agent was released after 24 hours, followed by a linear decline over 5 days of perilymph drug levels. In some embodiments, CGP is used as a biodegradable viscosity enhancing agent or gelling agent for controlled release of active agents from the formulations disclosed herein. In certain embodiments, when CGP is used as a viscosity enhancing agent or gelling agent, the compositions further comprise liposomes. Liposomes are added to further control the release of active agents from the formulations disclosed herein, whether they be hydrophobic or hydrophilic antimicrobial small molecules.

In some embodiments, other gel formulations are also contemplated to be useful depending upon the particular embodiment, and as such are considered to fall within the scope of the present disclosure. For example, other currently commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the formulations described herein. In some embodiments, gels include, but are not limited to, alginate hydrogels SAF-Gel (ConvaTec, Princeton, N.J.), Duoderm Hydroactive Gel (ConvaTec), Nu-gel (Johnson & Johnson Medical, Arlington, Tex.); Carrasyn (V) Acemannan Hydrogel (Carrington Laboratories, Inc., Irving, Tex.); glycerin gels Elta Hydrogel (Swiss-American Products, Inc., Dallas, Tex.) and K-Y Sterile (Johnson & Johnson). In one embodiment, a sterilized solution of sodium alginate is mixed with a sterilized solution of an auris-compatible calcium salt, the therapeutic agent(s), and a polysaccharide. Upon admixing, a gel is formed in a desired amount of time having a desired viscosity. In further embodiments, biodegradable biocompatible gels also represent compounds present in formulations disclosed and described herein. In some embodiments, a hardening agent (e.g., glutaraldehyde, formaldehyde) is added to a biodegradable hydrogel gel. Contemplated for use in formulations described herein are biodegradable hydrogels comprising, by way of example, 0.1, 0.5, 1, 1.5, 2, 2.5, 3, 3.5, 4, 4.5, 5, 6, 7, 8, 9, 10, 15, 20, 25, 30, 40, 50, 60, 70, 80, 90 or 100 mM glutaraldehyde (e.g., a gelatin gel and/or a glycerin gel and/or a chitosan hydrogel comprising 10 mM glutaraldehyde). In further embodiments, biodegradable biocompatible gels also represent compounds present in auris-acceptable formulations disclosed and described herein. For examples, of formulations and their characteristics see Table 1.

In some formulations developed for administration to a mammal, and for compositions formulated for human administration, the gel comprises substantially all of the weight of the composition. In other embodiments, the gel comprises as much as about 98% or about 99% of the composition by weight. In a further embodiment, this is desirous when a substantially non-fluid, or substantially viscous formulation is needed. In a further embodiment, when slightly less viscous, or slightly more fluid formulations are desired, the biocompatible gel portion of the formulation comprises at least about 50% by weight, at least about 60% by weight, at least about 70% by weight, or even at least about 80% or 90% by weight of the compound. Of course, all intermediate integers within these ranges are contemplated to fall within the scope of this disclosure, and in some embodiments, even more fluid (and consequently less viscous) gel compositions are formulated, such as for example, those in which the gel or matrix component of the mixture comprises not more than about 50% by weight, not more than about 40% by weight, not more than about 30% by weight, or even those in which comprise not more than about 15% or about 20% by weight of the composition.

If desired, the gels may also contain preservatives, cosolvents, suspending agents, viscosity enhancing agents, ionic-strength and osmolality adjustors and other excipients in addition to buffering agents. Suitable water soluble preservatives which are employed in the drug delivery vehicle are sodium bisulfate, sodium thiosulfate, ascorbate, benzalkonium chloride, chorobutanol, thimerosal, parabens, benzyl alcohol, phenylethanol and others. These agents are present, generally, in amounts of about 0.001% to about 5% by weight and, preferably, in the amount of about 0.01 to about 2% by weight.

Suitable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent can be as much as 5% on a weight basis of the total composition.

Cosolvents can be used to enhance drug solubility, however, some drugs are insoluble. These can often be suspended in the polymer vehicle with the aid of suitable suspending or viscosity enhancing agents.

Since the polymer systems of the thermoreversible gel dissolve more completely at reduced temperatures, the preferred methods of solubilization are to add the required amount of polymer to the amount of water to be used. Generally after wetting the polymer by shaking, the mixture is capped and placed in a cold chamber or in a thermostatic container at about 0-10° C. in order to dissolve the polymer. The mixture can be stirred or shaken to bring about a more rapid dissolution of the polymer. The active pharmaceutical ingredient and various additives such as buffers, salts, and preservatives can subsequently be added and dissolved. In some embodiments the pharmocologically active substance is suspended if it is insoluble in water. The pH is modulated by the addition of appropriate buffering agents.

In certain embodiments, the polymer systems of the thermoreversible gels are designed to remain liquids up to temperatures of about 15-25° C., about 18-22° C., or about 20° C. In some instances, the formulations described herein are manufactured under conditions such that the temperature of the manufacturing room is maintained below 25° C. to retain the temperature of a polymer solution at about 25° C., about 23° C., about 21° C., or about 19° C. In certain instances, the formulations described herein are manufactured under conditions such that the temperature of a manufacturing room is maintained at about 19° C. In some of such instances, the temperature of the polymer solution is maintained at or below about 19° C. up to 3 hours of the initiation of the manufacturing, without the need to chill/cool the container. In some instances, the temperature of the solution is maintained at or below about 19° C. up to 3 hours of the initiation of the manufacturing by use of a jacketed container for the polymer solution.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, that is, as the solvent in the injected gel formulation diffuses out the gel, a gel having the desired gel properties is formed. For example, a formulation that comprises sucrose acetate isobutyrate, a pharmaceutically acceptable solvent, one or more additives, and the auris therapeutic agent is administered at or near the round window membrane: diffusion of the solvent out of the injected formulation provides a depot having the desired gel properties. For example, use of a water soluble solvent provides a high viscosity depot when the solvent diffuses rapidly out of the injected formulation. On the other hand, use of a hydrophobic solvent (e.g., benzyl benzoate) provides a less viscous depot. One example of an auris-acceptable solvent release gel formulation is the SABER™ Delivery System marketed by DURECT Corporation.

Presented below are examples of potential controlled release excipients:

| Example Formulation | Example Characteristics |
|---|---|
| Chitosan glycerophosphate (CGP) | tunable degradation of matrix in vitro |
| | tunable VP2 modulator release in vitro: e.g., ~50% of drug released after 24 hrs |
| | biodegradable |
| | compatible with drug delivery to the inner ear |
| |

| Example Formulation | Example Characteristics |
|---|---|
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP formulation tolerates liposomes: e.g., up to 15 uM/mL liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

Auris Interna Mucoadhesive Excipients

Mucoadhesive characteristics may also be imparted to the gel or other auris-interna formulations disclosed herein, including a thermoreversible gel, by incorporation of mucoadhesive carbomers, such as Carbopol 934P, to the composition (Majithiya et al, AAPS PharmSciTech (2006), 7(3), p. E1; EP0551626).

The term 'mucoadhesion' is commonly used for materials that bind to the mucin layer of a biological membrane. To serve as mucoadhesive polymers, the polymers should possess some general physiochemical features such as predominantly anionic hydrophilicity with numerous hydrogen bond forming groups, suitable surface property for wetting mucus/mucosal tissue surfaces and sufficient flexibility to penetrate the mucus network. In some embodiments, mucoadhesive formulations described herein adhere to the round window and/or the oval window and/or any inner ear structure.

Mucoadhesive agents including, but not limited to, at least one soluble polyvinylpyrrolidone polymer (PVP); a water-swellable, but water-insoluble, fibrous, cross-linked carboxy-functional polymer; a crosslinked poly(acrylic acid) (e.g. Carbopol 947P); a carbomer homopolymer; a carbomer copolymer; a hydrophilic polysaccharide gum, maltodextrin, a cross-linked alignate gum gel, a water-dispersible polycarboxylated vinyl polymer, at least two particulate components selected from the group consisting of titanium dioxide, silicon dioxide, and clay, or a mixture thereof. The mucoadhesive agent are used in combination with a viscosity increasing excipient, or are used alone to increase the interaction of the composition with a mucosal layer. In one non-limiting example, the mucoadhesive agent is maltodextrin and/or an alginate gum. Those of ordinary skill in the art will recognize that the mucoadhesive character imparted to the composition should be at a level that is sufficient to deliver an effective amount of the composition to, for example, the mucosal membrane of the round window in an amount that may coat the mucosal membrane, and thereafter deliver the composition to the affected areas, including by way of example only, the vestibular and/or cochlear structures of the auris interna. Those of ordinary skill in the art can determine the mucoadhesive characteristics of the compositions provided herein, and may thus determine appropriate ranges. One method for determining sufficient mucoadhesiveness may include monitoring changes in the interaction of the composition with a mucosal layer, including but not limited to measuring changes in residence or retention time of the composition in the absence and presence of the excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference in its entirety.

In one non-limiting example, the mucoadhesive agent is maltodextrin. Maltodextrin is a carbohydrate produced by the hydrolysis of starch that are derived from corn, potato, wheat or other plant products. Maltodextrin are used either alone or in combination with other mucoadhesive agents to impart mucoadhesive characteristics on the compositions disclosed herein. In one embodiment, a combination of maltodextrin and a carbopol polymer are used to increase the mucoadhesive characteristics of the compositions disclosed herein.

In another non-limiting example, a mucoadhesive agent can be, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, are selected from the group consisting of fumed silicon dioxide, precipitated silicon dioxide, coacervated silicon dioxide, gel silicon dioxide, and mixtures thereof. Clay, if present, are kaolin minerals, serpentine minerals, smectites, illite or a mixture thereof. For example, clay can be laponite, bentonite, hectorite, saponite, montmorillonites or a mixture thereof.

Stabilizers

In one embodiment, stabilizers are selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In a further embodiment, the chosen stabilizer changes the hydrophobicity of the formulation (e.g., oleic acid, waxes), or improves the mixing of various components in the formulation (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In a further embodiment, stabilizers are present in sufficient amount to inhibit the degradation of the active pharmaceutical ingredient. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful auris-acceptable formulations include one or more anti-aggregation additives to enhance stability of otic formulations by reducing the rate of protein aggregation. The anti-aggregation additive selected depends upon the nature of the conditions to which the otic agents, for example anti-TNF antibodies are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as quarternary ammonium compounds, benzalkonium chloride, cetyltrimethylammonium bromide, and lauryldimethylbenzyl-ammonium chloride.

In a further embodiment, when one or more co-surfactants are utilized in the formulations of the present disclosure, they are combined, e.g., with a pharmaceutically acceptable vehicle and is present in the final formulation, e.g., in an amount ranging from about 0.1% to about 20%, from about 0.5% to about 10%. In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

Preservatives

In some embodiments, an auris controlled release formulation described herein is free of preservatives. In some embodiments, a composition disclosed herein comprises a preservative. Suitable auris-acceptable preservatives for use in a composition disclosed herein include, but are not limited to benzoic acid, boric acid, p-hydroxybenzoates, benzyl alcohol, lower alkyl alcohols (e.g., ethanol, butanol or the like), quaternary compounds, stabilized chlorine dioxide, mercurials, such as merfen and thiomersal, mixtures of the foregoing and the like. Suitable preservatives for use with a formulation disclosed herein are not ototoxic. In some embodiments, a formulation disclosed herein does not include a preservative that is ototoxic. In some embodiments, a formulation disclosed herein does not include benzalkonium chloride or benzethonium chloride.

In certain embodiments, any controlled release formulation described herein has an endotoxin level of less than 0.5 EU/kg, less than 0.4 EU/kg or less than 0.3 EU/kg. In certain embodiments, any controlled release formulation described herein has less than about 60 colony forming units (CFU), has less than about 50 colony forming units, has less than about 40 colony forming units, has less than about 30 colony forming units of microbial agents per gram of formulation. In certain embodiments, any controlled release formulation described herein is substantially free of pyrogens.

In a further embodiment, the preservative is, by way of example only, an antimicrobial agent, within the formulation presented herein. In one embodiment, the formulation includes a preservative such as by way of example only, methyl paraben. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the active pharmaceutical ingredient disclosed herein. In certain embodiments, the preservative employed in any auris-compatible formulation described herein is an antioxidant (e.g., butyl hydroxytoluene (BHT) or the like, as described herein). In certain embodiments, an antioxidant preservative is non-toxic and/or non-irritating to the inner ear environment.

Carriers

Suitable carriers for use in a formulation described herein include, but are not limited to, any pharmaceutically acceptable solvent. For example, suitable solvents include polyalkylene glycols such as, but not limited to, polyethylene glycol (PEG) and any combinations or mixtures thereof. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, benzalkonium chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithins, phospholipids, phosphatidyl cholines (c8-c18), phosphatidylethanolamines (c8-c18), phosphatidylglycerols (c8-c18), pharmaceutical acceptable salts thereof and combinations or mixtures thereof.

In further embodiments, the carrier is polyethylene glycol. Polyethylene glycol is available in many different grades having varying molecular weights. For example, polyethylene glycol is available as PEG 200; PEG 300; PEG 400; PEG 540 (blend); PEG 600; PEG 900; PEG 1000; PEG 1450; PEG 1540; PEG 2000; PEG 3000; PEG 3350; PEG 4000; PEG 4600 and PEG 8000. For purposes of the present disclosure, all grades of polyethylene glycol are contemplated for use in preparation of a formulation described herein. In some embodiments the polyethylene glycol used to prepare a formulation described herein is PEG 300.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based thickened formulations utilized in the preparation of pharmaceutical delivery vehicles that comprise at least one active pharmaceutical ingredient contains at least about 0.1% of the water-soluble glycerin compound or more. In some embodiments, the percentage of active pharmaceutical ingredient is varied between about 1% and about 95%, between about 5% and about 80%, between about 10% and about 60% or more of the weight or volume of the total pharmaceutical formulation. In some embodiments, the amount of the compound(s) in each therapeutically useful formulation is prepared in such a way that a suitable dosage will be obtained in any given unit dose of the compound. Factors such as solubility, bioavailability, biological half-life, route of administration, product shelf life, as well as other pharmacological considerations are contemplated herein and the preparation of such pharmaceutical formulations is presented herein.

Suspending Agents

In one embodiment is a active pharmaceutical ingredient in a pharmaceutically acceptable thickened formulation wherein the formulation comprises at least one suspending agent.

In one embodiment, at least one cytotoxic agent is included in a pharmaceutically acceptable enhanced viscosity formulation wherein the formulation further comprises at least one suspending agent, wherein the suspending agent assists in imparting controlled release characteristics to the formulation. In some embodiments, suspending agents also serve to increase the viscosity of the auris-acceptable cytotoxic agent formulations and compositions.

Suspending agents include by example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides compositions comprising a therapeutically effective amount of an active pharmaceutical ingredient in a hydroxyethyl cellulose gel. Hydroxyethyl cellulose (HEC) is obtained as a dry powder which can be reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% and about 2%.

In some embodiments, the formulations include excipients, other medicinal or pharmaceutical agents, carriers, adjuvants, such as preserving, stabilizing, wetting or emulsifying agents, solution promoters, and salts. In some embodiments, the excipients, carriers, adjuvants, are useful in forming a pharmaceutically acceptable thickened formulation. In some embodiments, the thickened formulation comprises a stabilizer. In another embodiment the formulation comprises a solubilizer. In a further embodiment the formulation comprises an antifoaming agent. In yet a further embodiment, the formulation comprises an antioxidant. In yet another embodiment, the formulation comprises a dispersing agent. In one embodiment, the formulation comprises a surfactant. In yet another embodiment, the formulation comprises a wetting agent.

Viscosity Enhancing Agents

In one embodiment is a thickened formulation comprising at least one active pharmaceutical ingredient and a viscosity agent. Also described herein are controlled release formulations comprising an aural pressure modulating agent and a viscosity enhancing agent. Suitable viscosity-enhancing agents include by way of example only, gelling agents and suspending agents. In one embodiment, the enhanced viscosity formulation does not include a pharmaceutically acceptable buffer. In other embodiments, the enhanced viscosity formulation includes a pharmaceutically acceptable buffer. Sodium chloride or other tonicity agents are optionally used to adjust tonicity, if necessary.

Described herein are formulations comprising an active pharmaceutical ingredient and a thickening agent. Suitable thickening agents include by way of example only, gelling agents and suspending agents. In one embodiment, the thickened formulation does not include a pharmaceutically acceptable buffer. In another embodiment, the thickened formulation includes a pharmaceutically acceptable buffer.

By way of example only, the auris-acceptable viscosity agent include hydroxypropyl methylcellulose, hydroxyethyl cellulose, polyvinylpyrrolidone (PVP: povidone), carboxymethyl cellulose, polyvinyl alcohol, sodium chondrointin sulfate, sodium hyaluronate. Other viscosity agents that are used in pharmaceutical compositions described herein include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, Splenda® (dextrose, maltodextrin and sucralose) or combinations thereof. In specific embodiments, the viscosity-enhancing excipient is a combination of methylcellulose (MC) and CMC. In another embodiment, the viscosity-enhancing agent is a combination of carboxymethylated chitosan, or chitin, and alginate. The combination of chitin and alginate with the CNS modulators disclosed herein acts as a controlled release formulation, restricting the diffusion of the CNS modulator from the formulation. Moreover, the combination of carboxymethylated chitosan and alginate is optionally used to assist in increasing the permeability of any active agent described herein through the round window membrane.

In one embodiment, the pharmaceutically acceptable thickened formulation comprises at least one gelling agent. In one embodiment, the pharmaceutical formulation is a thickened formulation comprising at least one active pharmaceutical ingredient wherein the compound is utilized at a concentration of about 0.005 mg to about 5 mg per gram of gelling agent. In another embodiment is an active pharmaceutical ingredient utilized at a concentration of about 1 mg to about 5 mg per gram of gelling agent. In another embodiment is an active pharmaceutical ingredient utilized at a concentration of about 0.005 mg to about 0.05 mg per gram of gelling agent. In another embodiment is an active pharmaceutical ingredient utilized at a concentration of about 0.05 mg to about 0.5 mg per gram of gelling agent. In another embodiment is an active pharmaceutical ingredient utilized at a concentration of about 0.5 mg to about 5 mg per gram of gelling agent. In another embodiment is an active pharmaceutical ingredient utilized at a concentration of about 0.1 mg to about 5 mg per gram of gelling agent.

In some embodiments is a thickened formulation comprising from about 0.1 mM and about 100 mM of an active pharmaceutical ingredient, a pharmaceutically acceptable viscosity agent, and water for injection, the concentration of the viscosity agent in the water being sufficient to provide a thickened formulation with a final apparent viscosity from about 100 to about 1,000,000 cP. In certain embodiments, the viscosity of the gel is in the range from about 100 to about 500,000 cP, about 100 cP to about 1,000 cP, about 500 cP to about 1500 cP, about 1000 cP to about 3000 cP, about 2000 cP to about 8,000 cP, about 4,000 cP to about 10,000 cP, about 10,000 cP to about 50,000 cP. In further embodiments, the auris gel formulation contains a viscosity enhancing agent sufficient to provide a viscosity of between about 500 and 1,000,000 centipoise, between about 750 and 1,000,000 centipoise; between about 1000 and 40,000 centipoise; between about 2000 and 35,000 centipoise; between about 3000 and 30,000 centipoise; between about 4000 and 25,000 centipoise; between about 5000 and 20,000 centipoise; or between about 6000 and 15,000 centipoise.

In other embodiments, when an even more viscous medium is desired, the biocompatible gel comprises at least about 35%, at least about 45%, at least about 55%, at least about 65%, at least about 70%, at least about 75%, or even at least about 80% or so by weight of the active pharmaceutical ingredient. In highly concentrated samples, the biocompatible thickened formulation comprises at least about 65%, at least about 75%, at least about 85%, at least about 90% or at least about 95% or more by weight of the active pharmaceutical ingredient.

Figure 2:
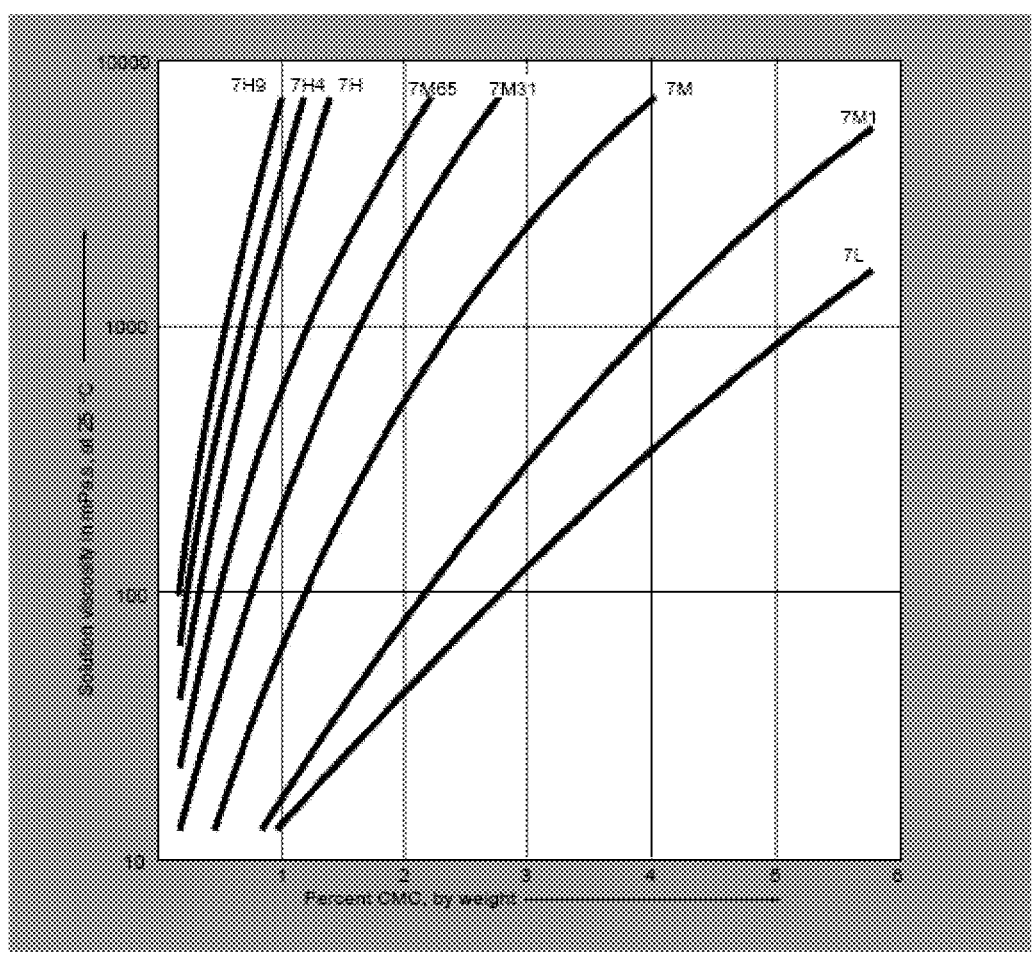
FIG. 2 illustrates the effect of concentration on viscosity of aqueous solutions of Blanos refined CMC.
Figure 3:
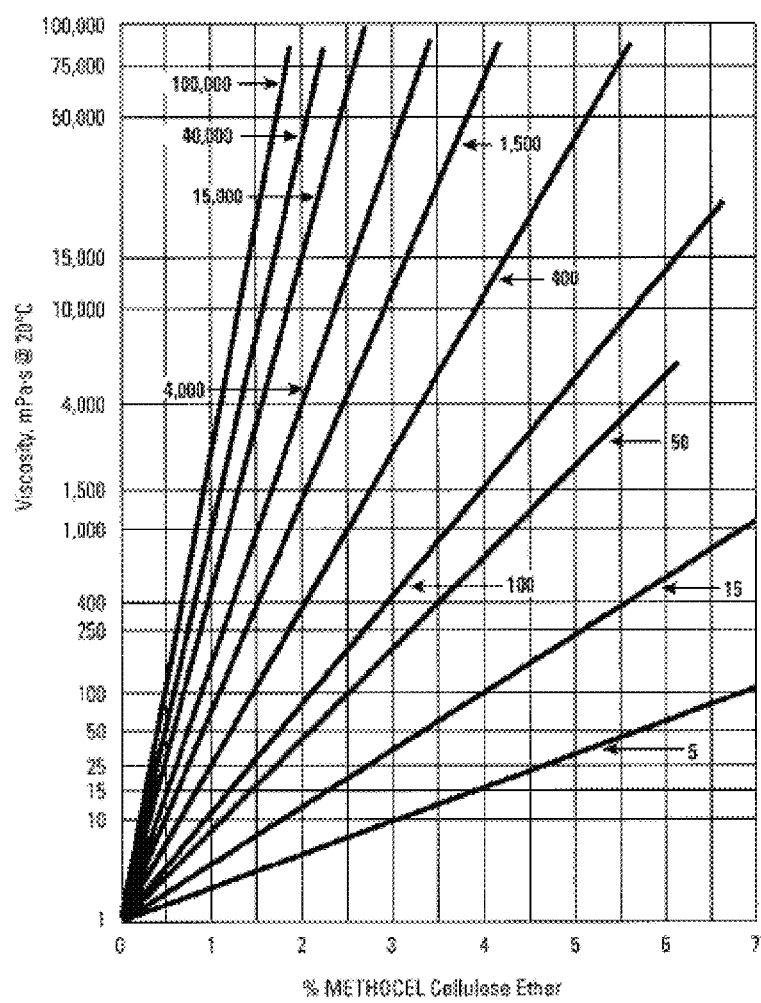
FIG. 3 illustrates the effect of concentration on viscosity of aqueous solutions of Methocel.
Figure 4:
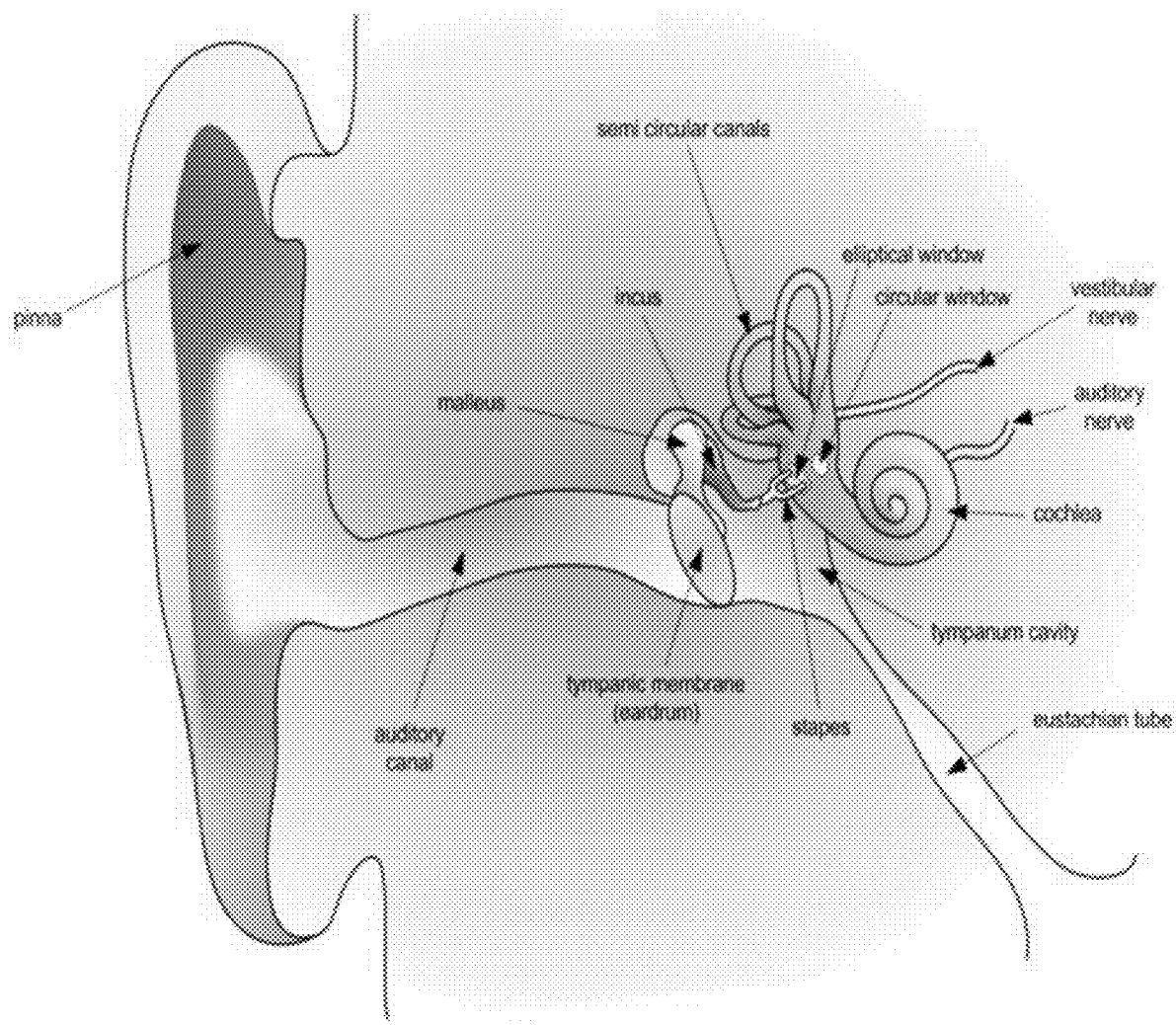
FIG. 4 illustrates the anatomy of the ear.

In some embodiments, the viscosity of any formulation described herein is designed to provide an optimal rate of release from a otic compatible gel. In some specific embodiments, a formulation viscosity of at least 700 cP (e.g., at 20° C., i.e, at 2 degrees below Tgel, measured at a shear rate of 0.6 s$^{-1}$) substantially decreases the release rate of an otic agent from a gel, i.e, substantially increases the mean dissolution time (MDT) of an otic agent. In specific embodiments, the rate of release of an otic agent from a formulation described herein is modulated by the incorporation of a secondary polymer. In specific embodiments, water soluble polymer, (e.g., cellulose based polymers (e.g., sodium carboxymethylcellulose), or poloxamer or the like) is incorporated as a secondary polymer for modulation of the release rate and/or mean dissolution time of an otic agent from a formulation described herein. In some instances, the concentration and grade of polymers is selected by the use of graphs shown in FIGS. 2 and 3 for commonly available water soluble polymers.

In some instances, a combination of polymers (e.g, a poloxamer and a cellulose based polymer) provides a viscosity that is greater than the viscocity of a formulation comprising a single polymer (e.g., a poloxamer). In specific embodiments, a combination of a poloxamer and a cellulose based polymer (e.g., sodium carboxymethylcellulose) provides a composition of viscosity above 500 cP, above 300 cP or above 100 cP.

In one embodiment the thickened formulation described herein is not a liquid at room temperature. In other embodiments, the thickened formulation described herein is a liquid at room temperature. In some embodiments, the viscosity of the gel formulations presented herein are measured by any means described herein. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature. In certain embodiments, the thickened formulation is characterized by a phase transition between room temperature and body temperature. In some embodiments, the phase transition occurs at 1° C. below body temperature, at 2° C. below body temperature, at 3° C. below body temperature, at 4° C. below body temperature, at 6° C. below body temperature, at 8° C. below body temperature, at 10° C. below body temperature.

In some embodiments, the gel formulations are designed to be liquids at or about room temperature. In some instances, intratympanic injection of cold formulations (e.g., formulation with temperatures of <20° C.) causes vertigo. In some embodiments, the gel formulations are injected as liquids at temperatures of about 15° C. to about 25° C., about 18° C. to about 22° C., or about 20° C.

In some instances, auris-acceptable gel formulations do not require the use of a thickening agent. Such gel formulations incorporate at least one pharmaceutically acceptable buffer. In one aspect is a gel formulation comprising an active pharmaceutical ingredient and a pharmaceutically acceptable buffer. In another embodiment, the pharmaceutically acceptable excipient or carrier is a gelling agent.

Auris-Acceptable Penetration Enhancers

In another embodiment the formulation further comprises one or more penetration enhancers.

Penetration into biological membranes can be enhanced by the presence of penetration enhancers. Penetration enhancers are chemical entities that facilitate transport of coadministered substances across biological membranes. Penetration enhancers can be grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates and the like, function as penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acyl-carnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, propylene glycol, polyethylene glycol, glycerol, propanediol and the like) also function as penetration enhancers. In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derviatives and enable drug absorption by passive transcellular diffusion without affecting the integrity of membranes or intercellular tight junctions. In some embodiments, a penetration enhancer is hyaluronic acid.

In some embodiments, the auris acceptable penetration enhancer is a surfactant. In some embodiments, the auris acceptable penetration enhancer is a surfactant comprising an alkyl-glycoside and/or a saccharide alkyl ester. As used herein, an "alkyl-glycoside" means a compound comprising any hydrophilic saccharide (e.g. glucose, fructose, sucrose, maltose, or glucose) linked to a hydrophobic alkyl. In some embodiments, the auris acceptable penetration enhancer is a surfactant comprising an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the auris acceptable penetration enhancer is a surfactant comprising hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea on an alkyl chain; long chain aliphatic carbonic acid ureides of sucrose β-amino-alkyl ethers and long chain aliphatic carbonic acid amides of sucrose β-amino-alkyl ethers. In some embodiments, the auris acceptable penetration enhancer is a surfactant comprising an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the auris acceptable penetration enhancer is a surfactant comprising an alkyl-glycoside wherein the alkyl glycoside is dodecylmaltoside, tridecylmaltoside, and tetradecylmaltoside. In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D- glucopyranosyl-β-glycopyranoside, and/or n-tetradecyl-4-O-α-D-glucopyranosyl-β-glycopyranoside. In some embodiments, the auris acceptable penetration enhancer is a surfactant comprising an alkyl-glycoside wherein the alkyl-glycoside has a critical miscelle concentration (CMC) of less than about 1 mM in poure water or in aqueous solutions. In some embodiments, the auris acceptable penetration enhancer is a surfactant comprising an alkyl-glycoside wherein an oxygen atom within the alkyl-glycoside is substituted with a sulfur atom. In some embodiments, the auris acceptable penetration enhancer is a surfactant comprising an alkyl-glycoside wherein the alkylglycoside is the β anomer. In some embodiments, the auris acceptable penetration enhancer is a surfactant comprising an alkyl-glycoside wherein the alkylglycoside comprises 90%, 91%, 92%, 93%, 94%, 95%, 96%, 97%, 98%, 99%, 99.1%, 99.5%, or 99.9% of the anomer.

In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)).

Foams and Paints

In some embodiments, the auris therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which are lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated in its entirety. The paints contemplated for use herein, are flexible such that they do not interfere with the propagation of pressure waves through the ear. Further, the paints are applied as a liquid (i.e. solution, suspension, or emulsion), a semisolid (i.e. a gel, foam, paste, or jelly) or an aerosol.

In some embodiments, the auris therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilised with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

Auris-Acceptable In-Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired auris therapeutic agent and placed within the auris media so as to provide controlled release of the auris therapeutic agent within the auris media, or in contact with the round window membrane so as to provide controlled release of the auris therapeutic agent into the auris interna. In some embodiments, the spongy material is biodegradable.

Cyclodextrin Formulations

In a specific embodiment, the formulation alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives. Some of the more common derivatives of cyclodextrin are hydroxypropyl ethers, sulfonates, and sulfoalkylethers. Shown below is the structure of β-cyclodextrin and the hydroxypropyl-β-cyclodextrin (HPβCD).

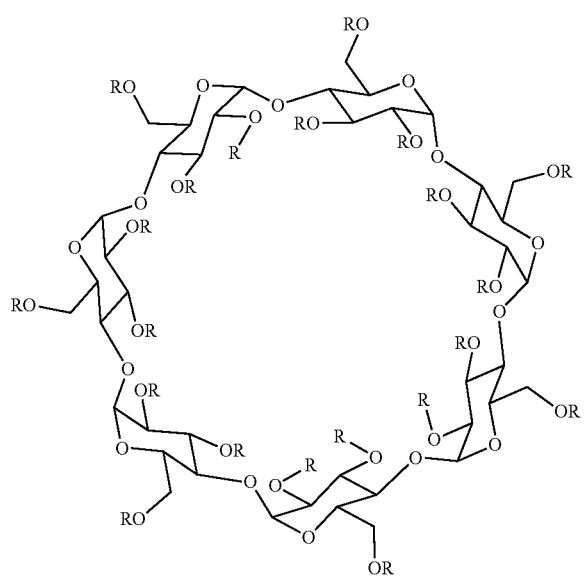

R = H
β-cyclodextrin

R = CH$_2$CH(OH)CH$_3$
hydroxypropyl β-cyclodextrin

The use of cyclodextrins in pharmaceutical compositions is well known in the art as cyclodextrins and cyclodextrin derivatives are often used to improve the solubility of a drug. Inclusion compounds are involved in many cases of enhanced solubility; however other interactions between cyclodextrins and insoluble compounds can also improve solubility. Hydroxypropyl-β-cyclodextrin (HPβCD) is commercially available as a pyrogen free product. It is a non-hygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the auris-acceptable otic agents within the formulations described herein. In other embodiments, cyclodextrins in addition serve as controlled release excipients within the formulations described herein.

Preferred cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein can vary according to the physiochemical properties, pharmacokinetic properties, side effect or adverse events, formulation considerations, or other factors associated with the therapeutically active agent, or a salt or prodrug thereof. The properties of other excipients in a composition may also be important. Thus, the concentration or amount of cyclodextrin used in accordance with the compositions and methods disclosed herein can vary.

In certain embodiments, the formulation further comprise a suitable viscosity agent, such as hydroxypropyl methylcellulose, hydroxyethyl cellulose, polyvinylpyrrolilidone, carboxymethyl cellulose, polyvinyl alcohol, sodium chondrointin sulfate, sodium hyaluronate etc. as a dispersant, if necessary. A nonionic surfactant such as polysorbate 80, polysorbate 20, tyloxapol, Cremophor, HCO 40 etc. is optionally used. In certain embodiments, the preparations optionally contain a suitable buffering system, such as phosphate, citrate, borate, tris, etc., and pH regulators such as sodium hydroxide and hydrochloric acid also are optionally used in the formulations of the inventions. Sodium chloride or other tonicity agents are also used to adjust tonicity, if necessary.

Auris Acceptable Microspheres and Nanospheres

Otic agents and/or other pharmaceutical agents disclosed herein are optionally incorporated within controlled release particles, lipid complexes, liposomes, nanoparticles, microspheres, nanocapsules or other agents which enhance or facilitate the localized delivery of the otic agent. In some embodiments, a single thickened formulation is used, in which at least one active pharmaceutical ingredient is present, while in other embodiments, a pharmaceutical formulation that comprises a mixture of two or more distinct thickened formulations is used, in which at least one active pharmaceutical ingredient is present. In some embodiments, combinations of sols, gels and/or biocompatible matrices are also employed to provide desirable characteristics of the thickened formulations. In certain embodiments, the thickened formulation compositions are cross-linked by one or more agents to alter or improve the properties of the composition.

Microspheres have been described in the following references, which are incorporated herein by reference: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. Nos. 4,758,435; 3,773,919; 4,474,572; G. Johns et al. "Broad Applicability of a Continuous Formation Process," Drug Delivery Technology vol. 4 (January/February 2004), each of which is hereby incorporated by reference for such disclosure. Examples of protein therapeutics formulated as microspheres include: U.S. Pat. Nos. 6,458,387; 6,268,053; 6,090,925; 5,981,719; and 5,578,709, and are herein incorporated by reference for such disclosure.

Microspheres usually have a spherical shape, although irregularly-shaped microparticles are possible. The microspheres vary in size, ranging from submicron to 1000 micron diameters. Preferably, submicron to 250 micron diameter microspheres, are desirable, allowing administration by injection with a standard gauge needle. The microspheres can thus be prepared by any method which produces microspheres in a size range acceptable for use in an injectable composition. Injection are accomplished with standard gauge needles used for administering liquid compositions.

Suitable examples of polymeric matrix materials include poly(glycolic acid), poly-d,l-lactic acid, poly-1-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are used in the method disclosed herein. For example, poly (d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. A preferred polymer for use is poly(d,l-lactide-co-glycolide). It is preferred that the molar ratio of lactide to glycolide in such a copolymer be in the range of from about 95:5 to about 50:50. In other embodiments, PLGA copolymers with polyethylene glycol (PEG) are suitable polymeric matrices for the formulations disclosed herein. For example, PEG-PLGA-PEG block polymers are biodegradable matrices for gel formation that provide high mechanical stability of the resulting gel. Mechanical stabilities of gels using PEG-PLGA-PEG block polymers have been maintained for more than one month in vitro. In some embodiments, PEG-PLGA-PEG block polymers are used to control the release rate of cytotoxic agents with different physical properties. Particularly, in some embodiments, hydrophilic cytotoxic agents are released more quickly, e.g., approximately 50% of drug release after 24 hours, the remainder released over approximately 5 days, whereas hydrophobic agents are released more slowly, e.g., approximately 80% after 8 weeks.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microsphere formulation can be made such that the resulting microspheres exhibit both diffusional release and biodegradation release properties. This is useful in affording multiphasic release patterns.

A variety of methods are known by which compounds can be encapsulated in microspheres. In these methods, the active pharmaceutical ingredient is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release formulations are made through the incorporation of the otic agents and/or other pharmaceutical agents into ethylene-vinyl acetate copolymer matrices. (See U.S. Pat. No. 6,083,534, incorporated herein for such disclosure). In another embodiment, otic agents are incorporated into poly (lactic-glycolic acid) or poly-L-lactic acid microspheres. In yet another embodiment, the otic agents are encapsulated into alginate microspheres. (See U.S. Pat. No. 6,036,978, incorporated herein for such disclosure). Biocompatible methacrylate-based polymers to encapsulate the otic agents or compositions are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb. 2008 (online publication)). In one embodiment, the enhanced viscosity auris-acceptable formulations described herein comprises otic agent microspheres wherein the microspheres are formed from a methacrylate polymer or copolymer. In an additional embodiment, the enhanced viscosity formulation described herein comprises otic agent microspheres wherein the microspheres are mucoadhesive. Other controlled release systems, including incorporation or deposit of polymeric materials or matrices onto solid or hollow spheres containing otic agents, are also explicitly contemplated within the embodiments disclosed herein. The types of controlled release systems available without significantly losing activity of the otic agent are determined using the teachings, examples, and principles disclosed herein An example of a conventional microencapsulation process for pharmaceutical preparations is shown in U.S. Pat. No. 3,737,337, incorporated herein by reference. The substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of active pharmaceutical ingredients, the microspheres form when the solvent containing an active agent and a polymer is emulsified or dispersed in an immiscible solution by stirring, agitating, vibrating, or some other dynamic mixing technique, often for a relatively long period of time.

Conventional methods for the construction of microspheres are also described in U.S. Pat. Nos. 4,389,330, and 4,530,840, incorporated herein by reference. The desired agent is dissolved or dispersed in an appropriate solvent. To the agent-containing medium is added the polymeric matrix material in an amount relative to the active ingredient which gives a product of the desired loading of active agent. Optionally, all of the ingredients of the microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

In some embodiments, the controlled-release auris-acceptable microspheres are combined in a controlled-release auris-acceptable increased-viscosity formulation, including a gel.

A suitable controlled-release auris-acceptable microsphere example for use with the auris-acceptable therapeutic agents disclosed herein includes CHRONIJECT™, a PLGA-based controlled release injectable drug delivery system. Chroniject microspheres are useful for both hydrophobic and hydrophilic auris therapeutic agents, with achieved durations of release ranging from as short as 1 week to as long as 1 year. Release profiles for the microspheres are achieved by modifying polymer and/or process conditions, with initial release or burst of the auris therapeutic agent also available. The manufacturing process is adaptable to aseptic conditions, allowing direct therapeutic use of the manufactured product. Chroniject manufacturing processes are described in U.S. Pat. Nos. 5,945,126; 6,270,802 and 6,3361,798, each of which is hereby incorporated by reference for such disclosure.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils can be used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly vinyl alcohol in water mixture. The dispersion is formed by mechanical agitation of the mixed materials. An emulsion can also be formed by adding small drops of the active agent-wall forming material solution to the continuous phase processing medium. The temperature during the formation of the emulsion is not especially critical but can influence the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process can be conducted at any temperature which maintains stable operating conditions, which preferred temperature being about 30° C. to 60° C., depending upon the drug and excipient selected.

The dispersion which is formed is a stable emulsion and from this dispersion the organic solvent immiscible fluid can optionally be partially removed in the first step of the solvent removal process. The solvent can easily be removed by common techniques such as heating, the application of a reduced pressure or a combination of both. The temperature employed to evaporate solvent from the microdroplets is not critical, but should not be that high that it degrades the agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid can be decanted from the microsphere or the microsphere suspension can be filtered. Still other, various combinations of separation techniques can be used if desired.

Following the isolation of the microspheres from the continuous-phase processing medium, the remainder of the solvent in the microspheres is removed by extraction. In this step, the microspheres can be suspended in the same continuous-phase processing medium used in step one, with or without surfactant, or in another liquid. The extraction medium removes the solvent from the microspheres and yet does not dissolve the microspheres. During the extraction, the extraction medium with dissolved solvent can optionally be removed and replaced with fresh extraction medium. This is best done on a continual basis. Obviously, the rate of extraction medium replenishment of a given process is a variable which can easily be determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the agent since core loadings of up to 80 wt. %, preferably up to 60 wt. % are obtained.

Alternatively, controlled release microspheres containing an active pharmaceutical agent can be prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer can be used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an active pharmaceutical agent, an organic phase and an aqueous phase are combined. The organic and aqueous phases are largely or substantially immiscible, with the aqueous phase constituting the continuous phase of the emulsion. The organic phase includes an active pharmaceutical agent as well as a wall-forming polymer or polymeric matrix material. The organic phase can be prepared by dissolving an active pharmaceutical agent in an organic or other suitable solvent, or by forming a dispersion or an emulsion containing the active agent. The organic phase and the aqueous phase are pumped so that the two phases flow simultaneously through a static mixer, thereby forming an emulsion which comprises microspheres containing the active pharmaceutical agent encapsulated in the polymeric matrix material. The organic and aqueous phases are pumped through the static mixer into a large volume of quench liquid to extract or remove the organic solvent. Organic solvent are removed from the microspheres while they are washing or being stirred in the quench liquid. After the microspheres are washed in a quench liquid, they are isolated, as through a sieve, and dried.

The process whereby microspheres are prepared using a static mixer is optionally carried out for a variety of techniques used to encapsulate active agents. The process is not limited to the solvent extraction technique discussed above, but can be used with other encapsulation techniques. For example, the process can also be used with a phase separation encapsulation technique. To do so, an organic phase is prepared that comprises an active pharmaceutical agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation may also include spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference. An alternative process involves the use of a static mixer with co-solvents. In this process for preparing biodegradable microspheres comprising a biodegradable polymeric binder and an active pharmaceutical agent, a blend of at least two substantially non-toxic solvents, free of halogenated hydrocarbons, is used to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. The process has the advantages that less extraction medium is required because the solubility of one solvent in water is substantially independent of the other and solvent selection is increased, especially with solvents that are particularly difficult to extract.

Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions can be sterilized as the nanoparticles are small enough to be subjected to sterilizing filtration (U.S. Pat. No. 6,139,870). Nanoparticles comprise at least one hydrophobic, water-insoluble and water-indispersible polymer or copolymer emulsified in a solution or aqueous dispersion of surfactants, phospholipids or fatty acids. The active pharmaceutical ingredient are introduced with the polymer or the copolymer into the nanoparticles.

Lipid nanocapsules act as controlled release structures, as well for penetrating the round window membrane and reaching auris interna targets, is also contemplated herein. See Zou et al. *J. Biomed. Materials Res.*, online pub. (Apr. 24, 2008). Lipid nanocapsules are formed by emulsifying 1.028 g capric and caprylic acid triglycerides (LABRAFAC WL 1349; avg. mw 512), 0.075 g soybean lecithin (LIPOID S75-3; 69% phosphatidylcholine and other phospholipids), 0.846 g surfactant (SOLUTOL HS15), mixture of polyethylene glycol 660 hydroxystearate and free polyethylene glycol 660; 0.089 g NaCl and 2.962 g water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate auris interna active agents, the agent are added just prior to the dilution with cold water.

Agents may also be inserted into the lipid nanocapsules by incubation for 90 minutes with an aqueous micellar solution of the auris interna active agent. The suspension is then vortexed every 15 minutes, and then quenched in an ice bath for 1 minute.

Suitable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) could also be used to prepare nanoparticles.

The phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

The fatty acids are chosen from, by way of example, from lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable surfactants can preferably be selected from known organic and inorganic pharmaceutical excipients. Such excipients include various polymers, low molecular weight oligomers, natural products, and surfactants. Preferred surface modifiers include nonionic and ionic surfactants. Two or more surface modifiers can be used in combination.

Representative examples of surfactants include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; polyethylene glycols, dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamnines, a charged phospholipid such as dimyristoyl phophatidyl glycerol, dioctylsulfosuccinate (DOSS); Tetronic 1508, dialkylesters of sodium sulfosuccinic acid, Duponol P, Tritons X-200, Crodestas F-110, p-isononylphenoxypoly-(glycidol), Crodestas SL-40® (Croda, Inc.); and SA9OHCO, which is $C_{18}H_{37}CH_2$ (CON $(CH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference.

The hydrophobic, water-insoluble and water-indispersible polymer or copolymer are chosen from biocompatible and biodegradable polymers, for example lactic or glycolic acid polymers and copolymers thereof, or polylactic/polyethylene (or polypropylene) oxide copolymers, preferably with molecular weights of between 1000 and 200000, polyhydroxybutyric acid polymers, polylactones of fatty acids containing at least 12 carbon atoms, or polyanhydrides.

In one embodiment, the nanoparticles are suitable for use with hydrophobic active principles. The active principles which can be used are chosen from the major classes of medicaments for use in human or veterinary medicine. In some embodiments, the active principles are chosen from principles for use in the cosmetics or agrifood industry or sports medicine or from diagnostic agents. By way of example, active principles which are of interest in the pharmaceutical industry are chosen, in a non-limiting manner, from antirheumatic, non-steroidal anti-inflammatory (e.g., NSAIDs), analgesic, antitussive and psychotropic agents, steroids, barbiturates, antimicrobial, antiallergenic, antiasthmatic, antispasmodic, antisecretory and cardiovascular agents, cerebral vasodilators, cerebral and hepatic protective agents, therapeutic agents of the gastrointestinal tract, anticancer or antiviral agents, vitamins, contraceptives, vaccines, etc.

The nanoparticles are obtained by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods can be employed to fabricate nanoparticles. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers can provide the necessary turbulence to ensure small particle size. One type of continuous flow mixing device that can be used to prepare nanoparticles has been described (Hansen et al. J Phys Chem 92, 2189-96, 1988). In other embodiments, ultrasonic devices, flow through homogenizers or supercritical CO2 devices are used to prepare nanoparticles.

If suitable nanoparticle homogeneity is not obtained on direct synthesis, then size-exclusion chromatography can be used to produce highly uniform drug-containing particles that are freed of other components involved in their fabrication. Size-exclusion chromatography (SEC) techniques, such as gel-filtration chromatography, can be used to separate particle-bound drug from free drug or to select a suitable size range of drug-containing nanoparticles. Various SEC media, such as Superdex 200, Superose 6, Sephacryl 1000 are commercially available and are readily employed by persons of skill in the art for the size-based fractionation of mixture. Additionally, nanoparticles can be purified by centrifugation, membrane filtration and by use of other molecular sieving devices, crosslinked gels/materials and membranes.

Liposomes or lipid particles may also be employed to encapsulate the otic agent formulations or compositions. Phospholipids that are gently dispersed in an aqueous medium form multilayer vesicles with areas of entrapped aqueous media separating the lipid layers. Sonication, or turbulent agitation, of these multilayer veiscules results in the formation of single layer vesicles, commonly refered to as liposomes, with sizes of about 10-1000 nm. These liposomes have many advantages as drug carriers. They are biologically inert, biodegradable, non-toxic and non-antigenic. Liposomes can be formed in various sizes and with varying compositions and surface properties. Additionally, they are able to entrap a wide variety of small molecule drugs and release the drug at the site of liposome collapse.

Suitable phospholipids for use in the present compositions are, for example, phosphatidyl cholines, ethanolamines and serines, sphingomyelins, cardiolipins, plasmalogens, phosphatictic acids and cerebrosides, in particular those which are soluble together with piroxicam in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation can range from about 10 to about 30%, preferably from about 15 to about 25% and in particular is about 20%.

Lipophilic additives are employed advantageously to modify selectively the characteristics of the liposomes. Examples of such additives include, for example, stearylamine, phosphatictic acid, tocopherol, cholesterol, cholesterol hemisuccinate and lanolin extracts. The amount of lipophilic additive used can range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the active ingredient piroxicam are employed in conjunction with a non-toxic, pharmaceutically acceptable organic solvent system which can dissolve said ingredients. Said solvent system not only must dissolve the active pharmaceutical ingredient completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol can range from about 2:1 to about 1:3, in particular from about 1:1 to about 1:2.5 and preferably is about 1:2. The amount of tetraglycol in the final composition thus can vary from 5 to 20%, in particular from 5 to 15% and preferably is approximately 10%. The amount of dimethylisosorbide in the final composition thus can range from 3 to 10%, in particular from 3 to 7% and preferably is approximately 5%.

The term "organic component" as used hereinafter refers to mixtures comprising said phospholipid, lipophilic additives and organic solvents.

The active pharmaceutical ingredient is dissolved in the organic component. It is advantageous to use micronized forms of the active ingredient to facilitate its dissolution. The amount of active ingredient in the final formulation ranges from 0.1 to 5.0%. In addition, other ingredients such as anti-oxidants are added to the organic component. Examples include tocopherol, butylated hydroxyanisole, butylated hydroxytoluene, ascorbyl palmitate, ascorbyl oleate and the like.

The aqueous component of the present formulation comprises mainly water and may contain various additives such as electrolytes, buffer systems, preservatives and the like. Suitable electrolytes include metal salts, in particular alkali metal and earth alkaline metal salts such as, for example, calcium chlorides, sodium chloride, potassium chloride, preferably sodium chloride. The concentration of the electrolytes may vary over a wide range and depends on the nature and the concentration of each of the ingredients in the final formulation and should be sufficient to stabilize the liposomal membranes. In the present composition the amount of sodium chloride can range from 0.05 to 0.2%. Buffer systems comprise mixtures of appropriate amounts of an acid such as phosphoric, succinic, or preferably citric acid, and a base, in particular sodium hydroxide. Said buffer systems should maintain the pH of the formulation within the range of 3 to 9, alternatively within the range or 6 to 8 or between the range of 5 to 7. Preservatives which can be employed in the present composition to prevent degradation by microorganisms may comprise benzoic acid, methylparaben and propylparaben.

Liposomal formulations are optionally prepared by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, in particular a high-shear mixer; and (d) adding a thickener to the resulting mixture while further homogenizing. Preferably, the aqueous component is placed in a suitable vessel which can be equiped with a homogenizer and homogenization is effected by creating great turbulence during the injection of the organic component. Any mixing means or homogenizer which exerts high shear forces on the mixture are employed. Generally, a mixer capable of speeds from about 1,500 to 20,000 rpm, in particular from about 3,000 to about 6,000 rpm are employed. Suitable thickening agents for use in process step (d) are for example, xanthan gum, hydroxypropyl cellulose, hydroxypropyl methylcellulose or mixtures thereof, cellulose derivatives being preferred. The amount of thickening agent depends on the nature and the concentration of the other ingredients and in general ranges from about 0.5 to 1.5%, and in particular is approximately 1.5%. In order to prevent degradation of the materials used during the preparation of the liposimal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

Auris-Acceptable Lipid Formulations

In some embodiments, the drug delivery formulation is a lipid-based formulation. In some embodiments, the lipid-based drug delivery formulation is a lipid emulsion (e.g., microemulsions and oil-in-water emulsions), a lipid vesicle (e.g., liposomes, liosomes, micelles and transfersomes) or a combination thereof. In some embodiments, the lipid-based drug delivery formulation is a lipid vesicle wherein the lipid vesicle is a liposome. In some embodiments, the lipid-based drug delivery formulation is a phospholipid-based formulation. In some embodiments, the lipid-based drug delivery formulation is a phospholipid-based formulation wherein the natural or synthetic phospholipid is phosphatidylethanolamine, phosphatidylserine, phosphatidylinositol, phosphatidylglycerol, phosphatidic acid, lysophospholipids, egg or soybean phospholipid, or a combination thereof. The phospholipid is optionally salted or desalted, hydrogenated or partially hydrogenated, natural, synthetic, or semisynthetic. In some embodiments, the lipid-based drug delivery formulation is a phospholipid-based formulation (e.g., hydrogenated or nonhydrogenated phospholipids, lecithins, phosphatidyl cholines (C8-C18), phosphatidylethanolamines (C8-C18), phosphatidylglycerols (C8-C18)) wherein the phospholipid is phospholipon 90H (1,2-dia-cyl-SN-glycero-3-phosphatidyl choline), egg phospholipids P123, Lipoid E80; Phospholipon 80H®, 80G®, 90H® and 100H®, or combinations thereof.

In some embodiments, the lipid-based drug delivery formulation comprises a water-soluble preservative (i.e., a component that prevents microbes from substantially growing and multiplying). In some embodiments, the lipid-based drug delivery formulation comprises a water-soluble preservative wherein the preservative is a benzethonium salt (e.g., benzethonium chloride), benzoic acid, and/or a benzylkonium salt (e.g., benzylkonium chloride). As used herein, water soluble means that the component has a solubility in water from about 100 µg/mL (0.01%) to about 0.01 mg/mL (0.1%).

In some embodiments, the lipid-based drug delivery formulation comprises a lipid soluble anti-oxidant anti-oxidant. In some embodiments, the lipid-based drug delivery formulation comprises vitamin E.

In some embodiments, the lipid-based drug delivery formulation comprises less than about 2% w/w, less than about 1.5%, less than about 1.0%, less than about 0.5%, or less than about 0.25% of a viscosity enhancing agent.

In some embodiments, the lipid-based drug delivery formulation has a viscosity of at least about 10,000 centipoise, at least about 20,000 centipoise, at least about 30,000 centipoise, at least about 40,000 centipoise, at least about 50,000 centipoise, at least about 60,000 centipoise, or at least about 70,000 centipoise, all at 58° C., without the presence of any methyl-cellulose or other viscosity enhancing agents. In some embodiments, the lipid-based drug delivery formulation comprises oleyl alcohol to enhance the transmembrane penetration.

In some embodiments, the lipid-based drug delivery formulation comprises a penetration enhancer (e.g., a low molecular weight alcohol (e.g., ethanol, oleyl alcohol), alkyl methanol sulphoxides, N-methyl-2-pyrrolidone, fatty amines (e.g., oleylamine), fatty acids (e.g., oleic acid, palmitoleic acid, linoleic acid, myristate acid), gluconic acid (the hexonic acid derived from glucose by oxidation of the aldehyde group at C-1 to a carboxyl group) and its derivatives, such as gluconolactone (especially, glucono-D-lactone, a chelating agent produced by the oxidation of glucose), azone and propylene glycol, singly or in combination). In some embodiments, the lipid-based drug delivery formulation comprises a penetration enhancer wherein the penetration enhancer is propylene glycol, either alone or in up to a 1:1 ratio with another enhancer, such as oleic acid or ethanol. In some embodiments, the lipid-based drug delivery formulation comprises a penetration enhancer wherein the penetration enhancer is gluconolactone (e.g., glucono-D-lactone), either alone or in up to a 1:1 ratio with another enhancer, such as propylene glycol.

In some embodiments, the lipid-based drug delivery formulation comprises about 25% v/v or less of any one or more chemical penetration enhancer(s), most preferably from about 2% to 15% v/v, although the exact formulation will vary depending on the presence and amounts of excipients, preservatives, water, pH modulators, and the like included therein.

In some embodiments, prepared liposomes loaded with the aural pressure modulators herein are gently mixed with viscosity, mucosal adhesives or absorption penetration enhancers. For example, aural pressure modulators loaded into liposomes are mixed with a chitosan-glycerophosphate composition, allowing in situ gelling of the composition at internal body temperatures of approximately 37° C. The liposome size are optionally increased or decreased to modulate the release kinetics of the controlled release particles. In additional aspects, release kinetics are altered by changing the lipid composition of the liposomes as described above.

The formulations described herein are adminstered in any suitable form. By way of non-limiting examples, the formulations are administered as otic drops, as intratympanic injections, as foams or as otic paints. The formulations are administered via canula and/or injection, via a drop dispenser, as a spray in the ear canal, or as a paint via a cotton tipped stick.

Controlled Release Kinetics

The goal of every drug delivery technique is to deliver the proper amount of drug to the site of action at the right time to obtain a therapeutic benefit. In general, controlled release drug formulations impart control over the release of drug with respect to site of release and time of release within the body. As discussed herein, controlled release refers to any release other than solely immediate release. In some instances, controlled release is delayed release, extended release, sustained release and/or pulsatile release (e.g., a combination of extended release and immediate release) or a combination thereof. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the at the site of disease. Still further, controlled release offers the opportunity to administer and release two or more different drugs, each having a unique release profile, or to release the same drug at different rates or for different durations, by means of a single dosage unit.

In a specific embodiment the formulations described herein provide a therapeutically effective amount of at least one active pharmaceutical ingredient at the site of disease with no systemic exposure. In an additional embodiment the formulations described herein provide a therapeutically effective amount of at least one active pharmaceutical ingredient at the site of disease with no detectable systemic exposure.

The formulation are designed to provide drug delivery over a desired period of time, including periods up to several weeks. As such, the patient will not need repeated administration of the drug, or at the least, fewer and less frequent administration of the drug.

Drugs delivered to the auris interna have commonly been administered systemically via oral, intravenous or intramuscular routes. However, systemic administration for pathologies local to the auris interna increases the likelihood of systemic toxicities and side effects and creates a nonproductive distribution of drug in which high levels drug are found in the serum and correspondingly lower levels are found at the auris interna.

In one embodiment, the formulations disclosed herein additionally provides an immediate release of an otic agent from the formulation, or within 1 minute, or within 5 minutes, or within 10 minutes, or within 15 minutes, or within 30 minutes, or within 60 minutes or within 90 minutes. In other embodiments, a therapeutically effective amount of at least one otic agent is released from the formulation immediately, or within 1 minute, or within 5 minutes, or within 10 minutes, or within 15 minutes, or within 30 minutes, or within 60 minutes or within 90 minutes. In certain embodiments the formulation comprises an auris-pharmaceutically acceptable gel formulation providing immediate release of at least one otic agent. Additional embodiments of the formulation may also include an agent that enhances the viscosity of the formulations included herein.

An immediate or rapid release option includes use of different viscosity-enhancing polymers, multi-component gels and nanospheres (or sub-micron spheres). In addition, the microspheres are optionally coated with an immediate-release component and a controlled-release component.

In certain embodiments the formulation comprises a gel formulation providing immediate release of at least one active pharmaceutical ingredient. Additional embodiments of the formulation may also include a thickener that thickens the formulations included herein. In other embodiments the thickened comprises a liposomal formulation providing immediate release of at least one active pharmaceutical ingredient. In certain other embodiments the formulation comprises a cyclodextrin-containing formulation providing immediate release of at least one active pharmaceutical ingredient. In additional embodiments the formulation comprises a microsphere formulation providing immediate release of at least one active pharmaceutical ingredient. In additional embodiments the formulation comprises a nanoparticle formulation providing immediate release of at least one active pharmaceutical ingredient.

In other or further embodiments, the formulation provides a controlled release formulation of at least one otic agent. In certain embodiments, diffusion of at least one otic agent from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one otic agent is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an otic agent. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first otic agent and an extended release of a second otic agent or other therapeutic agent. In yet other embodiments, the formulation provides an immediate release and extended release formulation of at least one otic agent, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first otic agent and second therapeutic agent, respectively.

In a specific embodiment the formulation provides a therapeutically effective amount of at least one otic agent at the site of disease with essentially no systemic exposure. In an additional embodiment the formulation provides a therapeutically effective amount of at least one otic agent at the site of disease with essentially no detectable systemic exposure. In other embodiments, the formulation provides a therapeutically effective amount of at least one otic therapeutic agent at the site of disease with little or no detectable detectable systemic exposure.

In some instances, upon administration (e.g., intratympanic injection) of a conventional otic formulation (e.g., DSP in a buffer), the concentration of a drug in the perilymph of an individual will rise sharply ($C_{max}$ at about 1-2 hours) and then taper off (FIG. 1) to below $C_{min}$. In some instances, administration of an otic formulation described herein lowers the ratio of $C_{max}$ to $C_{min}$ and provides a larger Area Under the Curve (AUC) with a prolonged PK profile based on the $C_{min}$ (FIG. 1). In certain instances, controlled release formulations described herein delay the time to $C_{max}$. In certain instances, the controlled steady release of a drug prolongs the time the concentration of the drug will stay above the minimum therapeutic concentration (i.e., $C_{min}$). In some instances, controlled release of an otic agent provided by the formulations described herein allows for release of an otic agent at concentrations greater than $C_{min}$ for a period of at least 3 days, 4 days, 5 days, 6 days, 7 days, 10 days, 14 days, 3 weeks or 1 month. In some embodiments, auris compositions described herein prolong the residence time of a drug in the inner ear. In certain instances, once drug exposure (e.g., concentration in the perilymph) of a drug reaches steady state, the concentration of the drug in the perilymph stays at or about the therapeutic dose for an extended period of time (e.g., one day, 2 days, 3 days, 4 days, 5 days, 6 days, or 1 week). In some embodiments, otic formulations described herein increase the bioavailability and/or steady state levels of a drug in auris structures (e.g., in inner ear and/or the endolymph and/or the perilymph).

In some instances, upon administration of a controlled release auris formulation described herein (e.g., a formulation comprising an anti-inflammatory agent (e.g., an anti-TNF agent)), drug concentrations relative to the binding constants of one or more otic receptors (e.g., corticoid receptors, NMDA receptors, glutamate receptors or the like, or any combination thereof) are relevant in determining a biologically meaningful PK profile or the minimum concentration of an active agent required for a therapeutic effect. In some instances, upon administration of a controlled release auris formulation described herein, drug concentrations relative to the binding constants of two receptors, such as, by way of example only, mineralcorticoid receptor (MR) and glucocorticoid receptor (GR), are relevant in determining the $C_{min}$ or the biologically most meaningful PK profile. In some instances, for example, a drug saturates a first receptor (e.g. GR) first, then saturates a second receptor (e.g., MR), and there is therapeutic benefit even when the first receptor is saturated and the second receptor is not yet saturated. In some instances, the drug concentration for saturation the second receptor is about the same as the $C_{min}$. In some of such instances, for example, a next dose is administered when drug concentration drops below saturation levels of the second receptor and/or the $C_{min}$ (FIG. 1).

The combination of immediate release, delayed release and/or extended release otic compositions or formulations are combined with other pharmaceutical agents, as well as the excipients, diluents, stabilizers, tonicity agents and other components disclosed herein. As such, depending upon the otic agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the otic formulations described herein are determined by injecting the formulation on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and the inner ear removed and tested for the presence of the otic agent. As needed, the level of otic agent is measured in other organs. In addition, the systemic level of the otic agent is measured by withdrawing a blood sample from the test animal. In order to determine whether the formulation impedes hearing, the hearing of the test animal is optionally tested.

Alternatively, an inner ear is provided (as removed from a test animal) and the migration of the otic agent is measured. As yet another alternative, an in vitro model of a round window membrane is provided and the migration of the otic agent is measured.

Modes of Otic Administration

Provided herein are modes of treatment for otic compositions that ameliorate or lessen otic disorders described herein. Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Provided herein are methods comprising the administration of said auris compositions on or near the round window membrane via intratympanic injection. In some embodiments, a composition disclosed herein is administered on or near the round window or the crista fenestrae cochleae through entry via a post-auricular incision and surgical manipulation into or near the round window or the crista fenestrae cochleae area. Alternatively, a composition disclosed herein is applied via syringe and needle, wherein the needle is inserted through the tympanic membrane and guided to the area of the round window or crista fenestrae cochleae. In some embodiments, a composition disclosed herein is then deposited on or near the round window or crista fenestrae cochleae for localized treatment. In other embodiments, a composition disclosed herein is applied via microcathethers implanted into the patient, and in yet further embodiments a composition disclosed herein is administered via a pump device onto or near the round window membrane. In still further embodiments, a composition disclosed herein is applied at or near the round window membrane via a microinjection device. In yet other embodiments, a composition disclosed herein is applied in the tympanic cavity. In some embodiments, a composition disclosed herein is applied on the tympanic membrane. In still other embodiments, a composition disclosed herein is applied onto or in the auditory canal. The formulations described herein, and modes of administration thereof, are also applicable to methods of direct instillation or perfusion of the inner ear compartments. Thus, the formulations described herein are useful in surgical procedures including, by way of non-limiting examples, cochleostomy, labyrinthotomy, mastoidectomy, stapedectomy, endolymphatic sacculotomy or the like.

Intratympanic Injections

In some embodiments, a surgical microscope is used to visualize the tympanic membrane. In some embodiments, the tympanic membrane is anesthetized by any suitable method (e.g., use of phenol, lidocaine, xylocaine). In some embodiments, the anterior-superior and posterior-inferior quadrants of the tympanic membrane are anesthetized.

In some embodiments, a puncture is made in the tympanic membrane to vent any gases behind the tympanic membrane. In some embodiments, a puncture is made in the anterior-superior quadrant of the tympanic membrane to vent any gases behind the tympanic membrane. In some embodiments, the puncture is made with a needle (e.g., a 25 gauge needle). In some embodiments, the puncture is made with a laser (e.g., a $CO_2$ laser). In one embodiment the delivery system is a syringe and needle apparatus that is capable of piercing the tympanic membrane and directly accessing the round window membrane or crista fenestrae cochleae of the auris interna.

In one embodiment, the needle is a hypodermic needle used for instant delivery of the gel formulation. The hypodermic needle are a single use needle or a disposable needle. In some embodiments, a syringe are used for delivery of the pharmaceutically acceptable gel-based otic agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the pharmaceutically acceptable otic gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the otic agent or other pharmaceutical compounds contained therein.

In some embodiments, the syringe comprises a cylindrical syringe body wherein the body is compartmentalized in that each compartment is able to store at least one component of the auris-acceptable otic gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an otic agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, a needle punctures the posterior-inferior quadrant of the tympanic membrane. In some embodiments, the needle is wider than a 18 gauge needle. In another embodiment, the needle gauge is from 18 gauge to 30 gauge. In a further embodiment, the needle is a 25 gauge needle. Depending upon the thickness or viscosity of a composition disclosed herein, the gauge level of the syringe or hypodermic needle are varied accordingly. In some embodiments, the formulations described herein are liquids and can be administered via narrow gauge needles or cannulae (e.g., 22 gauge needle, 25 gauge needle, or cannula), minimizing damage to the tympanic membrane upon administration. In some embodiments, the formulations described herein gel upon contact with auditory surfaces and/or at body temperature; there is no need for patients to lie on their side while the otic agent takes effect. The formulations described herein are administered with minimal discomfort to a patient.

In some embodiments, an otoendoscope (e.g., about 1.7 mm in diameter) is used to visualize the round window membrane. In some embodiments, any obstructions to the round window membrane (e.g., a false round window membrane, a fat plug, fibrous tissue) are removed.

In some embodiments, a composition disclosed herein is injected onto the round window membrane. In some embodiments, 0.4 to 0.5 cc of a composition disclosed herein is injected onto the round window membrane.

In some embodiments, the tympanic membrane puncture is left to heal spontaneously. In some embodiments, a paper patch myringoplasty is performed by a trained physician. In some embodiments, a tympanoplasty is performed by a trained physician. In some embodiments, an individual is advised to avoid water. In some embodiments, a cotton ball soaked in petroleum-jelly is utilized as a barrier to water and other environmental agents.

Other Delivery Routes

In some embodiments, a composition disclosed herein is administered to the inner ear. In some embodiments, a composition disclosed herein is administered to the inner ear via an incision in the stapes footplate. In some embodiments, a composition disclosed herein is administered to the cochlea via a cochleostomy. In some embodiments, a composition disclosed herein is administered to the vestibular apparatus (e.g., semicircular canals or vestibule).

In some embodiments, a composition disclosed herein is applied via syringe and needle. In other embodiments, a composition disclosed herein is applied via microcatheters implanted into the patient. In some embodiments, a composition disclosed herein is administered via a pump device. In still further embodiments, a composition disclosed herein is applied via a microinjection device. In some embodiments, a composition disclosed herein is administered via a prosthesis, a cochlear implant, a constant infusion pump, or a wick.

In some embodiments, the delivery device is an apparatus designed for administration of therapeutic agents to the middle and/or inner ear. By way of example only: GYRUS Medical GmbH offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

Dosage

The compositions containing the compound(s) described herein are administered for prophylactic and/or therapeutic treatments. In therapeutic applications, the compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

The amount of a given agent that will correspond to such an amount will vary depending upon factors such as the particular compound, disease condition and its severity, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-50 mg per administration, preferably 1-15 mg per administration. The desired dose may conveniently be presented in a single dose or as divided doses administered simultaneously (or over a short period of time) or at appropriate intervals.

Frequency of Administration

In the case wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds are given continuously; alternatively, the dose of drug being administered are temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday are from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

In some embodiments, the initial administration is of a particular formulation and the subsequent administration is of a different formulation or active pharmaceutical ingredient.

Kits and Other Articles of Manufacture

The disclosure also provides kits for preventing, treating or ameliorating the symptoms of a diseases or disorder in a mammal. Such kits generally will comprise one or more of the pharmaceutically acceptable gel-based compositions as disclosed herein, and instructions for using the kit. The disclosure also contemplates the use of one or more of the formulations, in the manufacture of medicaments for treating, abating, reducing, or ameliorating the symptoms of a disease, dysfunction, or disorder in a mammal, such as a human that has, is suspected of having, or at risk for developing an auris interna disorder.

In some embodiments, a kit disclosed herein comprises a needle that can penetrate a tympanic membrane and/or a round window. In some embodiments, a kit disclosed herein further comprises a hydrogel with a penetration enhancer (e.g., an alkylglycoside and/or a saccharide alkyl ester).

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by extended release administration of a therpeutic agent to the auris interna.

In some embodiments, a kit will typically includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Preparation of a Thermoreversible Gel Anti-TNF Formulation

| Ingredient | Quantity (mg/g of formulation) |
| --- | --- |
| Adalimumab | 10.0 |
| methylparaben | 1.0 |
| HPMC | 10.0 |
| Poloxamer 407 | 180.0 |
| TRIS HCl buffer (0.1M) | 789.0 |

Adalimumab is supplied in 40 mg/0.8 mL pre-filled glass syringes containing approximately 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 0.6 mg mannitol, 0.8 mg polysorbate 80 and water. All mixing vessels are siliconized or otherwise treated to prevent adalimumab from adhering to the vessel walls.

A 10-g batch of gel formulation containing 1.0% of adalimumab is prepared by suspending 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (2.89 g) is added and further stirring allowed until complete dissolution is observed. Adalimumab (100 mg) is added and mixed to maintain activity. The mixture is maintained below room temperature until use.

Examples 2-10

Thermoreversible gel formulations comprising VP2 antagonist lixivaptan, diazepam, methotrexate, amoxicillin, AMN082, SRT-501, Neramexane, JB004/A, KCNQ modulator Retigabine, are prepared using a procedure similar to the procedure in Example 1. In further examples, thermoreversible gel formulations comprising micronized VP2 antagonist lixivaptan, diazepam, methotrexate, amoxicillin, AMN082, SRT-501, Neramexane, JB004/A, KCNQ modulator Retigabine, are prepared using a procedure similar to the procedure in Example 1

Example 11—Preparation of a Mucoadhesive, Thermoreversible Gel Calcineurin Inhibitor Formulation

| Ingredient | Quantity (mg/g of formulation) |
| --- | --- |
| tacrolimus | 10.0 |
| methylparaben | 1.0 |
| HPMC | 10.0 |
| Carbopol 934P | 2.0 |
| Poloxamer 407 | 180.0 |
| TRIS HCl buffer (0.1M) | 787.0 |

A 10-g batch of mucoadhesive, gel formulation containing 1.0% of anti-TNF agent is prepared by suspending 20.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (2.87 g) are added and further stirring allowed until complete dissolution is observed. Tacrolimus (100 g) is added and mixed while maintaining activity. The mixture is maintained below room temperature until use.

Examples 12-18

Mucoadhesive thermoreversible gel formulations comprising diazepam, AMN082, D-methionine, Ganciclovir, SRT-501, neomycin, the KCNQ modulator XE-991 are prepared using a procedure similar to the procedure in Example 11. In further examples, mucoadhesive thermoreversible gel formulations comprising micronized diazepam, AMN082, D-methionine, Ganciclovir, SRT-501, neomycin, the KCNQ modulator XE-991 are prepared using a procedure similar to the procedure in Example 11.

Example 19—Preparation of a Mucoadhesive-Based TACE Inhibitor Formulation

| Ingredient | Quantity (mg/g of formulation) |
| --- | --- |
| BMS-561392 | 10.0 |
| paraffin oil | 200 |
| trihydroxystearate | 10 |

| Ingredient | Quantity (mg/g of formulation) |
|---|---|
| cetyl dimethicon copolyol | 30 |
| water | qs ad 1000 |
| phosphate buffer pH 7.4 | qs pH 7.4 |

The cream-type formulation is first prepared by gently mixing BMS-561392 with an organic solvent. A second system is prepared by mixing paraffin oil, trihydroxystearate and cetyl dimethicon copolyol with warming to 60° C. Upon cooling to room temperature, the lipid system is mixed with the aqueous phase for 30 minutes.

Examples 20-25

Mucoadhesive-based formulations lidocaine.HCl, methotrexate, benzthine penicillin G, piceatannol, cyclophosphamide and CNQX are prepared using a procedure similar to the procedure in Example 19.

Example 26—Preparation of a Mucoadhesive, Thermoreversible Gel IKK Inhibitor Formulation

| Ingredient | Quantity (mg/g of formulation) |
|---|---|
| BMS-345541 | 10.0 |
| methylparaben | 1.0 |
| Poloxamer 407 | 180.0 |
| Carbopol 934P | 2.0 |
| TRIS HCl buffer (0.1M) | 317.0 |

The Carbopol 934P and Poloxamer 407 (BASF Corp.) is first suspended in the TRIS HCl buffer (0.1 M) and the components are mixed under agitation overnight at 4° C. to ensure complete dissolution. The methylparaben is added and further stirring allowed until complete dissolution is observed. The BMS-345541 is mixed in while retaining activity. The mixture is maintained below room temperature until use.

Examples 27-28

Mucoadhesive thermoreversible gel formulation comprising methotrexate, alpha lipoic acid is prepared using a procedure similar to the procedure in Example 26.

Viscosity determinations of the pharmaceutical compositions described herein are performed at room temperature and 37° C. and are made using a Brookfield (spindle and cup) viscometer at 20 rpm.

Example 29—Preparation of an Enhanced Viscosity, Mucoadhesive Controlled Release Anti-TNF Formulation Poly (lactic-glycolic acid) (PLGA) microspheres, containing anti-TNF binding protein, are prepared by a modified solvent evaporation method using a double emulsion. (See U.S. Pat. No. 6,083,354, incorporated by reference for such disclosure; Cohen et al. *Pharm. Res.* (1991) 8:713-720). Briefly, anti-TNF binding protein (TBPI) solution or powder of TBPI and bovine serum albumin (TBPI solution added to BSA powder in double distilled water; freeze dried into powder and sieved to give particles of sizes ranging from 75 nm to 250-425 nm, is dissolved in double distilled water. PLGA is separately dissolved in methylene chloride. A mixture of the PLGA and TBPI is probe sonicated (model VC-250, Sonic & Materials Inc.) for 30 sec to form the first inner emulsion (W1/0). The emulsion is then poured, under vigorous mixing using a magnetic bar, into 2 mL aqueous it polyvinylalcohol (PVA) saturated with methylene chloride to form the second emulsion ((W1/0)W2). The resulting double emulsion is subsequently poured into 200 mL of 0.1% PVA and continuously stirred for 3 hr at room temperature until most of the methylene chloride evaporates, leaving solid microspheres. The microspheres are collected by centrifugation (1000 g for 10 min), sized using sieves with apertures of 100 μm and freeze dried (16 hr, Freeze Dryer, Lab Conco) into a powder. The microspheres are mixed into the enhanced viscosity mucoadhesive formulation of Example 19.

Example 30—Preparation of Liposomal VP2 Antagonist Formation

| Ingredient | Quantity (mg/g of cream) |
|---|---|
| Lixivaptan | 5.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| BHT | 0.1 |
| sodium chloride | 1.0 |
| HPMC | 15.0 |
| sodium hydroxide | 0.6 |
| citric acid | 1.0 |
| purified water, USP | 603.6 |

Heat the soya lecithin, tetraglycol and dimethyl isosorbide to about 70-75° C. Dissolve the lixivaptan, cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. The homogenizer is a Silverson high-shear mixer operating at approximately 3000 rpm. Single bilayered liposomes are formed. The white lipogel cream is ready for use.

Example 31—Preparation of a VP2 Antagonist Nanoparticle Formulation 750 mg (15 mg/mL theoretical) of a diblock copolymer consisting of the combination of a poly(d,l-lactic acid) of mass 30 kD and of a polyethylene glycol of mass 2 kD (PLA-PEG) and 250 mg (5 mg/mL theoretical) of tolvaptan is dissolved in 20 mL of ethyl acetate (solution A). 175 mg of lecithin E80 and 90 mg of sodium oleate is dispersed in 50 mL of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 mL (70 g). The ethyl acetate is removed using a rotary evaporator at reduced pressure (100 mm of mercury) to a suspension volume of about 45 mL (45 g).

Nanoparticle formulation of a KCNQ modulator flupirtine is prepared using a procedure similar to the procedure in Example 31.

Example 32—Preparation of a 5% Cyclodextrin VP2 Antagonist Formulation

To a suitable 150 mL glass vessel is added tolvaptan (5.0 g), sterile 2% dibasic sodium phosphate dodecahydrate solution (9.0 g) and hydroxypropyl-cyclodextrin (50 g). The resulting mixture is stirred until a clear solution is formed. To this solution is added sterile 2% polysorbate 80 solution (5 g), sterile 2% stock HPMC 2910 (E4M) solution (2.5 g) and 5% sterile sodium chloride solution (11 g), and stirring is continued until homogeneous. Sterile water for injection is added to get to 95% of batch size. The solution is stirred at room temperature for 30 min and pH is adjusted to 7.2. Finally, water for injection is added to get a final batch size of 100 g.

Example 33—Preparation of a 5% Cyclodextrin KCNQ Modulator Mucoadhesive Thermoreversible Gel Formulation A 5% CD solution of Flupirtine is prepared according to the procedure in Example 32 and added to the mucoadhesive thermoreversible gel formulation of Example 11.

Example 34—Preparation of a 50% VP2 Antagonist 95:5 d,l-PLGA Microsphere Formulation Twenty-five grams (25 g) of 95:5 d,l-PLGA and 25 g of OPC-31260 are codissolved in 196 g ethyl acetate in an Erlemeyer flask at 52° C. The drug/polymer solution is added to a 1000 mL glass jacketed reactor containing 550 g of 5% aqueous polyvinyl alcohol containing 9.7 g of ethyl acetate. Reactor contents are stirred with an overhead stir motor and the temperature is maintained at 52° C. by a circulating bath. The emulsion size is monitored by light microscopy and the stirring is stopped when the particle size is found to be in the desired size range (less than 300 microns), usually after about 2 minutes. The stir speed is reduced to avoid further size reduction of the sterilized emulsion. After stirring for a total of 4 minutes, the reactor contents are pressure-transferred into 40 liters of water at 12° C. After stirring for 20 minutes, the hardened microspheres are isolated and the product then transferred into 20 liters of water at 12° C. After approximately 3 hours, the second wash is transferred onto a sieve stack composed of 25, 45, 90, 150, and 212 micron openings. The product on the sieves is washed with copious amounts of cold water to separate the different sizes of microspheres. After drying on the sieves overnight, the different fractions are collected and drying was continued under vacuum at room temperature. Formulations with other drug levels are prepared by simply adjusting the polymer/drug ratio.

Example 35

Microspheres comprising KCNQ modulator XE-991 are prepared using a procedure similar to the procedure in Example 34.

Example 36—Preparation of a 50% VP2 Antagonist 65:35 d,l-PLGA Microsphere Formulation Microspheres are produced by the method of Example 34 except that a different biodegradable polymer matrix was utilized. A 65:35 d,l-PLGA polymer was used in place of the 95:5 polymer indicated in Example 34.

Example 37—Preparation of a Mucoadhesive, Cyclodextrin-Based VP2 Antagonist Formulation

| Ingredient | Quantity (mg/g of formulation) |
| --- | --- |
| Lixivaptan | 20.0 |
| HP ®CD | 500 |
| propylene glycol | 50 |
| paraffin oil | 200 |
| trihydroxystearate | 10 |
| cetyl dimethicon copolyol | 30 |
| water | qs ad 1000 |
| phosphate buffer pH 7.4 | qs pH 7.4 |

The cream-type formulation is prepared by solubilizing lixivaptan with propylene glycol and this solution is added to a suspension of HP®CD in water. A second system is prepared by mixing paraffin oil, trihydroxystearate and cetyl dimethicon copolyol with warming to 60° C. Upon cooling to room temperature, the lipid system is mixed with the aqueous phase in a homogenizer for 30 minutes.

Example 38—Preparation of a Cyclodextrin-Containing Thermoreversible Gel 2.5% VP2 Antagonist Formulation

| Ingredient | Quantity (mg/g of formulation) |
| --- | --- |
| 5% CD solution | 500.0 |
| methylparaben | 1.0 |
| Poloxamer 407 | 180.0 |
| TRIS HCl buffer (0.1M) | 317.0 |

The Poloxamer 407 (BASF Corp.) is suspended in the TRIS HCl buffer (0.1 M) and the components are mixed under agitation overnight at 4° C. to ensure complete dissolution. The cyclodextrin solution from Example 4 and methylparaben is added and further stirring allowed until complete dissolution is observed. The mixture is maintained below room temperature until use.

Example 39—Preparation of a Cyclodextrin-Containing Mucoadhesive, Thermoreversible Gel VP2 Antagonist Formulation

| Ingredient | Quantity (mg/g of formulation) |
|---|---|
| 5% CD solution | 500.0 |
| methylparaben | 1.0 |
| Poloxamer 407 | 180.0 |
| Carbopol 934P | 2.0 |
| TRIS HCl buffer (0.1M) | 317.0 |

The Carbopol 934P and Poloxamer 407 (BASF Corp.) is suspended in the TRIS HCl buffer (0.1 M) and the components are mixed under agitation overnight at 4° C. to ensure complete dissolution. The cyclodextrin solution from Example 32 and methylparaben is added and further stirring allowed until complete dissolution is observed. The mixture is maintained below room temperature until use.

Examples 40

A cyclodextrin containing thermoreversible gel formulation comprising 2.5% KCNQ modulator flupirtine is prepared using a procedure similar to the procedure in Example 38.

Example 41—Preparation of a Gel VP2 Antagonist Formulation

| Ingredient | Quantity (mg/g of formulation) |
|---|---|
| SR-121463 | 20.0 |
| chitosan | 20.0 |
| Glycerophosphate disodium | 80.0 |
| water | 880 |

A 5 mL solution of acetic acid is titrated to a pH of about 4.0. The chitosan is added to achieve a pH of about 5.5. The SR-121463 is then dissolved in the chitosan solution. This solution is sterilized by filtration. A 5 mL aqueous solution of glycerophosphate disodium is also prepared and sterilized. The two solutions are mixed and within 2 h at 37° C., the desired gel is formed.

Examples 42-49

Gel formulations comprising vestipitant, gabapentin, thalidomide, carbamazepine, gentamicin, SRT-2183 and P2X modulator A-317491 are prepared using a procedure similar to the procedure in Example 41.

Example 50—Preparation of a Gel/Liposome VP2 Antagonist Formulation

| Ingredient | Quantity |
|---|---|
| SR-121463 | 20.0 mg/g |
| Liposomes | 15 umol/mL |
| Chitosan-Glycerophosphate | 100.0 mg/g |

The liposomes are prepared in the presence of the VP2 antagonist SR-121463 by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sephadex G-50 column (Amersham Pharmacia Biotech, Uppsala, Sweden).

To prepare the chitosan-glycerophosphate formulation, a 5 mL solution of acetic acid is titrated to a pH of about 4.0. The chitosan is added to achieve a pH of about 5.5. This solution is sterilized by filtration. A 5 mL aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature.

Example 51—Preparation of a KCNQ Modulator Nanoparticle Formulation 750 mg (15 mg/mL theoretical) of a diblock copolymer consisting of the combination of a poly(d,l-lactic acid) of mass 30 kD and of a polyethylene glycol of mass 2 kD (PLA-PEG) and 250 mg (5 mg/mL theoretical) of flupirtine is dissolved in 20 mL of ethyl acetate (solution A). 175 mg of lecithin E80 and 90 mg of sodium oleate is dispersed in 50 mL of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 mL (70 g). The ethyl acetate is removed using a rotary evaporator at reduced pressure (100 mm of mercury) to a suspension volume of about 45 mL (45 g).

Example 52—Preparation of a Mucoadhesive, Thermoreversible Gel AL-15469A/AL-38905 Formulation

| Ingredient | Quantity (mg/g of formulation) |
|---|---|
| AL-15469A | 25.5 |
| AL-38905 | 25.5 |
| methylparaben | 2.55 |
| Hypromellose | 25.5 |
| Carbopol 934P | 5.1 |
| Poloxamer 407 | 459 |
| TRIS HCl buffer (0.1M) | 2006.85 |

Both AL-15469A and AL-38905 are supplied as solids. They are rehydrated in water to a final molarity of 10 mM. A 10-g batch of mucoadhesive gel formulation containing 1.0% of AL-15469A and 1% of AL-38905 is prepared by first suspending Poloxamer 407 (BASF Corp.) and Carbopol 934P in TRIS HCl buffer (0.1 M). The Poloxamer 407, Carbopol 934P and TRIS are mixed under agitation overnight at 4° C. to ensure complete dissolution of the Poloxamer 407 and Carbopol 934P in the TRIS. The hypromellose, methylparaben and additional TRIS HCl buffer (0.1 M)

is added. The composition is stirred until dissolution is observed. The AL-15469A and AL-38905 solutions are added and the composition is mixed until a homogenous gel is produced. The mixture is maintained below room temperature until use.

Example 53—Preparation of a Hydrogel-Based Vestipitant/Paroxitene Formulation

| Ingredient | Quantity (mg/g of formulation) |
|---|---|
| Vestipitant | 10.0 |
| Paroxetine | 10.0 |
| paraffin oil | 200.0 |
| trihydroxystearate | 10.0 |
| cetyl dimethicon copolyol | 30.0 |
| water | qs ad 1000 |
| phosphate buffer pH 7.4 | qs pH 7.4 |

Both Vestipitant and Paroxitene are supplied as solids. A solution of Vestipitant is prepared by gently mixing Vestipitant with water until it is dissolved. A solution of Paroxitene is prepared by gently mixing Paroxitene with water until it is dissolved.

Then, the oil base is prepared by mixing paraffin oil, trihydroxystearate and cetyl dimethicon copolyol at temperatures up to 60° C. The oil base is cooled to room temperature and the Vestipitant and Paroxitene solutions are added. The two phases are mixed until a homogenous, monophasic hydrogel is formed.

Example 54—Preparation of Liposomal JB004/A Modulator Formation

| Ingredient | Quantity (mg/g of cream) |
|---|---|
| JB004/A | 2.5 |
| soya lecithin | 100.0 |
| cholesterol | 10.0 |
| tetraglycol | 50.0 |
| dimethylisosorbide | 25.0 |
| methylparaben | 1.0 |
| propylparaben | 0.1 |
| BHT | 0.05 |
| sodium chloride | 0.5 |
| HPMC | 7.5 |
| sodium hydroxide | 0.3 |
| citric acid | 0.5 |
| purified water, USP | 302.55 |

Heat the soya lecithin, tetraglycol and dimethyl isosorbide to about 70-75° C. Dissolve the JB004/A, cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. The homogenizer is a Silverson high-shear mixer operating at approximately 3000 rpm. Single bilayered liposomes are formed. The white lipogel cream is ready for use.

Examples 55-56

Liposomal preparations of AMN082, KCNQ modulator retigabine are prepared using a procedure similar to the procedure in Example 54.

Example 57—Controlled/Immediate Release Antimicrobial Formulation

| Ingredient | Quantity (mg/g of formulation) |
|---|---|
| PLA Microspheres comprising ~30% Benzathine penicillin G | 15 |
| Propylene Glycol | 30 |
| Glycerin | 20 |
| Methylcellulose (METHOCEL ® A4M) | 20 |
| Benzathine penicillin G | 10 |
| Water | qs ad 1000 |

PLA (poly(L-lactide)) microspheres comprising benzathine penicillin G are prepared by adding sufficient PLA to 100 mL dichloromethane to produce a 3% wt/vol solution. 1.29 g benzathine penicillin G is added to the solution with mixing. The solution is then added dropwise to 2 L distilled water containing 0.5% wt/vol poly(vinyl alcohol) with stirring to produce an oil/water emulsion. Stirring is continued for a sufficient period to allow evaporation of the dichloromethane and the formation of solid microspheres. Microspheres are filtered, washed with distilled water, and dried until no weight loss is observed.

The immediate release portion of the formulation is prepared by generating a 2% methylcellulose solution in a water/propylene glycol/glycerin solvent system under stirring. Benzathine penicillin G is added to the solution while stirring is continued to yield a 1% benzathine penicillin G low-viscosity gel. The appropriate amount of microspheres comprising benzathine penicillin G is then mixed with the low-viscosity gel to yield a combination controlled/immediate release benzathine penicillin G otic formulation.

Example 58—Preparation of a Cyclosporine Thermoreversible Gel Formulation Comprising a Penetration Enhancer

| Ingredient | Quantity (mg/g of formulation) |
|---|---|
| Cyclosporine | 10.0 |
| Sodium citrate | 1.25 |
| Sodium ascorbate | 0.8 |
| Hyaluronidase PH20 | 10 |
| Poloxamer 407 | 15 |
| Water | qs ad 1000 |
| Phosphate buffer pH 7.4 | qs pH 7.4 |

The liquid formulation is prepared by mixing micronized cyclosporine and hyaluronidase PH20 with a buffer to form a first solution. A second system is prepared by mixing poloxamer 407, sodium citrate, and sodium ascorbate in water with warming to 60° C. The first solution is added to the second system and mixed well.

Example 59—Preparation of a SB656933 Thermoreversible Gel Formulation Comprising a Penetration Enhancer

| Ingredient | Quantity (mg/g of formulation) |
|---|---|
| SB656933 | 10.0 |
| Sodium citrate | 1.25 |
| Sodium ascorbate | 0.8 |
| Dodecyl maltoside | 10 |
| Poloxamer 407 | 15 |
| Carboxymethyl cellulose | 5 |
| Water | qs ad 1000 |
| Phosphate buffer pH 7.4 | qs pH 7.4 |

The liquid formulation is prepared by mixing SB656933 and dodecyl maltoside with a buffer to form a first solution. A second system is prepared by mixing poloxamer 407, carboxymethyl cellulose, sodium citrate, and sodium ascorbate in water with warming to 60° C. The first solution is added to the second system and mixed well. The solution is autoclaved at 120° C. for 2 hours.

Example 60—Preparation of a JB004/a Thermoreversible Gel Formulation for Visualization

| Ingredient | Quantity (mg/g of formulation) |
|---|---|
| JB004/A | 10.0 |
| Sodium citrate | 1.25 |
| Sodium ascorbate | 0.8 |
| Evans blue | 2 |
| Poloxamer 407 | 15 |
| Carboxymethyl cellulose | 5 |
| Water | qs ad 1000 |
| Phosphate buffer pH 7.4 | qs pH 7.4 |

The liquid formulation is prepared by mixing JB004/A and Evans blue with a buffer to form a first solution. A second system is prepared by mixing poloxamer 407, carboxymethyl cellulose, sodium citrate, and sodium ascorbate in water with warming to 60° C. The first solution is added to the second system and mixed well. The solution is autoclaved at 120° C. for 2 hours.

Example 61 Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% Poloxamer 407/2% Otic Agent in PBS pH of 5.3.

Take an aliquot (approximately 30 mL) of the above solution and adjust the pH to 5.3 by the addition of 1 M HCl.

17% Poloxamer 407/2% Otic Agent in PBS pH of 8.0.

Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolved with 1.5 mL of a 1:1 acetonitrile water mixture. Purity of the otic agent in the autoclaved samples is recorded.

In general the formulation should not have any individual impurity (e.g., degradation product of otic agent) of more than 2% and more preferably not more than one percent. In addition, the formulation should not precipitate during storage or change in color after manufacturing and storage.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to the procedure in Example 61, are tested using the above procedure to determine the effect of pH on degradation during the autoclaving step.

Example 62 Effect of Autoclaving on the Release Profile and Viscosity of a 17% Poloxamer 407NF/2% Otic Agent in PBS An aliquot of the sample from example 61 (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 μm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 μL of the sample is mixed with 1980 μL of a 15 mM cobalt thiocyanate solution and absorbance measured at 625 nm, using a Evolution 160 UV/Vis spectrophotometer (Thermo Scientific).

The released otic agent is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{-1/n}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to the procedure in Example 61, are tested using the above procedure to determine the effect of autoclaving on the release profile, Tgel and viscosity of the formulations.

Example 63 Effect of Addition of a Secondary Polymer on the Degradation Products and Viscosity of a Formulation Containing 2% Otic Agent and 17% Poloxamer 407NF after Heat Sterilization (Autoclaving)

Solution A.

A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 µL of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 µm), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to the procedure in Example 63, are tested using the above procedure to determine the effect addition of a secondary polymer on the degradation products and viscosity of a formulation containing 2% otic agent and 17% poloxamer 407NF after heat sterilization (autoclaving).

Example 64 Effect of Buffer Type on the Degradation Products for Formulations Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Stock Solution (pH 7.3) Containing 25% Poloxamer 407 Solution in PBS Buffer:

PBS buffer from example 61 is used. Dissolve 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Tables 1 and 2 list samples prepared using the procedures described in Example 64. An appropriate amount of otic agent is added to each sample to provide a final concentration of 2% otic agent in the sample.

TABLE 1

Preparation of samples containing TRIS buffer

| Sample | pH | 25% Stock Solution (g) | TRIS Buffer (g) |
|---|---|---|---|
| 20% P407/2 otic agent/TRIS | 7.45 | 8.01 | 1.82 |
| 18% P407/2 otic agent/TRIS | 7.45 | 7.22 | 2.61 |
| 16% P407/2 otic agent/TRIS | 7.45 | 6.47 | 3.42 |
| 18% P4072 otic agent/TRIS | 7.4 | 7.18 | 2.64 |
| 4% otic agent/TRIS | 7.5 | — | 9.7 |
| 2% otic agent/TRIS | 7.43 | — | 5 |
| 1% otic agent/TRIS | 7.35 | — | 5 |
| 2% otic agent/TRIS (suspension) | 7.4 | — | 4.9 |

TABLE 2

Preparation of samples containing PBS buffer (pH of 7.3)

| Sample | 25% Stock Solution in PBS (g) | PBS Buffer (g) |
|---|---|---|
| 20% P407/2 otic agent/PBS | 8.03 | 1.82 |
| 18% P407/2 otic agent/PBS | 7.1 | 2.63 |
| 16% P407/2 otic agent/PBS | 6.45 | 3.44 |
| 18% P407/2 otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 µL of sample and dissolving with 1.5 mL of a 1:1 acetonitrile water mixture. Purity of the otic agent in the autoclaved samples is recorded. The stability of formulations in TRIS and PBS buffers is compared.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition. Only formulations that show no change after autoclaving are analyzed.

Formulations comprising VP2 antagonist lixivaptan, diazepam, methotrexate, amoxicillin, SRT-501, Neramexane, JB004/A, KCNQ modulator Retigabine, and tacrolimus, prepared according to the procedure in Example 64, are tested using the above procedure to determine the effect addition of a secondary polymer on the degradation products and viscosity of a formulation containing 2% otic agent and 17% poloxamer 407NF after heat sterilization (autoclaving).

Formulations comprising micronized VP2 antagonist lixivaptan, diazepam, methotrexate, amoxicillin, AMN082, SRT-501, Neramexane, JB004/A, KCNQ modulator Retigabine, and tacrolimus, prepared according to the procedure in Example 64, are subjected to autoclaving. Stability of formulations containing micronized otic agent is compared to solution counterparts.

Example 65: Pulsed Release Otic Formulations

A combination of neramexane and neramexane hydrochloride (ratio of 1:1) is used to prepare a pulsed release otic agent formulation using the procedures described herein. 20% of the delivered dose of neramexane is solubilized in a 17% poloxamer solution of example 61 with the aid of beta-cyclodextrins. The remaining 80% of the otic agent is then added to the mixture and the final formulation is prepared using any procedure described herein.

Pulsed release formulations comprising VP2 antagonist lixivaptan, diazepam, methotrexate, amoxicillin, AMN082, SRT-501, JB004/A, KCNQ modulator Retigabine, and tacrolimus, prepared according to the procedures and examples described herein, are tested using procedures described herein to determine pulse release profiles.

Example 66: Preparation of a 17% Poloxamer 407/2% Otic Agent/78 ppm Evans Blue in PBS A Stock solution of Evans Blue (5.9 mg/mL) in PBS buffer is prepared by dissolving 5.9 mg of Evans Blue (Sigma Chemical Co) with 1 mL of PBS buffer (from example 61).

A Stock solution containing 25% Poloxamer 407 solution in PBS buffer from example 64 is used in this study. An appropriate amount of an otic agent is added to the stock solution from example 64 to prepare formulations comprising 2% of an otic agent (Table 3).

TABLE 3

| Preparation of poloxamer 407 samples containing Evans Blue | | | |
|---|---|---|---|
| Sample ID | 25% P407in PBS (g) | PBS Buffer (g) | Evans Blue Solution (μL) |
| 17% P407/2 otic agent/EB | 13.6 | 6 | 265 |
| 20% P407/2 otic agent/EB | 16.019 | 3.62 | 265 |
| 25% P407/2 otic agent/EB | 19.63 | — | 265 |

Formulations comprising VP2 antagonist lixivaptan, diazepam, methotrexate, amoxicillin, AMN082, SRT-501, Neramexane, JB004/A, KCNQ modulator Retigabine, and tacrolimus are prepared according to the procedure in Example 66 and are sterile filtered through 0.22 μm PVDF syringe filters (Millipore corporation), and autoclaved.

The above formulations are dosed to guinea pigs in the middle ear by procedures described herein and the ability of formulations to gel upon contact and the location of the gel is identified after dosing and at 24 hours after dosing.

Example 67: Terminal Sterilization of Poloxamer 407 Formulations with and without a Visualization Dye 17% Poloxamer 407/2% Otic Agent/in Phosphate Buffer, pH 7.3:

Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% Poloxamer 407/2% Otic Agent/59 ppm Evans Blue in Phosphate Buffer:

Take two mL of the 17% poloxamer 407/2% otic agent/in phosphate buffer solution and add 2 mL of a 5.9 mg/mL Evans blue (Sigma-Aldrich chemical Co) solution in PBS buffer.

25% Poloxamer 407/2% Otic Agent/in Phosphate Buffer:

Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% Poloxamer 407/2% Otic Agent/59 ppm Evans Blue in Phosphate Buffer:

Take two mL of the 25% poloxamer 407/2% otic agent/in phosphate buffer solution and add 2 mL of a 5.9 mg/mL Evans blue (Sigma-Aldrich chemical Co) solution in PBS buffer.

Place 2 mL of formulation into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 µm, 100 Å, 250×4.6 mm column) using a 30-95 methanol:acetate buffer pH 4 gradient (1-6 min), then isocratic for 11 minutes, for a total run of 22 minutes. Samples are diluted by taking 30 µL of sample and dissolved with 0.97 mL of water. The main peaks are recorded in the table below. Purity before autoclaving is always greater than 99% using this method.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to the procedure in Example 67, are tested using the above procedures to determine stability of the formulations.

Example 68: In Vito Comparison of Relase Profile

Dissolution is performed at 37° C. in snapwells (6.5 mm diameter polycarbonate membrane with a pore size of 0.4 µm), 0.2 mL of a gel formulation described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the formulations mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008,43(2):208-203] and Rank-order of mean dissolution time (MDT) as a function of % P407 is determined.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to the procedures described herein, are tested using the above procedure to determine the release profile of the otic agents.

Example 69: In Vitro Comparison of Gelation Temperature

The effect of Poloxamer 188 and an otic agent on the gelation temperature and viscosity of Poloxamer 407 formulations is evaluated with the purpose of manipulating the gelation temperature.

A 25% Poloxamer 407 stock solution in PBS buffer and the PBS solution from example 64 are used. Poloxamer 188NF from BASF is used. An appropriate amount of otic agent is added to the solutions described in Table 4 to provide a 2% formulation of the otic agent.

TABLE 4

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above formulations are measured using procedures described herein.

An equation is fitted to the data obtained and can be utilized to estimate the gelation temperature of F127/F68 mixtures (for 17-20% F127 and 0-10% F68).

$$T_{gel} = -1.8(\% \ F127) + 1.3(\% \ F68) + 53$$

An equation is fitted to the data obtained and can be utilized to estimate the Mean Dissolution Time (hr) based on the gelation temperature of F127/F68 mixtures (for 17-25% F127 and 0-10% F68), using results obtained in example 67 and 69.

$$MDT=-0.2(T_{gel})+8$$

Formulations comprising VP2 antagonist lixivaptan, diazepam, methotrexate, amoxicillin, AMN082, SRT-501, Neramexane, JB004/A, KCNQ modulator Retigabine, and tacrolimus are prepared by addition of an appropriate amount of otic agents to the solutions described in Table 4. The gel temperature of the formulations is determined using the procedure described above.

Example 70: Determination of Temperature Range for Sterile Filtration

The viscosity at low temperatures is measured to help guide the temperature range at which the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic formulation is estimated by:

$$\Delta T_{gel}=0.93[\% \text{ otic agent}]$$

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to procedures described herein, are tested using the above procedure to determine the temperature range for sterile filtration. The effect of addition of increased amounts of otic agent on the Tgel, and the apparent viscosity of the formulations is recorded.

Example 71: Determination of Manufacturing Conditions

TABLE 5

Viscosity of potential formulations at manufacturing/filtration conditions.

| Sample | Apparent Viscosity$^a$ (cP) | | Temperature |
|---|---|---|---|
| | 5° C. below Tgel | 20° C. | @ 100 cP |
| Placebo | 52 cP @ 17° C. | 120 cP | 19° C. |
| 17% P407/2% otic agent | 90 cP @ 18° C. | 147 cP | 18.5° C. |
| 17% P407/6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank was taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution
1) Sartopore 2, 0.2 μm 5445307HS-FF (PES), flow rate of 16 mL/min
2) Sartobran P, 0.2 μm 5235307HS-FF (cellulose ester), flow rate of 12 mL/min
3) Sartopore 2 XLI, 0.2 μm 5445307IS-FF (PES), flow rate of 15 mL/min Sartopore 2 filter 5441307H4-SS is used, filtration is carried out at the solution temperature using a 0.45, 0.2 μm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 6

Predicted filtration time for a 17% poloxamer 407 placebo at a solution temperature range of 6.5-14° C. using Sartopore 2, 0.2 μm filters at a pressure of 16 psi of pressure.

| Filter | Size (m$^2$) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is check before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer). Table 7 lists physicochemical properties of the above solutions before and after filtration. Table 7. Physicochemical properties of 17% poloxamer 407 placebo solution before and after filtration

| Sample | Tgel (° C.) | Viscosity$^a$ @ 19° C. (cP) | Absorbance @ 274 nm |
|---|---|---|---|
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 formulations, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 72 In Vitro Release of Otic Agent from an Autoclaved Micronized Sample 17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the formulation is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 μm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other formulations disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. Otic agent concentration in the supernatant is measured by UV at 245 nm against an external calibration standard curve.

Formulations comprising micronized otic agents VP2 antagonist lixivaptan, diazepam, methotrexate, amoxicillin, AMN082, SRT-501, Neramexane, JB004/A, KCNQ modulator Retigabine, and tacrolimus, prepared according to the procedures described herein, are tested using the above procedures to determine release rate of the otic agent from each formulation.

Example 73 Release Rate or MDT and Viscosity of Formulation Containing Sodium Carboxymethyl Cellulose 17% Poloxamer 407/2% Otic Agent/1% CMC (Hercules Blanose 7M):

A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing. A formulation comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% Poloxamer 407/2% Otic Agent/0.5% CMC (Blanose 7M65):

A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% Poloxamer 407/2% Otic Agent/0.5% CMC (Blanose 7H9):

A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min). Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 μm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. The release rate is compared to the formulation disclosed in example 63, MDT time is calculated for each of the above formulations.

Formulations comprising VP2 antagonist lixivaptan, diazepam, methotrexate, amoxicillin, AMN082, SRT-501, Neramexane, JB004/A, KCNQ modulator Retigabine, and tacrolimus, prepared according to procedures described above, are tested using the above procedures to determine relationship between release rate and/or mean dissolution time and viscosity of formulation containing sodium carboxymethyl cellulose. Any correlation between the mean dissolution time (MDT) and the apparent viscosity (measured at 2° C. below the gelation temperature) is recorded.

Example 74—Application of a Enhanced Viscosity Calcineurin Inhibitor Formulation onto the Round Window Membrane A formulation according to Example 11 is prepared and loaded into 5 mL siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the immunomodulator formulation applied directly onto the round-window membrane.

Examples 75-89

Enhanced Viscosity AL-15469A/AL-38905 Formulation of Example 52, cytotoxic agent methotrexate formulation of Example 4, AMN082 formulation of Example 13, Antimicrobial gentamicin formulation of Example 46, SRT-501 formulation of Example 16 are tested using a procedure similar to the procedure in Example 61.

Example 90—Evaluation of a Calcineurin Inhibitor Formulation in an AIED Animal Model Methods and Materials
Induction of Immune Response
Female albino National Institutes of Health-Swiss mice (Harlan Sprague-Dawley, Inc., Indianapolis, Inc.) weighing 20 to 24 g are used. Keyhole limpet hemocyanin (KLH; Pacific Biomarine Supply Co., Venice, Calif.) is suspended in phosphate-buffered saline (PBS) IpH 6.4), dialyzed aseptically against PBS and centrifuged twice. The precipitate (associated KLH) is dissolved in PBS and injected subcutaneously in the back of the animal (0.2 mg emulsified in Freund's complete adjuvant). The animals are given a booster (0.2 mg KLH in Freund's incomplete adjuvant, and then injected ten weeks later with 0.1 mg KLH in 5 µl PBS (pH 6.4) through a microhole drilled through the cochlear capsule. The cochlea is approached using an operating microscope and sterile technique. A postauricular incision is made, and a hole is drilled into the bullae to allow good visualization of the promontory of the cochlear basal turn, stapedial artery, and round window niche. The stapedial artery is cauterized and removed, and a 25 µm hole is drilled through the cochlear capsule into the scala tympani of the lateral basal turn. KLH or PBS control is slowly injected using a Hamilton syringe coupled with a plastic tube to a glass micropipette filled with the antigen or control. The hole is sealed with bone wax after injection, and excess fluid is removed. Only one cochlea per animal is treated with KLH.

Treatment
KLH and control mice are sorted into two groups (n=10 in each group). Calcineurin inhibitor formulation of Example 11 containing tacrolimus is applied to the round window membrane of one group of animals. Control formulation containing no tacrolimus is applied to the second group. The calcineurin inhibitor and control formulations are reapplied three days after the initial application. The animals are sacrificed after the seventh day of treatment.
Analysis of Results
Electrophysiologic Testing
The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Histochemical Analysis
Animals are anesthsized and sacrificed via intracardiac perfusion of heparinized warm saline followed by approximately 40 mL periodate-lysine-paraformaldehyde (4% paraformaldehyde final concentration) fixative. Right-side temproal bones are immediately removed and decalcified with buffered 5% ethylenediamine tetra-acetate (pH 7.2) for 14 days (4° C.). After decalcification, temporal bones are immersed sequentially in increasing concentrations (50%, 75%, 100%) of optimal cutting temperature (OCT) compound (Tissue-Tek, Miles Inc., Elkhart, Ind.), snap-frozen (−70° C.), and cryostat-sectioned (4 µm) parallel to the modiolus. Sections are collected for hematoxylin and eosin (H&E) staining and immunohistochemical analysis.

The severity of inflammation is assessed according to the amount of cellular infiltration of the scala tympani, and an unbiased score is given to each cochlea. A score of 0 indicates no inflammation, and a score of 5 indicates that all cochlear turns had severe infiltration of inflammatory cells.

Examples 91-92

Mucoadhesive thermoreversible gel formulation comprising Etanercept prepared according to Example 26, mucoadhesive thermoreversible gel formulation comprising antimicrobial ganciclovir of example 15 are evaluated in an AIED animal model using a procedure similar to the procedure in Example 67.

Example 93—Evaluation of a Calcineurin Inhibitor Formulation in an Otitis Media Animal Model Induction of Otitis Media
Healthy adult chinchillas weight 400 to 600 g with normal middle ears, ascertained by otoscopy and tympanometry are used for these studies. Eustachian tube obstruction is performed 24 hours before inoculation to prevent the inoculum from flowing out of the eustachian tube. One milliliter of type 3 *S. pneumoniae* strain at 4-h-log phase (containing approximately 40 colony forming units (CFU)) is placed directly into both middle ear hypotympanic bullae of the chinhillas. Control mice are inoculated with one milliliter sterile PBS.

Treatment
*S. pneumoniae* inoculated and control mice are sorted into two groups (n=10 in each group). A calcineurin inhibitor formulation of Example 2 containing tacrolimus is applied to the walls of the tympanic cavity of one group of animals. Control formulation containing no tacrolimus is applied to the second group. The anti-TNF and control formulations are reapplied three days after the initial application. The animals are sacrificed after the seventh day of treatment.
Analysis of Results
Auris media ear fluid (MEF) is sampled at 1, 2, 6, 12, 24, 48 and 72 hours after pneumoccal inocualtion. Quantitative MEF cultures are performed on sheep blood agar, with the quantitation threshold set at 50 CFU/mL. Inflammatory cells are quantitated with a hemocytometer, and differential cell enumeration performed with Wright's staining.

Examples 94-95

Mucoadhesive thermoreversible gel formulation comprising methotrexate of Example 27 and thermoreversible gel formulation comprising amoxicillin of Example 5 are evaluated in an Otitis Media animal model using a procedure similar to the procedure in Example 68.

Example 96—AIED Clinical Trials Using TACE Inhibitor Formulations

Ten adult patients are selected due to initial steroid responsiveness followed by recurrence of hearing loss when steroids are tapered or after completion of steroid treatment. The TACE inhibitor formulation of Example 3 containing 0.3 mg of BMS-561392 is administered to each patient's round window membrane through piercing of the tympanic membrane. Reapplication of the TACE inhibitor formulations is performed 7 days after the initial application, and again at 2 and 3 weeks of treatment.

Hearing evaluations consisting of pure tone audiometry (250-8000 Hz) and speech testing using dissyllabic word lists in French are administered to each patient. Testing is carried out both before the application of the TACE inhibitor formulation and at 1, 2,3 and 4 weeks post-initial treatment.

Example 97—Evaluation of VP2 Antagonist Formulations in an Endolymphatic Hydrops Animal Model The following procedure is used to determine the efficacy of the thermoreversible gel formulation of lixivaptan as prepared in Example 2.
Materials and Methods Thirty-five Hartley guinea pigs with a positive Preyer's reflex and weighing about 300 g are used. Five animals, which serve as controls (normal ear group), are fed for 5 weeks with neither operation nor treatment, and the remaining 30 serve as experimental animals. All experimental animals received electro-cauterization of the endolymphatic sac (Lee et al., Acta Otolaryngol. (1992) 112:658-666; Takeda et al., Equilib. Res. (1993) 9:139-143). Four weeks after surgery, these animals are divided into three groups of non-infusion hydropic ears, vehicle-treated hydropic ears and lixivaptan-treated hydropic ears, consisting of 10 animals each. The group of non-infusion hydropic ears receive no treatment except for electro-cauterization of the endolymphatic sac. In the groups of vehicle-treated hydropic ears and lixivaptan-treated hydropic ears, the thermoreversible gel formulation is applied to the round window membrane. One week after administration of the composition, all animals are sacrificed for assessment of the changes of the endolymphatic space. All animals are left undisturbed and freely moving in individual cages in a quiet room throughout the period, except during experimental procedures.

To assess the changes to the endolymphatic space, all animals are transcardially perfused with physiological saline solution under deep anesthesia by a peritoneal injection of pentobarbital, and fixation is performed with 10% formalin. The left temporal bones are removed and postfixed in 10% formalin solution for 10 days or more. Thereafter, they are decalcified with 5% trichloroacetic acid for 12 days and dehydrated in a graded ethanol series. They are embedded in paraffin and celloidin. The prepared blocks are cut horizontally into 6 µm sections. The sections are stained with hematoxylin and eosin and observed under a light microscope. Quantitative assessment of changes of the endolymphatic space is performed according to the method of Takeda (Takeda et al., Hearing Res. (2003) 182:9-18).

Example 98

KCNQ thermoreversible gel formulation of retigabine as prepared in Example 10 is tested in an Endolymphatic Hydrops Animal Model using a procedure similar to the procedure of Example 72.

Example 99—Evaluation of Lixivaptan Administration in Meniere's Patients

Study Objective
The primary objective of this study will be to assess the safety and efficacy of Lixivaptan (100 mg) in ameliorating Meniere's Disease in human subjects.
Methods
Study Design
This will be a phase 3, multicentre, double-blind, randomised, placebo-controlled, parallel group study comparing lixivaptan administration (100 mg) to placebo in the treatment of endolymphatic hydrops. Approximately 100 subjects will be enrolled in this study, and randomised (1:1) to 1 of 2 treatment groups based on a randomisation sequence prepared by the sponsor. Each group will receive either 100 mg lixivaptan+meclizine or meclizine treatment alone.

Subjects who do not complete the study will not be replaced. All patients will receive daily meclizine treatment for 8 weeks. Patients receiving the study drug (Lixivaptan 100 mg or matching placebo) will be administered a gel formulation directly onto the subjects' round window membrane for 8 weeks. Each patient will receive a vestibular and hearing evaluation before each treatment with meclizine and the study drug.

Example 100—Clinical Trials of Vestipitant/Paroxitene in Tinnitus Patients

Study Objective
The primary objective of this study will be to assess the safety and efficacy of Vestipitant/Paroxitene compared with that of placebo in ameliorating tinnitus symptoms in afflicted patients.
Study Design
This will be a phase 3, multicentre, double-blind, randomised, placebo-controlled, three-arm study comparing Vestipitant/Paroxitene to placebo in the treatment of tinnitus. Approximately 100 subjects will be enrolled in this study, and randomised (1:1) to 1 of 3 treatment groups based on a randomisation sequence prepared by sponsor. Each group will receive 280 mg Paroxitene/350 mg Vestipitant delivered in a thermoreversible gel, or controlled release placebo formulation. Release of Vestipitant/Paroxitene is controlled release and occurs over 14 days. Route of Administration will be intratympanic injection.
Primary Outcome Measure
Visual Analog Scales (VAS) to measure the change in tinnitus loudness as perceived at the moment of the measurement at 2 hrs after dosing (or at any other time point vs. pre-dose baseline).

Secondary Outcome Measures

VAS to measure tinnitus pitch, distress and anxiety. Pure Tone Audiometry & Psychoacoustic assessment. Sleep & Tinnitus questionnaires Safety, tolerability and pharmacokinetics of drug. [Time Frame: perceived at the moment of the measurement at 2 hrs after dosing (or at any other time point vs. pre-dose baseline).

Inclusion Criteria

Patients are included if they meet any of the following criteria:

Male or female subjects with a diagnosed tinnitus.

Subject with THI severity grade of 3 or 4.

Subjects willing to restrict alcohol intake.

Women of childbearing potential who abstain from intercourse OR agree to birth control.

Women of non-childbearing potential.

Exclusion Criteria

Patients will be excluded if they meet any of the following criteria:

Subject with THI severity grade=5 or less than or equal to 2.

Subject with pathologic level of anxiety or depression.

Subject with no audiogram deficit and with normal hearing.

Subjects that do not respond to the lidocaine infusion test or show a large variability in pre-infusion values.

Subjects with any serious medical disorder or condition that would preclude the administration of Vestipitant or Paroxetine.

Existence of any surgical or medical condition which might interfere with the PK of the drug.

Subjects with hepatic impairment or a history of liver dysfunction.

Subjects with renal impairment.

Subjects positive for HIV, hepatitis C or hepatitis B.

Subjects with abnormal laboratory, ECG or physical examination findings.

Subjects who are not euthyroid.

Subjects with a history of hepatic, cardiac, renal, neurologic, cerebrovascular, metabolic or pulmonary disease.

Subjects who have had a myocardial infarction.

Subjects with a history of seizure disorders.

Subjects with history of cancer.

Subjects with a history of drug or other allergy.

Subjects positive for drug use and/or a history of substance abuse or dependence.

Subjects who have taken psychotropic drugs or antidepressants within specified time frames.

Medication or foodstuff (e.g. grapefruit or grapefruit juice) which is known to interfere with liver enzymes.

The subject had a non-psychotropic medication with a serotonergic mechanism of action.

Subjects who have recently used an investigational drug or recently participated in a trial.

Subjects who have exhibited intolerance to NK1 antagonists or SSRIs.

Women who have a positive pregnancy test.

Female subjects who intend to get pregnant or male subjects who intend to father a child within the next 4 weeks following the last study drug administration in the study.

Subjects, who have donated a unit of blood or more within the previous month or who intend to donate blood within one month of completing the study.

Example 101—Clinical Trials of Neramexane in Tinnitus Patients

Study Objective

The primary objective of this study will be to assess the safety and efficacy of Neramexane compared with that of placebo in ameliorating tinnitus symptoms in afflicted patients.

Study Design

This will be a phase 3, multicentre, double-blind, randomised, placebo-controlled, three-arm study comparing Neramexane to placebo in the treatment of tinnitus. Approximately 250 subjects will be enrolled in this study, and randomised (1:1) to 1 of 3 treatment groups based on a randomisation sequence prepared by sponsor. Each group will receive 300 mg Neramexane delivered in a thermoreversible gel, or controlled release placebo formulation. Release of Neramexane is controlled release and occurs over 14 days. Route of Administration will be intratympanic injection.

Primary Outcome Measure

Visual Analog Scales (VAS) to measure the change in tinnitus loudness as perceived at the moment of the measurement at 2 hrs after dosing (or at any other time point vs. pre-dose baseline).

Secondary Outcome Measures

VAS to measure tinnitus pitch, distress and anxiety. Pure Tone Audiometry & Psychoacoustic assessment. Sleep & Tinnitus questionnaires Safety, tolerability and pharmacokinetics of drug. [Time Frame: perceived at the moment of the measurement at 2 hrs after dosing (or at any other time point vs. pre-dose baseline).

Inclusion Criteria

Patients are included if they meet any of the following criteria:

Male or female subjects with a persistent, subjective, uni or bi-lateral tinnitus tinnitus.

Subjects willing to restrict alcohol intake.

Women of childbearing potential who abstain from intercourse OR agree to birth control.

Women of non-childbearing potential.

Exclusion Criteria

Patients are excluded if they meet any of the following criteria:

Intermittent or pulsatile tinnitus

Subject with pathologic level of anxiety or depression.

Subject with no audiogram deficit and with normal hearing.

Subjects that do not respond to the lidocaine infusion test or show a large variability in pre-infusion values.

Existence of any surgical or medical condition which might interfere with the PK of the drug.

Subjects with hepatic impairment or a history of liver dysfunction.

Subjects with renal impairment.

Subjects positive for HIV, hepatitis C or hepatitis B.

Subjects with abnormal laboratory, ECG or physical examination findings.

Subjects who are not euthyroid.

Subjects with a history of hepatic, cardiac, renal, neurologic, cerebrovascular, metabolic or pulmonary disease.

Subjects who have had a myocardial infarction.

Subjects with a history of seizure disorders.

Subjects with history of cancer.

Subjects with a history of drug or other allergy.

Subjects positive for drug use and/or a history of substance abuse or dependence.

Subjects who have taken psychotropic drugs or antidepressants within specified time frames.

Medication or foodstuff (e.g. grapefruit or grapefruit juice) which is known to interfere with liver enzymes.

Subjects who have recently used an investigational drug or recently participated in a trial.

Women who have a positive pregnancy test.

Female subjects who intend to get pregnant or male subjects who intend to father a child within the next 4 weeks following the last study drug administration in the study.

Subjects, who have donated a unit of blood or more within the previous month or who intend to donate blood within one month of completing the study.

Example 102—Clinical Trials of AL-15469A/AL-38905 in Acute Otitis Externa Patients Study Objective The primary objective of this study will be to assess the safety and efficacy of AL-15469A/AL-38905 compared with that of placebo in ameliorating Acute Otitis Externa symptoms in afflicted patients.

Study Design

This will be a phase 3, multicentre, double-blind, randomised, placebo-controlled, three-arm study comparing AL-15469A/AL-38905 (100 mg and 200 mg) to placebo in the treatment of tinnitus.

Approximately 1500 subjects will be enrolled in this study, and randomised (1:1) to 1 of 3 treatment groups based on a randomisation sequence prepared by sponsor. Each group will receive 100 mg controlled release AL-15469A/AL-38905, 200 mg controlled release AL-15469A/AL-38905 or controlled release placebo formulation.

Primary Outcome Measures:

Clinical cure [Time Frame: Day 3 and Day 12]

Secondary Outcome Measures:

Microbiological success [Time Frame: Day 12]

Inclusion Criteria:

Patients must be at least 6 months of age or older. Further, patients must have a clinical diagnosis of AOE based on clinical observation and of presumed bacterial origin. Additionally, patients must demonstrate a minimum combined score of ≥4 in at least 1 affected ear at the Day 1 exam for tenderness, erythema, and edema.

Exclusion Criteria:

Patients will be excluded if they meet any of the following criteria:

Duration of pretherapy signs or symptoms of AOE greater than four (4) weeks.

Presence of a tympanostomy tube or perforated tympanic membrane in the treated ear(s). Patients with a history of tympanic membrane perforation should not be enrolled unless the absence of a current perforation is confirmed at Visit 1 prior to enrollment.

Clinically diagnosed chronic suppurative otitis media, acute otitis media, acute otorrhea in patients with tympanostomy tubes, or malignant otitis externa.

Known or suspected ear infection of fungal or mycobacterial origin.

Prior otologic surgery within 6 months of study entry. Seborrheic dermatitis or other skin conditions of the external auditory canal.

Current or prior history of an immunosuppressive disorder (e.g., HIV positive) or current immunosuppressive therapy (e.g., cancer chemotherapy) or known acute or chronic renal disorders or active hepatitis.

Diabetic patients (controlled or uncontrolled) based upon assessment by Investigator.

Any systemic disease or disorder, complicating factor or structural abnormality that would negatively affect the conduct or outcome of the study [e.g., cleft palate (including repairs), Downs Syndrome, and cranial facial reconstruction].

Any current known or suspected infection (other than AOE) requiring systemic antimicrobial therapy.

Use of prohibited medications or inadequate washout of any medication listed in protocol.

Concomitant use of topical or oral analgesics (i.e., NSAIDs and aspirin products) which may have anti inflammatory effects. Patients on low dose aspirin therapy (81 mg per day) at the time of enrollment are enrolled and continue the low dose aspirin during the study. Use of acetaminophen ("Tylenol") is permitted during the trial.

Example 103—Clinical Trials of JB004/A in Meniere's Disease Patients

Study Objective

The primary objective of this study will be to assess the safety and efficacy of JB004/A compared with that of placebo in ameliorating tinnitus symptoms in Meniere's Disease afflicted patients.

Study Design

This will be a phase 3, multicentre, double-blind, randomised, placebo-controlled, three-arm study comparing JB004/A to placebo in the treatment of tinnitus. Approximately 250 subjects will be enrolled in this study, and randomised (1:1) to 1 of 3 treatment groups based on a randomisation sequence prepared by sponsor. Each group will receive 300 mg JB004/A delivered in a thermoreversible gel, or controlled release placebo formulation. Release of JB004/A is controlled release and occurs over 30 days. Route of Administration will be intratympanic injection.

Primary Outcome Measure

Visual Analog Scales (VAS) to measure the change in tinnitus loudness as perceived at the moment of the measurement at 2 hrs after dosing (or at any other time point vs. pre-dose baseline). Alternatively, audiometry is used in the healthy ear to match the tone of the tinnitus in the affected ear.

Secondary Outcome Measures

VAS to measure tinnitus pitch, distress and anxiety. Pure Tone Audiometry & Psychoacoustic assessment. Sleep & Tinnitus questionnaires Safety, tolerability and pharmacokinetics of drug. [Time Frame: perceived at the moment of the measurement at 2 hrs after dosing (or at any other time point vs. pre-dose baseline).

Inclusion Criteria

Patients are included if they meet any of the following criteria:

Male or female subjects diagnosed with a tinnitus.

Subjects willing to restrict alcohol intake.

Women of childbearing potential who abstain from intercourse OR agree to birth control.

Women of non-childbearing potential.

Exclusion Criteria

Patients are excluded if they meet any of the following criteria:

Intermittent or pulsatile tinnitus

Subject with pathologic level of anxiety or depression.

Subject with no audiogram deficit and with normal hearing.

Subjects that do not respond to the lidocaine infusion test or show a large variability in pre-infusion values.

Existence of any surgical or medical condition which might interfere with the PK of the drug.

Subjects with hepatic impairment or a history of liver dysfunction.

Subjects with renal impairment.

Subjects positive for HIV, hepatitis C or hepatitis B.

Subjects with abnormal laboratory, ECG or physical examination findings.

Subjects who are not euthyroid.

Subjects with a history of hepatic, cardiac, renal, neurologic, cerebrovascular, metabolic or pulmonary disease.

Subjects who have had a myocardial infarction.

Subjects with a history of seizure disorders.

Subjects with history of cancer.

Subjects with a history of drug or other allergy.

Subjects positive for drug use and/or a history of substance abuse or dependence.

Subjects who have taken psychotropic drugs or antidepressants within specified time frames.

Medication or foodstuff (e.g. grapefruit or grapefruit juice) which is known to interfere with liver enzymes.

Subjects who have recently used an investigational drug or recently participated in a trial.

Women who have a positive pregnancy test.

Female subjects who intend to get pregnant or male subjects who intend to father a child within the next 4 weeks following the last study drug administration in the study.

Subjects, who have donated a unit of blood or more within the previous month or who intend to donate blood within one month of completing the study.

Example 104—Evaluation of Alpha Lipoic Acid in an Early Onset Age-Related Hearing Impairment DBA-Mouse Model DBA mice are administered an alpha-lipoic acid formulation of Example 3 directly onto the round window membrane, beginning 2, 4 or 8 weeks after birth. The hearing threshold for the auditory brainstem response threshold (ABR) to click stimuli for each ear of each animal is initially measured and on a weekly basis during and after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 105—Evaluation of Diazepam in an Endolymphatic Hydrops Animal Model

Methods and Materials

Induction of Endolymphatic Hydrops

Female albino National Institutes of Health-Swiss mice (Harlan Sprague-Dawley, Inc., Indianapolis, Inc.) weighing 20 to 24 g are used. Artificial endolymph is injected into the cochlear duct.

Treatment

The endolymphatic mice and control mice are sorted into two groups (n=10 in each group). The CNS modulating formulation of Example 5 containing diazepam is applied to the round window membrane of one group of animals. Control formulation containing no diazepam is applied to the second group. The CNS modulating and control formulations are reapplied three days after the initial application. The animals are sacrificed after the seventh day of treatment.

Analysis of Results

Electrophysiologic Testing

The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 106—Clinical Trial of Diazepam as a Treatment for Tinnitus

Active Ingredient: Diazepam

Dosage: 10 ng delivered in 10 µL of a thermoreversible gel. Release of diazepam is controlled release and occurs over thirty (30) days.

Route of Administration: Intratympanic injection

Treatment Duration: 12 weeks

Methodology

Monocentric

Prosepective

Randomized

Double-blind

Placebo-controlled

Parallel group

Adaptive

Inclusion Criteria

Male and female subjects between the 18 and 64 years of age.

Subjects experiencing subjective tinnitus.

Duration of tinnitus is greater than 3 months.

No treatment of tinnitus within 4 weeks.

Evaluation Criteria

Efficacy (Primary)

Total score of the Tinnitus Questionnaire

Efficacy (Secondary)

Audiometric measurements (mode, frequency, loudness of the tinnitus, pure tone audiogram, speech audiogram)

Quality of Life questionnaire

Safety

Treatment groups were compared with respect to incidence rates of premature termination, treatment-emergent adverse events, laboratory abnormalities, and ECG abnormalities.

Study Design

Subjects are divided into three treatment groups. The first group is the safety sample. The second group is the intent-to-treat (ITT) sample. The third group is the valid for efficacy (VfE) group.

For each group, one half of subjects to be given diazepam and the remainder to be given placebo.

Statistical Methods

The primary efficacy analysis is based on the total score of the Tinnitus Questionnaire in the ITT sample. The statistical analysis is based on an analysis of covariance (ANCOVA) with baseline as covariant and the last observation carried forward value as dependent variable. Factor is "treatment." The homogeneity of regression slopes is tested. The analysis is repeated for the VfE sample.

Audiometric measurements (mode, frequency, loudness of the tinnitus, pure tone audiogram, speech audiogram) as well as quality of life are also analyzed via the aforementioned model. The appropriateness of the model is not tested. P values are exploratory and are not adjusted for multiplicity.

Example 107—Evaluation of Cytotoxic Agent Formulations in an Ear Cancer Animal Model Cytotoxic agent formulations are tested in an ear cancer animal model, described in Arbeit, J. M., et al. Cancer Res. (1999), 59: 3610-3620. A cohort of K14-HPV16 transgenic mice is divided into control/untreated and test/treated mice groups for comparison of the effect of cytotoxic agent formulation administration on the development of ear cancer. The cytotoxic agent methotrexate formulation of Example 4 is administered to the ear of the test mice group starting at age 4 weeks. The chemopreventive effect of the cytotoxic agent formulation is assessed by sacrificing treated mice at age 8, 16, and 32 weeks, and comparing the number of lesions and histopathological and phenotypic markers (papillomatosis, dermal inflammatory cell infiltration, corneal parakeratosis, etc.) at the various stages of neoplastic progression to control mice of the same age. The effect of cytotoxic agent formulations on the progression of established, late-stage neoplasia is assessed by administering the cytotoxic agent formulation of Example 4 to K14-HPV16 transgenic mice starting at age 28 weeks. The mice are sacrificed at age 32 weeks, and the effect of the cytotoxic agent formulation is assessed by comparing the number of lesions and histopathological and phenotypic markers to control mice of the same age.

Example 108—AIED Clinical Trials Using Cytotoxic Agent Formulations

Ten adults patients are selected due to initial steroid responsiveness followed by recurrence of hearing loss when steroids are tapered or after completion of steroid treatment. The cytotoxic agent formulation of Example 4 containing methotrexate is administered to each patient's round window membrane through piercing of the tympanic membrane. Reapplication of the cytotoxic agent formulations is performed 7 days after the initial application, and again at 2 and 3 weeks of treatment.

Hearing evaluations consisting of pure tone audiometry (250-8,000 Hz) and speech testing using dissyllabic word lists in French are administered to each patient. Testing is carried out both before the application of the cytotoxic agent formulation and at 1, 2, 3 and 4 weeks post-initial treatment.

Example 109—Evaluation of N-acetylcysteine (NAC) in a Cisplatin-Induced Ototoxicity Mouse Model Methods and Materials Induction of Ototoxicity Twelve Harlan Sprague-Dawley mice weighing 20 to 24 g are used. Baseline auditory brainstem response (ABR) at 4-20 mHz is measured. The mice are treated with cisplatin (6 mg/kg of body weight). The cisplatin is delivered to the aorta by IV infusion.

Treatment

The control group (n=10) are administered saline following administration of the cisplatin. The experimental group (n=10) are administered NAC (400 mg/kg of body weight) following administration of the cisplatin.

Analysis of Results

Electrophysiologic Testing

The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated pre-amplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 110

L(+)-Ergothioneine was tested in a cisplatin-induced ototoxicity mouse model using a procedure similar to the procedure in Example 84.

Example 111—Evaluation of AMN082 on Cisplatin-Induced Ototoxicity

Study Objective

The primary objective of this study will be to assess the safety and efficacy of AMN082 (100 mg) compared with that of placebo in preventing Cisplatin-induced ototoxicity.

Methods

Study Design

This will be a phase 3, multicentre, double-blind, randomised, placebo-controlled, parallel group study comparing AMN082 (100 mg) to placebo in the treatment of Cisplatin-induced ototoxicity. Approximately 140 subjects will be enrolled in this study, and randomised (1:1) to 1 of 2 treatment groups based on a randomisation sequence prepared by sponsor. Each group will receive either AMN082 100 mg or placebo.

Subjects who do not complete the study will not be replaced. Patients will receive weekly chemotherapy (cisplatin at a dose of 70 mg/m$^2$ for 7 weeks and daily radiation. Following chemotherapy, patients will receive the study drug (AMN082 500 mg or matching placebo) administered as a gel formulation directly onto the subjects' round window membrane for 8 weeks.

Each patient will receive a hearing evaluation before each treatment with Cisplatin. Two to four weeks after the final dose of Cisplatin, each patient will receive a hearing evaluation. Pre-treatment audiogram will be compared with the post treatment audiogram to determine the degree of cisplatin-induced ototoxicity. Patients will thereafter receive a hearing evaluation at 4-week intervals concomitant with the AMN082 treatment.

Main Criteria for Inclusion

Male or female outpatients aged between 18 and 75 years receiving chemotherapy with Cisplatin. Patients expected to receive a minimum of 3 rounds of chemotherapy. If a subject becomes pregnant during the study, she will be immediately withdrawn and no study medication will be administered.

Exclusion Criteria

Patients who have had middle ear surgery. Patients who have active external or middle ear disease. Patients who have preceding pure tone average of >40 dB HL.

Example 112—Evaluation of Antimicrobial Agent Formulations in an Otitis Externa Animal Model Otitis externa is induced in 20 Sprague-Dawley rats using a plastic pipette to aggravate the tissue of the ear canal. All of the rats develop OE within one day. The antimicrobial formulation of Example 17 containing neomycin is administered to the ears of half of the rats using a needle and syringe, while the remaining rats receive the same formulation without the neomycin. The ear canal tissue is observed for redness and swelling that characterizes the condition. Light microscopy is used to analyze biopsy samples from the rats.

Example 113—Clinical Trial of Antimicrobial Agent Formulations for the Treatment of Otosyphilis Patients selected for the study present symptoms of cochleovestibular dysfunction and positive syphilis serology. Patients are divided into two groups, a test group receiving intratympanic administration of the formulation of Example 57 in conjunction with an intramuscular (IM) injection of 2.4 million units of benzathine penicillin G (the recommended treatment for syphilis), and a control group receiving only the carrier and microspheres of the otic formulation of Example 57 in conjunction with an IM injection of 2.4 million units of benzathine penicillin G. Patients are monitored for improvement of hearing, tinnitus, vertigo, and nystagmus following administration of the active agents. The primary outcome of the trial is improvement of cochleovestibular function at the 6 month post-treatment visit. The outcome for patients receiving the formulation of Example 6 and the recommended therapy is compared to the outcome for patients receiving only the carrier for the otic formulation and the recommended therapy in order to determine the efficacy of localized delivery of an antimicrobial agent formulation for the treatment of otic symptoms of syphilis.

Example 114—Clinical Trials of KCNQ Modulator in Vertigo Patients

Study Objective

The primary objective of this study will be to assess the safety and efficacy of retigabine compared with that of placebo in ameliorating vertigo symptoms in afflicted patients.

Methods

Study Design

This will be a phase 3, multicentre, double-blind, randomised, placebo-controlled, three-arm study comparing retigabine (100 mg and 200 mg) to placebo in the treatment of vertigo symptoms. Approximately 150 subjects will be enrolled in this study, and randomised (1:1) to 1 of 3 treatment groups based on a randomisation sequence prepared by sponsor. Each group will receive 200 mg controlled release retigabine, 400 mg controlled release retigabine or controlled release placebo formulation.

After a 1-week baseline phase, patients from each group will be randomized to a 16 week double treatment period (8-week treatment followed by an 8-week maintenance period). Primary efficacy will be measured as a percentage change in the frequency and intensity of vertigo symptoms, including dizziness, loss of balance and incidence of nystagmus after treatment as compared to baseline measurements.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. A pharmaceutical composition comprising: between about 0.1 mg/ml to about 20 mg/ml of one and no more than one growth factor selected from brain-derived neurotrophic factor (BDNF) or neurotrophin-3, or pharmaceutically acceptable salt thereof, wherein the pharmaceutical composition is a thermoreversible gel formulated for intratympanic administration, wherein the pharmaceutical composition comprises from 14% to 17% by weight of Poloxamer 407, and wherein the growth factor is not a glial cell-line derived neurotrophic factor (GDNF).

2. The pharmaceutical composition of claim 1, wherein the pharmaceutical composition has a gelation temperature of from 20° C. to 25° C.

3. The pharmaceutical composition of claim 1, wherein the pharmaceutical composition has a pH of from 7.0 to 8.0.

4. The pharmaceutical composition of claim 1, wherein the pharmaceutical composition has an osmolarity of from 250 mOsm/L to 320 mOsm/L.

5. The pharmaceutical composition of claim 1, wherein the pharmaceutical composition comprises from 15% to 16% by weight of Poloxamer 407.

6. The pharmaceutical composition of claim 1, wherein the growth factor is in the form of non-coated micronized particles.

7. The pharmaceutical composition of claim 1, wherein the pharmaceutical composition is formulated to provide sustained release of the growth factor into an inner ear for a period of at least 5 days following a single administration.

8. The pharmaceutical composition of claim 7, wherein the pharmaceutical composition is formulated to provide sustained release of the growth factor into an inner ear for a period of at least 7 days following a single administration.

9. The pharmaceutical composition of claim 1, wherein the growth factor is an otic hair cell growth factor.

10. The pharmaceutical composition of claim 9, wherein the growth factor is a neurotroph.

11. The pharmaceutical composition of claim 1, wherein the growth factor is neurotrophin-3.

12. The pharmaceutical composition of claim 1, wherein the growth factor is BDNF.

13. The pharmaceutical composition of claim 1, wherein the pharmaceutical composition comprises between about 0.1 mg/ml to about 5 mg/ml of the growth factor.

14. The pharmaceutical composition of claim 13, wherein the pharmaceutical composition comprises between about 0.5 mg/ml to about 5 mg/ml of the growth factor.

15. The pharmaceutical composition of claim 13, wherein the pharmaceutical composition comprises between about 0.1 mg/ml to about 0.5 mg/ml of the growth factor.

16. The pharmaceutical composition of claim 1, wherein the growth factor is dissolved in the pharmaceutical composition.

17. The pharmaceutical composition of claim 1, wherein the composition comprises: between about 0.1 mg/ml to about 10 mg/ml of the growth factor.

* * * * *